US012098400B2

(12) United States Patent
Vegge et al.

(10) Patent No.: US 12,098,400 B2
(45) Date of Patent: Sep. 24, 2024

(54) HIGHLY POTENT ISVD COMPOUNDS CAPABLE OF SUBSTITUTING FOR FVIII(A)

(71) Applicant: Novo Nordisk A/S, Bagsvaerd (DK)

(72) Inventors: Andreas Vegge, Frederiksberg (DK);
Daniele Granata, Copenhagen (DK);
Jais Rose Bjelke, Smoerum (DK);
Jacob Lund, Roskilde (DK); Philip Jonas Sassene, Copenhagen V (DK);
Per J. Greisen, Belmont, WA (US);
Thomas Egebjerg, Ganloese (DK);
Evelyn De Tavernier, Deurle (BE);
Soren Steffensen, Etterbeek (BE);
Marie-Ange Buyse, Merelbeke (BE);
Frantisek Hubalek, Herlev (DK);
Simone Fulle, Copenhagen (DK);
Mathias Norrman, Staffanstorp (SE)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 18/219,159

(22) Filed: Jul. 7, 2023

(65) Prior Publication Data

US 2024/0067944 A1 Feb. 29, 2024

(30) Foreign Application Priority Data

Jul. 8, 2022 (EP) ..................... 22183818
Jul. 8, 2022 (EP) ..................... 22183825

(51) Int. Cl.
*C12N 9/64* (2006.01)
*A61K 38/00* (2006.01)

(52) U.S. Cl.
CPC ........... *C12N 9/644* (2013.01); *C12N 9/6432* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 7,429,381 B2* | 9/2008 | Hansen | ............ | C07K 16/3007 424/9.34 |
| 9,334,331 B2 | 5/2016 | Gawa et al. | | |
| 10,759,870 B2 | 9/2020 | Teranishi et al. | | |
| 11,787,874 B2* | 10/2023 | Lund | ............ | C07K 16/36 424/133.1 |
| 2011/0123529 A1 | 5/2011 | Laeremans et al. | | |
| 2017/0107302 A1 | 4/2017 | Silence et al. | | |
| 2017/0349668 A1 | 12/2017 | Rattel et al. | | |
| 2021/0054097 A1 | 2/2021 | Lund et al. | | |
| 2021/0284715 A1 | 9/2021 | Kong et al. | | |
| 2023/0203185 A1* | 6/2023 | Owen | ............ | C07K 16/2896 424/141.1 |

FOREIGN PATENT DOCUMENTS

| | | |
|---|---|---|
| EP | 2267028 A2 | 12/2010 |
| EP | 2746290 A2 | 6/2014 |
| EP | 3299393 A1 | 3/2018 |
| WO | 199404678 A1 | 3/1994 |
| WO | 199749805 A2 | 12/1997 |
| WO | 2005044858 A1 | 5/2005 |
| WO | 2005052002 A2 | 6/2005 |
| WO | 2005118629 A1 | 12/2005 |
| WO | 2006040153 A2 | 4/2006 |
| WO | 2006122825 A2 | 11/2006 |
| WO | 2008074867 A2 | 6/2008 |
| WO | 2008149150 A2 | 12/2008 |
| WO | 2012067176 A1 | 5/2012 |
| WO | 2013174537 A1 | 11/2013 |
| WO | 2016102562 A1 | 6/2016 |
| WO | 2017158176 A1 | 9/2017 |
| WO | 2018098363 | 5/2018 |
| WO | 2018141863 A1 | 8/2018 |
| WO | 2018234575 A1 | 12/2018 |
| WO | 2019065795 | 4/2019 |
| WO | 2019215063 A1 | 11/2019 |
| WO | 2020025672 A1 | 2/2020 |
| WO | 2020114614 A1 | 6/2020 |
| WO | 2020114615 A1 | 6/2020 |
| WO | 2020115281 A1 | 6/2020 |
| WO | 2020128049 A1 | 6/2020 |
| WO | 2021152066 A1 | 8/2021 |

(Continued)

OTHER PUBLICATIONS

Abramson et al., "Oral delivery of systemic monoclonal antibodies, peptides and small molecules using gastric auto-injectors", Nature Biotechnology, Aug. 2021, vol. 40, pp. 103-109.
Anson et al., "The gene structure of human anti-haemophilic factor IX.", EMBO J., May 1984, vol. 3, No. 5, pp. 1053-1060.
Avery et al., "Establishing in vitro in vivo correlations to screen monoclonal antibodies for physicochemical properties related to favorable human pharmacokinetics", MAbs, Jan. 29, 2018, vol. 10, No. 2, pp. 244-255.
Dobson et al., "Engineering the surface properties of a human monoclonal antibody prevents self-association and rapid clearance in vivo", Nature, Dec. 20, 2016, vol. 6, Article No. 38644, pp. 1-14.
Dooley et al., "Antibody repertoire development in cartilaginous fish" Developmental & Comparative Immunology, Jul. 2005, vol. 30, pp. 43-56.

(Continued)

*Primary Examiner* — Sudhakar Katakam
*Assistant Examiner* — Zachary J Miknis
(74) *Attorney, Agent, or Firm* — Jianjie Hu

(57) ABSTRACT

The present invention provides ISVD polypeptide derivatives capable of binding coagulation Factor IX(a) and Factor X(a) which are highly potent and provide a sufficiently long half-life such to allow for effective subcutaneous—as well as peroral administration. The ISVD polypeptides derivatives disclosed herein are thus suitable for treatment of haemophilia A, haemophilia A with inhibitors and acquired haemophilia A by various routes of administration including subcutaneous and peroral administration.

9 Claims, 14 Drawing Sheets
Specification includes a Sequence Listing.

(56) References Cited

FOREIGN PATENT DOCUMENTS

WO      WO2024008904 A2 *    1/2024             C07K 16/36

OTHER PUBLICATIONS

Durocher et al. "High-Level and High-throughput recombinant protein production by transient transfection of suspension-growing human 293-EBNA1 cells" Nucleic Acids Research, Jan. 2002, vol. 30, No. 2, e9—pp. 1-9.

Graham et al., "The malmo polymorphism of coagulation factor IX, an immunologic polymorphism due to dimorphism of residue 148 that is in linkage disequilibrium with two other F.IX polymorphisms", Am. J. Hum. Genet., Apr. 1988, vol. 42, pp. 573-580.

Hemker et al., "The calibrated automated thrombogram (CAT): a universal routine test for hyper- and hypocoagulability", Pathophysiol Haemost Thromb, Sep.-Dec. 2002, vol. 32, pp. 249-253.

Igawa et al., "Reduced elimination of IgG antibodies by engineering the variable region", PEDS, Feb. 2010, vol. 23, No. 5, pp. 385-392.

Knight et al., "The role of emicizumab, a bispecific factor IXa- and factor X-directed antibody, for the prevention of bleeding episodes in patients with hemophilia A", Therapeutic Advances in Hematology, Oct. 2018, vol. 9, No. 10, pp. 319-334.

Kolkman et al.,"Insertion Loop 256-268 in Coagulation Factor IX Restricts Enzymatic Activity in the Absence but Not in the Presence of Factor VIII" Biochemistry, 2000, vol. 39, pp. 7398-7405.

Martin, "Chapter 3—Protein Sequence and Structure Analysis of Antibody Variable Domains", Antibody Engineering, 2010, vol. 2, pp. 33-51.

McGraw et al., "Evidence for a prevalent dimorphism in the activation peptide of human coagulation factor IX.", PNAS, May 1985, vol. 82, No. 9, pp. 2847-2851.

Muyldermans, "Nanobodies: natural single-domain antibodies", Annu Rev Biochem., Jun. 2013, vol. 82, pp. 775-797.

Needleman et al., "A general method applicable to the search for similarities in the amino acid sequence of two proteins", Journal of Molecular Biology, Mar. 1970, vol. 48, No. 3, pp. 443-453.

Østergaard et al., "A factor VIIIa-mimetic bispecific antibody, Mim8, ameliorates bleeding upon severe vascular challenge in hemophilia A mice", Blood, Jun. 2021, vol. 138, No. 14, pp. 1258-1268.

Sampei et al.,"Identification and Multidimensional Optimization of an Asymmetric Bispecific IgG Antibody Mimicking the Function of Factor VIII Cofactor Activity" PLOS One, 2013, vol. 8, No. 2, p. e57479.

SB van Witteloostuijn et al., "Half-Life Extension of Biopharmaceuticals using Chemical Methods: Alternatives to PEGylation," Chem Med Chem, Oct. 2016, vol. 11, pp. 2474-2495.

Scheiflinger et al., "Enhancement of the enzymatic activity of activated coagulation factor IX by anti-factor IX antibodies", J Thromb Haemost, Feb. 2008, vol. 6. pp. 315-322.

Shima et al., "Factor VIII-Mimetic Function of Humanized Bispecific Antibody in Hemophilia A", N Engl J Med, May 26, 2016, vol. 374, pp. 2044-2053.

Zogg et al., "Activation mechanisms of coagulation factor IX", Biol Chem, May 2009, vol. 390, No. 5-6, pp. 391-400.

* cited by examiner

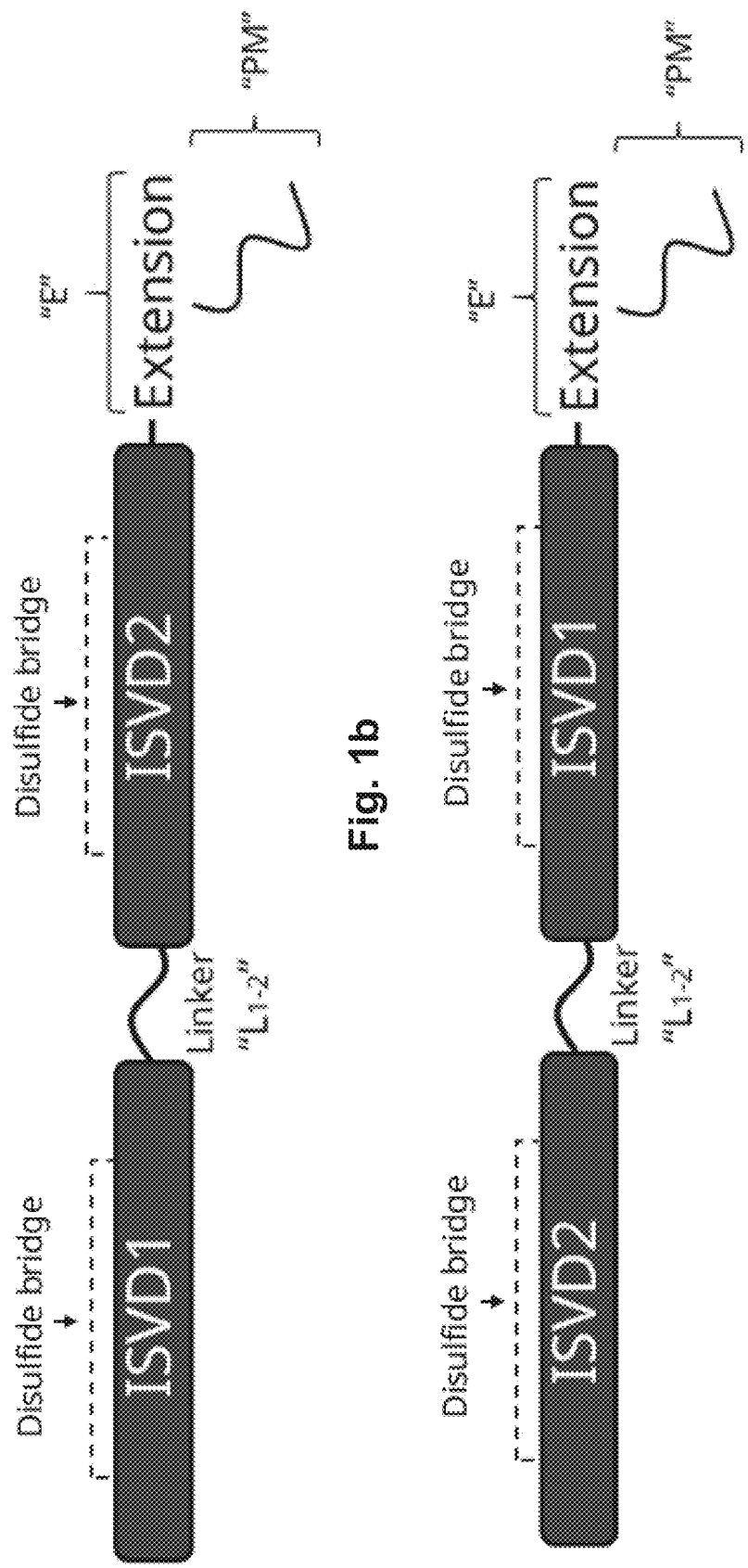

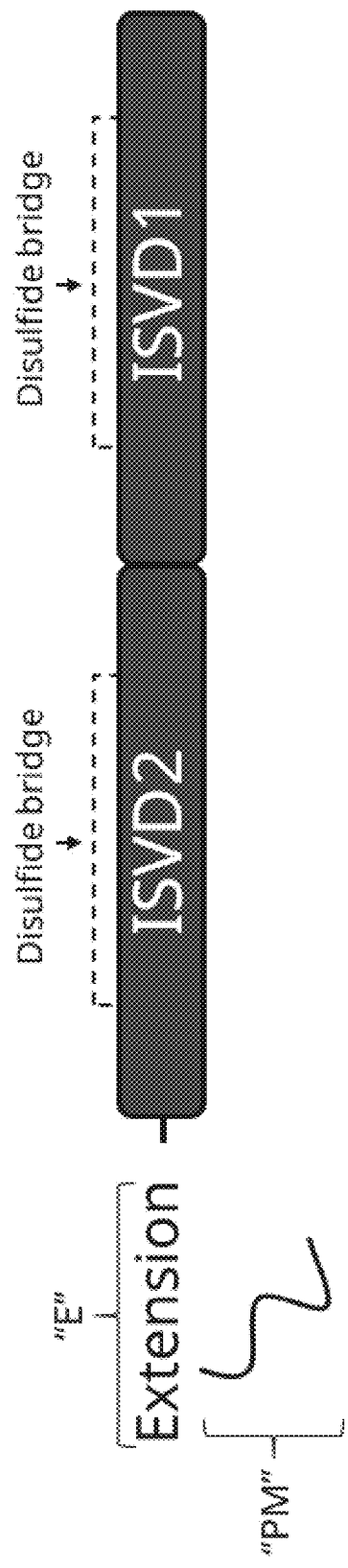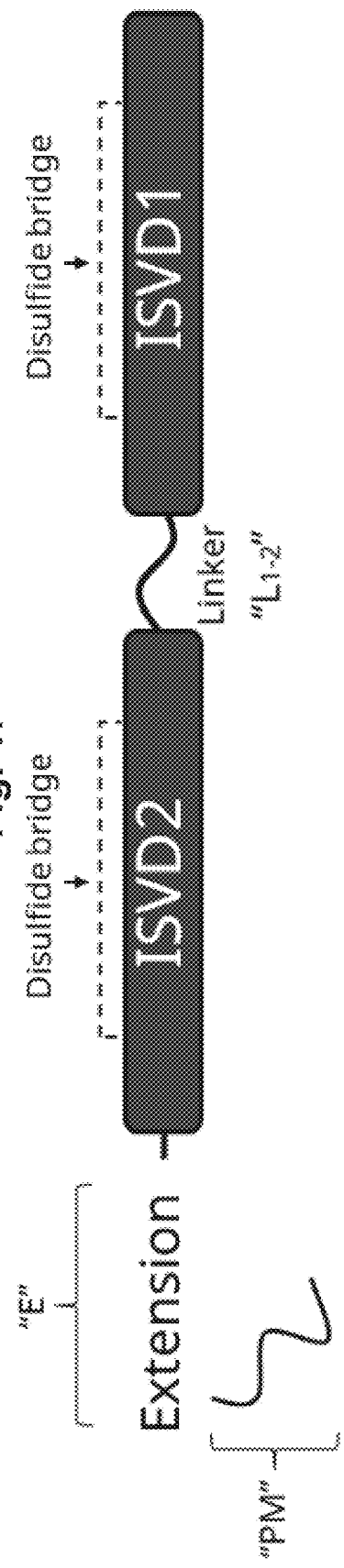

Compound: Cmpd #66

Compound: Cmpd #68

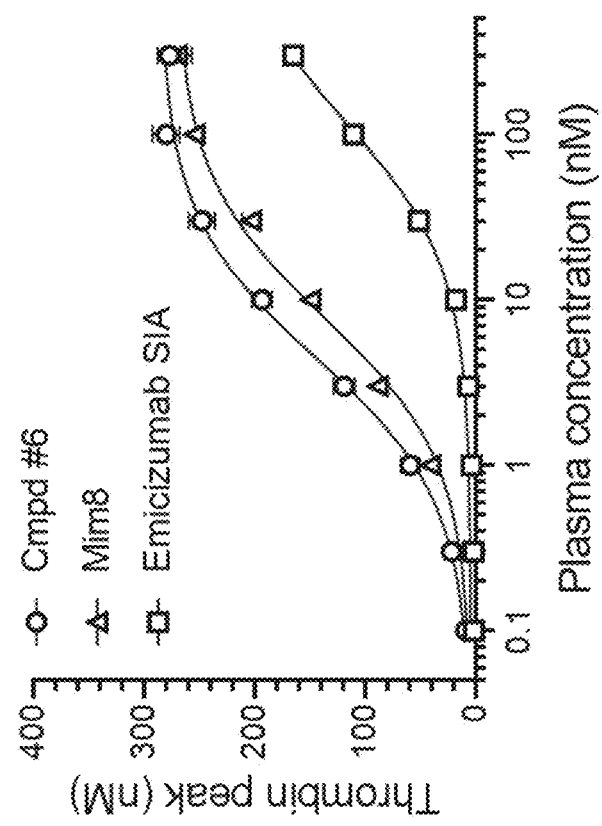

Fig. 5a

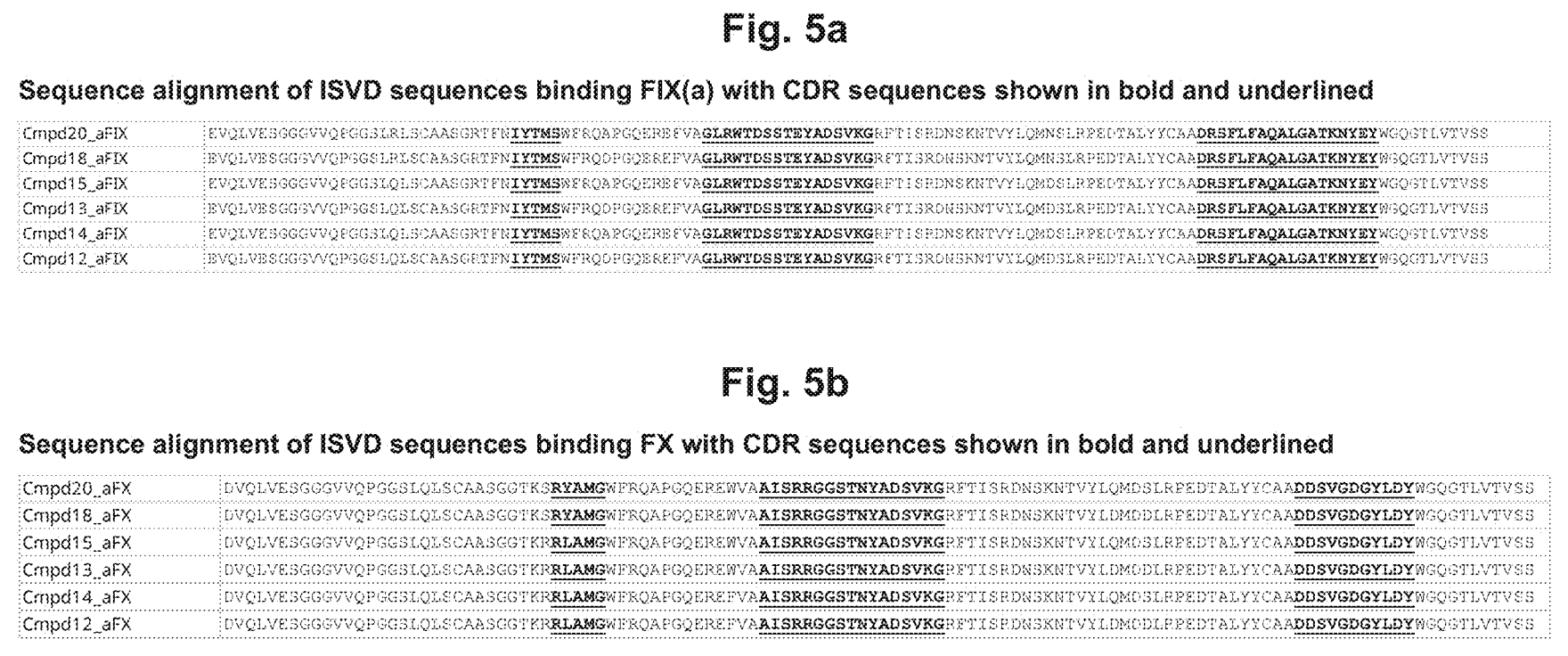

Sequence alignment of ISVD sequences binding FIX(a) with CDR sequences shown in bold and underlined

Fig. 5b

Sequence alignment of ISVD sequences binding FX with CDR sequences shown in bold and underlined

HIGHLY POTENT ISVD COMPOUNDS CAPABLE OF SUBSTITUTING FOR FVIII(A)

CROSS-REFERENCE TO RELATED APPLICATIONS

This application claims priority under 35 U.S.C. § 119 to European Patent Applications 22183825.3, filed Jul. 8, 2022 and 22183818.8, filed Jul. 8, 2022; the contents of which are incorporated herein by reference.

TECHNICAL FIELD

The invention relates to compounds capable of binding to coagulation Factor IX(a) and Factor X(a) and their use in the treatment of a coagulopathy, such as the various forms of haemophilia, including haemophilia A.

INCORPORATION-BY-REFERENCE OF THE SEQUENCE LISTING

The instant application contains a Sequence Listing which has been submitted in XML format via USPTO patent electronic filing system and is hereby incorporated by reference in its entirety. Said XML file, created on Jul. 7, 2023, is named "210022US01 XML seq listing", and is 914 kilobytes in size.

BACKGROUND

In patients with a coagulopathy, such as in human beings with haemophilia A (HA) and B (HB), various steps of the coagulation cascade are rendered dysfunctional due to, for example, the absence or insufficient presence of a functional coagulation factor. Such dysfunction of one part of the coagulation cascade results in insufficient blood coagulation and potentially life-threatening bleeding, or damage to internal organs, such as the joints. Coagulation Factor VIII (FVIII) deficiency, commonly referred to as haemophilia A, is a congenital bleeding disorder affecting approximately 420,000 people worldwide, of which around 105,000 are currently diagnosed. Haemophilia A has three grades of severity defined by factor FVIII plasma levels of 1% or less ("severe"), 2 to 5% ("moderate"), and 6 to 30% ("mild") (White et al. (2001) Thromb. Haemost. 85:560) or 5-<40% according to WFH "Guidelines for the management of haemophilia" 2nd edition Haemophilia; Epub 6 Jul. 2012. A bleed can appear spontaneously, or following trauma. Approximately half of all patients with haemophilia A are classified as having the severe haemophilia A and experience severe bleeding starting in early childhood, and frequent episodes of spontaneous or excessive bleeding later in life. Bleeding commonly occurs into joints and muscles, and without appropriate treatment, recurrent bleeding can lead to irreversible hemoarthropathy (Manco-Johnson et al. (2007) N. Engl. J. Med. 357: 535-44). Patients with haemophilia A may receive coagulation factor replacement therapy such as exogenous FVIII. Conventional treatment consists of replacement therapy, provided as prophylaxis or on demand treatment of bleeding episodes. Until recently prophylactic treatment for a patient with severe haemophilia A included up to three intravenous injections/week with either plasma derived FVIII or recombinant FVIII or long-acting variants thereof.

However, such patients are at risk of developing neutralizing antibodies, so-called inhibitors, to such exogenous factors, rendering formerly efficient therapy ineffective. Haemophilia A patients with inhibitors is a non-limiting example of a coagulopathy that is partly congenital and partly acquired. Patients that have developed inhibitors to FVIII cannot be treated with conventional replacement therapy. Exogenous coagulation factors may only be administered intravenously, which is of considerable inconvenience and discomfort to patients.

An inadequate FXa formation and decreased thrombin generation caused by reduced or absent FVIII activity is the reason underlying the bleeding diathesis in haemophilia A patients.

Proteolytic conversion of FX into its enzymatically active form FXa can be achieved by the intrinsic FX-activating complex comprising FIXa and its cofactor activated FVIII (FVIIIa). Cofactor binding increases the enzymatic activity of FIXa by about five orders of magnitude and is believed to result through multiple mechanisms as outlined by Scheiflinger et al. (2008) *J Thromb Haemost,* 6:315-322. Notably, FVIIIa has been found to stabilize a conformation of FIXa that has increased proteolytic activity towards FX (Kolkman J A, Mertens K (2000) *Biochemistry,* 39:7398-7405, Zögg T, Brandstetter H (2009) *Biol Chem,* 390:391-400).

In recent years, emicizumab (HEMLIBRA®) also known as ACE910, has been approved for subcutaneous prophylactic treatment of Haemophilia A with or without inhibitors against conventional replacement therapy factors. Emicizumab is a humanized, bispecific full-length anti-FIX(a)/anti-FX(a) monoclonal antibody developed by Chugai Pharmaceuticals/Roche Pharmaceuticals for the treatment of haemophilia A. Emicizumab is designed to mimic FVIII cofactor function (see Sampei et al. (2013) *PLoS One,* 8, e57479 and WO2012/067176). Treatment with 30-50 μg of emicizumab per milliliter plasma has been speculated correspond to at least 10 to 15 IU of equivalent factor VIII activity per decilitre plasma (Shima et al., N Engl J Med 2016; 374:2044-53). However, some patients have developed inhibitors (anti-drug antibodies) against emicizumab rendering treatment with this compound ineffective.

Besides the generation of inhibitors as exemplified for Emicizumab, other antibody properties are also important for achieving an effective antibody-based treatment for the patient. In particular, it has been demonstrated that antibodies with high propensity for non-specific binding may lead to safety issues in the clinic. In some reports, a high level of non-specific binding caused a several-fold reduction in circulating half-life of the antibody and led to ineffective and cumbersome dosing regimens for the patient (See Dobson et al., *Nature,* volume 6, art. no.: 38644 (2016) and Avery et al., *MAbs* 2018, Vol. 10, No. 2, 244-255).

WO2018/141863, WO2019/065795 (U.S. Ser. No. 10/759,870), WO2020/025672 and WO2021/152066 disclose anti-FIX(a)/anti-FX(a) bispecific full-length antibodies and their use as procoagulants for use in the treatment of haemophilia by way of subcutaneous administration. One such bispecific antibody is designated Mim8 (see Østergaard H et al. Blood. 2021; 138:1258-68 and WO2020/025672).

There are, however, still many very significant unmet medical needs in the haemophilia community, in particular, in subjects with coagulopathies and in particular there is a need for reduced treatment burden and improved compounds capable of substituting for FVIII(a) for use in the treatment of a coagulopathy such as haemophilia A and related diseases.

SUMMARY

The present invention provides procoagulant immunoglobulin single variable domain (ISVD) polypeptides derivatives, such as V$_H$H polypeptide derivatives, capable of binding coagulation Factor IX(a) and coagulation Factor X(a) which are highly potent and provide a sufficiently long half-life such to allow for effective subcutaneous administration as well as peroral administration. Thus, in one aspect the present invention relates to procoagulant immunoglobulin single variable domain (ISVD) polypeptide derivatives comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, one or more protraction moiety(ies) attached to one or more surface exposed residue(s), optionally a linker (L$_{1-2}$) linking ISVD1 and ISVD2, and optionally one or more extension(s) (E).

In one aspect the present invention relates to a procoagulant ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, at least one protraction moiety attached to a surface exposed residue, optionally a linker (L$_{1-2}$) linking ISVD1 and ISVD2, and optionally one or more extension(s) (E), wherein said first ISVD is capable of binding to an epitope on Factor IX (SEQ ID NO:1) or the activated form thereof comprising at least one of the amino acid residues E224, T225, G226, V250, I251, R252, I253, P255, H257 and N260 (consecutive numbering), and wherein said second ISVD is capable of binding to an epitope on Factor X (SEQ ID NO:2) comprising at least one of the amino acid residues N173, P174, F175, L177, L178 and D179 (consecutive numbering).

The ISVD polypeptide derivative can for example be a V$_H$H polypeptide derivative. Another aspect the present invention relates to pharmaceutical compositions comprising the ISVD polypeptides derivatives as disclosed herein. Another aspect of the invention relates to use of ISVD polypeptides derivatives disclosed herein and compositions comprising such compounds for the treatment of various forms of haemophilia and in particular haemophilia A, haemophilia A with inhibitors and acquired haemophilia A by various routes of administration including subcutaneous and peroral administration.

In a further aspect the invention relates to the individual component (intermediate) ISVDs or V$_H$H fragments that are part of an ISVD polypeptide derivative or V$_H$H polypeptide derivative, such as a particular anti-FIX(a) V$_H$H fragment or a particular anti-FX(a) V$_H$H fragment thereof.

A further aspect of the invention relates to the manufacture of the components (intermediates) of the compounds as disclosed herein including methods for modifying the isoelectric point of ISVD polypeptide derivatives capable of binding FIX(a) and FX(a) such to improve oral bioavailability of such polypeptide derivatives.

BRIEF DESCRIPTION OF FIGURES

FIGS. 1a-h show non-limiting examples of anti-FX(a)/FIX(a) ISVD polypeptide derivatives. E: Extension, PM: protraction moiety, L$_{1-2}$: linker connecting ISVD1 and ISVD2. The dashed lines indicate disulphide bonds.

Figure 1C:
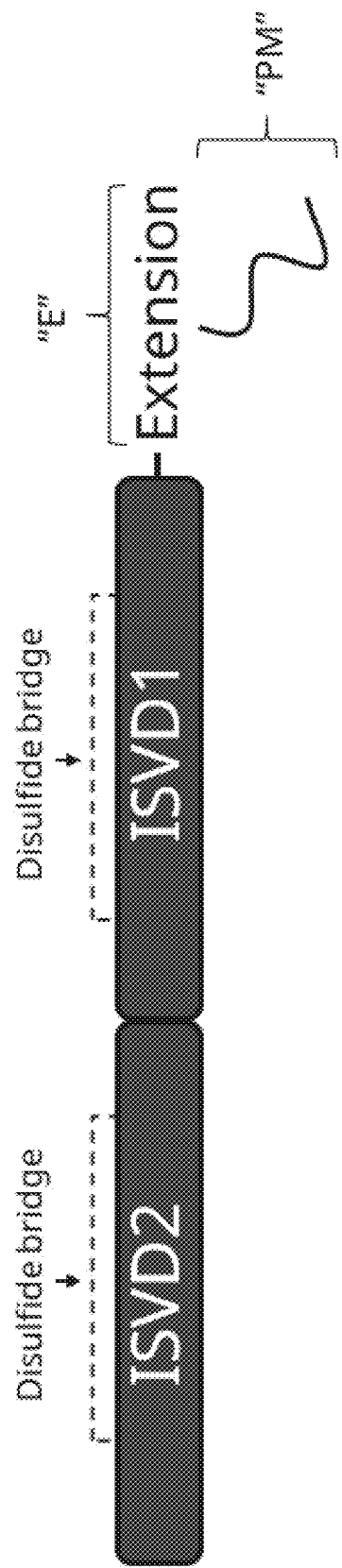

In a) the sequence of the V$_H$H1.20-L$_{1-2}$-V$_H$H2.20-E polypeptide is represented by SEQ ID NO:634 (cmpd #20).

In b) the sequence of the V$_H$H1.18-L$_{1-2}$-V$_H$H2.18-E polypeptide is represented by SEQ ID NO:632 (cmpd #18).

In c) the sequence of the V$_H$H1.15-L$_{1-2}$-V$_H$H2.15-E polypeptide is represented by SEQ ID NO:629 (cmpd #15).

In d) the sequence of the V$_H$H1.13-L$_{1-2}$-V$_H$H2.13-E polypeptide is represented by SEQ ID NO:627 (cmpd #13).

In e) the sequence of the V$_H$H1.14-L$_{1-2}$-V$_H$H2.14-E polypeptide is represented by SEQ ID NO:628 (cmpd #14).

In f) the sequence of the V$_H$H1.12-L$_{1-2}$-V$_H$H2.12-E polypeptide is represented by SEQ ID NO:626 (cmpd #12).

FIG. 4 shows an example of titration curves (activity as result of compound concentration) for cmpd #6, Mim8 and emicizumab SIA.

FIGS. 5a and 5b show sequence alignments of anti-FIX (a) and anti-FX ISVD (V$_H$H fragment) sequences, respectively, wherein CDR sequences are highlighted in bold and underlined.

BRIEF DESCRIPTION OF THE SEQUENCES

SEQ ID NO:1 represents the amino acid sequence of human coagulation Factor IX.

SEQ ID NO:2 represents the amino acid sequence of human coagulation Factor X.

SEQ ID NOs:3-13 and 690 represent the amino acid sequences of extensions (E).

SEQ ID NOs:14-26 and 691 represent the amino acid sequences of L$_{1-2}$ and L P linkers.

SEQ ID NOs:27-614 represent the amino acid sequences of V$_H$H fragments and Complementarity Determining Regions (CDRs) thereof.

SEQ ID NOs:615-691, 734 and 735 represent the amino acid sequences of V$_H$H polypeptides including any L$_{1-2}$ linkers and/or extensions.

SEQ ID NOs:692-733 represent the sequences of peptide fragments as disclosed in Example 4 herein.

SEQ ID NOs:736-739 represent the amino acid sequences of potential protractors.

DESCRIPTION

The present invention provides ISVD polypeptides derivatives capable of binding FIX(a) and FX(a) which are highly potent and provide a sufficiently long half-life such to allow for effective subcutaneous as well as peroral administration. The ISVD polypeptides derivatives disclosed herein are thus suitable for treatment of various forms of haemophilia, such as haemophilia A, haemophilia A with inhibitors and acquired haemophilia A by various routes of administration including subcutaneous and peroral administration.

In particular, the present invention relates to bispecific protracted ISVD polypeptides, such as $V_HH$ polypeptides, referred-to as ISVD polypeptide derivatives (or $V_HH$ polypeptide derivatives), that can bind coagulation FIXa and coagulation FX leading to formation of activated coagulation FX (FXa) in a way that mimics the co-factor activity of coagulation factor VIIIa (FVIIIa). The $V_HH$ polypeptide derivatives as disclosed herein show very high in vitro potency, which, for example, are orders-of-magnitude higher than the bi-specific antibody emicizumab sequence identical analogue (SIA). The $V_HH$ polypeptide derivatives also show prolonged half-life via introduced protractors, e.g. fatty acid conjugations and albumin-binder peptide fusions, in animal models such as rat, dog and pig. Non-protracted $V_HH$ polypeptides show very rapid clearance in dog and pig. Moreover, the $V_HH$ polypeptide derivatives have been engineered to enable a clinically relevant bioavailability following peroral administration via pI-lowering amino acid substitutions of surface exposed residues, and formulations using the excipients sodium N-(8-(2-hydroxybenzoyl) amino)caprylate (SNAC) and e.g. nicotinamide (NAM). Thus, upon peroral administration, the formulated and highly potent $V_HH$ polypeptide derivatives show levels of bioavailability in rat and dog animal models that are clinically relevant. Hitherto, therapeutic polypeptides such as ISVD polypeptide derivatives, such as $V_HH$ polypeptide derivatives, having a molecular weight of more than 10 kDa have not been considered suitable for peroral administration. However, the $V_HH$ polypeptide derivates as disclosed herein are suitable for novel oral treatment of coagulopathies, such as—but not limited to—haemophilia A with or without inhibitors.

Figure 1D:
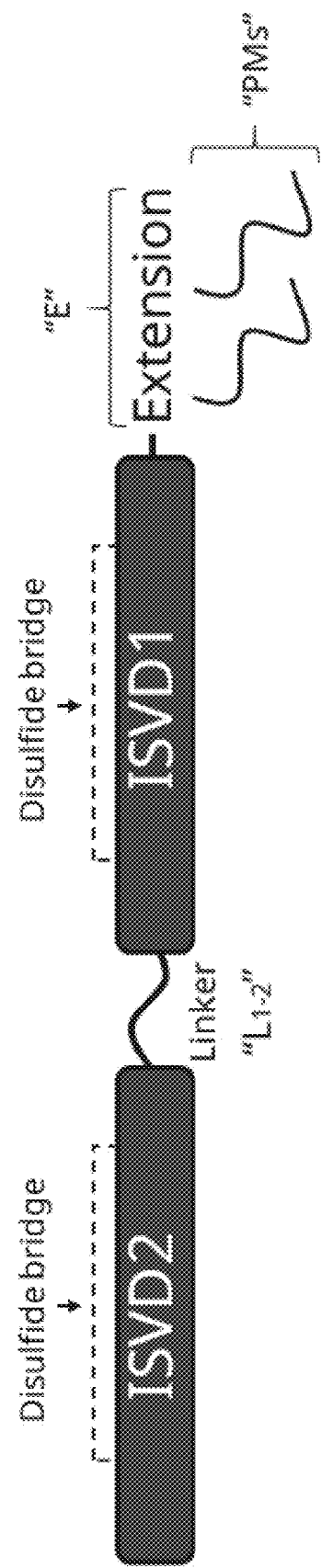

The present invention thus provides procoagulant immunoglobulin single variable domain (ISVD) polypeptides derivatives, such as $V_HH$ polypeptide derivatives, capable of binding coagulation Factor IX(a) and coagulation Factor X(a) which are highly potent and provide a sufficiently long half-life to allow for effective subcutaneous administration as well as peroral administration. Thus, in one aspect the present invention relates to procoagulant immunoglobulin single variable domain (ISVD) polypeptide derivatives comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, one or more protraction moiety(ies) attached to one or more surface exposed residue(s), optionally a linker ($L_{1-2}$) linking ISVD1 and ISVD2, and optionally one or more extension(s) (E). FIGS. 1a-f show non-limiting examples of anti-FX/FIX(a) ISVD polypeptide derivatives.

In one aspect the present invention relates to a procoagulant ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, at least one protraction moiety attached to a surface exposed residue, optionally a linker ($L_{1-2}$) linking ISVD1 and ISVD2, and optionally one or more extension(s) (E), wherein said first ISVD is capable of binding to an epitope on Factor IX (SEQ ID NO:1) or the activated form thereof comprising at least one of the amino acid residues E224, T225, G226, V250, I251, R252, I253, P255, H257 and N260 (consecutive numbering), and wherein said second ISVD is capable of binding to an epitope on Factor X (SEQ ID NO:2) comprising at least one of the amino acid residues N173, P174, F175, L177, and L178 and D179 (consecutive numbering).

In another aspect the present invention relates to a procoagulant $V_HH$ polypeptide derivative comprising
a first $V_HH$ ($V_HH1$) capable of binding to Factor IX (SEQ ID NO:1) or the activated form thereof,
a second $V_HH$ ($V_HH2$) capable of binding to Factor X (SEQ ID NO:2),
at least one protraction moiety attached to a surface exposed residue,
optionally a linker ($L_{1-2}$) linking $V_HH1$ and $V_HH2$, and optionally one or more extension(s) (E),
wherein $V_HH1$ comprises the sequence of
$V_HH$-2.20 (SEQ ID NO:171),
$V_HH$-2.18 (SEQ ID NO:155),
$V_HH$-2.15 (SEQ ID NO:131),
$V_HH$-2.13 (SEQ ID NO:115),
$V_HH$-2.14 (SEQ ID NO:123),
$V_HH$-2.12 (SEQ ID NO:107), or
$V_HH$-2.2 (SEQ ID NO:35),
and wherein $V_HH2$ comprises the sequence of
$V_HH$-1.20 (SEQ ID NO:167),
$V_HH$-1.18 (SEQ ID NO:151),
$V_HH$-1.15 (SEQ ID NO:127),
$V_HH$-1.13 (SEQ ID NO:111),
$V_HH$-1.14 (SEQ ID NO:119),
$V_HH$-1.12 (SEQ ID NO:103),
$V_HH$-1.3 (SEQ ID NO:31), or
$V_HH$-1.4 (SEQ ID NO:39).

In one such embodiment $V_HH1$ comprises the sequence of $V_HH$-2.20 (SEQ ID NO:171) and $V_HH2$ comprises the sequence of $V_HH$-1.20 (SEQ ID NO:167).

In another such embodiment $V_HH1$ comprises the sequence of $V_HH$-2.20 (SEQ ID NO:171) and $V_HH2$ comprises the sequence of $V_HH$-1.18 (SEQ ID NO:151).

In another such embodiment $V_HH1$ comprises the sequence of $V_HH$-2.20 (SEQ ID NO:171) and $V_HH2$ comprises the sequence of $V_HH$-1.15 (SEQ ID NO:127).

In another such embodiment $V_HH1$ comprises the sequence of $V_HH$-2.20 (SEQ ID NO:171) and $V_HH2$ comprises the sequence of $V_HH$-1.13 (SEQ ID NO:111).

In another such embodiment $V_HH1$ comprises the sequence of $V_HH$-2.20 (SEQ ID NO:171) and $V_HH2$ comprises the sequence of $V_HH$-1.12 (SEQ ID NO:103).

In another such embodiment $V_HH1$ comprises the sequence of $V_HH$-2.20 (SEQ ID NO:171) and $V_HH2$ comprises the sequence of $V_HH$-1.3 (SEQ ID NO:31).

In another such embodiment $V_HH1$ comprises the sequence of $V_HH$-2.20 (SEQ ID NO:171) and $V_HH2$ comprises the sequence of $V_HH$-1.4 (SEQ ID NO:39).

In one such embodiment $V_HH1$ comprises the sequence of $V_HH$-2.20 (SEQ ID NO:171) and $V_HH2$ comprises the sequence of $V_HH$-1.20 (SEQ ID NO:167).

In another such embodiment $V_HH1$ comprises the sequence of $V_HH$-2.18 (SEQ ID NO:155) and $V_HH2$ comprises the sequence of $V_HH$-1.18 (SEQ ID NO:151).

In another such embodiment $V_HH1$ comprises the sequence of $V_HH$-2.20 (SEQ ID NO:171) and $V_HH2$ comprises the sequence of $V_HH$-1.15 (SEQ ID NO:127).

In another such embodiment $V_HH1$ comprises the sequence of $V_HH$-2.20 (SEQ ID NO:171) and $V_HH2$ comprises the sequence of $V_HH$-1.13 (SEQ ID NO:111).

In another such embodiment $V_HH1$ comprises the sequence of $V_HH$-2.20 (SEQ ID NO:171) and $V_HH2$ comprises the sequence of $V_HH$-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In another such embodiment V$_H$H1 comprises the sequence of V$_H$H-2.15 (SEQ ID NO:131) and V$_H$H2 comprises the sequence of V$_H$H-1.18 (SEQ ID NO:151).

In another such embodiment V$_H$H1 comprises the sequence of V$_H$H-2.20 (SEQ ID NO:171) and V$_H$H2 comprises the sequence of V$_H$H-1.15 (SEQ ID NO:127).

In another such embodiment V$_H$H1 comprises the sequence of V$_H$H-2.20 (SEQ ID NO:171) and V$_H$H2 comprises the sequence of V$_H$H-1.13 (SEQ ID NO:111).

In another such embodiment V$_H$H1 comprises the sequence of V$_H$H-2.20 (SEQ ID NO:171) and V$_H$H2 comprises the sequence of V$_H$H-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In another such embodiment V$_H$H1 comprises the sequence of V$_H$H-2.13 (SEQ ID NO:115) and V$_H$H2 comprises the sequence of V$_H$H-1.18 (SEQ ID NO:151).

In another such embodiment V$_H$H1 comprises the sequence of V$_H$H-2.20 (SEQ ID NO:171) and V$_H$H2 comprises the sequence of V$_H$H-1.15 (SEQ ID NO:127).

In another such embodiment V$_H$H1 comprises the sequence of V$_H$H-2.20 (SEQ ID NO:171) and V$_H$H2 comprises the sequence of V$_H$H-1.13 (SEQ ID NO:111).

In another such embodiment V$_H$H1 comprises the sequence of V$_H$H-2.20 (SEQ ID NO:171) and V$_H$H2 comprises the sequence of V$_H$H-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In another such embodiment V$_H$H1 comprises the sequence of V$_H$H-2.14 (SEQ ID NO:123) and V$_H$H2 comprises the sequence of V$_H$H-1.18 (SEQ ID NO:151).

In another such embodiment V$_H$H1 comprises the sequence of V$_H$H-2.20 (SEQ ID NO:171) and V$_H$H2 comprises the sequence of V$_H$H-1.15 (SEQ ID NO:127).

In another such embodiment V$_H$H1 comprises the sequence of V$_H$H-2.20 (SEQ ID NO:171) and V$_H$H2 comprises the sequence of V$_H$H-1.13 (SEQ ID NO:111).

In another such embodiment V$_H$H1 comprises the sequence of V$_H$H-2.20 (SEQ ID NO:171) and V$_H$H2 comprises the sequence of V$_H$H-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In another such embodiment V$_H$H1 comprises the sequence of V$_H$H-2.12 (SEQ ID NO:107) and V$_H$H2 comprises the sequence of V$_H$H-1.18 (SEQ ID NO:151).

In another such embodiment V$_H$H1 comprises the sequence of V$_H$H-2.20 (SEQ ID NO:171) and V$_H$H2 comprises the sequence of V$_H$H-1.15 (SEQ ID NO:127).

In another such embodiment V$_H$H1 comprises the sequence of V$_H$H-2.20 (SEQ ID NO:171) and V$_H$H2 comprises the sequence of V$_H$H-1.13 (SEQ ID NO:111).

In another such embodiment V$_H$H1 comprises the sequence of V$_H$H-2.20 (SEQ ID NO:171) and V$_H$H2 comprises the sequence of V$_H$H-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In another such embodiment V$_H$H1 comprises the sequence of V$_H$H-2.2 (SEQ ID NO:135) and V$_H$H2 comprises the sequence of V$_H$H-1.18 (SEQ ID NO:151).

In another such embodiment V$_H$H1 comprises the sequence of V$_H$H-2.20 (SEQ ID NO:171) and V$_H$H2 comprises the sequence of V$_H$H-1.15 (SEQ ID NO:127).

In another such embodiment V$_H$H1 comprises the sequence of V$_H$H-2.20 (SEQ ID NO:171) and V$_H$H2 comprises the sequence of V$_H$H-1.13 (SEQ ID NO:111).

In another such embodiment V$_H$H1 comprises the sequence of V$_H$H-2.20 (SEQ ID NO:171) and V$_H$H2 comprises the sequence of V$_H$H-1.12 (SEQ ID NO:103).

In another such embodiment V$_H$H1 comprises the sequence of V$_H$H-2.20 (SEQ ID NO:171) and V$_H$H2 comprises the sequence of V$_H$H-1.3 (SEQ ID NO:31).

In another such embodiment V$_H$H1 comprises the sequence of V$_H$H-2.20 (SEQ ID NO:171) and V$_H$H2 comprises the sequence of V$_H$H-1.4 (SEQ ID NO:39).

In some embodiments the protraction moiety comprises the following structure:

wherein * designated the point of attachment on the ISVD polypeptide.

The ISVD polypeptide derivative can for example be a V$_H$H polypeptide derivative.

In another aspect, the present invention relates to pharmaceutical compositions comprising the ISVD polypeptides derivatives as disclosed herein. Another aspect of the invention relates to use of ISVD polypeptides derivatives disclosed herein and compositions comprising such compounds for the treatment of various forms of haemophilia and in particular haemophilia A, haemophilia A with inhibitors and acquired haemophilia A by various routes of administration including but not limited to subcutaneous and peroral administration.

In a further aspect the invention relates to the individual component (intermediate) ISVDs or $V_HH$ fragments that are part of an ISVD polypeptide derivative or $V_HH$ polypeptide derivative, such as a particular anti-FIX(a) $V_HH$ fragment or a particular anti-FX(a) $V_HH$ fragment thereof.

A further aspect of the invention relates to the manufacture of the components (intermediates) of the compounds as disclosed herein including methods for modifying the isoelectric point of ISVD polypeptide derivatives capable of binding FIX(a) and FX(a) such to improve oral bioavailability of such polypeptide derivatives.

Definitions

In order that the present invention may be more readily understood, certain terms are defined below.

Greek letters may be represented by their symbol or the corresponding written name, for example: α=alpha; β=beta; ε=epsilon; γ=gamma; ω=omega; etc. Also, the Greek letter of μ may be represented by "u", e.g. in μl=ul, or in μM=uM.

An asterisk (*) in a chemical formula designates a point of attachment.

The term "a" or "an" is intended to mean "one or more." The term "comprise" and variations thereof such as "comprises" and "comprising" when preceding the recitation of a step or an element, are intended to mean that the addition of further steps or elements is optional and not excluded.

The term "about" is used herein to mean approximately, roughly, or around. When the term "about" is used in conjunction with a numerical range, it modifies that range by extending the boundaries above and below the numerical values set forth. In general, the term "about" can modify a numerical value above and below the stated value by 10 percent, up or down (higher or lower).

The term "backbone" as used herein refers to an ISVD polypeptide or $V_HH$ polypeptide amino acid sequence including any $L_{1-2}$ linker and extension(s), but excluding a protraction moiety and for the avoidance of doubt excluding any protraction moiety suitable for being fused to the backbone.

The term "binding affinity" is a measure of the strength of a non-covalent interaction between two molecules, e.g. an ISVD, such as a $V_HH$ fragment and an antigen. The term is used to describe monovalent interactions. Binding affinity between two molecules, e.g. an ISVD, such as a $V_HH$, through a monovalent interaction may be quantified by determining the equilibrium dissociation constant ($K_D$). $K_D$ can be determined by measurement of the kinetics of complex formation and dissociation, e.g. by the Surface Plasmon Resonance (SPR) method or the Isothermal Titration calorimetry (ITC) method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$.

Following the above definition, binding affinities associated with different molecular interactions, such as the binding affinity of different ISVDs for a given antigen, may be compared by comparison of the $K_D$ values for the individual antibody/antigen complexes. The value of the dissociation constant can be determined directly by well-known methods. Standard assays to evaluate the binding ability of ligands such as ISVDs towards targets are known in the art and include, for example, ELISAs, Western blots, RIAs, and flow cytometry analysis. The binding kinetics and binding affinity of the ISVD also can be assessed by standard assays known in the art, such as SPR.

A competitive binding assay can be conducted in which the binding of the ISVD, such as a $V_HH$, to the target is compared to the binding of the target in the presence of another ligand of that target, such as another ISVD.

Unless contradicted by context, the $K_D$ is preferably determined by Surface Plasmon Resonance as described herein (see example 7).

Preferably, the $K_D$ value of an ISVD capable of binding to FIX(a) is 3 μM or less, such as 15 nM or less, such as 11.7 nM or less.

Preferably, the $K_D$ value of an ISVD capable of binding to FX(a) is 3 μM or less, such as 350 nM or less, such as 300 nM or less.

A "cross-species reactive" ISVD (or $V_HH$ fragment) binds to e.g. FIX from all indicated species (e.g. human and cynomolgus monkey) with comparable affinity, in particular with a $K_D$ in the range of a factor of 100, such as within a range of a factor of 50, within a range of a factor of 20, or within a range of a factor of 10. Within a $K_D$ range of a defined factor X means that the highest affinity for a particular listed species is not more than X-times higher than the lowest affinity measured for binding to a different listed species. A person skilled in the art will understand that any method for measuring affinity can be used to verify that a cross-species reactive ISVD binds to the target antigen from all listed species within a given $K_D$ factor range as described herein as long as the same conditions are applied to the $K_D$ measurement for all listed species. Preferably, the $K_D$ values are measured using SPR, in particular at 25° C. Preferably, the affinities are measured using the cross-species reactive ISVD, such as an $V_HH$.

Amino acids are molecules containing an amine group and a carboxylic acid group, and, optionally, one or more additional groups, often referred to as a side chain.

The term "amino acid" includes canonical amino acids (which are genetically encoded), and unnatural amino acids. Non-limiting examples of unnatural amino acids are Aib (α-aminoisobutyric acid), deamino histidine (alternative name 3-(imidazol-4-yl)propanoic acid, abbreviated Imp (imidazopropionyl) and the d-isomers of the canonical amino acids. All amino acid residues within the polypeptide for which the optical isomer is not stated is herein to be understood to mean the I-isomer, unless otherwise specified.

The term "antibody" herein refers to a protein, comprising or derived from an immunoglobulin sequence, which is capable of binding to an antigen or a portion thereof An "antibody" includes—but is not limited to—full-length antibodies comprising at least four polypeptide chains: two heavy chains (HC) and two light chains (LC) that are connected by disulphide bonds as well as antibodies comprising at least three polypeptide chains: two heavy chains (HC) and one light chain (LC) that are connected by disulphide bonds. One class of immunoglobulins is the IgGs. In humans, the IgG class may be divided into four subclasses IgG1, IgG2, IgG3 and IgG4, based on the sequence of their heavy chain constant regions. The light chains can be divided into two types, kappa and lambda chains, based on differences in their sequence composition. IgG molecules are composed of two heavy chains, interlinked by two or more disulphide bonds, and two light chains, each attached to a heavy chain by a disulphide bond. The term "antibody"

also encompasses single-domain antibodies such as $V_HH$ fragments and V-NAR fragments.

The term "hypervariable region" as used herein refer to the amino acid residues of an antibody which are responsible for antigen-binding. The hypervariable region comprises the "complementarity determining regions" also known as the "CDRs".

"Framework" or "FR" regions are those variable domain regions other than the hypervariable region residues. Thus, an antibody or ISVD comprises from N- to C-terminus the domains FR1, CDR1, FR2, CDR2, FR3, CDR3, and FR4. The CDR3 of the heavy chain is the region which typically contributes most to antigen binding.

The term "epitope" as used herein means a protein determinant capable of specific binding to an antibody. Epitopes usually consist of surface elements of molecules, such as amino acids or sugar side chains, and usually have specific three-dimensional structural characteristics, as well as specific charge characteristics. Conformational and non-conformational epitopes are distinguished in that the binding to the former but not the latter is lost in the presence of denaturing agents capable of disrupting the structure of the protein.

In the context of an X-ray derived crystal structure defined by spatial coordinates of a complex between an ISVD, a $V_HH$ fragment, and its target, the term epitope is herein, unless otherwise specified or contradicted by context, specifically defined as ISVD residues characterized by having a heavy atom (i.e. a non-hydrogen atom) within a distance of 4 Å from a heavy atom in FIX/FIXa or FX/FXa.

The epitope for a given ISVD/antigen pair may be identified by routine methods, such as those described in the examples. For example, the ISVD and antigen may be combined and the ISVD/antigen complex may be crystallised. The crystal structure of the complex may be determined and used to identify specific sites of interaction between the ISVD and its antigen.

In one embodiment an ISVD polypeptide derivative as described herein comprises a first ISVD capable of binding to an epitope on FIX or the activated form thereof comprising at least one of the amino acid residues E224, T225, G226, V250, I251, R252, I253, P255, H257 and N260 (SEQ ID NO:1) and a second ISVD is capable of binding to an epitope on FX (SEQ ID NO:2) comprising at least one of the amino acid residues N173, P174, F175, L177 and L178 (consecutive numbering).

In one embodiment the ISVD polypeptide derivative comprises a first ISVD capable of binding to an epitope on Factor IX (SEQ ID NO:1) or the activated form thereof comprising at least one of the amino acid residues E224, T225, G226, V250, I251, R252, I253, P255, H257 and N260 (consecutive numbering), and a second ISVD capable of binding to an epitope on Factor X (SEQ ID NO:2) comprising at least one of the amino acid residues N173, P174, F175, L177, L178 (consecutive numbering) or comprising at least one of the amino acid residues N173, P174, F175, L177, L178 and D179.

Coagulation Factor IX (FIX) is a vitamin K-dependent coagulation factor with structural similarities to Factor VII, prothrombin, Factor X, and Protein C. FIX circulates in plasma as a single-chain zymogen (SEQ ID NO:1). The circulating zymogen form consists of 415 amino acids divided into four distinct domains comprising an N-terminal γ-carboxyglutamic acid-rich (Gla) domain, two EGF domains and a C-terminal trypsin-like serine protease domain. Activation of FIX occurs by limited proteolysis at Arg145 and Arg180 to release the activation peptide (residues 146 to 180 of SEQ ID NO:1). Thus, activated FIX (FIXa) is composed of residues 1-145 of SEQ ID NO:1 (light chain) and residues 181-415 of SEQ ID NO:1 (heavy chain).

Circulating FIX molecules thus comprise the FIX zymogen and the activated form of FIX which are herein generally referred to as FIX and FIXa with reference to SEQ ID NO:1.

Activated Factor IX is referred to as Factor IXa or FIXa. The term "FIX (SEQ ID NO:1) and/or the activated form thereof (FIXa)" may also be referred to as "FIX/FIXa" or simply "FIX(a)".

FIXa is a trypsin-like serine protease that serves a key role in haemostasis by generating, as part of the tenase complex, most of the Factor Xa required to support proper thrombin formation during coagulation.

FIX is herein represented by SEQ ID NO:1 corresponding to the Ala148 allelic form of human FIX (Anson et al. EMBO J. 1984 3:1053-1060; McGraw et al., Proc Natl Acad Sci USA. 1985 82:2847-2851; Graham et al. Am. J. Hum. Genet. 1988 42:573-580). In the present invention FIX is intended to cover all natural variants of FIX, such as the T148 variant (Uniprot ID P00740).

FX is a vitamin K-dependent coagulation factor with structural similarities to Factor VII, prothrombin, FIX, and protein C. FX circulates in plasma as a two-chain zymogen including residues 1-139 of SEQ ID NO:2 (light chain) and residues 143-448 of SEQ ID NO:2 (heavy chain). Human FX zymogen comprises four distinct domains comprising an N-terminal gamma-carboxyglutamic acid rich (Gla) domain (residues 1-45), two EGF domains, EGF1 (residues 46-82) and EGF2 (residues 85-125), respectively, and a C-terminal trypsin-like serine protease domain (residues 195-448). Activation of FX occurs by limited proteolysis at Arg194, which results in the release of the activation peptide (residues 143-194). Thus, activated FX (FXa) is composed of residues 1-139 of SEQ ID NO:2 (light chain) and residues 195-448 of SEQ ID NO:2 (activated heavy chain). Circulating Factor X molecules thus comprises the FX zymogen and the activated form of FX which are herein referred to as FX and FXa, respectively, with reference to SEQ ID NO:2. In the present invention FX is intended to cover all natural variants of FX. The term "FX (SEQ ID NO:2) and/or the activated form thereof (FXa)" may also be referred to as "FX/FXa" or "FX(a)".

The term "conservative substitution" as used herein refers to the case where an amino acid may be substituted to an amino acid with similar biochemical properties, for example, a basic amino acid may be substituted to another basic amino acid (e.g. lysine to arginine), an acidic amino acid may be substituted to another acidic amino acid (e.g glutamate to aspartate), a neutral amino acid may be substituted to another neutral amino acid (e.g. threonine to serine), a charged amino acid may be substituted to another charged amino acid (e.g. glutamate to aspartate), a hydrophilic amino acid may be substituted to another hydrophilic amino acid (e.g. asparagine to glutamine), a hydrophobic amino acid may be substituted to another hydrophobic amino acid (e.g. alanine to valine), a polar amino acid may be substituted to another polar amino acid (e.g. serine to threonine), an aromatic amino acid may be substituted to another aromatic amino acid (e.g. phenylalanine to tryptophan) and an aliphatic amino acid may be substituted to another aliphatic amino acid (e.g. leucine to isoleucine).

The term "excipient" as used herein refers to an inert substance added to a pharmaceutical composition to further facilitate administration of an active ingredient. Examples, without limitation, of excipients include calcium carbonate, calcium phosphate, various sugars and types of starch, L-arginine, nicotinamide, SNAC, cellulose derivatives, gelatin, vegetable oils and polyethylene glycols.

The term "extension" (E) as used herein refers to a peptide or polypeptide suitable for being attached to an ISVD polypeptide.

The extension can be of a few amino acids, 1 to 10 amino acids, it can be longer, 10 to 30 amino acids, or it can be very long, more than 30 amino acids. An extension is preferably present in the N-terminal end (N-terminal extension) or in the C-terminal end (C-terminal extension), or both, of an ISVD polypeptide, ISVD polypeptide derivative, $V_HH$ polypeptide or $V_HH$ polypeptide derivative. Alternatively, the extension is attached elsewhere in the ISVD polypeptide outside the CDR sequences, such as in one or more framework regions or in a linker $L_{1-2}$.

The extension(s) is/are preferably recombinantly fused to the ISVD polypeptide. In other embodiments the extension(s) is/are conjugated to the ISVD polypeptide.

Non-limiting examples include cpmd #22 which has a 6-amino acid C-terminal extension composed of GQACPC (SEQ ID NO:9), cpmd #6 which has a 13-amino acid C-terminal extension composed of GGGGCSCHHHHHH (SEQ ID NO:8), and an 11-amino acid C-terminal extension composed of GGGGSHHHHHH (SEQ ID NO:7).

The purpose of the extension is to provide a point of attachment for protraction moieties and/or to provide a means for purification. Thus, the term extension does not encompass protractors and protraction moieties.

For example, a protractor including any protractor linker (L P) recombinantly fused to the N- or C-terminal end of the polypeptide is not regarded as an extension.

The term "fusion" as used herein refers to in-frame joining of two or more DNA sequences which originally encode separate proteins or peptides or fragments hereof. Translation of the fusion polypeptide DNA sequence will result in a single polypeptide sequence which may have functional properties derived from each of the original proteins or peptides. DNA sequences encoding fusion proteins may be created artificially by standard molecular biology methods such as overlapping PCR or DNA ligation. The resulting fusion polypeptides DNA sequence may be inserted into an appropriate expression vector that supports the heterologous fusion protein expression in host organisms such as bacteria, yeast, fungus, insect cells or mammalian cells. Protraction moieties may for example be fused to the C-terminal or N-terminal of an ISVD polypeptide or $V_HH$ polypeptide backbone.

The term "host cell" as used herein covers any kind of cellular system which can be engineered to generate the ISVDs disclosed herein. Host cells include—but is not limited to—cultured cells, e.g., mammalian cultured cells, such as CHO cells, HEK293T cells, BHK cells, NSO cells, SP2/0 cells, YO myeloma cells, P3X63 mouse myeloma cells, PER cells, PER.C6 cells or hybridoma cells, yeast cells, fungal cells, and insect cells.

The term "identity" as known in the art, refers to a relationship between the sequences of two or more polypeptides, as determined by comparing the sequences. In the art, "identity" also means the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. In the present invention similarity and identity were determined using Needleman (Needleman et al. J. Mol. Biol. 1970; 48:443-453) from EMBOSS-6.6.0 using the parameters 10 and 0.5 for gaps opening and extensions, respectively (gapopen=10, gapextend=0.5).

The term "Immunoglobulin Single Variable Domain" or "ISVD" is used as a general term to include antigen-binding domains or fragments such as VH and VL domains, respectively.

The ISVD can thus be a light chain variable domain sequence (e.g. a VL-sequence), or heavy chain variable domain sequence (e.g. a VH-sequence); for example a heavy chain variable domain sequence that is derived from a conventional four-chain antibody or a light chain variable domain sequence that is derived from a conventional four-chain antibody.

A particular type of ISVD is a $V_HH$ fragment which was originally identified as a type of immunoglobulin defined as an antibody fragment consisting of a single monomeric variable antibody domain. A $V_HH$ fragment is a single-domain antibody that encompasses the antigen-binding variable region of heavy-chain-only antibodies, which can be obtained from camelids. $V_HH$ fragments have a size of around 15 kDa. They contain a single chain molecule that can bind its cognate antigen using a single domain. The antigen-binding surfaces of $V_HH$ fragments are usually more convex (or protruding) than those of conventional antibodies, which are usually flat or concave. $V_HH$ fragments are composed of four Framework Regions (or FRs) whose sequences and structures are defined as conserved, and three Complementarity Determining Regions (or CDRs) showing high variability both in sequence content and structure conformation, which are involved in antigen binding and provide antigen specificity.

Another type of ISVD can be obtained from IgNARs of cartilaginous fish and a single-domain antibody thereof is designated a "V-NAR fragment".

$V_HH$- and V-NAR fragments do not comprise constant domains and therefore have no Fc-region which is typically part of partial/full-length and/or engineered/natural heavy-chain-only antibodies [Dooley et al. (2006) Dev. Comp. Immunol. 30:43-56; Muyldermans S. (2013) Annu Rev Biochem. 82:775-97].

A general description of camelid $V_HH$ fragments and methods for their production and/or isolation and/or use is found inter alia in the following references WO94/04678 and WO97/49805. A general description of heavy chain immunoglobulins from cartilaginous fish and the variable regions thereof and methods for their production and/or isolation and/or use is found inter alia in WO2005/118629.

The total number of amino acid residues in a $V_HH$ fragment is typically in the range of 110-140. It should, however, be noted that parts, fragments, or analogues of a $V_HH$ are not particularly limited as to their length and/or size, if such parts, fragments, or analogues meet the further requirements outlined hereinbelow and are also preferably suitable for the purposes described herein. The molecular weight of a $V_HH$ fragment is typically in the range 12-15 kDa. pI for $V_HH$ fragments is generally basic, as antibodies generally are, meaning that pI values are generally above 7, often between 7.5 and 8.5. A $V_HH$ fragment usually encompasses at least one disulphide bridge typically formed by conserved cysteine pairs positioned in framework regions 1 and 3. Such disulphide bridge(s) ensure(s) correct folding and stability of the $V_HH$ fragment, and it is desirable to retain such disulphide bridge(s), if, for example, side-chain modifications and/or conjugations is conducted in such a way that it targets an introduced unpaired cysteine(s) in a $V_HH$ polypeptide.

In the present document, CDR sequences of ISVDs such as $V_HH$ fragments are determined using the Kabat definition (Kontermann and Dübel, 2010, Eds., Antibody Engineering, vol 2, Springer Verlag Heidelberg Berlin, Martin, Chapter 3, pp. 33-51). According to this method, the CDRs of the variable domain is defined as position 31-35 (CDR1), position 50-65 (CDR2) and position 95-102 (CDR3). However, when referring to specific amino acid residue positions in the polypeptide compounds described herein including CDRs and framework (FR) regions in the ISVD polypeptides or $V_HH$ polypeptides consecutive numbering is used unless otherwise stated.

The term "ISVD polypeptide" as used herein refers to a polypeptide comprising two or more ISVDs, such as a first ISVD (ISVD1) and a second ISVD (ISVD2), e.g. connected by a linker ($L_{1-2}$) of any appropriate composition and length as required or without any linker at all as a direct domain fusion.

The term "linker" as used herein refers to at least one atom that forms a covalent bond between chemical entities. If the chemical entities are linked solely through peptide bonds, the linker can be referred to as a "peptide linker". Otherwise, the linker can be referred to as a "chemical linker".

An example of an ISVD polypeptide is two ISVDs connected via a linker ($L_{1-2}$).

Another example of an ISVD polypeptide is two ISVDs connected via a linker ($L_{1-2}$) further comprising one or more extensions.

Another example of an ISVD polypeptide is two ISVDs connected without a linker ($L_{1-2}$) and further comprising one or more extensions, such as—but not limited to—a C-terminal and/or N-terminal extension.

The linker ($L_{1-2}$) may for example be composed of an amino acid sequence, comprising no or multiple repeats.

For example, a linker may comprise 2 to 50 amino acids, 5 to 40 amino acids, or 10 to 30 amino acids.

Non-limiting examples of linkers include *-GGGGS-* linker, *-GQAPGQ-* linker (SEQ ID NO:20), *-QAPGQA-* linker (SEQ ID NO:16), *-GI-* linker, *-GV-* linker, *-GT-* linker, *-GL-* linker, or another amino acid composite linker. Two examples of linkers are x2 and x6 repeat composites of GGGGS, being 10 and 30 amino acid residues in length, respectively.

For the avoidance of doubt, the subscript $_{1-2}$ in $L_{1-2}$ does not imply a particular direction of ISVDs being linked, i.e. a $L_{1-2}$ can—for example—link ISVD1 to ISVD2, or ISVD2 to ISVD1 (N- to C-terminal).

SEQ ID NOs:14-24 represent non-limiting examples of $L_{1-2}$ linkers.

In some embodiment the ISVD polypeptide comprises an extension (E) as outlined in any of the below formulas.

ISVD1-ISVD2, or

ISVD1-ISVD2-E, or

ISVD2-ISVD1-E, or

E-ISVD1-ISVD2, or

ISVD1-$L_{1-2}$-ISVD2-E, or

ISVD2-$L_{1-2}$-ISVD1-E, or

E-ISVD1-$L_{1-2}$-ISVD2,

The extension (E) may for example be attached to an ISVD polypeptide as outlined in any of the below formulas (N- to C-terminal):

ISVD1-ISVD2, or

ISVD1-ISVD2-E, or

ISVD2-ISVD1-E, or

E-ISVD1-ISVD2, or

ISVD1-$L_{1-2}$-ISVD2-E, or

ISVD2-$L_{1-2}$-ISVD1-E, or

E-ISVD1-$L_{1-2}$-ISVD2

An ISVD polypeptide preferably comprises a protraction moiety. In such cases the ISVD polypeptide is referred-to as an ISVD polypeptide derivative.

In some embodiments the first ISVD serves as attachment point for one or more protraction moieties.

In some embodiments the second ISVD serves as attachment point for one or more protraction moieties.

In some embodiments the $L_{1-2}$ linker serves as attachment point for one or more protraction moieties.

For the avoidance of doubt, when a protraction moiety includes a linker ($L_P$) attached to an extension (E) to an ISVD1-$L_{1-2}$-ISVD2, the linker $L_P$ is not considered part of the "extension".

In some aspects, ISVD polypeptides are chemically conjugated with a non-ISVD, for example a small chemical non-polypeptide molecule, a carbohydrate, a fatty acid or oligopeptide or polypeptide or a protein, such as an antibody or preferably an antibody fragment.

In one embodiment an ISVD polypeptide is connected to an Fc domain from an IgG antibody without use of a linker.

In another embodiment an ISVD polypeptide is connected to an Fc domain or fragment thereof from an IgG antibody by a linker.

In preferred embodiments the extension(s) is/are fused to the ISVD polypeptide and thus not connected to the ISVD polypeptide by way of chemical conjugation.

In some embodiments the protraction moiety(ies) is/are fused to the ISVD polypeptide and thus not connected to the ISVD polypeptide by way of chemical conjugation.

The term "isoelectric point" or "pI" as used herein refers to the pH value where the overall net charge of a protein—such as an antibody—is zero. In proteins there may be many charged groups, and at the isoelectric point the sum of all these charges is zero. At a pH above the isoelectric point the overall net charge of the protein will be negative, whereas at pH values below the isoelectric point the overall net charge of the protein will be positive.

The pI may be either a theoretical or an experimentally determined isoelectric point. The skilled person is aware of methods to determine the isoelectric point of a protein.

Most commonly, the isoelectric point of a protein is computed based on the amino acid sequence of the protein. Numerous (online) tools allowing the determination of the isoelectric point of a protein are available, such as "ExPASy Compute pI/Mw"; see Protein Identification and Analysis Tools on the ExPASy Server; Gasteiger E., Hoogland C., Gattiker A., Duvaud S., Wilkins M. R., Appel R. D., Bairoch A.; (In) John M. Walker (ed): The Proteomics Protocols Handbook, Humana Press (2005) pp. 571-607. Preferably, the algorithm of Skoog & Wichman, 1986. pKa of amino acid residues is used for calculating pI.

The pI can also be determined experimentally and charge variants can, for example, be separated using charged based-separation techniques such as isoelectric focusing (IEF) gel electrophoresis, capillary isoelectric focusing (cIEF) gel electrophoresis.

In one embodiment the first and second ISVD in an ISVD polypeptide are V-NAR fragments and such compounds are designated "V-NAR polypeptides".

In another embodiment the first and second ISVD in an ISVD polypeptide are $V_HH$ fragments and such compounds are designated "$V_HH$ polypeptides". In one such embodiments the first $V_HH$ fragment is capable of binding FIX/FIXa and the second $V_HH$ fragment is capable of binding FX/FXa. In a preferred embodiment the $V_HH$ polypeptide is a bispecific $V_HH$ polypeptide.

For the avoidance of doubt, the terms multi-, tri- or bispecific are intended to reflect the number of antigens bound by the ISVDs, such as $V_HH$ fragments, i.e. not including molecules bound by a protraction moiety (if present), such as—but not limited—to albumin.

In one embodiment the molecular weight of a $V_HH$ polypeptide without a protraction moiety is in the range 27 to 29 kDa.

In preferred embodiments the molecular weight of a $V_HH$ polypeptide including one or more protraction moiety(ies) (a $V_HH$ polypeptide derivative) and optionally one or more an extension is in the range 28 to 33 kDa.

A person skilled in the art will appreciate that the above embodiments are similarly applicable to V-NAR polypeptides.

The term "free cysteine" as used herein is a cysteine residue in a polypeptide chain that is available for reaction e.g. chemical conjugation and, thus, not part of a natural or an engineered internal disulphide bridge. In essence, free cysteines can be used for conjugation, albeit free cysteine residues, including recombinantly introduced free cysteines, are often blocked with small thiols, such as cysteine, homocysteine, or glutathione, during recombinant expression of polypeptides in host cells. This is also observed in the recombinant production of ISVD polypeptides wherein one or more free cysteine(s) has/have been introduced. Thus, a reduction reaction using a proper reducing agent, such as bis(p-sulfonatophenyl)phenylphosphine dihydrate or tris(2-carboxyethyl)phosphine hydrochloride, can be used to liberate and prepare the free cysteine for conjugation to a moiety of interest, such as—but not limited to—a protraction moiety, such as a C18 diacid gamma-Glu 2xOEG fatty acid moiety.

The ISVD polypeptides, such as a $V_HH$ polypeptide, as disclosed herein can be multispecific such as—but not limited to—bispecific or trispecific.

The terms "bispecific ISVD polypeptide" or "bispecific $V_HH$ polypeptide" as used herein, refers to an ISVD polypeptide or a $V_HH$ polypeptide, respectively, which is capable of binding to two different antigens or two different epitopes on the same antigen.

The terms "trispecific ISVD polypeptide" or "trispecific $V_HH$ polypeptide" as used herein, refers to a ISVD polypeptide or a $V_HH$ polypeptide, respectively, which is capable of binding to three different antigens or three different epitopes on the same antigen or three different epitopes present on two different antigens.

The terms "multispecific ISVD polypeptide" or "multispecific $V_HH$ polypeptide" as used herein, refers to a ISVD polypeptide or a $V_HH$ polypeptide, respectively, which is capable of binding to two or more different antigens or two or more different epitopes on the same antigen. Multispecific ISVD polypeptides or multispecific $V_HH$ polypeptides thus comprise bi- and trispecific ISVD polypeptides or $V_HH$ polypeptides, respectively.

A person skilled in the art will appreciate that the above also applies to polypeptide derivatives (i.e. including a protraction moiety).

The term "oral bioavailability" or "peroral bioavailability" as used herein refers to the amount of administered drug in systemic circulation after peroral administration (estimated as the area under the plasma concentration of the administrated drug versus time curve) relative to the amount of administered drug in systemic circulation after intravenous administration of said drug.

The term "paratope" as used here in refers to the area or region on the ISVD to which an antigen specifically binds, i.e. to which it makes physical contact to the antigen.

In the context of an X-ray derived crystal structure defined by spatial coordinates of a complex between an ISVD, a $V_HH$ fragment, and its target, the term paratope is herein, unless otherwise specified or contradicted by context, specifically defined as ISVD residues characterized by having a heavy atom (i.e. a non-hydrogen atom) within a distance of 4 Å from a heavy atom in FIX/FIXa or FX/FXa.

The paratope (and epitope) for a given ISVD/antigen pair may be identified by routine methods, such as those described in the examples. For example, the ISVD and antigen may be combined and the ISVD/antigen complex may be crystallised. The crystal structure of the complex may be determined and used to identify specific sites of interaction between the ISVD and its antigen.

The term "pharmaceutically acceptable excipient" means an excipient that is useful in preparing a pharmaceutical composition that is generally safe, non-toxic and includes excipients that are acceptable for human pharmaceutical use. Such excipients can for example be solid, liquid or semi-solid.

The term "plasma half-life" as used herein refers to the time required for half the quantity of a substance administered to a patient to be metabolized or eliminated from the serum or plasma of the patient by normal biological processes.

The term "preferentially binds" as used herein shall be taken to mean that a binding region on the ISVD, such as a $V_HH$ fragment, binds to one component (e.g. activated FIX) in preference to, or in favour of, another component. As such, "preferential binding" does not necessarily require exclusive binding or non-detectable binding of the other component. For example, an anti-FIX(a) ISVD, such as an anti-FIX(a) $V_HH$ fragment, may preferentially bind to activated FIX as compared to non-activated FIX.

The term "procoagulant antibody" refers to an antibody which potentiates blood coagulation for example by accelerating the process of blood coagulation and/or increasing the enzymatic activity of one or more coagulation factors.

The term "procoagulant activity" as used herein refers to the ability of a compound, such as an antibody, to potentiate blood coagulation for example by accelerating the process of blood coagulation and/or increasing the enzymatic activity of one or more coagulation factors. Accordingly, the term "procoagulant activity" encompasses (but is not limited to) one or more of the activities listed below:

Enhancing Factor IXa-mediated Factor X activation, as measured by an amidolytic (chromogenic or fluorogenic) assay based on FIXa-mediated FX activation. The assay measures FXa through cleavage of an FXa specific peptide substrate. The substrate is produced, giving a colour that can be measured photometrically by absorbance. Shortening of clotting times, as measured by clotting assays such as Activated partial thromboplastin time (APTT) measure the activity of the intrinsic and common pathways of coagulation. Plasma is preincubated with an APTT reagent containing a contact activator, e.g. ellagic acid or kaolin, and phospholipid. Calcium chloride is added to promote fibrin clot formation. Possible readouts are clotting time or clot wave form.

Enhancing thrombin generation, as measured in a thrombin generation assay such as Calibrated Automated Thrombography (CAT). The thrombogram describes the concentration of thrombin in clotting plasma and is therefore a functional test of the hemostatic system. The assay is based on the measurement of fluorescence that is generated by the cleavage of the fluorogenic substrate Z G G R AMC by thrombin over time. See also the method as used in Example 8 herein.

Enhancing global visco-elastic properties of clot formation as measured by viscoelastic hemostatic methods e.g. in whole blood under shear stress by assays such as ROTEM (Rotational thromboelastometry). In the instrument, a ball-bearing pin rotates in a stationary cup. The fibrin strands in the sample form between the wall of the cup and the pin during coagulation and the strength of the strands will affect the movement of the pin, which is detected.

tractor or protraction moiety thus serves the purpose of the extending half-life of the ISVD polypeptides disclosed herein.

A protraction moiety (PM) comprises a protractor "P" and an optional linker ($L_P$).

Each protraction moiety preferably attaches to a surface exposed lysine or a cysteine residue in the polypeptide backbone of the compound. The attachment point is generally referred to as R1 (and in case of attachment of more than one protraction moiety R2, R3 and so forth wherein R1≠R2 ≠R3 and so forth).

The skilled person will be able to identify other surface exposed residue(s) suitable for attachment.

A protraction moiety may consist of one protractor.

A protraction moiety may comprise one linker ($L_P$) and one protractor (P).

A protraction moiety may comprise one linker and two or more protractors.

When the linker ($L_P$) is present, the protraction moiety attaches to the ISVD polypeptide backbone via $L_P$. When the linker ($L_P$) is absent, P attaches to the polypeptide backbone. In one embodiment a first and a second protraction moiety are present wherein said first protraction moiety comprises the structure:

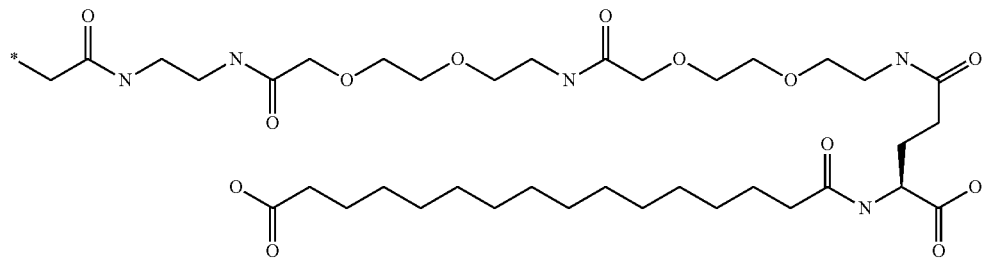 [SMILES: *CC(=O)NCCNC(=O)COCCOCCNC(=O)COCCOCCNC(=O)CC[C@H](NC(=O)CCCCCCCCCCCCCCC(=O)O)C(=O)O]

Shortening of the whole blood closure time (WBCT), as measured by a platelet function analyzer, which is based on and wherein said second protraction moiety comprises the structure

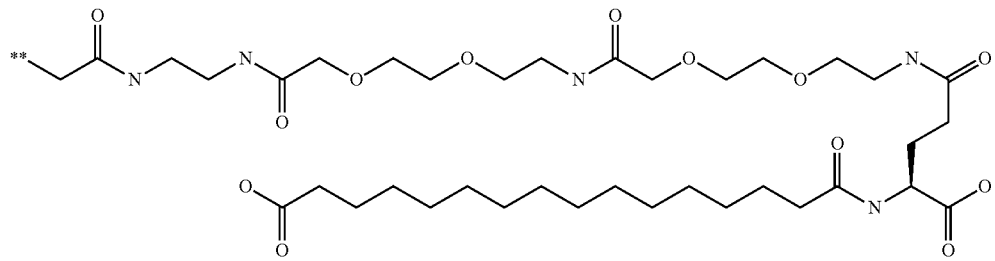

Von Willebrand Factor (VWF)-mediated platelet adhesion to collagen after platelet activation. High shear stress is produced which leads to platelet adhesion and platelet aggregation. The time from the beginning to end of blood flow is measured.

The ISVD polypeptides disclosed herein preferably comprises one, two, three or four "protraction moieties" (PM). More preferably one or two protraction moieties.

The term "protraction moiety" as used herein refers to a moiety having half-life extending properties and comprising a "protractor" (P) and an optional "linker" ($L_P$). The term "protraction" thus refers to half-life extension and a prowherein '*' (R1) represents the point of attachment on the ISVD polypeptide for the first protraction moiety, and wherein '**' (R2) represents the point of attachment on the ISVD polypeptide for the second protraction moiety, wherein '*' is Cys in position 257 of SEQ ID NO:629, and wherein '**' is Cys in position 259 of SEQ ID NO:629.

The ISVD polypeptide disclosed herein may comprise a single cysteine or lysine residue, to which a single protraction moiety is attached/conjugated.

The ISVD polypeptide disclosed herein may comprise two lysine residues and two protraction moieties.

The ISVD polypeptide disclosed herein may comprise two lysine residues and two identical protraction moieties.

The ISVD polypeptide disclosed herein may comprise two lysine residues and two non-identical protraction moieties.

The ISVD polypeptide disclosed herein may comprise three lysine residues and three protraction moieties.

The ISVD polypeptide disclosed herein may comprise three lysine residues and three identical protraction moieties.

The ISVD polypeptide disclosed herein may comprise three lysine residues and three non-identical protraction moieties (for example, the first and second protraction moieties may be identical and the third protraction moiety different form said first and second moieties)

The ISVD polypeptide disclosed herein may comprise two cysteine residues and two protraction moieties.

The ISVD polypeptide disclosed herein may comprise two cysteine residues and two identical protraction moieties.

The ISVD polypeptide disclosed herein may comprise two cysteine residues and two non-identical protraction moieties.

The ISVD polypeptide disclosed herein may comprise three cysteine residues and three protraction moieties.

The ISVD polypeptide disclosed herein may comprise three cysteine residues and three identical protraction moieties.

The ISVD polypeptide disclosed herein may comprise three cysteine residues and three non-identical protraction moieties (for example, the first and second protraction moieties may be identical and the third protraction moiety different form said first and second moieties).

Where the ISVD polypeptide comprises two or three protraction moieties, the protracting moieties are preferably similar, more preferably substantially identical, or, most preferably, identical.

In the context of chemical moieties such as the protraction moieties disclosed herein, similarity and/or identity may be determined using any suitable computer program and/or algorithm known in the art.

Compounds comprising a protraction moiety may be referred as "derivatives". For example, an "ISVD polypeptide derivative" is understood to be an ISVD polypeptide comprising a protraction moiety, a "$V_HH$ polypeptide derivative" a $V_HH$ polypeptide comprising a protraction moiety, and a "V-NAR polypeptide derivative" a V-NAR polypeptide comprising a protraction moiety.

The protraction moiety may be capable of non-covalently binding to albumin, thereby promoting the circulation of the ISVD polypeptide derivative in the blood stream and prolonging its half-life. Thus, in one embodiment the protraction moiety is an albumin binding moiety.

The protractor (P) may comprise an acyl group. The acyl group may be branched or unbranched. The acyl group may be saturated or unsaturated. The protractor may comprise a fatty acyl group. The acyl group may be branched or unbranched. The acyl group may be saturated or unsaturated.

The protractor may comprise a distal carboxylic acid group.

The protractor may comprise a fatty acid group.

The protractor may comprise a fatty acid group and an amide group.

The protractor may comprise a distal carboxylic acid group and an amide group.

The protractor may comprise an alkyl group.

The protractor may comprise an aryl group.

The protractor may comprise a tetrazole group.

The protractor may comprise a sulfonic acid group.

The protractor may comprise a phenoxy group.

The protractor may comprise a benzoic acid group.

The protractor may comprise 8-30 carbon atoms. The protractor may comprise 8, 9, 10, 11, 12, 13, 14, 15, 16, 17, 18, 19, 20, 21, 22, 23, 24, 25, 26, 27, 28, 29 or 30 carbon atoms.

The protractor may comprise 6-30 consecutive —$CH_2$— groups. The protractor may comprise a carbon chain comprising at least 6, 7, 8, 9, 10, 11, 12, 13, 14, 15, 16, 17, 18, 19, 20, 21, 22, 23, 24, 25, 26, 27, 28, 29 or 30 consecutive —$CH_2$— groups.

The protractor may comprise 12-26 carbon atoms. The "protractor" may comprise 12, 13, 14, 15, 16, 17, 18, 19, 20, 21, 22, 23, 24, 25 or 26 carbon atoms.

The protractor may comprise 10-26 consecutive —$CH_2$— groups. The protractor may comprise a carbon chain comprising 10, 11, 12, 13, 14, 15, 16, 17, 18, 19, 20, 21, 22, 23, 24, 25 or 26 consecutive —$CH_2$— groups.

The protractor may comprise 16-22 carbon atoms.

The protractor may comprise 14-20 consecutive —$CH_2$— groups. The protractor may comprise a carbon chain comprising 14, 15, 16, 17, 18, 19 or 20 consecutive —$CH_2$— groups.

The protractor may comprise 16-22 consecutive carbon atoms and 14-20 consecutive —$CH_2$— groups.

The protractor may comprise 16 consecutive carbon atoms and 14 consecutive —$CH_2$— groups.

The protractor may comprise 18 consecutive carbon atoms and 16 consecutive —$CH_2$— groups.

The protractor may comprise 20 consecutive carbon atoms and 18 consecutive —$CH_2$— groups.

The protractor may comprise 22 consecutive carbon atoms and 20 consecutive —$CH_2$— groups.

In some embodiments the protractor comprises a group defined by:

$$HOOC-(CH_2)_n-CO-* \qquad \text{Chem. a:}$$

wherein n is an integer in the range of 8-30, which may also be referred to as a C(n+2) diacid or as Chem. a1:

$$HO-\underset{O}{\overset{O}{\|}}C-(CH_2)_n-\underset{O}{\overset{O}{\|}}C-*,$$

wherein n is an integer in the range of 8-30.

The protractor may comprise an oligopeptide. In one embodiment, the protractor oligopeptide is 10 to 40 amino acids, such as 10 to 30 amino acids, such as 15 to 25 amino acids, and, preferably, 20 amino acids. The protractor oligopeptide sequence composition may for example be QRL-MEDICLPRWGCLWEDDF (SEQ ID NO:736), exemplified as fusion sequence in SEQ ID NO:3 and 4 [see also WO01/45746 A2]. Cmpd #71—for example—comprises a 50-amino acid N-terminal protraction moiety composed of QRLMEDICLPRWGCLWEDDFGGGGS-GGGGSGGGGSGGGGSGGGGSGGGGS (SEQ ID NO: 4) wherein residues 1-20 is the protractor (P) and residues 21-50 is the linker ($L_P$).

The protractor may be attached to the ISVD or ISVD polypeptide via an amino acid linker $L_P$.

In one embodiment $L_P$ may join the protractor (P) to the side chain of a lysine or cysteine residue in the ISVD polypeptide backbone.

The ISVD polypeptide derivative may comprise two protraction moieties, each of which comprises 14, 15, 16, 17, 18, 19 or 20 carbon atoms. The ISVD polypeptide may comprise two protraction moieties, wherein each protractor (P) comprises 12, 13, 14, 15, 16, 17 or 18 consecutive —CH$_2$— groups.

The ISVD polypeptide derivative may comprise two C14 diacids, two C16 diacids or two C18 diacids.

The ISVD polypeptide derivative may comprise three protraction moieties, each of which comprises a protractor comprising 12, 13, 14, 15, 16, 17, 18, 19 or 20 carbon atoms. The ISVD polypeptide may comprise three protraction moieties, wherein the protractor comprises 10, 11, 12 13, 14, 15, 16, 17 or 18 consecutive —CH$_2$— groups.

For the avoidance of doubt a protraction moiety even if capable of binding e.g. albumin, it is not considered a binder in terms of defining whether an ISVD polypeptide as disclosed herein is bi-, tri- or multispecific.

In some embodiments an ISVD polypeptide as disclosed herein may comprise a protractor which is selected from any one of those depicted in Table 1.

In Table 2, L$_P$ represents the optional linker which connects the depicted protractor (P) to the ISVD polypeptide backbone. R1 represents the site of attachment in the ISVD polypeptide.

TABLE 1

Examples of protractors (P) ('*' represents the point of attachment to L$_P$ or R1)

| Protractor ID | Structure | Used in compounds |
| --- | --- | --- |
| P1 | C12 diacid | Cmpd #65 |
| P2 | C16 diacid | Cmpd #6, #7, #8, #9, #10, #11, #12, #13, #14, #15, #16, #17, #18, #19, #20, #21, #22 |
| P3 | C18 diacid | Cmpd #4, #5, #24, #26, #28, #30, #32, #34, #36, #38, #40, #58, #59, #60, #61, #62, #63, #66 |
| P4 | C20 diacid | Cmpd #67 |
| P5 | Tetrazole | Cmpd #68 |
| P6 | QRLMEDICLPRWGCLWEDDF Albumin-binder oligopeptide, exemplified as fusion sequence in SEQ ID NO: 3 and 4. SEQ ID NO: 3 describes the albumin-binder oligopeptide together with a 10 amino acid long glycine-serine linker while SEQ ID NO: 4 describes the albumin-binder oligopeptide together with a 30 amino acid long glycine-serine linker. | Cmpd #70, #71, #72, #73 |

In one embodiment the protractor is conjugated directly onto the ISVD polypeptide, i.e. without use of a linker $L_P$ (i.e. by way of a covalent bond).

In other embodiments the protractor is conjugated directly onto the ISVD polypeptide using a linker $L_P$. Non-limiting examples are provided below.

The $L_P$ linker—when present—may comprise Ado, Aeep or Aeeep, sulfonamide, Trx, ε-Lys, Ahx, Glu, γGlu, Gly, Ser, Ala and/or Thr.

The $L_P$ linker may comprise at least a moiety which may be represented by the following chemical formula:

*—NH—$(CH_2)_2$—(O—$(CH_2))_k$—O—$(CH_2)_n$—CO—*  Chem. 1:

or

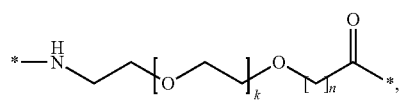

Chem. 2 wherein k is an integer in the range of 1-5, and n is an integer in the range of 1-5.

When k=1 and n=1, the linker element may be designated Ado, or 8-amino-3,6-dioxaoctanoyl, which may be represented by the following chemical formula:

*—NH—$(CH_2)_2$—O—$(CH_2)_2$—O—$CH_2$—CO—*  Chem. 3:

or

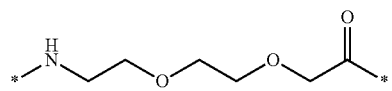

Chem. 4

When k=1 and n=2, the linker element may be designated Aeep, which may be represented by the following chemical formula:

*—NH—$(CH_2)_2$—O—$(CH_2)_2$—O—$(CH_2)_2$—CO—*  Chem. 5:

or

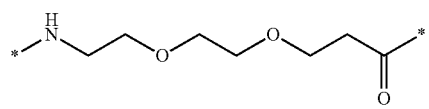

Chem. 6

When k=2 and n=2, the linker element may be designated Aeeep, which may be represented by the following chemical formula:

*—NH—$(CH_2)_2$—O—$(CH_2)_2$—O—$(CH_2)_2$—O—$(CH_2)_2$—CO—*  Chem. 7:

or

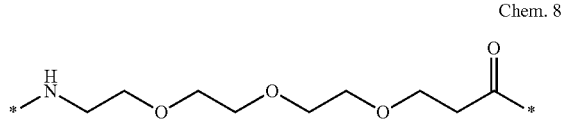 [SMILES: *NCCOCCOCCOCCC(*)=O]

Chem. 8

The optional linker ($L_P$) may comprise an 8-amino-3,6-dioxa-octanoic acid (OEG) group having the following chemical formula

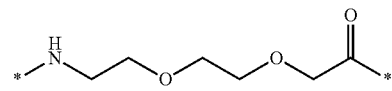

Chem 8a

The optional linker ($L_P$) may comprise a sulfonamide-C4 moiety. A sulfonamide-C4 group is a sulfonamide group attached to a 4-butanoyl group, having the following chemical formula:

*—NH—$S(O)_2$—$CH_2$—$CH_2$—$CH_2$—CO—*  Chem. 9:

or

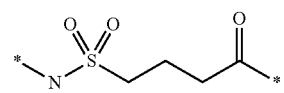

Chem 10

The optional linker $L_P$ may comprise Trx. Trx is also referred to as Tranexamic acid, trans-4-(aminomethyl)cyclohexanecarboxylic acid, having the following chemical formula:

*—NH—$CH_2$—$(C_6H_{10})$—CO—*  Chem. 11:

or

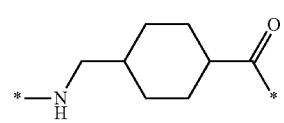

Chem. 12

The linker $L_P$ may comprise epsilon-lysine (ε-Lys).
The linker $L_P$ may comprise lysine (Lys).
The linker $L_P$ may comprise Ahx. Ahx is also referred to as Aminocaproic acid, 6-aminohexanoic acid and is defined by

*—NH—$(CH_2)_5$—CO—*  Chem 13:

or

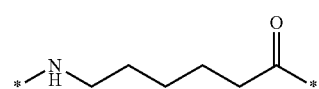

Chem 14

The linker $L_P$ may comprise a Glu di-radical, such as

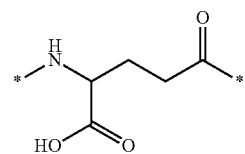

Chem. 15 wherein the Glu di-radical may be included p times, where p is an integer in the range of 1-3.

Chem. 15 may also be referred to as gamma-Glu, or briefly γGlu, due to the fact that it is the gamma carboxy group of the amino acid glutamic acid which is here used for connection to the epsilon-amino group of lysine. As explained above, the other linker element may, for example, be another Glu residue, or an Ado molecule. The amino group of Glu in turn forms an amide bond with the carboxy group of the protracting moiety, or with the carboxy group of, e.g., an Ado molecule, if present, or with the gamma-carboxy group of, e.g., another Glu, if present.

Alternatively, the ISVD polypeptide derivatives disclosed herein may comprise a linker ($L_P$) which is selected from any one of those depicted in Table 2 below. R1 represents the residue in the ISVD polypeptide to which the protraction moiety is attached and P represents the protractor.

The protraction moiety may attach to a cysteine or lysine residue in the first ISVD portion of the ISVD polypeptide backbone.

The protraction moiety may attach to a cysteine or lysine residue in the second ISVD portion of the ISVD polypeptide backbone.

The protraction moiety may attach to a cysteine or lysine residue in the optional linker ($L_{1-2}$) portion of the ISVD polypeptide backbone.

The protraction moiety may be covalently attached to a lysine residue in the ISVD polypeptide backbone. The protraction moiety may be attached via an amide bond formed between a carboxylic acid group in the protraction moiety and the epsilon amino group of the lysine residue.

The protraction moiety may be covalently attached to a cysteine residue in the ISVD polypeptide backbone. The protraction moiety may be attached via a thioether bond

TABLE 2

Examples of (optional) protraction moiety linkers ("$L_P$")

| Linker ($L_P$) ID | Structure | Used in derivative Cmpd# |
|---|---|---|
| $L_P$1 | [Structure: Glu-based linker with 2×OEG and ethylenediamine-acetyl to R1, with P attached via amide to Glu alpha-amino] | Cmpd #4, #5, #24, #26, #28, #30, #32, #34, #36, #38, #40, #58, #59, #60, #61, #62, #63, #65, #66, #67, #6, #7, #8, #9, #10, #11, #12, #13, #14, #15, #16, #17, #18, #19, #20, #21, #22 |
| $L_P$2 | [Structure: similar linker with 2×OEG and ethylenediamine-acetyl to R1, with P attached via sulfonamide] | Cmpd #68 |
| $L_P$3 | "R1"-GGGGSGGGGS (SEQ ID NO: 25)-"P" or "P"-GGGGSGGGGS (SEQ ID NO: 25)-"R1" | Cmpd #70, #72 |
| $L_P$4 | "R1"-GGGGSGGGGSGGGGSGGGGSGGGGSGGGGS (SEQ ID NO: 26)-"P" or "P"-GGGGSGGGGSGGGGSGGGGSGGGGSGGGGS (SEQ ID NO: 26)-"R1" | Cmpd #71, #73 |

Based on the disclosure herein, the skilled person will be able to determine the optimal L P and $L_{1-2}$ linker(s) for use in a specific ISVD polypeptide derivative as disclosed herein, optionally after some limited routine experiments. For example, the linkers are preferably such that it allows each ISVD, such as a $V_HH$ fragment, in the ISVD polypeptide to bind to its target. Again, based on the disclosure herein, the skilled person will be able to determine the optimal linker(s) for use in a specific ISVD polypeptide derivative as disclosed herein, optionally after some limited routine experiments.

An amino acid residue in the ISVD or ISVD polypeptide backbone to which attachment takes place is designated R1 herein. In case of more than one protraction moiety being attached, the further attachment site(s) may be designated R2, R3 and so forth.

formed between the protraction moiety and the sulphur atom of the cysteine residue in the polypeptide.

Thus, in some embodiments the compounds disclosed herein may comprise one, two or three lysine or cysteine residues and one, two or three protraction moieties, wherein each protraction moiety is attached to a side chain of a single lysine or cysteine residue.

When attachment takes place via cysteine residue, the cysteine is preferably a free cysteine.

A free cysteine, in some embodiments introduced by recombinant DNA technology, may serve as a conjugation site for attaching one or more C16-, C17- or C18 diacid gamma-Glu 2×OEG fatty acid moiety.

In a preferred embodiment a free cysteine, optionally introduced by recombinant DNA technology, may serve as a conjugation site for attaching one, two or three C18 diacid gamma-Glu 2×OEG fatty acid moiety (IUPAC name S{Beta-AA#}-[2-[2-[[2-[2-[2-[[2-[2-[2-[[(4S)-4-carboxy-4-(17-carboxyheptadecanoyl-amino)butanoyl]amino]ethoxy]ethoxy]acetyl]amino]ethoxy]ethoxy] acetyl]amino]-ethyl-amino]-2-oxoethyl], AA #amino acid attachment).

In another preferred embodiment a free cysteine, optionally introduced by recombinant DNA technology, may serve as a conjugation site for attaching one, two or three C17 diacid gamma-Glu 2×OEG fatty acid moiety (IUPAC name S{Beta-AA#}-[2-[2-[[2-[2-[2-[[2-[2-[2-[[(4S)-4-carboxy-4-(16-carboxyhexadecanoyl-amino)butanoyl]amino]ethoxy]ethoxy]acetyl]amino]ethoxy] ethoxy]acetyl]amino]-ethyl-amino]-2-oxoethyl], AA #amino acid attachment).

In a most preferred embodiment a free cysteine, introduced by recombinant DNA technology, may serve as a conjugation site for attaching one, two or three C16 diacid gamma-Glu 2×OEG fatty acid moiety (IUPAC name S{Beta-AA#}-[2-[2-[[2-[2-[2-[[2-[2-[2-[[(4S)-4-carboxy-4-(15-carboxypentadecanoyl-amino)butanoyl]amino]ethoxy]ethoxy]acetyl]amino]ethoxy] ethoxy]acetyl]amino]-ethyl-amino]-2-oxoethyl], AA #amino acid attachment).

The term "standard chromatography" as used herein encompasses standard chromatographic methods, such as protein A, cation exchange, anion exchange, hydrophobic interaction, and hydroxyapatite chromatography.

The term "surface exposed amino acid residue" as used herein refers to amino acid residues whose side chain can be in contact with solvent molecules (which in general may be mostly water molecules). However, the side chain does not necessarily have to be wholly in contact with solvent molecules, and when even a portion of the side chain is in contact with the solvent molecules, the amino acid residue is defined as an "amino acid located on the surface". The amino acid residues located on the surface of a polypeptide can also include amino acid residues located close to the ISVD surface and thereby can have a mutual electric charge influence from other amino acid residue(s) whose side chain, even partly, is in contact with the solvent molecules. Those of ordinary skill in the art can prepare a homology model or a machine learning based three-dimensional molecular model of a polypeptide or antibody by for example homology modelling or machine learning using commercially or publicly available softwares. Alternatively, it is possible to use methods such as X-ray crystallography for three-dimensional molecular model generation. The amino acid residues that may be exposed on the surface can be determined, for example, using coordinates from a three-dimensional molecular model of an antibody using a computer program such as MOE (Chemical Computing Group) or Bioluminate (Schrödinger). Surface exposed sites may be determined using algorithms known in the technical field (for example, Lee and Richards (1971) J. Mol. Biol. 55:379-400; Connolly, J. Appl. Cryst. (1983) 16:548-558). Surface exposable sites can be determined using software suitable for protein modelling and analysis of three-dimensional structure information obtained from the antibody. Software available for such purposes includes, for example, the MOE (Chemical Computing Group) or Bioluminate (Schrödinger). The solvent accessible surface (in A 2) area are calculated using a water probe with a probe radius of 1.4 Å. Furthermore, methods for determining surface exposed regions and areas using software for personal computers have been described by Pacios (Pacios, Comput. Chem. 18(4):377-386 (1994); J. Mol. Model. 1:46-53 (1995)). Based on such information as described above, appropriate amino acid residues located on the surface of an antibody in contact with solvent can be selected.

Pharmaceutical Compositions

The $V_HH$ polypeptide derivatives as disclosed herein may be prepared in pharmaceutical compositions. In some embodiments such composition comprises at least one pharmaceutically acceptable excipient.

The term "excipient" as used herein broadly refers to any component other than the active therapeutic ingredient (API). The excipients may serve various purposes, e.g. as a carrier, vehicle, filler, binder, lubricant, glidant, disintegrant, flow control agent, crystallization inhibitors, solubilizer, stabilizer, colouring agent, flavouring agent, surfactant, emulsifier, delivery agent, hydrotrope or combinations thereof and/or to improve administration, and/or absorption of the active pharmaceutical ingredient(s).

The amount of each excipient used may vary within ranges conventional in the art. Techniques and excipients which may be used to formulate oral dosage forms are described in Handbook of Pharmaceutical Excipients, 8th edition, Sheskey et al., Eds., American Pharmaceuticals Association and the Pharmaceutical Press, publications department of the Royal Pharmaceutical Society of Great Britain (2017); and Remington: the Science and Practice of Pharmacy, 22nd edition, Remington and Allen, Eds., Pharmaceutical Press (2013).

In preferred embodiments the composition comprising a $V_HH$ polypeptide further comprises a delivery agent and a hydrotrope.

A preferred delivery agent is a salt of N-(8-(2-hydroxybenzoyl)amino)caprylic acid (NAC). In some embodiments the delivery agent is a salt of N-(8-(2-hydroxybenzoyl)amino)caprylic acid as described in WO2007/121318. In some embodiments the delivery agent is sodium N-(8-(2-hydroxybenzoyl)amino)caprylate (referred to as "SNAC" herein), also known as sodium 8-(salicyloylamino)octanoate.

The pharmaceutical compositions preferably comprise one or more hydrotropes. Hydrotropes, like a surfactant, include both a hydrophilic part and a hydrophobic and can form micelles and self-aggregate, however they solubilize solutes without micellar solubilization. In one embodiment the hydrotrope is capable of increasing the solubility of SNAC. In one embodiment the hydrotrope is nicotinamide (NAM).

In one embodiment the composition is a solid composition. The composition may be in a form suitable for peroral administration, such as a tablet, sachet or capsule. In one such embodiment the composition is formulated as a tablet. The solid compositions provided herein allow for an accelerated dissolution and thereby enables fast uptake of the active pharmaceutical ingredient.

Administration and Dosages

A compound as disclosed herein, such as a $V_HH$ polypeptide derivative, may be administered parenterally, such as intravenously, such as intramuscularly, such as subcutaneously in an appropriate pharmaceutical composition. The compound may be administered via a non-parenteral route and preferably perorally (PO). The compound may be administered prophylactically. The compound may be administered therapeutically (on demand).

Subcutaneous Administration

The dose of the compounds to be delivered by subcutaneous administration may be from about 0.01 mg to 1 mg of the compound per day, preferably from about 0.05 mg to 5 mg per day, and more preferably from about 0.1 mg to about 10 mg per day, per every second day, per every third day, per fourth day, per fifth day, per every sixth day or once weekly depending on the severity of the condition. A suitable dose may also be adjusted for a particular compound based on the properties of that compound, including its in vivo half-life or mean residence time and its biological activity.

In one embodiment the present invention relates to an injection device with content of said composition.

Peroral (PO) Administration

The dose of the compounds to be delivered PO may be from about 1 mg to about 300 mg of the compound per day, per every second day, per every third day depending on the severity of the condition. A suitable dose may also be adjusted for a particular compound based on the properties of that compound, including its in vivo half-life or mean residence time and its biological activity.

The compositions containing the compounds as disclosed herein can be administered for prophylactic and/or in some embodiments therapeutic treatments. In therapeutic applications, compositions are administered to a subject already suffering from a disease, such as any bleeding disorder as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject.

EMBODIMENTS

1. A procoagulant immunoglobulin single variable domain (ISVD) polypeptide derivative comprising
   a first ISVD (ISVD1) capable of binding to Factor IX (SEQ ID NO:1) or the activated form thereof,
   a second ISVD (ISVD2) capable of binding to Factor X (SEQ ID NO:2) or the activated form thereof,
   at least one protraction moiety,
   optionally a linker ($L_{1-2}$) linking ISVD1 and ISVD2, and
   optionally one or more extension(s) (E).

2. The ISVD polypeptide derivative according to embodiment 1 having the formula

ISVD1-ISVD2, or

ISVD1-ISVD2-E, or

ISVD2-ISVD1-E, or

E-ISVD1-ISVD2, or

ISVD1-$L_{1-2}$-ISVD2-E, or

ISVD2-$L_{1-2}$-ISVD1-E, or

E-ISVD1-$L_{1-2}$-ISVD2,

3. The ISVD polypeptide derivative according to embodiment 1 having the formula (N- to C-terminal)

ISVD1-ISVD2, or

ISVD2-ISVD1, or

ISVD1-ISVD2-E, or

ISVD2-ISVD1-E, or

E-ISVD1-ISVD2, or

E-ISVD2-ISVD1, or

ISVD1-$L_{1-2}$-ISVD2, or

ISVD2-$L_{1-2}$-ISVD1, or

ISVD1-$L_{1-2}$-ISVD2-E, or

ISVD2-$L_{1-2}$-ISVD1-E, or

E-ISVD1-$L_{1-2}$-ISVD2, or

E-ISVD2-$L_{1-2}$-ISVD1.

4. The ISVD polypeptide derivative according to any of the former embodiments wherein the at least one protraction moiety(ies) is/are attached to one or more surface exposed residue(s).

5. The ISVD polypeptide derivative according to any of the former embodiments having the formula (N- to C-terminal)

ISVD2-$L_{1-2}$-ISVD1-E wherein one or more protraction moiety(ies) is/are attached to one or more surface exposed residue.

6. The ISVD polypeptide derivative according to any of the former embodiments having the formula (N- to C-terminal)

ISVD2-$L_{1-2}$-ISVD1-E wherein two protraction moieties are attached to one or more surface exposed residue(s) on E.

7. The ISVD polypeptide derivative according to any of the former embodiments having the formula (N- to C-terminal)

ISVD2-$L_{1-2}$-ISVD1-E further comprising
   a first protraction moiety and a second protraction moiety being attached to a first surface exposed residue and a second surface exposed residue in E, respectively.

8. The ISVD polypeptide derivative according to any of the former embodiments, wherein $L_{1-2}$ comprises a ratio of hydrophobic to hydrophilic amino acids of "40 to 60%" to "60 to 40%".

9. The ISVD polypeptide derivative according to any of the former embodiments, wherein the first ISVD is capable of binding to an epitope on Factor IX (SEQ ID NO:1) or the activated form thereof comprising at least one of the amino acid residues E224, T225, G226, V250, I251, R252, I253, P255, H257 and N260 (consecutive numbering).

10. The ISVD polypeptide derivative according to any of the former embodiments, wherein the first ISVD is capable of binding to an epitope on Factor IX (SEQ ID NO:1) or the activated form thereof comprising at least 4, 5, 6, 7 or 8 of the amino acid residues E224, T225, G226, V250, I251, R252, I253, P255, H257 and N260 (consecutive numbering).

11. The ISVD polypeptide derivative according to any of the former embodiments, wherein the first ISVD is capable of binding to an epitope on Factor IX (SEQ ID NO:1) or the activated form thereof comprising the amino acid residues E224, T225, G226, V250, I251, R252, I253, P255, H257 and N260 (consecutive numbering).

12. The ISVD polypeptide derivative according to any of the former embodiments, wherein the second ISVD is capable of binding to an epitope on Factor X (SEQ ID NO:2) comprising at least one of the amino acid residues N173, P174, F175, L177, L178 and D179 (consecutive numbering).

13. The ISVD polypeptide derivative according to any of the former embodiments, wherein the second ISVD is capable of binding to an epitope on Factor X (SEQ ID NO:2) comprising the amino acid residues N173, P174, F175, L177 and L178 (consecutive numbering).
14. The ISVD polypeptide derivative according to any of the former embodiments, wherein the second ISVD is capable of binding to an epitope on Factor X (SEQ ID NO:2) comprising at least one of the amino acid residues N173, P174, F175, L177, L178 and D179 (consecutive numbering).
15. The ISVD polypeptide derivative according to any of the former embodiments, wherein the second ISVD is capable of binding to an epitope on Factor X (SEQ ID NO:2) comprising at least 3, 4, 5 or 6 of the amino acid residues N173, P174, F175, L177, L178 and D179 (consecutive numbering).
16. The ISVD polypeptide derivative according to any of the former embodiments, wherein the second ISVD is capable of binding to an epitope on Factor X (SEQ ID NO:2) comprising the amino acid residues N173, P174, F175, L177, L178 and D179 (consecutive numbering).
17. The ISVD polypeptide derivative according to any of the former embodiments, wherein the first ISVD is capable of binding to an epitope on Factor IX (SEQ ID NO:1) or the activated form thereof comprising at least one of the amino acid residues E224, T225, G226, V250, I251, R252, I253, P255, H257 and N260 (consecutive numbering), and the second ISVD is capable of binding to an epitope on Factor X (SEQ ID NO:2) comprising at least one of the amino acid residues N173, P174, F175, L177, and L178 (consecutive numbering).
18. The ISVD polypeptide derivative according to any of the former embodiments, wherein
the first ISVD is capable of binding to an epitope on Factor IX (SEQ ID NO:1) or the activated form thereof comprising the amino acid residues E224, T225, G226, V250, I251, R252, I253, P255, H257 and N260 (consecutive numbering), and the second ISVD is capable of binding to an epitope on Factor X (SEQ ID NO:2) comprising the amino acid residues N173, P174, F175, L177, L178 and D179 (consecutive numbering).
19. The ISVD polypeptide derivative according to any of embodiments 1-9, wherein the first ISVD comprises a paratope comprising amino acid residues F29, N30, Y32, T54, D99, R100, S101, F102, L103, F104, Q106, A107 and N113 (SEQ ID NO:35), and wherein the second ISVD comprises a paratope comprising amino acid residues
a) D32, A33, M34, G35, Y37, L47, V48, A49, G50, I51, M52, N57, T58, N59, Y60, T61, K97, V99, R101 and P102 (SEQ ID NO:27), or
b) A33, M34, G35, W47, V48, A49, A50, I51, S52, S57, T58, N59, Y60, A61, A97, A98, D99, G105, L107 and Y109 (SEQ ID NO:734)
(consecutive numbering).
20. The ISVD polypeptide derivative according to any of embodiments 1-9, wherein said first ISVD comprises
1)
CDR1: IYTMS (SEQ ID NO:172), optionally comprising one or two amino acid substitutions,
CDR2: GLRWTDSSTEYADSVKG (SEQ ID NO:173), optionally comprising one, two or three amino acid substitutions,
CDR3: DRSFLFAQALGATKNYEY (SEQ ID NO:174), optionally comprising one, two or three amino acid substitutions (Kabat definition).
21. The ISVD polypeptide derivative according to of embodiments 1-9, wherein said second ISVD comprises
(A)
CDR1: RYAMG (SEQ ID NO:168), optionally comprising one or two substitutions,
CDR2: AISRRGGSTNYADSVKG (SEQ ID NO:169), optionally comprising one, two or three amino acid substitutions,
CDR3: DDSVGDGYLDY (SEQ ID NO:170), optionally comprising one, two or three amino acid substitutions; or
(B)
CDR1: RLAMG (SEQ ID NO:128), optionally comprising one or two amino acid substitutions,
CDR2: AISRRGGSTNYADSVKG (SEQ ID NO:129), optionally comprising one, two or three substitutions,
CDR3: DDSVGDGYLDY (SEQ ID NO:130), optionally comprising one, two or three amino acid substitutions
(Kabat definition).
22. The ISVD polypeptide derivative according to any of embodiments 1-9, wherein said first ISVD comprises
1)
CDR1: IYTMS (SEQ ID NO:172), optionally comprising one or two amino acid substitutions,
CDR2: GLRWTDSSTEYADSVKG (SEQ ID NO:173), optionally comprising one, two or three amino acid substitutions,
CDR3: DRSFLFAQALGATKNYEY (SEQ ID NO:174), optionally comprising one, two or three amino acid substitutions; or
and wherein said second ISVD comprises
(A)
CDR1: RYAMG (SEQ ID NO:168), optionally comprising one or two substitutions,
CDR2: AISRRGGSTNYADSVKG (SEQ ID NO:169), optionally comprising one, two or three substitutions,
CDR3: DDSVGDGYLDY (SEQ ID NO:170), optionally comprising one, two or three amino acid substitutions; or
(B)
CDR1: RLAMG (SEQ ID NO:128), optionally comprising one or two substitutions,
CDR2: AISRRGGSTNYADSVKG (SEQ ID NO:129), optionally comprising one, two or three substitutions,
CDR3: DDSVGDGYLDY (SEQ ID NO:130), optionally comprising one, two or three amino acid substitutions
(Kabat numbering).
23. The ISVD polypeptide derivative according to any of embodiments 20-22, wherein said substitution(s) is/are conservative substitution(s).
24. The ISVD polypeptide derivative according to any of the former embodiments, wherein the sequence of said first ISVD is at least 90, 91, 92, 93, 94, 95, 96, 97, 98 or 99% identical to the sequence identified by SEQ ID NO:107, 115, 123, 131, 155 or 171, respectively.
25. The ISVD polypeptide derivative according to any of the former embodiments, wherein the sequence of said second ISVD is at least 90, 91, 92, 93, 94, 95, 96, 97, 98 or 99% identical to the sequence identified by SEQ ID NO:103, 111, 119, 127, 151 or 167, respectively.

26. The ISVD polypeptide derivative according to any of the former embodiments, wherein the sequence of said first ISVD is at least 90, 91, 92, 93, 94, 95, 96, 97, 98 or 99% identical to the sequence identified by SEQ ID NO:107, 115, 123, 131, 155 or 171, respectively, and wherein the sequence of said second ISVD is at least 90, 91, 92, 93, 94, 95, 96, 97, 98 or 99% identical to the sequence identified by SEQ ID NO:103, 111, 119, 127, 151 or 167, respectively.

27. The ISVD polypeptide derivative according to any of the former embodiments, wherein said first ISVD comprises the sequence of
$V_HH$-2.20 (SEQ ID NO:171),
$V_HH$-2.18 (SEQ ID NO:155),
$V_HH$-2.15 (SEQ ID NO:131),
$V_HH$-2.13 (SEQ ID NO:115),
$V_HH$-2.14 (SEQ ID NO:123), or
$V_HH$-2.12 (SEQ ID NO:107).

28. The ISVD polypeptide derivative according to any of the former embodiments, wherein said second ISVD comprises the sequence of
$V_HH$-1.20 (SEQ ID NO:167),
$V_HH$-1.18 (SEQ ID NO:151),
$V_HH$-1.15 (SEQ ID NO:127),
$V_HH$-1.13 (SEQ ID NO:111),
$V_HH$-1.14 (SEQ ID NO:119), or
$V_HH$-1.12 (SEQ ID NO:103).

29. The ISVD polypeptide derivative according to any of the former embodiments, wherein said first ISVD comprises the sequence of
$V_HH$-2.20 (SEQ ID NO:171),
$V_HH$-2.18 (SEQ ID NO:155),
$V_HH$-2.15 (SEQ ID NO:131),
$V_HH$-2.13 (SEQ ID NO:115),
$V_HH$-2.14 (SEQ ID NO:123), or
$V_HH$-2.12 (SEQ ID NO:107)
and wherein
said second ISVD comprises the sequence of
$V_HH$-1.20 (SEQ ID NO:167),
$V_HH$-1.18 (SEQ ID NO:151),
$V_HH$-1.15 (SEQ ID NO:127),
$V_HH$-1.13 (SEQ ID NO:111),
$V_HH$-1.14 (SEQ ID NO:119), or
$V_HH$-1.12 (SEQ ID NO:103).

30. The ISVD polypeptide derivative according to embodiment 29, wherein said first ISVD comprises the sequence of $V_HH$-2.20 (SEQ ID NO:171), and wherein said second ISVD comprises the sequence of $V_HH$-1.20 (SEQ ID NO:167).

31. The ISVD polypeptide derivative according to embodiment 29, wherein said first ISVD comprises the sequence of $V_HH$-2.18 (SEQ ID NO:155), and wherein said second ISVD comprises the sequence of $V_HH$-1.18 (SEQ ID NO:151).

32. The ISVD polypeptide derivative according to embodiments 2929, wherein said first ISVD comprises the sequence of $V_HH$-2.15 (SEQ ID NO:131), and wherein said second ISVD comprises the sequence of $V_HH$-1.15 (SEQ ID NO:127).

33. The ISVD polypeptide derivative according to embodiment 29, wherein said first ISVD comprises the sequence of $V_HH$-2.13 (SEQ ID NO:115), and wherein said second ISVD comprises the sequence of $V_HH$-1.13 (SEQ ID NO:111).

34. The ISVD polypeptide derivative according to embodiment 29, wherein said first ISVD comprises the sequence of $V_HH$-2.14 (SEQ ID NO:123), and wherein said second ISVD comprises the sequence of $V_HH$-1.14 (SEQ ID NO:119).

35. The ISVD polypeptide derivative according to embodiment 29, wherein said first ISVD comprises the sequence of $V_HH$-2.12 (SEQ ID NO:107), and wherein said second ISVD comprises the sequence of $V_HH$-1.12 (SEQ ID NO:103).

36. The ISVD polypeptide derivative according to any of the former embodiments, wherein the protraction moiety(ies) comprises a protractor selected from the groups consisting of
a) a C16 diacid, C17 diacid, C18 diacid, C19 diacid, C20 diacid, C21 diacid or C22 diacid,
b) tetrazole,
c) an albumin-binder peptide, such as RLIEDICLPRWGCLWEDD (SEQ ID NO:737)
d) an FcRn-binder peptide, such as QRFCTGHFGGLYPCNG (SEQ ID NO:738), and
e) a Fc-binder peptide, such as FNMQQQRRFYEALHDPNLNEEQRNAKIKSIRDDN (SEQ ID NO:739).

37. The ISVD polypeptide derivative according to any of the former embodiments, wherein the protraction moiety(ies) comprises a protractor selected from the group consisting of C16 diacid, C17 diacid, C18 diacid, C19 diacid and C20 diacid.

38. The ISVD polypeptide derivative according to embodiment 34, wherein the protractor(s) is/are a C16 diacid protractor.

39. The ISVD polypeptide derivative according to any of the former embodiments, wherein the protraction moiety comprises a linker $L_P$ attaching the protractor to ISVD1, $L_{1-2}$, ISVD2 or E.

40. The ISVD polypeptide derivative according to embodiment 39, wherein $L_P$ is selected from the group consisting of

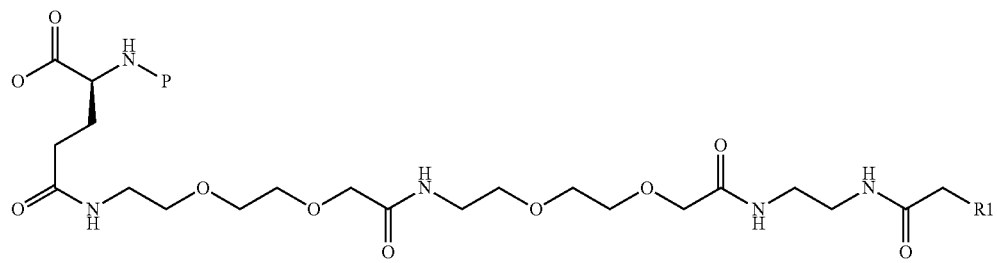

$L_{P}1$

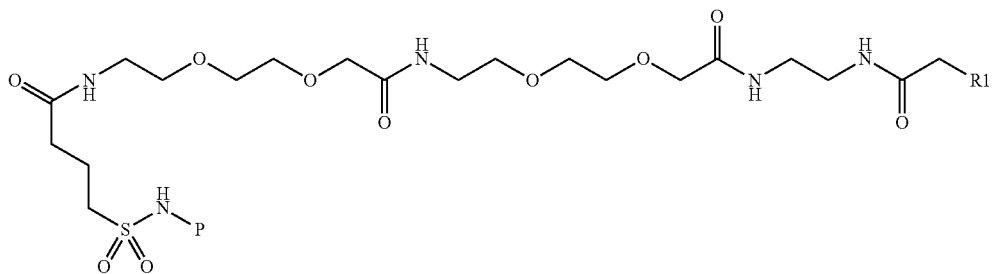

$L_{p2}$

"R1"-GGGGSGGGGS (SEQ ID NO: 25)-"P"
or
"P"-GGGGSGGGGS (SEQ ID NO: 25)-"R1"

$L_{p3}$

"R1"-GGGGSGGGGSGGGGSGGGGSGGGGSGGGGS (SEQ ID NO: 26)-"P"
or
"P"-GGGGSGGGGSGGGGSGGGGSGGGGSGGGGS (SEQ ID NO: 26)-"R1"

$L_{p4}$

41. The ISVD polypeptide derivative according to any of the former embodiments, wherein the protraction moiety(ies) is/are attached to position 13 in ISVD2 and/or one or more of positions 12, 14, 15, 42, 44, 63, and/or 85 on ISVD1 (consecutive numbering).

42. The ISVD polypeptide derivative according to any of embodiments 1-40, wherein the ISVD polypeptide derivative comprises a C-terminal extension, wherein the protraction moiety(ies) is/are attached to said C-terminal extension.

43. The ISVD polypeptide derivative according to any of the former embodiments, wherein the ISVD polypeptide derivative comprises a first and a second protraction moieties and a C-terminal extension, wherein the first protraction moiety and the second protraction moiety are attached to the C-terminal extension.

44. The ISVD polypeptide derivative according to embodiment 43, wherein the C-terminal extension is attached to ISVD1.

45. The ISVD polypeptide derivative according to embodiment 43, wherein the C-terminal extension is attached to ISVD2.

46. The ISVD polypeptide derivative according to any of the former embodiments, wherein the protraction moieties are identical.

47. The ISVD polypeptide derivative according to any of the former embodiments, wherein one or more protraction moiety(ies) is/are attached to a surface exposed residue.

48. The ISVD polypeptide derivative according to any of the former embodiments, wherein one or more protraction moiety(ies) is/are attached to a surface exposed residue wherein said surface exposed residue is not a residue in a CDR region.

49. The ISVD polypeptide derivative according to any of the former embodiments, wherein one or more protraction moiety(ies) is/are attached at one or more cysteine or lysine residue(s).

50. The ISVD polypeptide derivative according to embodiment 43 wherein said ISVD polypeptide derivative comprises SEQ ID NO:629, and
wherein
said first protraction moiety comprises the structure:

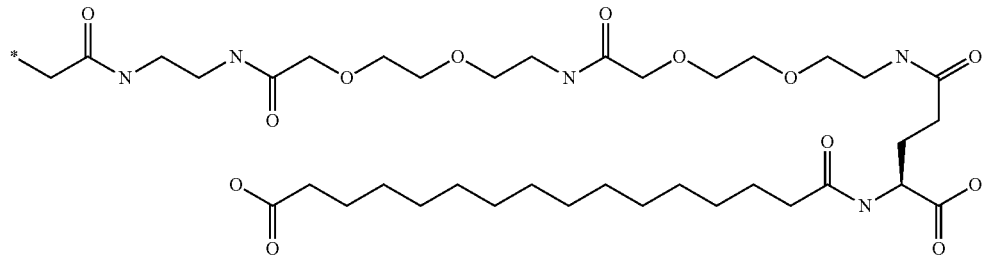 [SMILES: *CC(=O)NCCNC(=O)COCCOCCNC(=O)COCCOCCNC(=O)CC[C@H](NC(=O)CCCCCCCCCCCCCCC(=O)O)C(=O)O]

and wherein said second protraction moiety comprises the structure

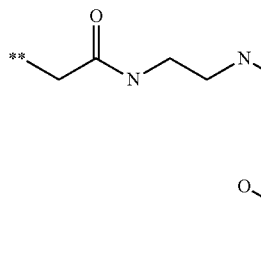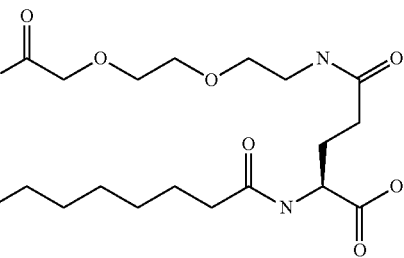

wherein '*' (R1) represents the point of attachment on the ISVD polypeptide for the first protraction moiety, and wherein '**' (R2) represents the point of attachment on the ISVD polypeptide for the second protraction moiety, wherein '*' is Cys in position 257 of SEQ ID NO:629, and wherein '**' is Cys in position 259 of SEQ ID NO:629.

51. The ISVD polypeptide derivative according to any of the former embodiments, wherein the isoelectric point of said polypeptide, as determined using isoelectric focusing, is 6.5 or less.

52. The ISVD polypeptide derivative according to any of the former embodiments wherein said polypeptide derivative is a multispecific polypeptide derivative such as a bi- or trispecific polypeptide derivative.

53. The ISVD polypeptide derivative according to any of the former embodiments wherein said polypeptide derivative is a bispecific polypeptide derivative.

54. The ISVD polypeptide derivative according to any of the former embodiments wherein said polypeptide derivative has a molecular weight in the range of 12-50 kDa, such as 12-48 kDa, such as 12-43 kDa, such as 12-37 kDa, such as 12-35 kDa, such as 12-32 kDa, such as 12-27 kDa, such as 12-22 kDa, such as 12-18 kDa, such as 14-50 kDa, such as 14-48 kDa, such as 14-43 kDa, such as 14-37 kDa, such as 14-35 kDa, 14-32 kDa, such as 14-27 kDa, such as 14-22 kDa, such as 14-18 kDa, such as 22-50 kDa, 22-48 kDa, such as 22-43 kDa, such as 22-37 kDa, such as 22-35 kDa, such as 22-32 kDa, such as 22-31 kDa, such as 22-30 kDa, such as 22-29 kDa, such as 22-28 kDa, such as 22-27 kDa, such as 24-50 kDa, 24-48 kDa, such as 24-43 kDa, such as 24-37 kDa, such as 24-35, such as 24-32 kDa, such as 24-31 kDa, 24-30 kDa, 24-29 kDa, 24-28 kDa, such as 24-27 kDa, such as 36-48 kDa, such as 36-43 kDa, such as 36-37 kDa, such as 28-36 kDa, such as 29-33 kDa, such as 29-30 such as about 29, such as 29, such as about 30, such as 30, such as 30-32 kDa, or such as 31 kDa.

55. The ISVD polypeptide derivative according to any of the former embodiments, which is not a membrane targeted ISVD polypeptide derivative.

56. The ISVD polypeptide derivative according to any of the former embodiments wherein said protraction moiety is not capable of binding components of a plasma membrane, such as aminophospholipid, such as a phosphatidylserine and/or phosphatidylethanolamine.

57. The ISVD polypeptide derivative according to any of the former embodiments, wherein said protraction moiety is not capable of binding platelet surface proteins such as GPIb-IX, collagen chaperone HSP47, ephrin B1, thiol isomerase protein ERP5, Hematopoietic progenitor kinase 1-interacting protein of 55 (HIP-55), glycoprotein VI, platelet glycoprotein 1b, platelet-derived growth factor receptor, platelet endothelial aggregation receptor I, CD31, CD36, MARKS, multimerin, integrin alpha IIb/beta 3, triggering receptor expressed on myeloid cells (TREM) like transcript-1 (TLT-1), integrin-linked kinase (ILK), zyxin, collagen, P-selectin, Factor XIII, P-selectin glycoprotein ligand-1, integrin alpha 6 beta 1, thrombospondin, von Willebrand factor, G6B, CD42b, syntaxin binding protein 2, phosphatidylethanolamine, fibrinogen/fibrin, filamin, stomatin, sphingolipid, CD31, CD36, CD40, CD41, CD42c, CD42, CD49b, CD61, CD62P, CD63, CD69, CD107a, CD107b, CD109, CD154, PECAM-1, and/or ERP5.

58. The ISVD polypeptide derivative according to any of the former embodiments, wherein said protraction moiety is not capable of binding a membrane associated polypeptide, such as glycoproteins, GPIIb/IIIa, β2GP1, TLT-1, selectins, a coagulation factor or coagulation factor complex and/or a selectin.

59. The ISVD polypeptide derivative according to any of the former embodiments, wherein the mean residence time terminal half-life in blood is prolonged by at least 12 hours, at least 24 hours, at least 48 hours, at least 3, 4, 5, or 7 days as compared to the ISVD polypeptide without said protraction moiety.

60. The ISVD polypeptide derivative according to any of the former embodiments, wherein said first and/or second ISVD is/are a $V_HH$ fragment.

61. The ISVD polypeptide derivative according to any of embodiments 1-59, wherein said first and/or second ISVD is a V-NAR fragment.

62. The ISVD polypeptide derivative according to any embodiments 1-60, wherein said ISVD polypeptide derivative is a $V_HH$ polypeptide derivative.

63. A procoagulant $V_HH$ polypeptide derivative comprising a first $V_HH$ capable of binding to Factor IX (SEQ ID NO:1) or the activated form thereof, a second $V_HH$ capable of binding to Factor X (SEQ ID NO:2), a linker ($L_{1-2}$) linking said first $V_HH$ and said second $V_HH$, and a C-terminal extension (E), and one or two protraction moiety(ies), having the formula (N- to C-terminal):

"second $V_HH$"-$L_{1-2}$-"first $V_HH$"-E wherein

I)
```
said first V_HH comprises
CDR1:
                         (SEQ ID NO: 172)
IYTMS,

CDR2:
                         (SEQ ID NO: 173)
GLRWTDSSTEYADSVKG,

CDR3:
                         (SEQ ID NO: 174)
DRSFLFAQALGATKNYEY,
and said second V_HH comprises
CDR1:
                         (SEQ ID NO: 168)
RYAMG,

CDR2:
                         (SEQ ID NO: 169)
AISRRGGSTNYADSVKG,

CDR3:
                         (SEQ ID NO: 170)
DDSVGDGYLDY;
or

II)
said first V_HH comprises
CDR1:
                         (SEQ ID NO: 132)
IYTMS,

CDR2:
                         (SEQ ID NO: 133)
GLRWTDSSTEYADSVKG,

CDR3:
                         (SEQ ID NO: 134)
DRSFLFAQALGATKNYEY,
and said second V_HH comprises
CDR1:
                         (SEQ ID NO: 128)
RLAMG,

CDR2:
                         (SEQ ID NO: 129)
AISRRGGSTNYADSVKG,

CDR3:
                         (SEQ ID NO: 130)
DDSVGDGYLDY;
or (Kabat definition).
```

64. The procoagulant $V_HH$ polypeptide derivative according to embodiment 63, wherein I)
said first $V_HH$ comprises the sequence of $V_HH$-2.20 (SEQ ID NO:171), and
said second $V_HH$ comprises the sequence of $V_HH$-1.20 (SEQ ID NO:167).

II)
said first $V_HH$ comprises the sequence of $V_HH$-2.18 (SEQ ID NO:155), and
said second $V_HH$ comprises the sequence of $V_HH$-1.18 (SEQ ID NO:151).

III)
said first $V_HH$ comprises the sequence of $V_HH$-2.15 (SEQ ID NO:131), and
said second $V_HH$ comprises the sequence of $V_HH$-1.15 (SEQ ID NO:127).

IV)
said first $V_HH$ comprises the sequence of $V_HH$-2.13 (SEQ ID NO:115), and
said second $V_HH$ comprises the sequence of $V_HH$-1.13 (SEQ ID NO:111).

V)
said first $V_HH$ comprises the sequence of $V_HH$-2.14 (SEQ ID NO:123), and
said second $V_HH$ comprises the sequence of $V_HH$-1.14 (SEQ ID NO:119).

VI)
said first $V_HH$ comprises the sequence of $V_HH$-2.12 (SEQ ID NO:107), and
said second $V_HH$ comprises the sequence of $V_HH$-1.12 (SEQ ID NO:103).

65. The procoagulant $V_HH$ polypeptide derivative according to any of embodiments 1-60 and 62-64 wherein said $V_HH$ polypeptide derivative is a bispecific $V_HH$ polypeptide derivative.

66. The procoagulant $V_HH$ polypeptide derivative according to any of embodiments 63-65 wherein the linker $L_{1-2}$ comprises the amino acid residues GQAPGQ (SEQ ID NO:20).

67. The procoagulant $V_HH$ polypeptide derivative according to any of embodiments 63-65, wherein the extension (E) comprises the amino acid residues GQACPC (SEQ ID NO:9).

68. The procoagulant $V_HH$ polypeptide derivative according to any of embodiments 63-67, wherein two protraction moieties are attached to E in positions 4 and 6 (SEQ ID NO:9), respectively.

69. The procoagulant $V_HH$ polypeptide derivative according to any of embodiments 63-68, wherein said two protraction moieties are identical.

70. The procoagulant $V_HH$ polypeptide derivative according to any of embodiments 63-69, wherein said two protraction moieties comprise the structure:

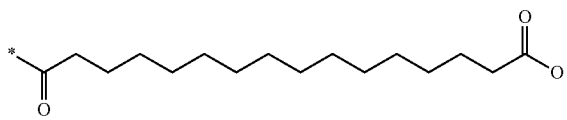 [SMILES: *C(=O)CCCCCCCCCCCCCCC(=O)O]

71. The procoagulant $V_HH$ polypeptide derivative according to any of embodiments 63-70 comprising a first and a second protraction moiety
wherein said first protraction moiety comprises the structure:

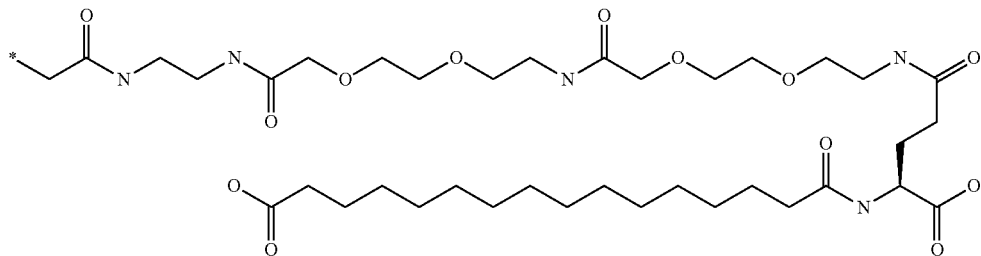 [SMILES: *CC(=O)NCCNC(=O)COCCOCCNC(=O)COCCOCCNC(=O)CC[C@H](NC(=O)CCCCCCCCCCCCCCC(=O)O)C(=O)O]

and wherein said second protraction moiety comprises the structure

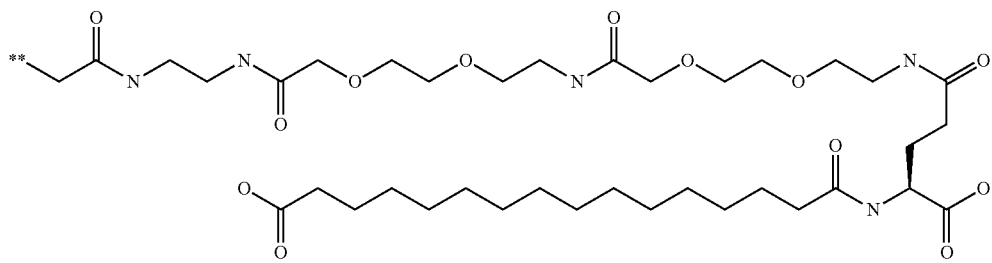

wherein '*' (R1) represents the point of attachment on the V$_H$H polypeptide derivative for the first protraction moiety, and
wherein '**' (R2) represents the point of attachment on the V$_H$H polypeptide derivative for the second protraction moiety,
wherein '*' is Cys in position 257 of SEQ ID NO:629, and
wherein '**' is Cys in position 259 of SEQ ID NO:629.

72. A pharmaceutical composition comprising the ISVD polypeptide derivative or V$_H$H polypeptide derivative according to any of embodiments 1-71.

73. A pharmaceutical composition for peroral administration comprising the ISVD polypeptide derivative or V$_H$H polypeptide derivative according to any of embodiments 1-7071.

74. The pharmaceutical composition according to embodiment 72 or 73, wherein the ISVD polypeptide derivative is a V$_H$H polypeptide derivative.

75. The pharmaceutical composition according to embodiment 72 or 73, wherein the ISVD polypeptide derivative is a V-NAR polypeptide derivative.

76. The pharmaceutical composition according to any of embodiments 72-75, wherein said composition comprises a salt of N-(8-(2-hydroxybenzoyl)amino) caprylic acid.

77. The pharmaceutical composition according to embodiment 76, wherein said salt of N-(8-(2-hydroxybenzoyl)amino)caprylic acid is sodium N-(8-(2-hydroxybenzoyl)amino)caprylate (SNAC).

78. The pharmaceutical composition according to any of embodiments 76 to 77 further comprising nicotinamide (NAM).

79. The pharmaceutical composition according to any of embodiments 74-78, wherein said composition comprises a V$_H$H polypeptide derivative, sodium N-(8-[2-hydroxybenzoyl] amino) caprylate (SNAC), nicotinamide (NAM) and magnesium stearate.

80. The pharmaceutical composition according to any of embodiments 74-78, wherein said composition comprises about 7% w/w V$_H$H polypeptide derivative, about 55% w/w sodium N-(8-[2-hydroxybenzoyl] amino) caprylate (SNAC), about 36% w/w nicotinamide (NAM) and about 0.5% w/w magnesium stearate.

81. The pharmaceutical composition according to any of embodiments 73-80, wherein said composition is a liquid composition.

82. The pharmaceutical composition according to any of embodiments 73-80, wherein said composition is a solid composition.

83. The pharmaceutical composition according to embodiment 82 82, wherein said composition is a tablet, losenge or capsule.

84. A method of treating a patient in need thereof comprising administering the ISVD polypeptide derivative, V$_H$H polypeptide derivative or pharmaceutical composition according to any of embodiments 1-83.

85. The method of treatment according to embodiment 84, wherein the patient is a patient suffering from haemophilia A with or without inhibitors or acquired haemophilia A.

86. The method of treatment according to embodiment 84 or 85, wherein the treatment is a prophylactic treatment.

87. The method of treatment according to any of embodiments 84-86 wherein the ISVD polypeptide derivative, V$_H$H polypeptide derivative or pharmaceutical composition is administered perorally.

88. The method of treatment according to any of embodiments 84-86, wherein the ISVD polypeptide derivative, V$_H$H polypeptide derivative or pharmaceutical composition is administered by subcutaneous injection.

89. The ISVD polypeptide derivative, V$_H$H polypeptide derivative or pharmaceutical composition according to any of embodiments 1-83 for use in medicine.

90. The ISVD polypeptide derivative, V$_H$H polypeptide derivative or composition according to any of embodiments 1-83 for use in the treatment of haemophilia, such as haemophilia A with or without inhibitors, or such as acquired haemophilia A.

91. The ISVD polypeptide derivative, $V_HH$ polypeptide derivative or composition according to any of embodiments 1-83 for use in the treatment of haemophilia A with or without inhibitors.

92. The ISVD polypeptide derivative, $V_HH$ polypeptide derivative or composition for use according to any of embodiments 89-92, wherein the treatment is prophylactic treatment.

93. The ISVD polypeptide derivative, $V_HH$ polypeptide derivative or composition for use according to any of embodiments 89-92, wherein said derivative or composition is administered perorally.

94. The ISVD polypeptide derivative, $V_HH$ polypeptide derivative or composition for use according to any of embodiments 89-92, wherein said derivative or composition is administered by subcutaneous injection.

95. A method for producing a procoagulant immunoglobulin single variable domain (ISVD) polypeptide derivative comprising
    a first ISVD (ISVD1) capable of binding to Factor IX (SEQ ID NO:1) or the activated form thereof,
    a second ISVD (ISVD2) capable of binding to Factor X (SEQ ID NO:2) or the activated form thereof,
    one or more protraction moiety(ies),
    optionally a linker capable of linking ISVD1 and ISVD2 ("$L_{1-2}$"), and
    optionally one or more extension(s) ("E") comprising the steps of
    a. modifying a nucleic acid encoding the amino acid residues of a ISVD polypeptide or ISVD polypeptide derivative such that the isoelectric point of the ISVD polypeptide or ISVD polypeptide derivative is reduced
    b. culturing host cells to express the nucleic acid encoding the ISVD polypeptide or ISVD polypeptide derivative,
    c. collecting the ISVD polypeptide or ISVD polypeptide derivative from the host cell culture,
    d. purifying the ISVD polypeptide or ISVD polypeptide derivative from the host cell culture using standard chromatography, and
    e. attaching a protraction moiety to the ISVD polypeptide, unless such moiety is already present.

96. A method for producing a procoagulant immunoglobulin single variable domain (ISVD) polypeptide or ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, a protraction moiety, optionally a linker capable of linking ISVD1 and ISVD2 ("$L_{1-2}$"), and optionally one or more extension(s) ("E") comprising the steps of
    a. modifying a nucleic acid encoding the amino acid residues of the ISVD polypeptide or ISVD polypeptide derivative such that the isoelectric point of the ISVD polypeptide or ISVD polypeptide derivative is 6.5 or less,
    b. culturing host cells to express the nucleic acid encoding ISVD polypeptide or ISVD polypeptide derivative,
    c. collecting the ISVD polypeptide or ISVD polypeptide derivative from the host cell culture,
    d. purifying the ISVD polypeptide or ISVD polypeptide derivative from the host cell culture using standard chromatography, and
    e. attaching a protraction moiety to the ISVD polypeptide, unless such moiety is already present.

97. A method for increasing the oral bioavailability of a procoagulant immunoglobulin single variable domain (ISVD) polypeptide or ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, a protraction moiety, optionally a linker capable of linking ISVD1 and ISVD2 ("$L_{1-2}$"), and optionally one or more extension(s) ("E") comprising the steps of
    a. modifying a nucleic acid encoding the amino acid residues of the ISVD polypeptide or ISVD polypeptide derivative such that the isoelectric point of the ISVD polypeptide or ISVD polypeptide derivative is reduced,
    b. culturing host cells to express the nucleic acid encoding the ISVD polypeptide or ISVD polypeptide derivative,
    c. collecting the ISVD polypeptide or ISVD polypeptide derivative from the host cell culture,
    d. purifying the ISVD polypeptide or ISVD polypeptide derivative from the host cell culture using standard chromatography, and
    e. attaching a protraction moiety to the ISVD polypeptide, unless such moiety is already present.

98. A method for increasing the oral bioavailability of a procoagulant immunoglobulin single variable domain (ISVD) polypeptide or ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, a protraction moiety, optionally a linker capable of linking ISVD1 and ISVD2 ("$L_{1-2}$"), and optionally one or more extension(s) ("E") comprising the steps of
    a. modifying a nucleic acid encoding the amino acid residues of the ISVD polypeptide or ISVD polypeptide derivative such that the isoelectric point of the ISVD polypeptide or ISVD polypeptide derivative is 6.5 or less,
    b. culturing host cells to express the nucleic acid encoding the ISVD polypeptide or ISVD polypeptide derivative,
    c. collecting the ISVD polypeptide or ISVD polypeptide derivative from the host cell culture,
    d. purifying the ISVD polypeptide or ISVD polypeptide derivative from the host cell culture using standard chromatography, and
    e. attaching a protraction moiety to the ISVD polypeptide, unless such moiety is already present.

99. The method according to any of embodiments 95-98, wherein the isoelectric point is reduced by at least 0.5 pH units, such as at least 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3. 3.1, 3.2, 3.3, 3.4, 3.5, 3.6, 3.7, 3.8, 3.9 or 4 pH units.

100. The method according to any of embodiments 95-99, wherein step e) does not lead to an increase the isoelectric point of the ISVD polypeptide or ISVD polypeptide derivative.

101. The method according to any of embodiments 95-100, wherein the isoelectric point is determined using isoelectric focusing.
102. The method according to any of embodiments 95-101, wherein the ISVD polypeptide or ISVD polypeptide derivative is encoded by a single nucleic acid.
103. The method according to any of embodiments 95-101, wherein the ISVD polypeptide or ISVD polypeptide derivative is a conjugate of a first and second ISVD, wherein said first and second ISVD are encoded by separate nucleic acids. 104. The method according to any of embodiments 95-103, wherein the ISVD polypeptide or ISVD polypeptide derivative is a $V_HH$ polypeptide or $V_HH$ polypeptide derivative.
105. An ISVD polypeptide or ISVD polypeptide derivative produced using the method according to any of embodiments 95-103.
106. An ISVD polypeptide or ISVD polypeptide derivative obtainable using the method according to any of embodiments 95-103.
107. A $V_HH$ polypeptide or $V_HH$ polypeptide derivative produced using the method according to any of embodiments 95-104.
108. A $V_HH$ fragment capable of binding to FIX (SEQ ID NO:1) or the activated form thereof (FIXa) wherein
  a. the CDR1 sequence is identified by SEQ ID NO:172, optionally comprising one or two amino acid substitutions,
    the CDR2 sequence is identified by SEQ ID NO:173, optionally comprising one, two or three amino acid substitutions,
    the CDR3 sequence is identified by SEQ ID NO:174, optionally comprising one, two or three amino acid substitutions; or
  b. the CDR1 sequence is identified by SEQ ID NO:156, optionally comprising one or two amino acid substitutions,
    the CDR2 sequence is identified by SEQ ID NO:157, optionally comprising one, two or three amino acid substitutions,
    the CDR3 sequence is identified by SEQ ID NO:158, optionally comprising one, two or three amino acid substitutions; or
  c. the CDR1 sequence is identified by SEQ ID NO:132, optionally comprising one or two amino acid substitutions,
    the CDR2 sequence is identified by SEQ ID NO:133, optionally comprising one, two or three amino acid substitutions,
    the CDR3 sequence is identified by SEQ ID NO:134, optionally comprising one, two or three amino acid substitutions; or
  d. the CDR1 sequence is identified by SEQ ID NO:116, optionally comprising one or two amino acid substitutions,
    the CDR2 sequence is identified by SEQ ID NO:117, optionally comprising one, two or three amino acid substitutions,
    the CDR3 sequence is identified by SEQ ID NO:118, optionally comprising one, two or three amino acid substitutions; or
  e. the CDR1 sequence is identified by SEQ ID NO:124, optionally comprising one or two amino acid substitutions,
    the CDR2 sequence is identified by SEQ ID NO:125, optionally comprising one, two or three amino acid substitutions,
    the CDR3 sequence is identified by SEQ ID NO:126, optionally comprising one, two or three amino acid substitutions; or
  f. the CDR1 sequence is identified by SEQ ID NO:108, optionally comprising one or two amino acid substitutions,
    the CDR2 sequence is identified by SEQ ID NO:109, optionally comprising one, two or three amino acid substitutions,
    the CDR3 sequence is identified by SEQ ID NO:110, optionally comprising one, two or three amino acid substitutions;
  (Kabat definition).
109. A $V_HH$ fragment capable of binding to FX (SEQ ID NO:2) wherein
  a. the CDR1 sequence is identified by SEQ ID NO:152, optionally comprising one or two amino acid substitutions,
    the CDR2 sequence is identified by SEQ ID NO:153, optionally comprising one, two or three amino acid substitutions,
    the CDR3 sequence is identified by SEQ ID NO:154, optionally comprising one, two or three amino acid substitutions; or
  b. the CDR1 sequence is identified by SEQ ID NO:128, optionally comprising one or two amino acid substitutions,
    the CDR2 sequence is identified by SEQ ID NO:129, optionally comprising one, two or three amino acid substitutions,
    the CDR3 sequence is identified by SEQ ID NO:130, optionally comprising one, two or three amino acid substitutions.
110. The $V_HH$ fragment according to embodiment 108 or 109 wherein said substitution(s) is/are conservative substitution(s).
111. The $V_HH$ fragment according to any of embodiments 108-110 wherein said $V_HH$ fragment is an intermediate for use in the manufacture of a $V_HH$ polypeptide or $V_HH$ polypeptide derivative which is capable of binding to FIX (SEQ ID NO:1) or the activated form thereof (FIXa), and capable of binding to FX (SEQ ID NO:2) or the activated form thereof (FXa).
112. The $V_HH$ polypeptide according to any of embodiments 108-110 wherein said $V_HH$ polypeptide is an intermediate for use in the manufacture of an ISVD polypeptide derivative.
113. The ISVD or $V_HH$ according to embodiment 109 or 110 wherein the activity is improved in terms of making FX more prone to proteolysis by FIXa as compared to any of the anti-FX ISVD compounds as described in WO2019/096874.
114. A procoagulant immunoglobulin single variable domain (ISVD) polypeptide derivative comprising
  a first ISVD (ISVD1) capable of binding to Factor IX (SEQ ID NO:1) or the activated form thereof,
  a second ISVD (ISVD2) capable of binding to Factor X (SEQ ID NO:2) or the activated form thereof,
  at least one protraction moiety,
  optionally a linker ($L_{1-2}$) linking ISVD1 and ISVD2, and
  optionally one or more extension(s) (E), wherein said ISVD polypeptide is selected from the group consisting of: SEQ ID NO:615-691, 734 or 735.

115. A V$_H$H fragment comprising the sequence of any of SEQ ID NOs:27-614.

116. A V$_H$H polypeptide derivative comprising the sequence of any of SEQ ID NOs:615-691 or 734-735.

117. A procoagulant immunoglobulin single variable domain (ISVD) polypeptide derivative comprising
a first ISVD (ISVD1) capable of binding to Factor IX (SEQ ID NO:1) or the activated form thereof,
a second ISVD (ISVD2) capable of binding to Factor X (SEQ ID NO:2) or the activated form thereof,
at least one protraction moiety,
optionally a linker (L$_{1-2}$) linking ISVD1 and ISVD2, and
optionally one or more extension(s) (E).

118. The ISVD polypeptide derivative according to embodiment 117 having the formula (N- to C-terminal)

ISVD2-L$_{1-2}$-ISVD1-E wherein one or more protraction moiety(ies) is/are attached to one or more surface exposed residue.

119. The ISVD polypeptide derivative according to embodiment 118 or 119 having the formula (N- to C-terminal)

ISVD2-L$_{1-2}$-ISVD1-E wherein two protraction moieties are attached to one or more surface exposed residue(s) on E, and
wherein the molecular weight of the derivative is in the range 20-35 kDa.

120. The ISVD polypeptide derivative according to any of embodiments 117-119, wherein
the first ISVD is capable of binding to an epitope on Factor IX (SEQ ID NO:1) or the activated form thereof comprising the amino acid residues E224, T225, G226, V250, I251, R252, I253, P255, H257 and N260 (consecutive numbering), and
the second ISVD is capable of binding to an epitope on Factor X (SEQ ID NO:2) or the activated form thereof comprising the amino acid residues N173, P174, F175, L177, and L178 (consecutive numbering).

121. The ISVD polypeptide derivative according to any of embodiments 117-119, wherein said first ISVD comprises
1)
CDR1: IYTMS (SEQ ID NO:172), optionally comprising one or two substitutions,
CDR2: GLRWTDSSTEYADSVKG (SEQ ID NO:173), optionally comprising one, two or three substitutions,
CDR3: DRSFLFAQALGATKNYEY (SEQ ID NO:174), optionally comprising one, two or three substitutions; or
2)
CDR1: IYTMS (SEQ ID NO:156), optionally comprising one or two substitutions,
CDR2: GLRWTDSSTEYADSVKG (SEQ ID NO:157), optionally comprising one, two or three substitutions,
CDR3: DRSFLFAQALGATKNYEY (SEQ ID NO:158), optionally comprising one, two or three substitutions; or
3)
CDR1: IYTMS (SEQ ID NO:132), optionally comprising one or two substitutions,
CDR2: GLRWTDSSTEYADSVKG (SEQ ID NO:133), optionally comprising one, two or three substitutions,
CDR3: DRSFLFAQALGATKNYEY (SEQ ID NO:134), optionally comprising one, two or three substitutions; or
4)
CDR1: IYTMS (SEQ ID NO:116), optionally comprising one or two substitutions,
CDR2: GLRWTDSSTEYADSVKG (SEQ ID NO:117), optionally comprising one, two or three substitutions,
CDR3: DRSFLFAQALGATKNYEY (SEQ ID NO:118), optionally comprising one, two or three substitutions; or
5)
CDR1: IYTMS (SEQ ID NO:124), optionally comprising one or two substitutions
CDR2: GLRWTDSSTEYADSVKG (SEQ ID NO:125), optionally comprising one, two or three substitutions,
CDR3: DRSFLFAQALGATKNYEY (SEQ ID NO:126), optionally comprising one, two or three substitutions; or
6)
CDR1: IYTMS (SEQ ID NO:108), optionally comprising one or two substitutions,
CDR2: GLRWTDSSTEYADSVKG (SEQ ID NO:109), optionally comprising one, two or three substitutions,
CDR3: DRSFLFAQALGATKNYEY (SEQ ID NO:110), optionally comprising one, two or three substitutions;
and wherein said second ISVD comprises
(A)
CDR1: RYAMG (SEQ ID NO:168), optionally comprising one or two substitutions,
CDR2: AISRRGGSTNYADSVKG (SEQ ID NO:169), optionally comprising one, two or three substitutions,
CDR3: DDSVGDGYLDY (SEQ ID NO:170), optionally comprising one, two or three substitutions; or
(B)
CDR1: RYAMG (SEQ ID NO:152), optionally comprising one or two substitutions,
CDR2: AISRRGGSTNYADSVKG (SEQ ID NO:153), optionally comprising one, two or three substitutions,
CDR3: DDSVGDGYLDY (SEQ ID NO:154), optionally comprising one, two or three substitutions; or
(C)
CDR1: RLAMG (SEQ ID NO:128), optionally comprising one or two substitutions,
CDR2: AISRRGGSTNYADSVKG (SEQ ID NO:129), optionally comprising one, two or three substitutions,
CDR3: DDSVGDGYLDY (SEQ ID NO:130), optionally comprising one, two or three substitutions; or
(D)
CDR1: RLAMG (SEQ ID NO:112), optionally comprising one or two substitutions,
CDR2: AISRRGGSTNYADSVKG (SEQ ID NO:113), optionally comprising one, two or three substitutions, CDR3: DDSVGDGYLDY (SEQ ID NO:114), optionally comprising one, two or three substitutions; or (E)
CDR1: RLAMG (SEQ ID NO:120), optionally comprising one or two substitutions,
CDR2: AISRRGGSTNYADSVKG (SEQ ID NO:121), optionally comprising one, two or three substitutions,
CDR3: DDSVGDGYLDY (SEQ ID NO:122), optionally comprising one, two or three substitutions; or (F)
CDR1: RLAMG (SEQ ID NO:104), optionally comprising one or two substitutions,
CDR2: AISRRGGSTNYADSVKG (SEQ ID NO:105), optionally comprising one, two or three substitutions,
CDR3: DDSVGDGYLDY (SEQ ID NO:106), optionally comprising one, two or three substitutions
(Kabat definition).

122. The ISVD polypeptide derivative according to embodiment 121, wherein said substitution(s) is/are conservative substitution(s).

123. The ISVD polypeptide derivative according to any of embodiments 117-122, wherein said first ISVD comprises the sequence of
$V_HH$-2.20 (SEQ ID NO:171),
$V_HH$-2.18 (SEQ ID NO:155),
$V_HH$-2.15 (SEQ ID NO:131),
$V_HH$-2.13 (SEQ ID NO:115),
$V_HH$-2.14 (SEQ ID NO:123), or
$V_HH$-2.12 (SEQ ID NO:107)
and wherein
said second ISVD comprises the sequence of
$V_HH$-1.20 (SEQ ID NO:167),
$V_HH$-1.18 (SEQ ID NO:151),
$V_HH$-1.15 (SEQ ID NO:127),
$V_HH$-1.13 (SEQ ID NO:111),
$V_HH$-1.14 (SEQ ID NO:119), or
$V_HH$-1.12 (SEQ ID NO:103).

124. A procoagulant $V_HH$ polypeptide derivative comprising
a first $V_HH$ capable of binding to Factor IX (SEQ ID NO:1) or the activated form thereof,
a second $V_HH$ capable of binding to Factor X (SEQ ID NO:2) or the activated form thereof,
a linker ($L_{1-2}$) linking said first $V_HH$ and said second $V_HH$, and
a C-terminal extension (E), and
one or two protraction moiety(ies),
having the formula (N- to C-terminal):
"second $V_HH$"-$L_{1-2}$-"first $V_HH$"-E
wherein I)
said first $V_HH$ comprises
CDR1:
(SEQ ID NO: 172)
IYTMS,

CDR2:
(SEQ ID NO: 173)
GLRWTDSSTEYADSVKG,

CDR3:
(SEQ ID NO: 174)
DRSFLFAQALGATKNYEY,
and said second $V_HH$ comprises
CDR1:
(SEQ ID NO: 168)
RYAMG,

CDR2:
(SEQ ID NO: 169)
AISRRGGSTNYADSVKG,

CDR3:
(SEQ ID NO: 170)
DDSVGDGYLDY;
or

II)
said first $V_HH$ comprises
CDR1:
(SEQ ID NO: 156)
IYTMS,

CDR2:
(SEQ ID NO: 157)
GLRWTDSSTEYADSVKG,

CDR3:
(SEQ ID NO: 158)
DRSFLFAQALGATKNYEY,
and said second $V_HH$ comprises
CDR1:
(SEQ ID NO: 152)
RYAMG,

CDR2:
(SEQ ID NO: 153)
AISRRGGSTNYADSVKG,

CDR3:
(SEQ ID NO: 154)
DDSVGDGYLDY;
or

III)
said first $V_HH$ comprises
CDR1:
(SEQ ID NO: 132)
IYTMS,

CDR2:
(SEQ ID NO: 133)
GLRWTDSSTEYADSVKG,

CDR3:
(SEQ ID NO: 134)
DRSFLFAQALGATKNYEY,
and said second $V_HH$ comprises
CDR1:
(SEQ ID NO: 128)
RLAMG,

CDR2:
(SEQ ID NO: 129)
AISRRGGSTNYADSVKG,

CDR3:
(SEQ ID NO: 130)
DDSVGDGYLDY;
or

IV)
said first $V_HH$ comprises
CDR1:
(SEQ ID NO: 116)
IYTMS,

CDR2:
(SEQ ID NO: 117)
GLRWTDSSTEYADSVKG,

-continued

```
CDR3:
                              (SEQ ID NO: 118)
DRSFLFAQALGATKNYEY,
and said second V_HH comprises
CDR1:
                              (SEQ ID NO: 112)
RLAMG,

CDR2:
                              (SEQ ID NO: 113)
AISRRGGSTNYADSVKG,

CDR3:
                              (SEQ ID NO: 114)
DDSVGDGYLDY;
or

V)
said first V_HH comprises
CDR1:
                              (SEQ ID NO: 124)
IYTMS,

CDR2:
                              (SEQ ID NO: 125)
GLRWTDSSTEYADSVKG,

CDR3:
                              (SEQ ID NO: 126)
DRSFLFAQALGATKNYEY,
and said second V_HH comprises
CDR1:
                              (SEQ ID NO: 120)
RLAMG,

CDR2:
                              (SEQ ID NO: 121)
AISRRGGSTNYADSVKG,

CDR3:
                              (SEQ ID NO: 122)
DDSVGDGYLDY;
or

VI)
said first V_HH comprises
CDR1:
                              (SEQ ID NO: 108)
IYTMS,

CDR2:
                              (SEQ ID NO: 109)
GLRWTDSSTEYADSVKG,

CDR3:
                              (SEQ ID NO: 110)
DRSFLFAQALGATKNYEY,
and said second V_HH comprises
CDR1:
                              (SEQ ID NO: 104)
RLAMG,

CDR2:
                              (SEQ ID NO: 105)
AISRRGGSTNYADSVKG,

CDR3:
                              (SEQ ID NO: 106)
DDSVGDGYLDY (Kabat definition).
```

125. A pharmaceutical composition comprising the ISVD polypeptide derivative or $V_HH$ polypeptide derivative according to any of embodiments 117-124.

126. The pharmaceutical composition according to embodiment 125, wherein said composition comprises a salt of N-(8-(2-hydroxybenzoyl)amino) caprylic acid.

127. The pharmaceutical composition according to embodiments 126 wherein said salt of N-(8-(2-hydroxybenzoyl)amino)caprylic acid is sodium N-(8-(2-hydroxybenzoyl)amino)caprylate (SNAC).

128. The pharmaceutical composition according to any of embodiments 125-127 further comprising nicotinamide (NAM).

129. The pharmaceutical composition according to any of embodiments 125-128 wherein said composition is a solid composition.

130. The ISVD polypeptide derivative, $V_HH$ polypeptide derivative or composition according to any of embodiments 117-129 for use in the treatment of haemophilia, such as haemophilia A with or without inhibitors, or such as acquired haemophilia A.

131. The ISVD polypeptide derivative, $V_HH$ polypeptide derivative or composition for use according to any of embodiments 130 wherein said polypeptide derivative or composition is administered perorally.

132. A method for increasing the oral bioavailability of a procoagulant immunoglobulin single variable domain (ISVD) polypeptide or ISVD polypeptide derivative comprising a first ISVD (ISVD1) capable of binding to Factor IX (SEQ ID NO:1) or the activated form thereof, a second ISVD (ISVD2) capable of binding to Factor X (SEQ ID NO:2) or the activated form thereof, a protraction moiety, optionally a linker capable of linking ISVD1 and ISVD2 ("$L_{1-2}$"), and optionally one or more extension(s) ("E") comprising the steps of
   a. modifying a nucleic acid encoding the amino acid residues of the ISVD polypeptide or ISVD polypeptide derivative such that the isoelectric point thereof is reduced,
   b. culturing host cells to express the nucleic acid encoding the ISVD polypeptide or ISVD polypeptide derivative,
   c. collecting the ISVD polypeptide or ISVD polypeptide derivative from the host cell culture,
   d. purifying the ISVD polypeptide or ISVD polypeptide derivative from the host cell culture using standard chromatography, and
   e. attaching a protraction moiety to the ISVD polypeptide, unless such moiety is already present.

In a preferred embodiment the compound obtained using said method for increasing the oral bioavailability of a procoagulant immunoglobulin single variable domain (ISVD) polypeptide or ISVD polypeptide derivative is formulated in a pharmaceutical composition comprising SNAC and optionally also NAM.

In a preferred embodiment an ISVD polypeptide derivative, comprises an anti-FX ISVD connected to an anti-FIX (a) $V_HH$ ISVD in a N-terminal to C-terminal direction (N- to C-terminal).

Figure 2A:
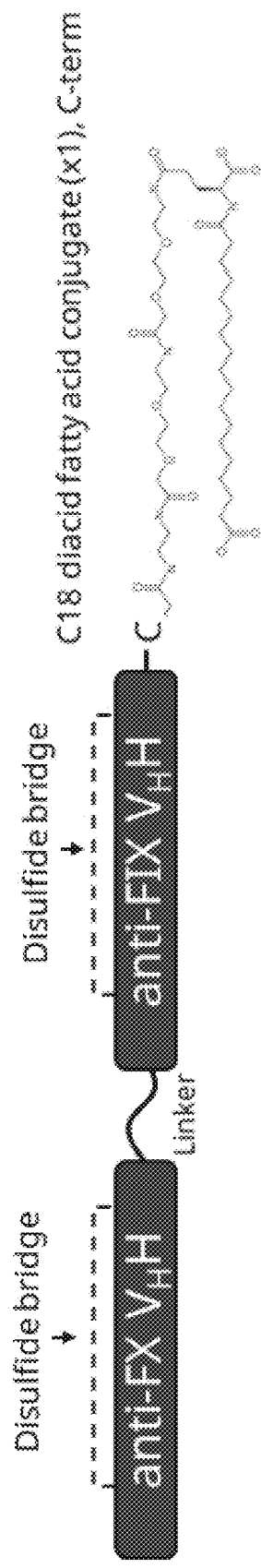
FIG. 2a shows a non-limiting example of an anti-FX/FIX (a) V$_H$H polypeptide derivative comprising a single C18 diacid fatty acid-based protraction moiety conjugated to a C-terminal extension by way of a protraction moiety linker (L$_P$), ID: L$_P$1. The dashed lines indicate disulphide bonds.
Figure 2B:
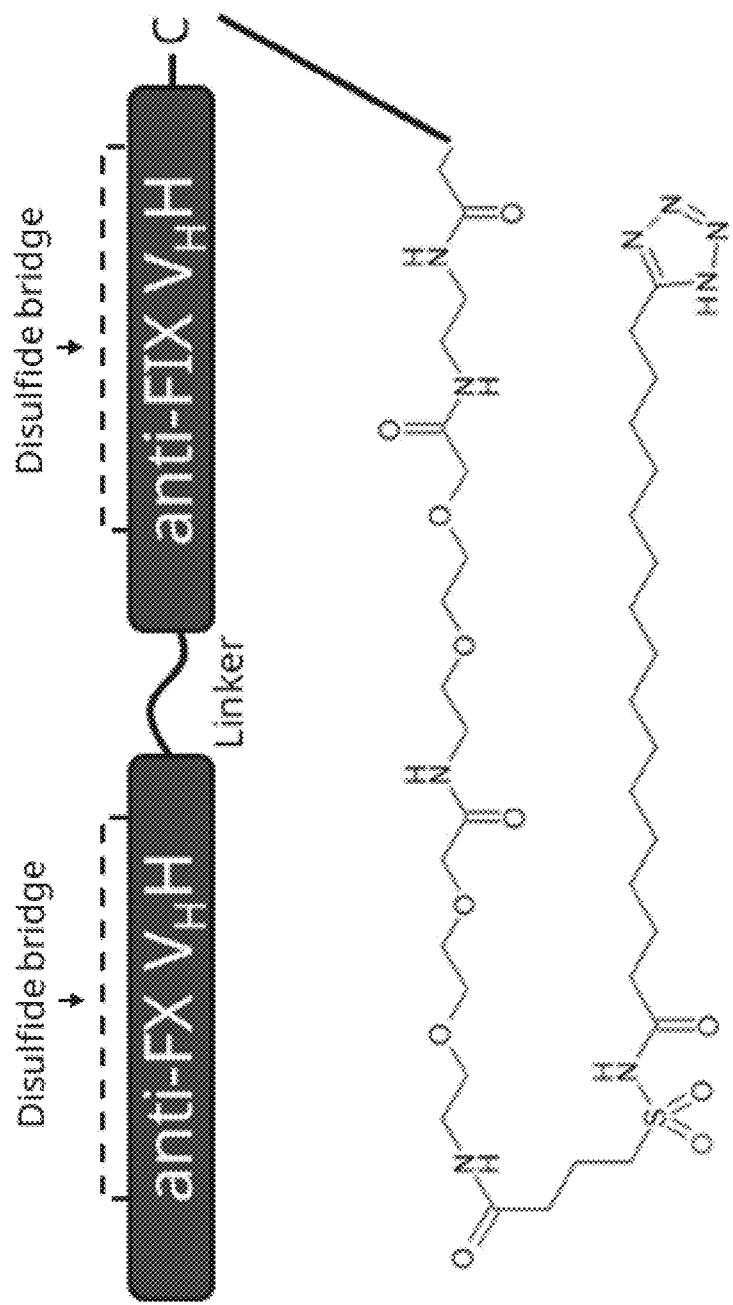
FIG. 2b shows a non-limiting example of an anti-FX/FIX (a) V$_H$H polypeptide derivative comprising a single tetrazole-based protraction moiety conjugated to a C-terminal extension by way of a protraction moiety linker (L$_P$), ID: L$_P$2. The dashed lines indicate disulphide bonds.
Figure 3A:
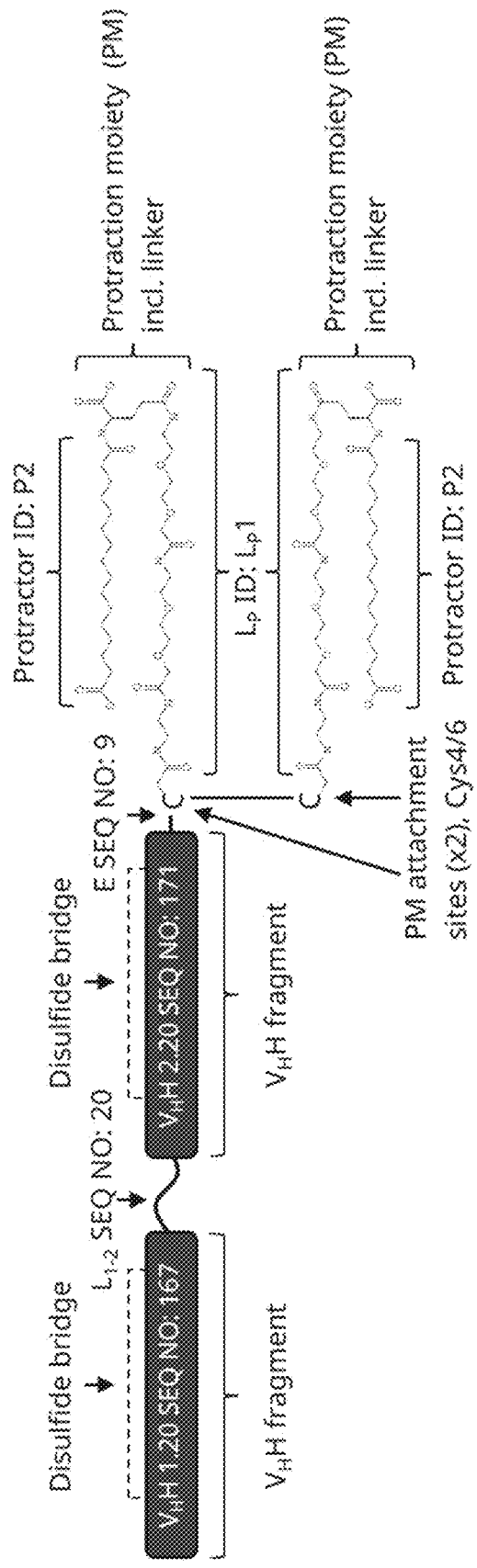
FIGS. 3a-f show a detailed figurative description of compounds cmpd #20 (a), cmpd #18 (b), cmpd #15 (c), cmpd #13 (d), cmpd #14 (e) and cmpd #12 (f), which are non-limiting examples of anti-FX/FIX(a) V$_H$H polypeptide derivatives comprising a double C16 diacid fatty acid-based protraction moiety conjugated to a C-terminal extension (E) by way of a protraction moiety linker (L$_P$), ID L$_P$1. The dashed lines indicate disulphide bonds. The extension (E) (SEQ NO:9) was used in these V$_H$H polypeptide derivatives. The extension comprises two cysteine residues in positions 4 and 6, respectively, which serve as attachment points for the protraction moieties (PM).
Figure 3B:
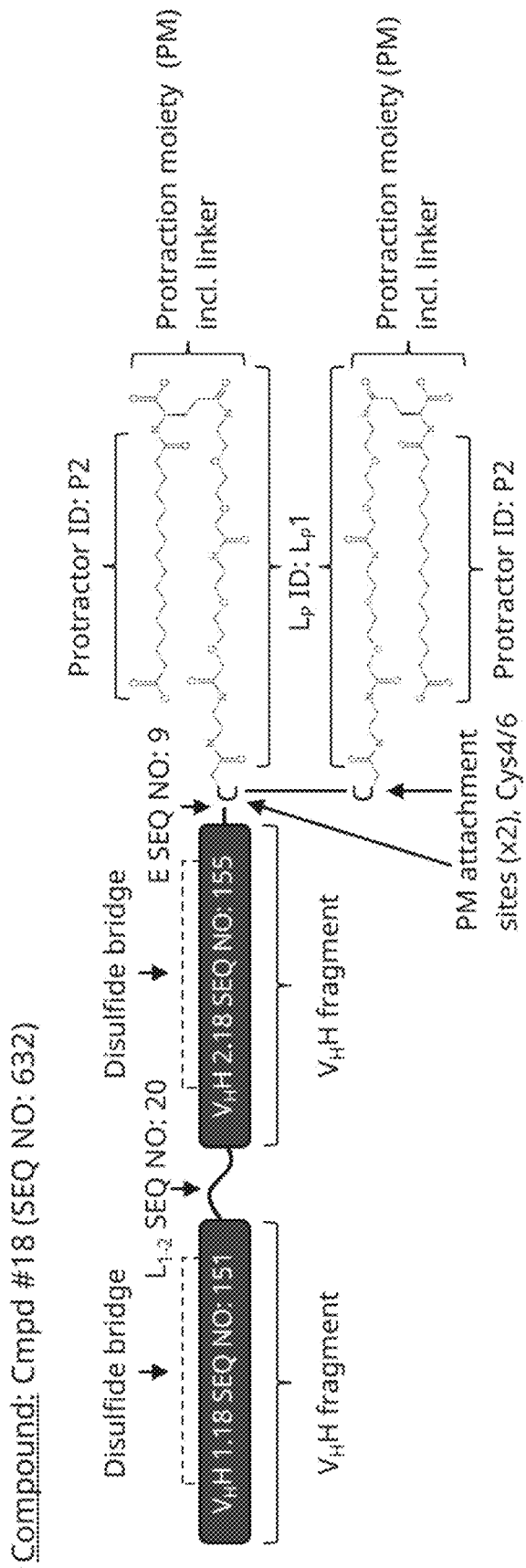
Figure 3C:
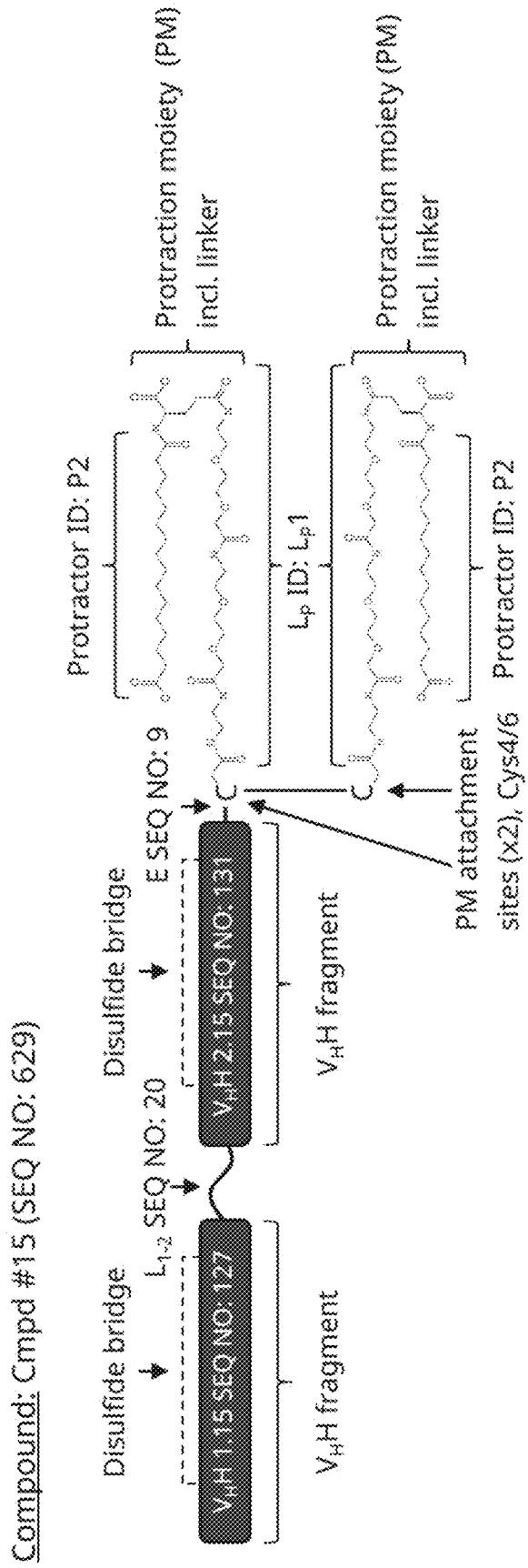
Figure 3D:
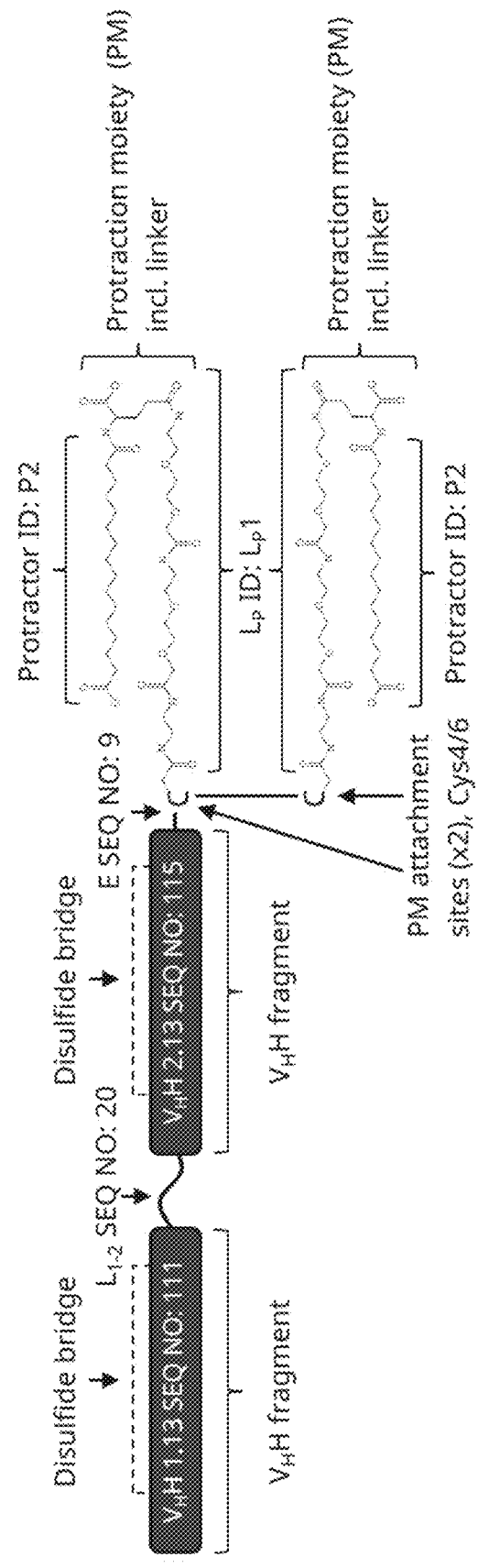
Figure 3E:
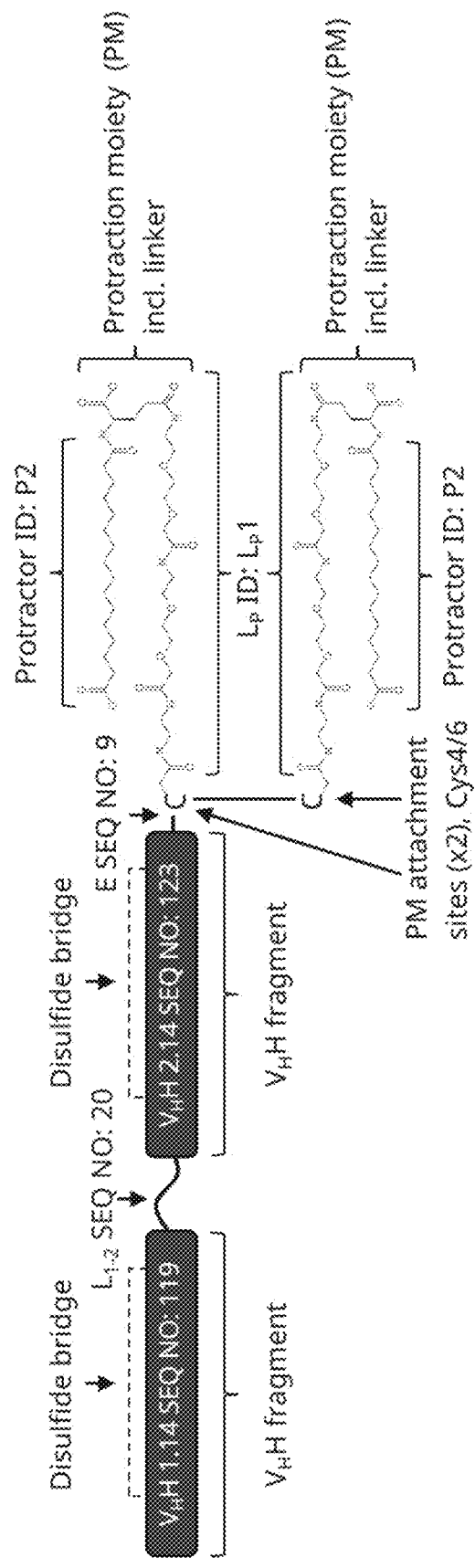
Figure 3F:
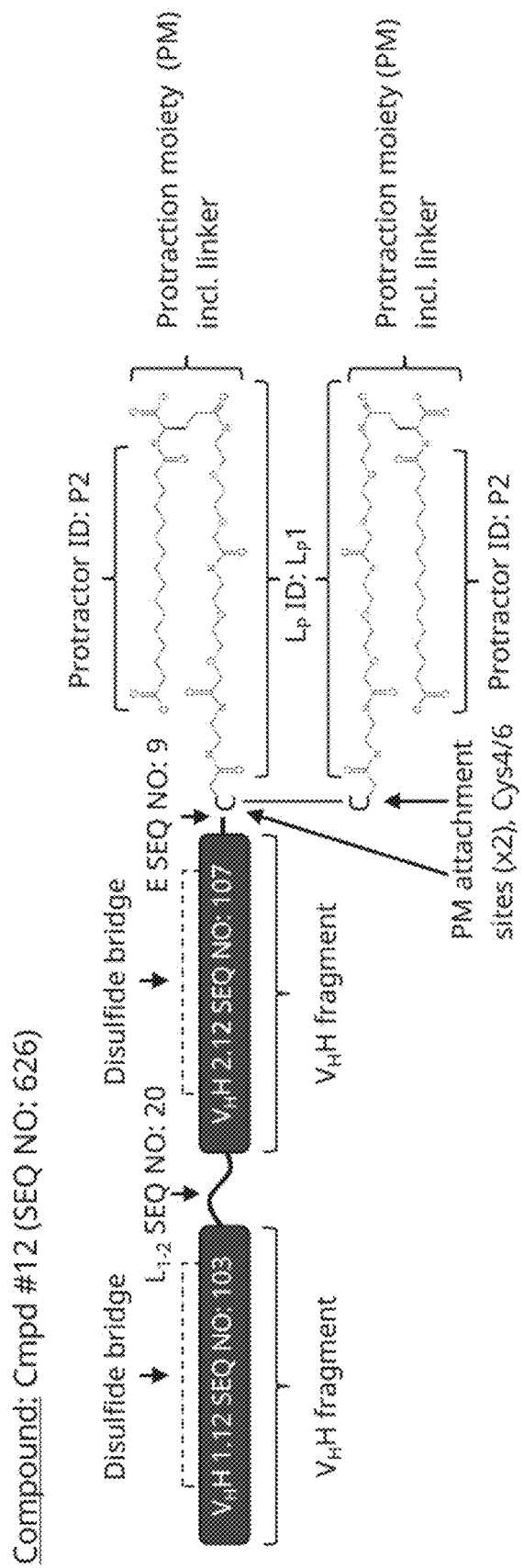

In one such preferred embodiment an ISVD polypeptide derivative, comprises an anti-FX $V_HH$ fragment connected to an anti-FIX(a) $V_HH$ fragment in a N-terminal to C-terminal direction (N- to C-terminal), see for example FIGS. 2a, 2b and 3a-f.

In preferred embodiments the ISVDs or $V_HH$ fragments capable of binding to FIX(a) preferentially binds to activated FIX (FIXa).

In preferred embodiments the ISVDs or V$_H$H fragments capable of binding to FX preferentially binds to FX zymogen, i.e. FX which has not been activated.

In one embodiment the ISVD polypeptide (derivatives) or V$_H$H polypeptide (derivatives) of the invention is/are capable of stimulating the enzymatic activity of FIXa towards FX. In one such embodiment the stimulatory properties of said ISVD polypeptide (derivatives) or V$_H$H polypeptide (derivatives) is derived from the ISVD or V$_H$H capable of binding FIX(a). FIGS. 5a and 5b show sequence alignments of preferred anti-FIX(a) and anti-FX ISVD (V$_H$H fragment) sequences, respectively, wherein CDR sequences are highlighted in bold and underline.

The present invention encompasses substitution variants of the ISVDs or V$_H$H fragments as disclosed herein, which may comprise 1, 2, 3, 4, 5, 6, 7, 8, 9, 10, 11, 12, 13, 14, 15, 16, 17, 18, 19 or 20 amino acid substitutions and/or deletions and/or insertions in the individual sequences disclosed herein. In some embodiments said substitutions and/or deletions and/or insertions are in one or more of the CDR sequences as disclosed herein. In some embodiments one or more of the CDR sequences is subject to amino acid substitution. In some embodiments the individual CDR sequences may comprise 0, 1, 2 or 3 amino acid substitutions each. For example, in the V$_H$H fragment according to SEQ ID NO:559, CDR1 may comprise no substitutions, CDR2 may comprise 3 substitutions and CDR3 may comprise 1 substitution. Substitution variants preferably involve the replacement of one or more amino acid(s) with the same number of amino acid(s). In some embodiments the substitution is a conservative substitution.

In one embodiment the ISVD polypeptide derivative, such as a V$_H$H polypeptide derivative comprises at least one protraction moiety which is not capable of binding components of a plasma membrane, such as aminophospholipid, such as a phosphatidylserine and/or phosphatidylethanolamine.

In one embodiment the protraction moiety comprises the structure:

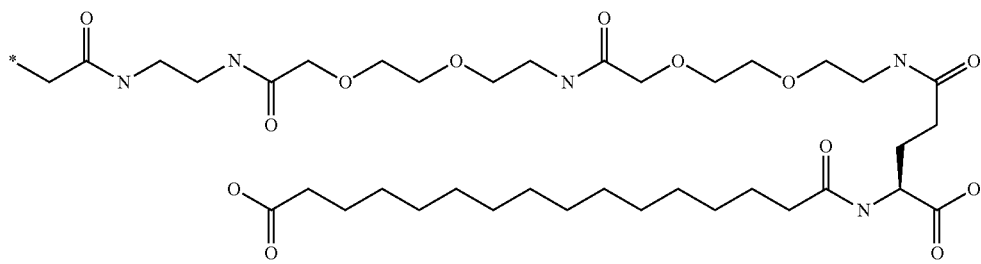 [SMILES: *CC(=O)NCCNC(=O)COCCOCCNC(=O)COCCOCCNC(=O)CC[C@H](NC(=O)CCCCCCCCCCCCCCC(=O)O)C(=O)O]

wherein '*' represents a point of attachment to the V$_H$H polypeptide.

In one embodiments the ISVD polypeptide derivative, such as a V$_H$H polypeptide derivative comprises a protraction moiety which is not capable of binding platelet surface proteins/markers, such as GPIb-IX, collagen chaperone HSP47, ephrin B1, thiol isomerase protein ERP5, Hematopoietic progenitor kinase 1-interacting protein of 55 (HIP-55), glycoprotein VI, platelet glycoprotein 1b, platelet-derived growth factor receptor, platelet endothelial aggregation receptor I, CD31, CD36, MARKS, multimerin, integrin alpha IIb/beta 3, triggering receptor expressed on myeloid cells (TREM) like transcript-1 (TLT-1), integrin-linked kinase (ILK), zyxin, collagen, P-selectin, Factor XIII, P-selectin glycoprotein ligand-1, integrin alpha 6 beta 1, thrombospondin, von Willebrand factor, G6B, CD42b, syntaxin binding protein 2, phosphatidylethanolamine, fibrinogen/fibrin, filamin, stomatin, sphingolipid, CD31, CD36, CD40, CD41, CD42c, CD42, CD49b, CD61, CD62P, CD63, CD69, CD107a, CD107b, CD109, CD154, PECAM-1, and/or ERP5.

In one embodiment the ISVD polypeptide derivative, such as a V$_H$H polypeptide derivative comprises a protraction moiety which is not capable of binding membrane associated polypeptides, such as glycoproteins, GPIIb/IIIa, β2GP1, TLT-1, selectins, a coagulation factor or coagulation factor complex and/or a selectin.

In one embodiment the ISVD polypeptide derivatives, such as V$_H$H polypeptide derivatives, of the invention do not interfere with the effect of FVIII, such as recombinant FVIII administered to a patient suffering from haemophilia A, when said polypeptide derivatives are used in clinically relevant dosages in the treatment of haemophilia A.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

List of Abbreviations
AIEX: Anion-exchange
CC: Pearson correlation coefficient
CDR: Complementarity Determining Region
CHO: Chinese Hamster Ovary
CMK: Chloromethylketone
EC$_{50}$: Half maximal effective concentration
EDTA: Ethylenediaminetetraacetic acid
ELISA: Enzyme-Linked Immunosorbent Assay
FACS: Fluorescence-Activated Cell Sorter
FIX: Coagulation Factor IX
FIXa: Coagulation Factor IXa
FX: Coagulation Factor X
FXa: Coagulation Factor Xa
FR: Framework Region
GS: Glutamine Synthetase
HA: Haemophilia A
HB: Haemophilia B
ISVD: Immunoglobulin Single Variable Domain
IV: Intravenously
KO: Knock-Out
MSX: L-Methionine sulfoximine
MRTHL: Mean residence time terminal half-life
NAM: Nicotinamide OEG: 8-amino-3,6-dioxa-octanoic acid
PBMC: Peripheral Blood Mononuclear Cells
PCR: Polymerase Chain Reaction
pI: Isoelectric point
PK: Pharmacokinetic
PO: Perorally
ROUT: Robust regression and Outlier removal (Graph Pad Prism function)
RMS: Root-mean-square
RT-PCR: Reverse Transcriptase Polymerase Chain Reaction
RP-UPLC: Reverse-Phase Ultra-Performance Liquid Chromatography
SIA: Sequence Identical Analogue
SC: Subcutaneous
SNAC: Sodium N-(8-[2-hydroxybenzoyl] Amino) Caprylate
SPR: Surface Plasmon Resonance
TGT: Thrombin Generation Test
TLS: Translation-libration-screw-rotation
TVT: Tail-Vein Transection
UPLC: Ultra-Performance Liquid Chromatography Example 1: General Methods & Preparation of $V_HH$ Fragments and Other Recombinant Proteins General Molecular Biology For general molecular biology techniques, see Molecular Cloning: A Laboratory Manual (4$^{th}$ Edition, 2014, Sambrook, Fritsch and Maniatis eds., CSHL Press, Cold Spring Harbor, NY USA).

Immunizations and Libraries

After approval of the Ethical Committee of the Ablynx Camelid Facility (LA1400575), two llama and two alpaca were immunized with human FIX and FX (Haemotologic Technologies, VT USA), respectively.

Cloning of heavy chain-only antibody fragment repertoires and preparation of phage immune libraries was performed as follows.

Following the final immunogen injection, blood samples were collected. From these blood samples, peripheral blood mononuclear cells (PBMCs) were prepared using Ficoll-Hypaque according to the manufacturer's instructions (Amersham Biosciences, Piscataway, NJ, US). From the PBMCs, total RNA was extracted and used as starting material for RT-PCR to amplify the $V_HH$ fragment-encoding DNA segments, essentially as described in WO2005/044858. In short, the $V_HH$ fragment-encoding DNA fragments were cloned into phagemid vector pAX212 enabling production of phage particles displaying $V_HH$ fragments fused with $His_6$- and $FLAG_3$-tags. Subsequently, phages were prepared and stored according to standard protocols.

Synthetic Libraries

Synthetic libraries were generated by cloning synthetic $V_HH$ gene fragments obtained and cloned from the immunizations into phagemid vector pAX190, which has the same features as the above described pAX212, but with differences in the multiple cloning site.

Library Screening of $V_HH$ Fragments Binding to FX or FIX $V_HH$ fragment Phage Display selections were performed with the generated immune and synthetic libraries. The libraries were subjected to one to four successive rounds of enrichment against different concentrations of immobilized human FIX and FX such to enrich clone screening to obtain better binders to FIX and FX (Haemotologic Technologies, VT USA) and cynomolgus FIX and FX (Novo Nordisk generated in house). In order to specifically enrich for $V_HH$ fragments that were selective for FIXa and FX versus FIX and FXa, respectively, in certain experiments excess soluble FIX and FXa was used for competition during the incubation of the libraries with the immobilized FIXa and FX.

In order to specifically enrich for $V_HH$ fragments that were selective for FIX and FX versus other structurally related coagulation factors, in certain experiments excess soluble FX and FIX, respectively, was used for competition during the incubation of the libraries with the immobilized FIX and FX.

Approximately 4500 individual clones from the selection outputs were screened for binding in ELISA (using periplasmic extracts from E. coli cells expressing the $V_HH$ fragments) against human and cynomolgus FX, FXa, FIX and FIXa. Approximately 1500 clones each that showed specific binding to human FX and FIXa/FIX were identified, of which the majority showed cross-binding to cynomolgus FX and FIX. Some clones showed preferential binding to FX versus FXa and FIXa versus FIX. Sequence analysis of the ELISA positive clones identified approximately 700 unique sequences of $V_HH$ fragments binding to FIXa/FIX or FX/FXa. To optimize compounds further, intensive $V_HH$ CDR and FR mutagenesis combined with protractor additions, linker and extension combinations were conducted with focus on enhancing the haemostatic potency via mutational screenings using a thrombin-generation assay, avoid target-mediated drug-disposition via screening for compounds with altered affinities, reducing immunogenicity via screening for risk sites using a MHC-associated peptide proteomics assay and enhancing in vivo oral bioavailability via pI lowering substitutions of surface-exposed residues.

Expression Construct Generation of $V_HH$ Fragments Binding to FX or FIX

Sequence analysis of $V_HH$ fragments from phage display selection outputs was done according to commonly known procedures (Pardon et al. (2014) Nat Protoc 9: 674). $V_HH$ fragment-containing DNA fragments, obtained by PCR with specific combinations of forward FR1 and reverse FR4 primers each carrying a unique restriction site, were digested with the appropriate restriction enzymes and ligated into the matching cloning cassettes of $V_HH$ polypeptide expression vectors as $His_6$- and/or $FLAG_3$-tagged formats for E. coli or P. pastoris expression. The ligation mixtures were then transformed to electrocompetent Escherichia coli TG1 (60502, Lucigen, Middleton, WI) or TOP10 (C404052, ThermoFisher Scientific, Waltham, MA) cells which were then grown under the appropriate antibiotic selection pressure (kanamycin or Zeocin). Resistant clones were verified by Sanger sequencing of a plasmid DNA (LGC Genomics, Berlin, Germany).

Generic Expression of $V_HH$ Fragments Binding to FX or FIX in E. coli $V_HH$ fragments were expressed in E. coli TG1 from a plasmid expression vector containing the lac promoter, a resistance gene for kanamycin, an E. coli replication origin and a $V_HH$ fragment cloning site preceded by the coding sequence for the OmpA signal peptide. In frame with the $V_HH$ polypeptide coding sequence, the vector codes for a C-terminal FLAG S and $His_6$ tag. The signal peptide directs the expressed $V_HH$ fragments to the periplasmic compartment of the bacterial host.

E. coli TG-1 cells containing the $V_HH$ fragment constructs of interest were grown for 2 hours at 37° C. followed by 29 hours at 30° C. in baffled shaker flasks containing "5052" auto-induction medium (0.5% glycerol, 0.05% glucose, 0.2% lactose+3 mM $MgSO_4$). Overnight frozen cell pellets from *E. coli* expression cultures were then dissolved in PBS (1/12.5th of the original culture volume) and incubated at 4° C. for 1 hour while gently rotating. Finally, the cells were pelleted down once more and the supernatant, containing the proteins secreted into the periplasmic space, stored.

Generic Expression of $V_HH$ Fragments in *P. pastoris*

*P. pastoris* cells containing $V_HH$ fragment constructs of interest were grown for two days (at 30° C., 200 rpm) in BGCM medium. On the third day, the medium was switched to BMCM and the constructs were further grown (at 30° C., 200 rpm) and induced with 0.5% v/v methanol after 8 hours. Next day the constructs were induced with 0.5% v/v methanol in the morning, at noon and in the evening. On the fifth day, the cells were spun down and the supernatant (containing the secreted $V_HH$ fragment) collected.

Generic Expression of $V_HH$ and Antibodies Binding to FX or FIX and Other Recombinant Proteins in HEK Cells Expression plasmids for transient expression in HEK293 cells were purchased from either Twist Biosciences or Thermo Fisher Scientific. Plasmids from Twist Biosciences were based on the pTT vector described in Durocher, Y. et al., (2002) Nucleic Acid Res, 30: E9 while plasmids from ThermoFisherScientific were based on the pcDNA34-Topo vector (Thermo Fisher Scientific). Hiss-tagged or non-tagged $V_HH$ polypeptide compounds were transfected into HEK293 suspension cells in order to transiently express $V_HH$ polypeptide compounds. Equivalent expression constructs harbouring sequences coding for anti-GLA FIX and anti-GLA FX antibodies (Novo Nordisk in-house generated), emicizumab (Hoffmann-La Roche Ltd, Switzerland) sequence identical analogue (SIA) and Mim8 (Novo Nordisk, Denmark) were also expressed in HEK293 using the method described below.

Transient transfection of HEK293 suspension cells (Expi293 expression system, Thermo Fisher Scientific, catalogue number A14635) were performed essentially following manufacturer's instructions. HEK293 cells were typically subcultivated every 3-4 days in Expi293 expression medium (Gibco, catalogue number A14351-01) supplemented with 1% P/S (GIBCO, catalogue number 15140-122). HEK293 cells were transfected at a cell density of 2.5-3 mill/mL using Expifectamine. For each litre of HEK293 cells, the transfection was performed by diluting a total of 1 mg of plasmid DNA into 50 mL Optimem (GIBCO, catalogue number 51985-026, dilution A) and by diluting 2.7 mL Expifectamine into 50 mL Optimem (dilution B). For co-transfections (i.e. for antibodies), plasmids were used in a 1:1 ratio. Dilution A and B were mixed and incubated at room temperature for 10-20 minutes. The transfection mix was hereafter added to the HEK293 cells and cells were incubated at 37° C. in a humidified incubator with orbital rotation (85-140 rpm). One day post-transfection, transfected cells were supplemented with 5 ml of ExpiFectamine 293 Transfection Enhancer 1 and 50 ml of ExpiFectamine 293 Transfection Enhancer 2. Cell culture supernatants were typically harvested 4-5 days post-transfection by centrifugation followed by filtration.

Generic Expression of $V_HH$ Fragments and Antibodies Binding to FX and FIX(a) in CHO Cells Anti-FIX and anti-FX $V_HH$ compounds and antibodies were produced in a Chinese Hamster Ovary (CHO) cells using glutamine synthetase (GS) selection. CHO cells were transfected with GS expression plasmids using electroporation and hereafter subjected to selection using glutamine deprival together with MSX supplement in CD-CHO medium (Thermo Fisher Scientific, catalogue number 10743029). Stable CHO cell pools were typically obtained after 3 weeks of culturing and pools were hereafter single-cell cloned into 384 well plates. CHO clones arising in 384 well plates were typically expanded into 96 well plates and screened for productivity. Selected producer clones were upscaled for cultivation in bioreactors at 1-L to 15-L scale using a pre-defined proprietary cell culture media (Novo Nordisk A/S). Cell viability was kept high during cultivation with a progressive decrease following this until cell culture harvest.. Here, cell supernatants were cleared by centrifugation and/or depth-filter filtration using MD0HC23CL3 and MX0HC01FS1 filters (Millipore) depending on cultivation scale before proceeding with chromatography-based protein purification.

Generic Purification and Characterization of $V_HH$ Fragments Binding to FX or FIX His6-tagged or non-tagged $V_HH$ compounds were purified by MabSelectSure Protein-A resin (Cytiva) or immobilized metal affinity chromatography (IMAC) on either Ni-Excel (Cytiva) resin with Imidazole (for the latter) or acidic elution (for the former) followed by a desalting step (PD columns with Sephadex G25 resin, Cytiva) and if necessary, gel filtration chromatography (Superdex200 column, Cytiva) in PBS or HBS. Non-His6-tagged $V_HH$ compounds and antibodies targeting the GLA domains of FIX and FX, respectively (generated in-house at Novo Nordisk) and emicizumab SIA (Hoffmann-La Roche Ltd, Switzerland) were purified by Protein-A resins MabSelectSure (Cytiva) or multimodal resins (Cytiva) with acidic elution followed by a desalting step (e.g. PD columns with Sephadex G25 resin, Cytiva) and if necessary, gel filtration chromatography (e.g. Superdex200 column, Cytiva) in PBS or HBS. Protein integrity was analysed using a Size-Exclusion High-Performance Liquid Chromatographic (SE-HPLC) method setup on an Agilent LC 1100/1200 system and using a BIOSEP (column for separation biomolecules)-SEC-53000 300×7.8 mm column (Phenomenex, cat. no. OOH-2146-K0) and a running buffer composed of 200 mM NaPhosphate pH 6.9, 300 mM NaCl and 10% isopropanol. The molecular masses of the purified $V_HH$ polypeptide batches weres analysed using ElectroSpray Ionization Time of Flight Mass Spectrometry (ESI-TOF-MS) on a 6280 Agilent system (Agilent Technologies) with a MassPREP Desalt (Waters) column run at 0.4 ml/min in A-buffer composed of MQ-$H_2O$/0.1% formic acid and B-buffer composed of acetonitrile/0.1% formic acid for step elution. To measure the final protein concentration, a Nano-Drop™ spectrophotometer (Thermo Scientific) was used with theoretical calculated extinction coefficients.

Example 2: Conjugation of Protraction Moiety to $V_HH$ Polypeptide Cysteine Residue In order to protract $V_HH$ polypeptides to improve pharmacokinetic properties, $V_HH$ polypeptide compounds were engineered such to comprise Cysteine (Cys) substituents in various backbone positions e.g. in N- or C-terminal extensions with one or two introduced Cys residues used for conjugation with one or more fatty acid protraction moiety(ies) as described further below.

In order to attach the protraction moiety to the $V_HH$ polypeptide compounds, an intermediate reagent in the form of a modified protraction moiety was used.

The intermediate reagent comprising the protraction moiety was prepared as described in WO2016/102562 and non-limiting examples of such intermediate reagents are shown in table 3 below:

TABLE 3

Examples of intermediate reagents comprising protraction moieties (incl. linker ($L_P$))

| ID | Intermediate reagent structure and IUPAC name (short name) | $V_HH$ polypeptide derivative ID |
|---|---|---|
| C1 | 11-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethyl-carbamoyl]propylcarbamoyl}undecanoic acid (C12 diacid linker reagent) | Cmpd #65 |
| C2 | 15-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethyl-carbamoyl]propylcarbamoyl}pentadecanoic acid (C16 diacid linker reagent) | Cmpd #6, #7, #8, #9, #10, #11, #12, #13, #14, #15, #16, #17, #18, #19, #20, #21, #22 |
| C3 | 17-{(S)-1-carboxy-3-[2-(2-{[2-(2-{[2-(2-bromoacetyl-amino)ethylcarbamoyl]methoxy}ethoxy)ethylcarbamoyl]methoxy}ethoxy)ethyl-carbamoyl]propylcarbamoyl}heptadecanoic acid (C18 diacid linker reagent) | Cmpd #4, #5, #24, #26, #28, #30, #32, #34, #36, #38, #40, #58, #59, #60, #61, #62, #63, #66 |
| C4 | 19-{(S)-1-carboxy-3-[2-(2-{[2-(2-{[2-(2-bromoacetyl-amino) ethylcarbamoyl]methoxy}ethoxy)ethylcarbamoyl]methoxy}ethoxy)ethyl-carbamoyl]propylcarbamoyl}nonadecanoic acid (C20 diacid linker reagent) | Cmpd #67 |
| C5 | N-[4-[2-[2-[2-[2-[2-[2-[2-[(2-bromoacetyl)amino]ethylamino]-2-oxo-ethoxy]ethoxy]ethylamino]-2-oxo-ethoxy]ethoxy]ethylamino]-4-oxo-butyl]sulfonyl-16-(1H-tetrazol-5-yl)hexadecanamide (Tetrazole linker reagent) | Cmpd #68 |

Conjugation, Purification, and Analysis

To the water solution containing the $V_HH$ polypeptide with one or more introduced cysteine residue(s) for conjugation, 5 eq. BSPP (Bis(p-sulfonatophenyl)phenylphosphine dihydrate dipotassium salt) or 1.1 eq TCEP (Tris(2-carboxyethyl)phosphine hydrochloride) per capped cysteine was added. After 1-2 h of stirring, pH was adjusted to 8.5 with aq. NaOH and 5 eq. of e.g. intermediate reagent Cl in 0.1 M NaHCO$_3$ (aq.) per free cysteine in the respective $V_HH$ polypeptide were added. The mixture was stirred gently in the dark for 1.5-16 hours. The reaction mixture was diluted with water before purification by anion exchange (AIEX) method using an Äkta system. The $V_HH$ polypeptide with the side-chain conjugation was purified using an AIEX chromatography separation method. Thus, the AIEX resin Source 30Q packed in a suitable column was used together with a sodium chloride gradient program setup on an Akta Avant chromatography system. The buffer systems used were an equilibration buffer composed of 20 mM Tris, pH 8.5 and an elution buffer composed of 20 mM Tris, 1 M NaCl, pH 8.5. The reaction mixture was adjusted to pH 8.5 and diluted to a conductivity below 4 mS/cm using MilliQ-H$_2$O or equilibration buffer. The sample was applied to the column and the column was washed after application with 5 to 10 column volumes of equilibration buffer. Separation chromatography was then performed using a shallow gradient of 30 to 50 column volumes. The gradient used was from 0% and up to 50% depending on pI of the $V_HH$ polypeptide derivative that was purified. Generally, the non-conjugated parental $V_HH$ polypeptides eluted early in the gradient, $V_HH$ polypeptides with single conjugation eluted in the middle of the gradient and $V_HH$ polypeptides with multi-conjugations, meaning more than one side-chain conjugation per $V_HH$ polypeptide molecule, eluted late in the gradient. Pooling of fractions over the main peak was conducted in a way, so high purities between 90 to 99% of $V_HH$ polypeptide with single or double conjugate preparations were obtained. The purity analysis was performed using a reverse-phase ultra-performance liquid chromatography (RP-UPLC) method based on HALO DiPhenyl column 1000 Å, 2.7 μm, 150×2.1 mm (Scantec Nordic USDPF001316) and running buffers composed of A) 0.1% v/v TFA in water and B) 0.09% v/v TFA in acetonitrile setup on a Waters Acquity UPLC system with UV and FLD detector. Column temperature was set to 60° C. The gradient program was 1) 0.0-8.0 min: 20-50% B, 2) 8.0-8.1 min: 50-80% B, 3) 8.1-9.0 min: 80% B, 4) 9.0-9.1 min: 80-20% B, and 5) 9.1-11.0 min: 20% B. The un-conjugated parental $V_HH$ polypeptide eluted between 4.6-4.8 min. The $V_HH$ polypeptide derivative with single conjugation eluted between 5.1-5.6 min with main peak at approx. 5.3 min. $V_HH$ polypeptide derivative with double conjugations eluted between 5.7-5.8 and later for offsite multi-conjugated $V_HH$ polypeptides. Integrity of $V_HH$ polypeptides with conjugation(s) were analysed using a SE-HPLC method setup on an Agilent LC 1100/1200 system and a BIOSEP-SEC-3000 300×7.8 mm column (Phenomenex, cat. no. 00H-2146-KO) and a running buffer composed of 200 mM NaPhosphate pH 6.9, 300 mM NaCl and 10% isopropanol. The molecular masses of $V_HH$ polypeptide with conjugation(s) were analysed using ESI-TOF-MS on a 6280 Agilent system (Agilent Technologies) with a MassPREP Desalt (Waters) column run at 0.4 ml/min in A-buffer composed of MilliQ-H$_2$O/0.1% formic acid and B-buffer composed of acetonitrile/0.1% formic acid for step elution. Peptide-mapping for sequence verification was performed using a combination of chymotrypsin and trypsin based digests. LC-MS system consisted of a waters Aquity UPLC combined to a Thermo Orbitrap Fusion instrument. On-line LC-MS analysis of the digests was done using a CSH C-18 column 1.7 μm, 150×2.1 mm and an acetonitril/formic acid gradient. Column temperature was 60 C. Buffer A: 0.1% FA Water and Buffer B: 0.1% FA Acetonitrile. The gradient program was: 1) 0.0-2.0 min: 1% B, 2) 2-50 min: 1-35% B, 3) 50-51 min: 100% B and 4) 51-60 min: 100-1% B with a flow of 120 μl/min. Data were analysed using a Genedata Refiner peptide mapping workflow. Full coverage of the primary sequence was obtained. To measure protein concentration of batch preparations of $V_HH$ polypeptide derivative with conjugation(s), a NanoDrop™ spectrophotometer (Thermo Scientific) was used with theoretical calculated extinction coefficients.

Figure 1G:
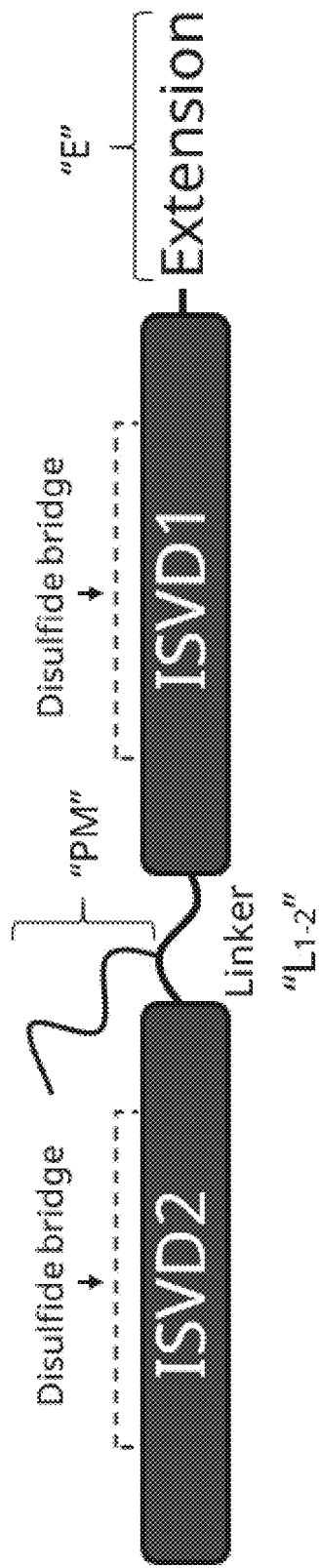
Figure 1H:
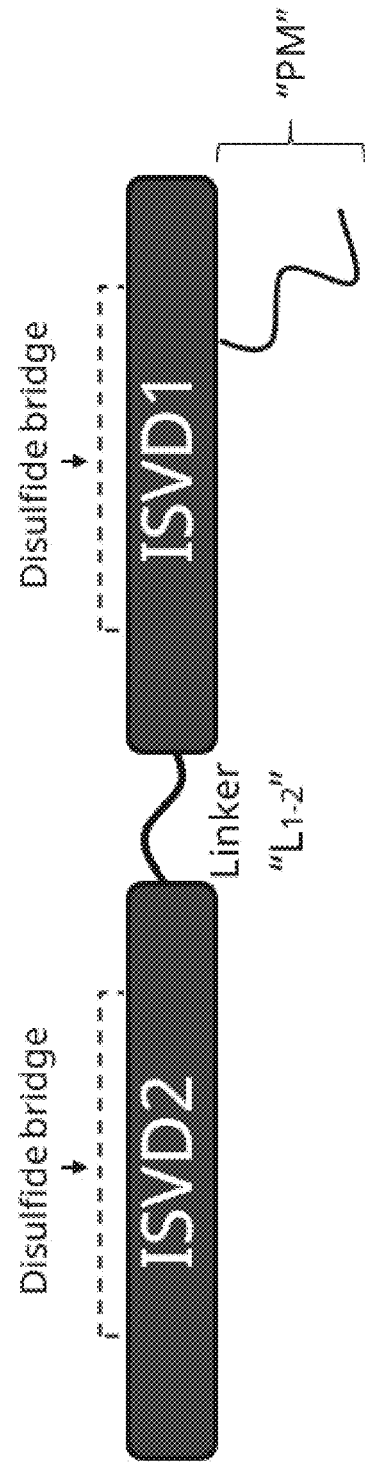

FIGS. 1, 2 and 3 show—with increasing level of details—non-limiting examples of ISVD- and $V_HH$ polypeptide derivatives.

Example 3: Tables of Sequences and Anti-FX/Anti-FIX(A) $V_HH$ Polypeptides

TABLE 4

Overview of compounds and SEQ ID NOs ($V_HH$ & CDR sequences) without protractor

| $V_HH$ polypeptide ID | N-term. extension SEQ ID NOs | Anti-FX $V_HH$ (N-terminal) $V_HH$ ID | SEQ ID NOs $V_HH$ (CDR1, 2, 3) (Kabat definition) | Linker (L$_{1-2}$) SEQ ID NOs | Anti-FIX(a) $V_HH$ (C-terminal) $V_HH$ ID | SEQ ID NOs $V_HH$ (CDR1, 2, 3) (Kabat definition) | C-term. extension SEQ ID NOs |
|---|---|---|---|---|---|---|---|
| Cmpd #1 (monovalent) | none | VHH-1.1 | 27 (28, 29, 30) | none | none | none | 5 |
| Cmpd #2 (monovalent) | none | none | none | none | VHH-2.2 | 35 (36, 37, 38) | 6 |
| Cmpd #3 (monovalent) | none | VHH-1.3 | 31 (32, 33, 34) | none | none | none | 6 |
| Cmpd #4 | none | VHH-1.4 | 39 (40, 41, 42) | 14 | VHH-2.4 | 43 (44, 45, 46) | 7 |
| Cmpd #5 | none | VHH-1.5 | 47 (48, 49, 50) | 14 | VHH-2.5 | 51 (52, 53, 54) | 7 |
| Cmpd #6 | none | VHH-1.6 | 47 (48, 49, 50) | 14 | VHH-2.6 | 51 (52, 53, 54) | 8 |
| Cmpd #7 | none | VHH-1.7 | 63 (64, 65, 66) | 20 | VHH-2.7 | 67 (68, 69, 70) | 9 |

TABLE 4-continued

Overview of compounds and SEQ ID NOs (V$_H$H & CDR sequences) without protractor

| | | Anti-FX V$_H$H (N-terminal) | | | Anti-FIX(a) V$_H$H (C-terminal) | | |
|---|---|---|---|---|---|---|---|
| V$_H$H polypeptide ID | N-term. extension SEQ ID NOs | V$_H$H ID | SEQ ID NOs V$_H$H (CDR1, 2, 3) (Kabat definition) | Linker (L$_{1-2}$) SEQ ID NOs | V$_H$H ID | SEQ ID NOs V$_H$H (CDR1, 2, 3) (Kabat definition) | C-term. extension SEQ ID NOs |
| Cmpd #8 | none | VHH-1.8 | 63 (64, 65, 66) | 20 | VHH-2.8 | 51 (52, 53, 54) | 9 |
| Cmpd #9 | none | VHH-1.9 | 79 (80, 81, 82) | 20 | VHH-2.9 | 83 (84, 85, 86) | 9 |
| Cmpd #10 | none | VHH-1.10 | 87 (88, 89, 90) | 20 | VHH-2.10 | 67 (68, 69, 70) | 9 |
| Cmpd #11 | none | VHH-1.11 | 95 (96, 97, 98) | 20 | VHH-2.11 | 83 (84, 85, 86) | 9 |
| Cmpd #12 | none | VHH-1.12 | 103 (104, 105, 106) | 20 | VHH-2.12 | 107 (108, 109, 110) | 9 |
| Cmpd #13 | none | VHH-1.13 | 111 (112, 113, 114) | 20 | VHH-2.13 | 115 (116, 117, 118) | 9 |
| Cmpd #14 | none | VHH-1.14 | 119 (120, 121, 122) | 20 | VHH-2.14 | 123 (124, 125, 126) | 9 |
| Cmpd #15 | none | VHH-1.15 | 127 (128, 129, 130) | 20 | VHH-2.15 | 131 (132, 133, 134) | 9 |
| Cmpd #16 | none | VHH-1.16 | 111 (112, 113, 114) | 20 | VHH-2.16 | 139 (140, 141, 142) | 9 |
| Cmpd #17 | none | VHH-1.17 | 143 (144, 145, 146) | 20 | VHH-2.17 | 107 (108, 109, 110) | 9 |
| Cmpd #18 | none | VHH-1.18 | 151 (152, 153, 154) | 20 | VHH-2.18 | 155 (156, 157, 158) | 9 |
| Cmpd #19 | none | VHH-1.19 | 159 (160, 161, 162) | 20 | VHH-2.19 | 51 (52, 53, 54) | 9 |
| Cmpd #20 | none | VHH-1.20 | 167 (168, 169, 170) | 20 | VHH-2.20 | 171 (172, 173, 174) | 9 |
| Cmpd #21 | none | VHH-1.21 | 79 (80, 81, 82) | 20 | VHH-2.21 | 107 (108, 109, 110) | 9 |
| Cmpd #22 | none | VHH-1.22 | 111 (112, 113, 114) | 20 | VHH-2.22 | 83 (84, 85, 86) | 9 |
| Cmpd #23 | 690 | VHH-1.23 | 191 (192, 193, 194) | 14 | VHH-2.23 | 43 (44, 45, 46) | 10 |
| Cmpd #24 | 690 | VHH-1.24 | 191 (192, 193, 194) | 14 | VHH-2.24 | 43 (44, 45, 46) | 10 |
| Cmpd #25 | 690 | VHH-1.25 | 207 (208, 209, 210) | 14 | VHH-2.25 | 43 (44, 45, 46) | 11 |
| Cmpd #26 | 690 | VHH-1.26 | 207 (208, 209, 210) | 14 | VHH-2.26 | 43 (44, 45, 46) | 11 |
| Cmpd #27 | 690 | VHH-1.27 | 223 (224, 225, 226) | 14 | VHH-2.27 | 227 (228, 229, 230) | 11 |
| Cmpd #28 | 690 | VHH-1.28 | 223 (224, 225, 226) | 14 | VHH-2.28 | 227 (228, 229, 230) | 11 |
| Cmpd #29 | 690 | VHH-1.29 | 223 (224, 225, 226) | 14 | VHH-2.29 | 243 (244, 245, 246) | 11 |
| Cmpd #30 | 690 | VHH-1.30 | 223 (224, 225, 226) | 14 | VHH-2.30 | 243 (244, 245, 246) | 11 |
| Cmpd #31 | 690 | VHH-1.31 | 223 (224, 225, 226) | 14 | VHH-2.31 | 259 (260, 261, 262) | 11 |
| Cmpd #32 | 690 | VHH-1.32 | 223 (224, 225, 226) | 14 | VHH-2.32 | 259 (260, 261, 262) | 11 |
| Cmpd #33 | 690 | VHH-1.33 | 223 (224, 225, 226) | 14 | VHH-2.33 | 275 (276, 277, 278) | 11 |
| Cmpd #34 | 690 | VHH-1.34 | 223 (224, 225, 226) | 14 | VHH-2.34 | 275 (276, 277, 278) | 11 |
| Cmpd #35 | 690 | VHH-1.35 | 223 (224, 225, 226) | 14 | VHH-2.35 | 291 (292, 293, 294) | 11 |
| Cmpd #36 | 690 | VHH-1.36 | 223 (224, 225, 226) | 14 | VHH-2.36 | 291 (292, 293, 294) | 11 |
| Cmpd #37 | 690 | VHH-1.37 | 223 (224, 225, 226) | 14 | VHH-2.37 | 307 (308, 309, 310) | 11 |
| Cmpd #38 | 690 | VHH-1.38 | 223 (224, 225, 226) | 14 | VHH-2.38 | 307 (308, 309, 310) | 11 |
| Cmpd #39 | 690 | VHH-1.39 | 223 (224, 225, 226) | 14 | VHH-2.39 | 323 (324, 325, 326) | 11 |
| Cmpd #40 | 690 | VHH-1.40 | 223 (224, 225, 226) | 14 | VHH-2.40 | 323 (324, 325, 326) | 11 |
| Cmpd #41 | none | VHH-1.41 | 335 (336, 337, 338) | 16 | VHH-2.41 | 51 (52, 53, 54) | 7 |

TABLE 4-continued

Overview of compounds and SEQ ID NOs (V$_H$H & CDR sequences) without protractor

| V$_H$H polypeptide ID | N-term. extension SEQ ID NOs | Anti-FX V$_H$H (N-terminal) | | Linker (L$_{1-2}$) SEQ ID NOs | Anti-FIX(a) V$_H$H (C-terminal) | | C-term. extension SEQ ID NOs |
|---|---|---|---|---|---|---|---|
| | | V$_H$H ID | SEQ ID NOs V$_H$H (CDR1, 2, 3) (Kabat definition) | | V$_H$H ID | SEQ ID NOs V$_H$H (CDR1, 2, 3) (Kabat definition) | |
| Cmpd #42 | none | VHH-1.42 | 335 (336, 337, 338) | 17 | VHH-2.42 | 51 (52, 53, 54) | 7 |
| Cmpd #43 | none | VHH-1.43 | 335 (336, 337, 338) | 18 | VHH-2.43 | 51 (52, 53, 54) | 7 |
| Cmpd #44 | none | VHH-1.44 | 335 (336, 337, 338) | 19 | VHH-2.44 | 51 (52, 53, 54) | 7 |
| Cmpd #45 | none | VHH-1.45 | 335 (336, 337, 338) | 20 | VHH-2.45 | 51 (52, 53, 54) | 7 |
| Cmpd #46 | none | VHH-1.46 | 335 (336, 337, 338) | 14 | VHH-2.46 | 379 (380, 381, 382) | 7 |
| Cmpd #47 | none | VHH-1.47 | 335 (336, 337, 338) | 16 | VHH-2.47 | 379 (380, 381, 382) | 7 |
| Cmpd #48 | none | VHH-1.48 | 335 (336, 337, 338) | 21 | VHH-2.48 | 379 (380, 381, 382) | 7 |
| Cmpd #49 | none | VHH-1.49 | 335 (336, 337, 338) | 18 | VHH-2.49 | 379 (380, 381, 382) | 7 |
| Cmpd #50 | none | VHH-1.50 | 335 (336, 337, 338) | 19 | VHH-2.50 | 379 (380, 381, 382) | 7 |
| Cmpd #51 | none | VHH-1.51 | 335 (336, 337, 338) | 14 | VHH-2.51 | 419 (420, 421, 422) | 7 |
| Cmpd #52 | none | VHH-1.52 | 335 (336, 337, 338) | 16 | VHH-2.52 | 419 (420, 421, 422) | 7 |
| Cmpd #53 | none | VHH-1.53 | 335 (336, 337, 338) | 23 | VHH-2.53 | 419 (420, 421, 422) | 7 |
| Cmpd #54 | none | VHH-1.54 | 335 (336, 337, 338) | 21 | VHH-2.54 | 419 (420, 421, 422) | 7 |
| Cmpd #55 | none | VHH-1.55 | 335 (336, 337, 338) | 18 | VHH-2.55 | 419 (420, 421, 422) | 7 |
| Cmpd #56 | none | VHH-1.56 | 335 (336, 337, 338) | 19 | VHH-2.56 | 419 (420, 421, 422) | 7 |
| Cmpd #57 | none | VHH-1.57 | 335 (336, 337, 338) | 20 | VHH-2.57 | 419 (420, 421, 422) | 7 |
| Cmpd #58 | none | VHH-1.58 | 471 (472, 473, 474) | 14 | VHH-2.58 | 475 (476, 477, 478) | 7 |
| Cmpd #59 | none | VHH-1.59 | 479 (480, 481, 482) | 14 | VHH-2.59 | 51 (52, 53, 54) | 7 |
| Cmpd #60 | none | VHH-1.60 | 487 (488, 489, 490) | 14 | VHH-2.60 | 475 (476, 477, 478) | 7 |
| Cmpd #61 | none | VHH-1.61 | 495 (496, 497, 498) | 14 | VHH-2.61 | 499 (500, 501, 502) | 7 |
| Cmpd #62 | none | VHH-1.62 | 503 (504, 505, 506) | 14 | VHH-2.62 | 507 (508, 509, 510) | 7 |
| Cmpd #63 | none | VHH-1.63 | 511 (512, 513, 514) | 14 | VHH-2.63 | 507 (508, 509, 510) | 7 |
| Cmpd #64 | 690 | VHH-1.64 | 223 (224, 225, 226) | 14 | VHH-2.64 | 43 (44, 45, 46) | 10 |
| Cmpd #65 | 690 | VHH-1.65 | 223 (224, 225, 226) | 14 | VHH-2.65 | 43 (44, 45, 46) | 10 |
| Cmpd #66 | 690 | VHH-1.66 | 223 (224, 225, 226) | 14 | VHH-2.66 | 43 (44, 45, 46) | 10 |
| Cmpd #67 | 690 | VHH-1.67 | 223 (224, 225, 226) | 14 | VHH-2.67 | 43 (44, 45, 46) | 10 |
| Cmpd #68 | 690 | VHH-1.68 | 223 (224, 225, 226) | 14 | VHH-2.68 | 43 (44, 45, 46) | 10 |
| Cmpd #69 | none | VHH-1.69 | 39 (40, 41, 42) | 14 | VHH-2.69 | 43 (44, 45, 46) | 7 |
| Cmpd #70 | 3 | VHH-1.70 | 223 (224, 225, 226) | 14 | VHH-2.70 | 43 (44, 45, 46) | 11 |
| Cmpd #71 | 4 | VHH-1.71 | 223 (224, 225, 226) | 14 | VHH-2.71 | 43 (44, 45, 46) | 11 |
| Cmpd #72 | none | VHH-1.72 | 223 (224, 225, 226) | 14 | VHH-2.72 | 43 (44, 45, 46) | 12 |
| Cmpd #73 | none | VHH-1.73 | 223 (224, 225, 226) | 14 | VHH-2.73 | 43 (44, 45, 46) | 13 |
| Cmpd #74 | 690 | VHH-1.74 | 599 (600, 601, 602) | 691 | VHH-2.74 | 603 (604, 605, 606) | 7 |

TABLE 4-continued

Overview of compounds and SEQ ID NOs (V$_H$H & CDR sequences) without protractor

| V$_H$H polypeptide ID | N-term. extension SEQ ID NOs | Anti-FX V$_H$H (N-terminal) V$_H$H ID | SEQ ID NOs V$_H$H (CDR1, 2, 3) (Kabat definition) | Linker (L$_{1-2}$) SEQ ID NOs | Anti-FIX(a) V$_H$H (C-terminal) V$_H$H ID | SEQ ID NOs V$_H$H (CDR1, 2, 3) (Kabat definition) | C-term. extension SEQ ID NOs |
|---|---|---|---|---|---|---|---|
| Cmpd #75 | none | VHH-1.75 | 607 (608, 609, 610) | 14 | VHH-2.75 | 35 (36, 37, 38) | none |
| Cmpd #76 (monovalent) | none | VHH-1.15 | 127 (128, 129, 130) | none | none | none | 11 |
| Cmpd #77 (monovalent) | none | VHH-1.13 | 111 (112, 113, 114) | none | none | none | 11 |

TABLE 5

Overview of anti-FX/anti-FIX(a) V$_H$H polypeptide derivatives (including protraction moiety)

| V$_H$H polypeptide ID | Protractor (P) | Protraction moiety linker (L$_P$) | Site(s) of protraction moiety attachment ("R1(/R2)") | Cmpd # backbone SEQ ID NO (without protraction moiety) |
|---|---|---|---|---|
| Cmpd #1 | None | None | None | 615 |
| Cmpd #2 | None | None | None | 616 |
| Cmpd #3 | None | None | None | 617 |
| Cmpd #4 | P3 | L$_P$1 | Cys6 in C-term extension (SEQ ID NO: 7) | 618 |
| Cmpd #5 | P3 | L$_P$1 | Cys6 in C-term extension (SEQ ID NO: 7) | 619 |
| Cmpd #6 | P2 | L$_P$1 | Cys5 and Cys7 in C-term extension (SEQ ID NO: 8) | 620 |
| Cmpd #7 | P2 | L$_P$1 | Cys4 and Cys6 in C-term extension (SEQ ID NO: 9) | 621 |
| Cmpd #8 | P2 | L$_P$1 | Cys4 and Cys6 in C-term extension (SEQ ID NO: 9) | 622 |
| Cmpd #9 | P2 | L$_P$1 | Cys4 and Cys6 in C-term extension (SEQ ID NO: 9) | 623 |
| Cmpd #10 | P2 | L$_P$1 | Cys4 and Cys6 in C-term extension (SEQ ID NO: 9) | 624 |
| Cmpd #11 | P2 | L$_P$1 | Cys4 and Cys6 in C-term extension (SEQ ID NO: 9) | 625 |
| Cmpd #12 | P2 | L$_P$1 | Cys4 and Cys6 in C-term extension (SEQ ID NO: 9) | 626 |
| Cmpd #13 | P2 | L$_P$1 | Cys4 and Cys6 in C-term extension (SEQ ID NO: 9) | 627 |
| Cmpd #14 | P2 | L$_P$1 | Cys4 and Cys6 in C-term extension (SEQ ID NO: 9) | 628 |
| Cmpd #15 | P2 | L$_P$1 | Cys4 and Cys6 in C-term extension (SEQ ID NO:9) | 629 |
| Cmpd #16 | P2 | L$_P$1 | Cys4 and Cys6 in C-term extension (SEQ ID NO: 9) | 630 |
| Cmpd #17 | P2 | L$_P$1 | Cys4 and Cys6 in C-term extension (SEQ ID NO: 9) | 631 |
| Cmpd #18 | P2 | L$_P$1 | Cys4 and Cys6 in C-term extension (SEQ ID NO: 9) | 632 |
| Cmpd #19 | P2 | L$_P$1 | Cys4 and Cys6 in C-term extension (SEQ ID NO :9) | 633 |
| Cmpd #20 | P2 | L$_P$1 | Cys4 and Cys6 in C-term extension (SEQ ID NO: 9) | 634 |
| Cmpd #21 | P2 | L$_P$1 | Cys4 and Cys6 in C-term extension (SEQ ID NO: 9) | 635 |
| Cmpd #22 | P2 | L$_P$1 | Cys4 and Cys6 in C-term extension (SEQ ID NO: 9) | 636 |
| Cmpd #23 | None | None | None | 637 |
| Cmpd #24 | P3 | L$_P$1 | Cys10 in C-term extension (SEQ ID NO: 10) | 638 |
| Cmpd #25 | None | None | None | 639 |
| Cmpd #26 | P3 | L$_P$1 | Cys30 in cmpd #26 (SEQ ID NO: 640) | 640 |
| Cmpd #27 | None | None | None | 641 |
| Cmpd #28 | P3 | L$_P$1 | Cys158 in cmpd #28 (SEQ ID NO: 642) | 642 |

TABLE 5-continued

Overview of anti-FX/anti-FIX(a) $V_HH$ polypeptide derivatives (including protraction moiety)

| $V_HH$ polypeptide ID | Protractor (P) | Protraction moiety linker ($L_P$) | Site(s) of protraction moiety attachment ("R1(/R2)") | Cmpd # backbone SEQ ID NO (without protraction moiety) |
|---|---|---|---|---|
| Cmpd #29 | None | None | None | 643 |
| Cmpd #30 | P3 | $L_P$1 | Cys160 in cmpd #30 (SEQ ID NO: 644) | 644 |
| Cmpd #31 | None | None | None | 645 |
| Cmpd #32 | P3 | $L_P$1 | Cys161 in cmpd #32 (SEQ ID NO: 646) | 646 |
| Cmpd #33 | None | None | None | 647 |
| Cmpd #34 | P3 | $L_P$1 | Cys188 in cmpd #34 (SEQ ID NO: 648) | 648 |
| Cmpd #35 | None | None | None | 649 |
| Cmpd #36 | P3 | $L_P$1 | Cys190 in cmpd #36 (SEQ ID NO: 650) | 650 |
| Cmpd #37 | None | None | None | 651 |
| Cmpd #38 | P3 | $L_P$1 | Cys209 in cmpd #38 (SEQ ID NO:652) | 652 |
| Cmpd #39 | None | None | None | 653 |
| Cmpd #40 | P3 | $L_P$1 | Cys231 in cmpd #40 (SEQ ID NO: 654) | 654 |
| Cmpd #41 | None | None | None | 655 |
| Cmpd #42 | None | None | None | 656 |
| Cmpd #43 | None | None | None | 657 |
| Cmpd #44 | None | None | None | 658 |
| Cmpd #45 | None | None | None | 659 |
| Cmpd #46 | None | None | None | 660 |
| Cmpd #47 | None | None | None | 661 |
| Cmpd #48 | None | None | None | 662 |
| Cmpd #49 | None | None | None | 663 |
| Cmpd #50 | None | None | None | 664 |
| Cmpd #51 | None | None | None | 665 |
| Cmpd #52 | None | None | None | 666 |
| Cmpd #53 | None | None | None | 667 |
| Cmpd #54 | None | None | None | 668 |
| Cmpd #55 | None | None | None | 669 |
| Cmpd #56 | None | None | None | 670 |
| Cmpd #57 | None | None | None | 671 |
| Cmpd #58 | P3 | $L_P$1 | Cys6 in C-term extension (SEQ ID NO: 7) | 672 |
| Cmpd #59 | P3 | $L_P$1 | Cys6 in C-term extension (SEQ ID NO: 7) | 673 |
| Cmpd #60 | P3 | $L_P$1 | Cys6 in C-term extension (SEQ ID NO: 7) | 674 |
| Cmpd #61 | P3 | $L_P$1 | Cys6 in C-term extension (SEQ ID NO: 7) | 675 |
| Cmpd #62 | P3 | $L_P$1 | Cys6 in C-term extension (SEQ ID NO: 7) | 676 |
| Cmpd #63 | P3 | $L_P$1 | Cys6 in C-term extension (SEQ ID NO: 7) | 677 |
| Cmpd #64 | None | None | None | 678 |
| Cmpd #65 | P1 | $L_P$1 | Cys10 in C-term extension (SEQ ID NO: 10) | 679 |
| Cmpd #66 | P3 | $L_P$1 | Cys10 in C-term extension (SEQ ID NO: 10) | 680 |
| Cmpd #67 | P4 | $L_P$1 | Cys10 in C-term extension (SEQ ID NO: 10) | 681 |
| Cmpd #68 | P5 | $L_P$2 | Cys10 in C-term extension (SEQ ID NO: 10) | 682 |
| Cmpd #69 | None | None | None | 683 |
| Cmpd #70 | P6 ("P"-"R1") | $L_P$3 ("P"-"$L_P$"-"R1") | Asp1 in VHH-1.70 (SEQ ID NO: 567) | 684 |
| Cmpd #71 | P6 ("P"-"R1") | $L_P$4 ("P"-"$L_P$"-"R1") | Asp1 in VHH-1.71 (SEQ ID NO: 575) | 685 |
| Cmpd #72 | P6 ("R1"-"P") | $L_P$3 ("R1"-"$L_P$"-"P") | Ser127 in VHH-2.72 (SEQ ID NO: 587) | 686 |
| Cmpd #73 | P6 ("R1"-"P") | $L_P$4 ("R1"-"$L_P$"-"P") | Ser127 in VHH-2.73 (SEQ ID NO: 595) | 687 |
| Cmpd #74 | None | None | None | 688 |
| Cmpd #75 | None | None | None | 689 |

Example 4: Epitope of Anti-FX V$_H$H Polypeptides Based on ELISA Experiment

To determine whether the binding epitope of the anti-FX V$_H$H polypeptide designated "cmpd #1" are located inside the activation peptide (AP) of human FX (SEQ ID NO:2), an ELISA assay was setup. 41 unique 12-mer peptide fragments spanning the 52 residues of the activation peptide with one amino acid spacing were immobilized in microtiter plate wells followed by incubation with the V$_H$H polypeptide to be tested, and detection of bound ligand was performed by addition of a secondary HRP-labelled antibody.

The peptides were C-terminally conjugated to biotin and 50 μL of 1 μg/mL peptide solution was used for immobilization in discrete wells of the microtiter plate which was pre-coated with 1 μg/mL streptavidin. Each well was washed with washing buffer (10 mM Tris, 150 mM NaCl, 2.5 mM CaCl$_2$), 0.05% Tween 20, pH 8.60) followed by addition of 50 μL of 2 μg/mL FLAG-tagged anti-FX V$_H$H polypeptide or IgG antibody to be tested. After 1 hour non-bound V$_H$H polypeptide was washed off using washing buffer.

Bound anti-FX activation peptide ligand was detected by first binding a HRP-labelled secondary antibody (for FLAG-tagged V$_H$H polypeptide: Anti-FLAG mAb M2-Peroxidase (HRP) (Sigma Aldrich, US) for 1 hour, and then adding 100 μL TMB-1 ELISA substrate (Kem-En-Tec Diagnostics, Denmark).

The minimal epitopes were then deduced from the set of peptides giving rise to a signal above baseline by identifying the common sequence covered by the set of peptides (table 6) bound by each FX binder. The first residue of the epitope was defined by the last amino acid in the first consecutive, ELISA-positive peptide, while the last residue of the epitope was defined as the first residue of the last consecutive, ELISA-positive peptide. Thus, table hereunder shows ELISA signal from consecutive peptides spanning the entire FX AP for initial anti-FX V$_H$H polypeptides tested corresponding to Cmpd #1. ELISA signals have been normalized relative to the background signal.

The underlined and bold numbers mark the positive binding signals used for determining the minimal epitope, which were identified as the sequence NPFDLLDF (SEQ ID NO:692).

The identified epitope sequence of the FX activation peptide for cmpd #1 was used for high-resolution structure determining experiments of the epitope:paratope interactions as outlined in example 6.

TABLE 6

Epitope identification

| Epitope residues (SEQ ID NO) | Cmpd#1 |
| --- | --- |
| empty | 1.00 |
| SVAQATSSSGEA (693) | 0.96 |
| VAQATSSSGEAP (694) | 1.02 |
| AQATSSSGEAPD (695) | 0.97 |
| QATSSSGEAPDS (696) | 0.96 |
| ATSSSGEAPDSI (697) | 0.98 |
| TSSSGEAPDSIT (698) | 0.77 |
| SSSGEAPDSITW (699) | 0.86 |
| SSGEAPDSITWK (700) | 0.88 |
| SGEAPDSITWKP (701) | 0.88 |
| GEAPDSITWKPY (702) | 0.93 |
| EAPDSITWKPYD (703) | 0.97 |
| APDSITWKPYDA (704) | 1.06 |
| PDSITWKPYDAA (705) | 1.05 |
| DSITWKPYDAAD (706) | 1.08 |
| SITWKPYDAADL (707) | 1.08 |
| ITWKPYDAADLD (708) | 1.10 |
| TWKPYDAADLDP (709) | 1.13 |
| WKPYDAADLDPT (710) | 0.89 |
| KPYDAADLDPTE (711) | 0.80 |
| PYDAADLDPTEN (712) | 0.83 |
| YDAADLDPTENP (713) | 0.87 |
| DAADLDPTENPF (714) | 0.88 |
| AADLDPTENPFD (715) | 0.88 |
| ADLDPTENPFDL (716) | 0.91 |
| DLDPTENPFDLL (717) | 1.00 |
| LDPTENPFDLLD (718) | 1.11 |
| DPTENPFDLLDF (719) | 4.16 |
| PTENPFDLLDFN (720) | 4.58 |
| TENPFDLLDFNQ (721) | 4.84 |
| ENPFDLLDFNQT (722) | 4.00 |
| NPFDLLDFNQTQ (723) | 3.13 |
| PFDLLDFNQTQP (724) | 4.95 |
| FDLLDFNQTQPE (725) | 4.38 |
| DLLDFNQTQPER (726) | 3.08 |
| LLDFNQTQPERG (727) | 1.88 |
| LDFNQTQPERGD (728) | 0.97 |
| DFNQTQPERGDN (729) | 0.94 |
| FNQTQPERGDNN (730) | 1.00 |
| NQTQPERGDNNL (731) | 0.92 |
| QTQPERGDNNLT (732) | 0.88 |
| TQPERGDNNLTR (733) | 1.05 |

Example 5: Crystallization and Paratope/Epitope Mapping of Anti-FIX V$_H$H Fragment Cmpd #2

The purpose of the present study was to determine the paratope and epitope residues of the V$_H$H fragment designated cmpd #2.

Crystallisation

Crystals of the V$_H$H polypeptide cmpd #2 mixed in a 1:1 molar ratio with human EGR-CMK-inhibited Factor IXa Gla-domain-less (wild-type) (purchased from Cambridge ProteinWorks Lot #hGDFIXAWTEGR_11) were grown using the sitting drop vapour diffusion technique at 18° C. A protein solution of 100 nl 8.4 mg/ml complex in 20 mM Tris-HCl, pH 7.4, 50 mM NaCl and 2.5 mM CaCl$_2$) was mixed with 100 nl of 0.2 M Li sulphate, 0.1 M Tris-HCl, pH 8.5, 30% (w/v) PEG 4000 as precipitant and incubated over 60 µl precipitant. Crystals appeared within two weeks.

Diffraction Data Collection

The crystal was cryo-protected by addition of 1 µl of precipitant added 20% of ethylene glycol to the crystallisation drop prior to flash cooling in liquid nitrogen. Diffraction data were collected at 100K at the Swiss Light Source beamline X06DA (1.0000 Å wavelength) using a Pilatus 2M pixel detector from Dectris. Autoindexing, integration and scaling of the data were performed with programmes from the XDS package (diffracting data statistics are summarised in Table 7).

Structure Determination and Refinement

The asymmetric unit contains two cmpd #2:EGR-CMK-inhibited Factor IXa Gla-domain-less complex as judged by Matthews coefficient analysis. The structure was determined by molecular replacement using Phaser as implemented in the programme suite Phenix using a structure of a predetermined V$_H$H:FIXa complex as search model. The correct amino acid sequence was model built using COOT and thereafter the structure was refined using steps of Phenix refinement and manual rebuilding in COOT. The refinement statistics are found in Table 7.

TABLE 7

Data collection and refinement statistics

| | |
|---|---|
| Wavelength (Å) | 1.0000 |
| Resolution range (Å) | 43.26-2.7 (2.797-2.7) |
| Space group | P 1 |
| Unit cell (Å, deg) | 56.51 64.47 64.72 |
| | 76.115 87.449 85.761 |
| Total reflections | 42366 (4277) |
| Unique reflections | 23473 (2340) |
| Multiplicity | 1.8 (1.8) |
| Completeness (%) | 96.66 (96.77) |
| Mean I/sigma(I) | 6.44 (1.40) |
| Wilson B-factor (Å$^2$) | 40.75 |
| R-merge | 0.1042 (0.5247) |
| R-meas | 0.1473 (0.7416) |
| R-pim | 0.1041 (0.5241) |
| CC1/2 | 0.986 (0.594) |
| CC* | 0.997 (0.863) |
| Reflections used in refinement | 23455 (2340) |
| Reflections used for R-free | 1176 (115) |
| R-work | 0.2260 (0.2951) |
| R-free | 0.2825 (0.3665) |
| CC(work) | 0.922 (0.745) |
| CC(free) | 0.829 (0.421) |
| Number of non-hydrogen atoms | 6622 |
| macromolecules | 6394 |
| ligands | 54 |
| solvent | 174 |
| Protein residues | 823 |
| RMS(bonds) (Å) | 0.004 |
| RMS(angles) (deg) | 0.87 |
| Ramachandran favored (%) | 94.82 |
| Ramachandran allowed (%) | 5.18 |
| Ramachandran outliers (%) | 0.00 |
| Rotamer outliers (%) | 6.39 |

TABLE 7-continued

Data collection and refinement statistics

| | |
|---|---|
| Clashscore | 9.91 |
| Average B-factor (Å$^2$) | 42.93 |
| macromolecules | 43.06 |
| ligands | 42.44 |
| Number of TLS groups | 38.49 |

Statistics for the highest-resolution shell are shown in parentheses.

Determination of Epitope and Paratope

The epitope of cmpd #2, defined as FIX(a) residues characterized by having a heavy atom (i.e. a non-hydrogen atom) within a distance of 4.0 Å from a heavy atom in the V$_H$H polypeptide, comprises the following residues from protease domain of FIX(a):

E224, T225, G226, V250, I251, R252, I253, P255, H257 and N260 according to FIX sequence (consecutive numbering) (SEQ ID NO:1).

The paratope of cmpd #2, defined as residues characterized by having a heavy atom (i.e. a non-hydrogen atom) within a distance of 4.0 Å from a heavy atom in FIX(a), comprises the following residues from cmpd #2:

F29, N30, Y32, T54, D99, R100, S101, F102, L103, F104, Q106, A107 and N113 (SEQ ID NO:35) (consecutive numbering).

Example 6: Crystallization and Paratope/Epitope Mapping Anti-FX V$_H$H Fragment Cmpd #1

The purpose of the present study was to determine the paratope and epitope residues of the V$_H$H fragment designated cmpd #1.

Crystallisation

Crystals of the V$_H$H polypeptide cmpd #1 mixed in a 1:14 molar ratio with a synthetic peptide N-term-NPFDLLD-C-term, corresponding to the activation peptide sequence aa31-37 of human FX (purchased from Schafer-N ApS) as identified in example 4, were grown using the sitting drop vapour diffusion technique at 18° C. A protein solution of 150 nl 4.0 mg/ml complex in 20 mM Tris-HCl, pH 7.4, 50 mM NaCl was mixed with 50 nl of 0.2 M NaCl, 2 M ammonium sulphate, 0.1 M sodium cacodylate, pH 6.5 as precipitant and incubated over 60 µl precipitant. Crystals appeared within a week.

Diffraction Data Collection

The crystal was cryo-protected by addition of 1 µl of precipitant added 20% of ethylene glycol to the crystallisation drop prior to flash cooling in liquid nitrogen. Diffraction data were collected at 100K at the Swiss Light Source beamline X06DA (1.0000 Å wavelength) using a Pilatus 2M pixel detector from Dectris. Autoindexing, integration and scaling of the data were performed with programmes from the XDS package (diffracting data statistics are summarised in Table 8).

Structure Determination and Refinement

The asymmetric unit contains one cmpd #1:peptide complex. The structure was determined by molecular replacement using Phaser as implemented in the programme suite Phenix using the V$_H$H polypeptide structure designated with Protein Data Bank ID 4641 (chain A) as search model. The correct amino acid sequence of cmpd #1 was introduced and difference electron density for the synthetic peptide was identified and model built manually, all using COOT. Thereafter the structure was refined using steps of Phenix refinement and manual rebuilding in COOT. The refinement statistics are found in Table 8.

TABLE 8

Data collection and refinement statistics

| | |
|---|---|
| Wavelength (Å) | 1.0000 |
| Resolution range (Å) | 47.61-3.183 (3.297-3.183) |
| Space group | P6$_1$22 |
| Unit cell (Å, deg) | 83.65 83.65 126.32 90 90 120 |
| Total reflections | 80989 (3197) |
| Unique reflections | 4667 (353) |
| Multiplicity | 17.4 (9.1) |
| Completeness (%) | 97.57 (76.08) |
| Mean I/sigma(I) | 8.69 (1.55) |
| Wilson B-factor (Å$^2$) | 50.39 |
| R-merge | 0.4146 (1.447) |
| R-meas | 0.4271 (1.516) |
| R-pim | 0.1004 (0.4227) |
| CC1/2 | 0.985 (0.651) |
| CC* | 0.996 (0.888) |
| Reflections used in refinement | 4664 (353) |
| Reflections used for R-free | 234 (18) |
| R-work | 0.1948 (0.2689) |
| R-free | 0.2500 (0.3981) |
| CC(work) | 0.957 (0.685) |
| CC(free) | 0.934 (0.389) |
| Number of non-hydrogen atoms | 986 |
| macromolecules | 981 |
| ligands | 5 |
| solvent | 0 |
| Protein residues | 130 |
| RMS(bonds) (Å) | 0.003 |
| RMS(angles) (deg) | 0.59 |
| Ramachandran favored (%) | 96.83 |
| Ramachandran allowed (%) | 3.17 |
| Ramachandran outliers (%) | 0.00 |
| Rotamer outliers (%) | 0.00 |
| Clashscore | 8.68 |
| Average B-factor (Å$^2$) | 44.41 |
| macromolecules | 44.18 |
| ligands | 88.79 |
| Number of TLS groups | 1 |

Statistics for the highest-resolution shell are shown in parentheses.

Determination of the Epitope and Paratope

The epitope of the synthetic peptide, defined as the FX activation peptide residues characterized by having a heavy atom (i.e. a non-hydrogen atom) within a distance of 4.0 Å from a heavy atom in the V$_H$H polypeptide cmpd #1, comprises the following residues from the synthetic peptide N173, P174, F175, L177, and L178 according to the corresponding FX activation peptide sequence based on consecutive numbering (SEQ ID NO:2).

The paratope of V$_H$H polypeptide cmpd #1, defined as cmpd #1 residues characterized by having a heavy atom (i.e. a non-hydrogen atom) within a distance of 4.0 Å from a heavy atom in the synthetic peptide, comprises the following residues from cmpd #1: D32, A33, M34, G35, Y37, L47, V48, A49, G50, I51, M52, N57, T58, N59, Y60, T61, K97, V99, R101 and P102 (SEQ ID NO:27) (consecutive numbering).

Construction of a homology model of the V$_H$H polypeptide cmpd #3 in complex with the synthetic peptide was performed, since cmpd #3 was used as the parental V$_H$H polypeptide sequence for rational sequence- and structure-based optimizations.

The crystal structure of cmpd #1 in complex with the synthetic peptide from the above described experiment was used as a starting model for the homology model of cmpd #3 in complex with the synthetic peptide. The amino acid sequences of cmpd #1 and cmpd #3 were aligned and amino acid residues differing between the two sequences were mutated in COOT to create a starting model for cmpd #3. This model, including cmpd #3, was pre-processed, optimised and run through a restrained minimisation in MAESTRO from SCHRÖDINGER.

The model showed the same epitope and paratope residues as described above, since sequences were identical at these positions.

Example 7: SPR Analysis of Anti-FX/Anti-FIX(a) V$_H$H Polypeptides

The purpose of the present study was to estimate the binding constants of selected anti-FX/anti-FIX(a) V$_H$H polypeptide compounds with human plasma-derived FX and Benefix® by Surface Plasmon Resonance (SPR) analysis.

Binding of purified anti-FX/FIX(a) V$_H$H polypeptide compounds to human plasma-derived FX (Haematologic Technologies Inc, USA) was probed by SPR.

Briefly, an anti-GLA-FX, prepared recombinantly as described above, was immobilised on a CM4 sensor chip or a Xantec HLC200M using standard amine coupling chemistry at pH 5. 10 nM FX (Haematologic Technologies, USA) was injected at a flow rate of 10 µL/min for 30 seconds. Subsequently 1000, 100, 10, 1, 0.1 and 0 nM of V$_H$H polypeptide compound, according to Table 9, below were injected at a flow rate of 50 µL/min for 200 seconds to allow for binding to FX followed by a flow of 10 minutes with a running buffer (10 mM HEPES, 150 mM NaCl, 5 mM CaCl$_2$), 0.05% (v/v) Surfactant P20, 1 mg/mL bovine serum albumin, pH 7.4) injection allowing for dissociation from FX. The running buffer was also used for dilution of anti-FX V$_H$H polypeptide compounds. Regeneration of the chip was achieved using a regeneration buffer consisting of 50 mM EDTA in running buffer, 30 seconds contact time, and a 30 µL/min flow rate. The binding data were collected at 25° C. and were analysed according to a 1:1 model using BiaEvaluation 4.1 supplied by the manufacturer (Biacore AB, Uppsala or Bruker Analyser).

In all cases, the binding sensograms displayed a fast on and a fast off binding kinetic profile precluding K$_D$ determination based on kinetic analysis. Therefore, the reported K$_D$ values are determined based on steady state analysis. Analysis resulted in the binding constants reported in Table 9 below.

Binding of purified anti-FX/FIX(a) V$_H$H polypeptide compounds to Benefix® (Pfizer Inc, USA) was probed by SPR. Briefly, anti-GLA-FIX, prepared recombinantly as described above, was immobilised on a CM4 sensor chip or a Xantec HLC200M using standard amine coupling chemistry at pH 5. FIX (10 nM) was injected at a flow rate of 10 µL/min for 1 minute. Subsequently 1000, 100, 10, 1, 0.1 and 0 nM of V$_H$H polypeptide compound were injected at a flow rate of 30 µL/min for 4 minutes to allow for binding to the FIX (Benefix®) followed by a flow of 5 minutes running buffer (10 mM HEPES, 150 mM NaCl, 5 mM CaCl$_2$), 0.05% (v/v) Surfactant P20, 1 mg/mL bovine serum albumin, pH 7.4) injection allowing for dissociation from FIX. The running buffer was also used for dilution of anti-FIX V$_H$H polypeptide compounds. Regeneration of the chip was achieved using a regeneration buffer consisting of 50 mM EDTA in running buffer, 30 seconds contact time, and a 30 µL/min flow rate. The binding data were collected at 25° C. and were analysed according to a 1:1 model using BiaEvaluation 4.1 supplied by the manufacturer (Biacore AB, Uppsala).

In all cases, the binding sensograms displayed a fast on and a fast off binding kinetic profile precluding K$_D$ determination based on kinetic analysis. Therefore, the reported K$_D$ values are determined based on steady state analysis.

Binding constant analysis of a series of compounds are reported in Table 9. Binding affinities of FIX were generally at low-nM $K_D$ for all compounds, while a range of compounds displayed high-nM $K_D$ for binding of FX. Target-mediated drug disposition is therefore expected to be absent for FX, while FIX interaction would be expected but limited to the required steady-state plasma concentration of the outlined compounds. Thus, the expected required plasma concentration for obtaining meaningful haemostatic coverage for the listed compounds is expected to be at low nM concentration given the high potency for the listed compounds.

TABLE 9

Estimated binding constants of selected $V_HH$ polypeptide compounds
Estimated binding constants based on steady state analysis for the interaction of selected anti-FX/anti-FIX(a) $V_HH$ polypeptide compounds with human plasma-derived FX and Benefix ® as determined by SPR analysis.

| Compound ID | FX binder $K_D$ (nM) | FIX binder $K_D$ (nM) |
|---|---|---|
| Cmpd #4 | 229 | 11.7 |
| Cmpd #5 | 199 | 2.7 |
| Cmpd #6 | 232 | 4.8 |
| Cmpd #7 | 82 | 2.3 |
| Cmpd #8 | 96 | 2.5 |
| Cmpd #9 | 70 | 1.1 |
| Cmpd #10 | 190 | 5.5 |
| Cmpd #11 | 42 | 6.4 |
| Cmpd #12 | 26 | 7.8 |
| Cmpd #13 | 300 | 2.0 |
| Cmpd #14 | 42 | 1.6 |
| Cmpd #15 | 350 | 3.0 |

Example 8: Activity of Anti-FX/Anti-FIX(a) $V_HH$ Polypeptides in Thrombin Generation Test (TGT) Assay The procoagulant activity of anti-FX/anti-FIX(a) $V_HH$ polypeptide derivatives was determined based on their ability to promote thrombin generation in the presence of procoagulant synthetic phospholipid membranes according to the principles described by Hemker et al. (Pathophysiol Haemost Thromb, 2002; 32:249-253). An emicizumab sequence identical analogue (SIA) was included for comparison. Each $V_HH$ polypeptide derivative was tested in a TGT assay using normal human platelet-poor plasma (NHP) supplemented with neutralizing anti-FVIII polyclonal antibody (hereafter named HA-PPP). TGTs in NHP (from healthy volunteers) supplemented with sheep anti-human FVIII polyclonal antibody (pAb, Haematologic Technologies Inc., VT, USA) were performed by standard calibrated automated thrombography using a 96-well plate fluorometer (Fluoroscan Ascent FL, Thermolabsystems, Helsinki, Finland). Reaction mixtures contained 36 µl NHP preincubated with 0.1 µg/ml anti-FVIII pAb, 4 µl test compound dilution (diluted in 20 mM HEPES, 140 mM NaCl, pH 7.4, 2% BSA), 10 µl of either 1 pM tissue factor (TF, pppLow, from Thrombinoscope BV, Maastricht, The Netherlands) or 1 to 8.3 U/ml human factor XIa (Enzyme Research Laboratories, IN, USA) and 10 µl FluCa Substrate (Thrombinoscope BV, Maastricht, The Netherlands). The TGT assay was calibrated using Thrombin calibrator (Thrombinoscope BV, Maastricht, The Netherlands), where 10 µl Thrombin calibrator was mixed with 36 µl NHP preincubated with 0.1 µg/ml anti-FVIII pAb, 4 µl buffer (20 mM HEPES, 140 mM NaCl, pH 7.4, 2% BSA). Generally, TGT was performed at 8 concentrations of test compound (0.1, 0.3, 1, 3, 10, 30, 100, and 300 nM, final plasma concentration, or similar) or added buffer (20 mM HEPES, 140 mM NaCl, pH 7.4, 2% BSA) only (representing control). Normal control levels in TGT were measured using NHP added buffer (20 mM HEPES, 140 mM NaCl, pH 7.4, 2% BSA) only. The TGT was allowed to proceed for a total of 60 minutes and the TGT parameter Peak Thrombin Height (nM) was analysed by Thrombinoscope software (Thrombinoscope BV). See FIG. 4 for representative titration curves for a selected test $V_HH$ polypeptide derivative, cmpd #6, and comparators emicizumab SIA and Mim8. Assessments of difference of activity level were conducted as difference in $EC_{50}$ relative to comparators, e.g. emicizumab SIA, or as difference in maximum thrombin peak height for a given $V_HH$ polypeptide compound relative to maximum thrombin peak height for emicizumab SIA. The latter approach was used for screening larger numbers of $V_HH$ polypeptide derivatives.

To boost activity of the $V_HH$ polypeptide derivatives, optimal combinations of CDR mutations were identified for generating maximum activity effect. Crystal structure models such as those described in examples 5 and 6 were used to identify important paratope residues as well as for identifying surface exposed residues suited for being substituted with cysteine, as conjugation sites, and pI-lowering substitutions to enhance bioavailability. Different linkers and different conjugation types were also investigated. In the following tables, activity profiles of a series of $V_HH$ polypeptide derivatives addressing each of these parameters are outlined and will be described individually.

In table 10, potency $EC_{50}$ values obtained from optimized $V_HH$ polypeptide derivatives that were optimized for activity boosting mutations are shown. Principal component computational and random forest algorithms were used for mutational combinations to boost activities. The $V_HH$ polypeptide cmpd #24 was the initial derivative without boosting mutations and compared to this $V_HH$ polypeptide derivative and to emicizumab SIA, an increase of up to 40-fold and up to 76-fold better potencies, respectively, were obtained among the best $V_HH$ polypeptide derivatives developed.

TABLE 10

TGT activity of $V_HH$ polypeptides derivatives, optimization of activity

| Compound ID | Protraction moiety P and $L_P$ (no. of protraction moieties) | pI | TGT activity $EC_{50}$ potency (nM) |
|---|---|---|---|
| Emicizumab SIA | — | — | 113.9 |
| Mim8 | — | — | 7.8 |
| Cmpd #4 | P3 and $L_P1$ (1) | 8.36 | 4.1 |
| Cmpd #6 | P2 and $L_P1$ (2) | 6.56 | 4.4 |
| Cmpd #7 | P2 and $L_P1$ (2) | 5.38 | 2.4 |
| Cmpd #8 | P2 and $L_P1$ (2) | 5.05 | 2.3 |
| Cmpd #9 | P2 and $L_P1$ (2) | 4.97 | 2.1 |
| Cmpd #10 | P2 and $L_P1$ (2) | 5.69 | 2.7 |
| Cmpd #11 | P2 and $L_P1$ (2) | 5.08 | 2.0 |
| Cmpd #12 | P2 and $L_P1$ (2) | 4.89 | 2.2 |
| Cmpd #13 | P2 and $L_P1$ (2) | 4.89 | 2.7 |
| Cmpd #14 | P2 and $L_P1$ (2) | 5.20 | 2.2 |
| Cmpd #15 | P2 and $L_P1$ (2) | 5.20 | 2.5 |
| Cmpd #16 | P2 and $L_P1$ (2) | 5.08 | 4.5 |
| Cmpd #17 | P2 and $L_P1$ (2) | 4.80 | 4.2 |
| Cmpd #18 | P2 and $L_P1$ (2) | 4.97 | 4.6 |
| Cmpd #19 | P2 and $L_P1$ (2) | 5.05 | 3.8 |
| Cmpd #20 | P2 and $L_P1$ (2) | 5.38 | 3.6 |
| Cmpd #21 | P2 and $L_P1$ (2) | 4.80 | 2.5 |
| Cmpd #22 | P2 and $L_P1$ (2) | 5.08 | 2.6 |
| Cmpd #24 | P3 and $L_P1$ (1) | 7.31 | 87.0 |
| Cmpd #69 | None | 8.36 | 1.5 |

In table 11, screening for optimal conjugation sites on $V_HH$ polypeptides (outside CDR1-3) that retained activity of the $V_HH$ polypeptides following substitution with cysteine (with and without conjugation with a C18 diacid fatty acid protraction moiety P3 attached via a linker $L_P1$) was performed.

A total of 95 surface-exposed sites were tested with introduction of Cys substitution. Based on consecutive numbering using cmpd #23/24 as reference (representing $V_HH$ polypeptides without any boosting mutations in CDRs), a screening for optimal site of conjugation was carried out. The following residue substitutions were tested: G27C, V28C, V29C, Q30C, P31C, G32C, S34C, L35C, R36C, S38C, A40C, S42C, R55C, Q56C, A57C, P58C, G59C, K60C, E61C, R62C, Y77C, A78C, D79C, V81C, K82C, G83C, R84C, F85C, T86C, S88C, D90C, N91C, S92C, K93C, T95C, Y97C, Q99C, M100C, N101C, S102C, L103C, R104C, P105C, E106C, D107C, T108C, G156C, V157C, V158C, Q159C, P160C, G161C, G162C, S163C, L164C, R165C, S167C, A169C, S171C, R184C, Q185C, A186C, P187C, G188C, K189C, E190C, R191C, Y206C, A207C, D208C, S209C, V210C, K211C, G212C, R213C, F214C, T215C, S217C, D219C, N220C, S221C, K222C, T224C, Y226C, Q228C, M229C, N230C, S231C, L232C, R233C, P234C, E235C, D236C, T237C and Cys introduced into a C-terminal extension.

Of these, the following 41 $V_HH$ polypeptides could be expressed using a HEK293 expression system and successfully conjugated with reagent C3 that comprises a C18 diacid protractor moiety: Q30C, P31C, Q56C, A57C, K60C, E61C, A78C, D79C, K82C, N91C, S92C, Q99C, R104C, G156C, V158C, Q159C, P160C, G161C, G162C, S163C, A169C, S171C, Q185C, A186C, P187C, G188C, K189C, E190C, A207C, D208C, S209C, V210C, T215C, S217C, D219C, N220C, S221C, K222C, S231C, R233C and Cys introduced into a C-terminal extension. These 41 $V_HH$ polypeptides with and without conjugations were tested for activity in a TGT assay. The relative activity levels, expressed as the maximum thrombin peak height of the $V_HH$ polypeptide derivative relative to the maximum thrombin peak height of emicizumab SIA, of the $V_HH$ polypeptide (derivatives) with and without conjugations are set forward in table 11. Thus, the following 9 sites were identified as optimal for introduction of a free Cys for conjugation with a protraction moiety, e.g. using C3 as a reagent, based on retained activities before and after conjugation: Cys introduced into a C-terminal extension (Cmpd #23/24), Q30C (Cmpd #25/26), V158C (Cmpd #27/28), P160C (Cmpd #29/30), G161C (Cmpd #31/32), G188C (Cmpd #33/34), E190C (Cmpd #35/36), S209C (Cmpd #37/38) and S231C (Cmpd #39/40).

TABLE 11

TGT activity of $V_HH$ polypeptides derivatives, protraction moiety conjugation site screening

| $V_HH$ polypeptide derivatives (cmpd#23/24 variants w/o C-term extension) Cys conjugation sites (consecutive numbering) | TGT activity, max. peak ratio (relative to emicizumab SIA) |
|---|---|
| Emicizumab SIA, reference control | 1.0 |
| $V_HH$ polypeptide_1, Cys in C-term linker extension SGGGGSGGGSCHHHHHH (SEQ ID NO: 23) | 1.4 |
| $V_HH$ polypeptide_1 with C18 diacid fatty acid conjugation | 1.3 |
| $V_HH$ polypeptide_2, Cys substitution Q30C | 1.8 |
| $V_HH$ polypeptide_2 with C18 diacid fatty acid conjugation | 1.5 |
| $V_HH$ polypeptide_3, Cys substitution P31C | 1.9 |

TABLE 11-continued

TGT activity of $V_HH$ polypeptides derivatives, protraction moiety conjugation site screening

| $V_HH$ polypeptide derivatives (cmpd#23/24 variants w/o C-term extension) Cys conjugation sites (consecutive numbering) | TGT activity, max. peak ratio (relative to emicizumab SIA) |
|---|---|
| $V_HH$ polypeptide_3 with C18 diacid fatty acid conjugation | 1.0 |
| $V_HH$ polypeptide_4, Cys substitution E58C | 1.9 |
| $V_HH$ polypeptide_4 with C18 diacid fatty acid conjugation | 0.5 |
| $V_HH$ polypeptide_5, Cys substitution A78C | 2.1 |
| $V_HH$ polypeptide_5 with C18 diacid fatty acid conjugation | 0.3 |
| $V_HH$ polypeptide_6, Cys substitution K82C | 1.7 |
| $V_HH$ polypeptide_6 with C18 diacid fatty acid conjugation | 0.4 |
| $V_HH$ polypeptide_7, Cys substitution N91C | 2.3 |
| $V_HH$ polypeptide_7 with C18 diacid fatty acid conjugation | 0.9 |
| $V_HH$ polypeptide_8, Cys substitution S92C | 2.3 |
| $V_HH$ polypeptide_8 with C18 diacid fatty acid conjugation | 0.7 |
| $V_HH$ polypeptide_9, Cys substitution Q99C | 2.1 |
| $V_HH$ polypeptide_9 with C18 diacid fatty acid conjugation | 1.2 |
| $V_HH$ polypeptide_10, Cys substitution R104C | 1.7 |
| $V_HH$ polypeptide_10 with C18 diacid fatty acid conjugation | 0.6 |
| $V_HH$ polypeptide_11, Cys substitution G156C | 0.1 |
| $V_HH$ polypeptide_11 with C18 diacid fatty acid conjugation | 0.2 |
| $V_HH$ polypeptide_12, Cys substitution V158C | 1.6 |
| $V_HH$ polypeptide_12 with C18 diacid fatty acid conjugation | 1.4 |
| $V_HH$ polypeptide_13, Cys substitution Q159C | 1.9 |
| $V_HH$ polypeptide_13 with C18 diacid fatty acid conjugation | 1.4 |
| $V_HH$ polypeptide_14, Cys substitution P160C | 2.0 |
| $V_HH$ polypeptide_14 with C18 diacid fatty acid conjugation | 1.9 |
| $V_HH$ polypeptide_15, Cys substitution G161C | 1.8 |
| $V_HH$ polypeptide_15 with C18 diacid fatty acid conjugation | 1.6 |
| $V_HH$ polypeptide_16, Cys substitution G162C | 1.9 |
| $V_HH$ polypeptide_16 with C18 diacid fatty acid conjugation | 1.3 |
| $V_HH$ polypeptide_17, Cys substitution S163C | 1.8 |
| $V_HH$ polypeptide_17 with C18 diacid fatty acid conjugation | 1.4 |
| $V_HH$ polypeptide_18, Cys substitution A169C | 2.0 |
| VHV$_H$ H polypeptide_18 with C18 diacid fatty acid conjugation | 1.0 |
| $V_HH$ polypeptide_19, Cys substitution S171C | 2.1 |
| $V_HH$ polypeptide_19 with C18 diacid fatty acid conjugation | 0.8 |
| $V_HH$ polypeptide_20, Cys substitution Q185C | 1.1 |
| $V_HH$ polypeptide_20 with C18 diacid fatty acid conjugation | 0.3 |
| $V_HH$ polypeptide_21, Cys substitution A186C | 1.0 |
| $V_HH$ polypeptide_21 with C18 diacid fatty acid conjugation | 0.4 |
| $V_HH$ polypeptide_22, Cys substitution P187C | 2.2 |
| $V_HH$ polypeptide_22 with C18 diacid fatty acid conjugation | 1.6 |
| $V_HH$ polypeptide_23, Cys substitution G188C | 2.0 |
| $V_HH$ polypeptide_23 with C18 diacid fatty acid conjugation | 1.8 |
| $V_HH$ polypeptide_24, Cys substitution K189C | 1.7 |
| $V_HH$ polypeptide_24 with C18 diacid fatty acid conjugation | 0.4 |
| $V_HH$ polypeptide_25, Cys substitution E190C | 1.8 |
| $V_HH$ polypeptide_25 with C18 diacid fatty acid conjugation | 1.5 |
| $V_HH$ polypeptide_26, Cys substitution A207C | 1.9 |
| $V_HH$ polypeptide_26 with C18 diacid fatty acid conjugation | 1.4 |

TABLE 11-continued

TGT activity of V$_H$H polypeptides derivatives, protraction moiety conjugation site screening

| V$_H$H polypeptide derivatives (cmpd#23/24 variants w/o C-term extension) Cys conjugation sites (consecutive numbering) | TGT activity, max. peak ratio (relative to emicizumab SIA) |
|---|---|
| V$_H$H polypeptide_27, Cys substitution D208C | 2.3 |
| V$_H$H polypeptide_27 with C18 diacid fatty acid conjugation | 1.5 |
| V$_H$H polypeptide_28, Cys substitution S209C | 1.9 |
| V$_H$H polypeptide_28 with C18 diacid fatty acid conjugation | 1.7 |
| V$_H$H polypeptide_29, Cys substitution V210C | 1.9 |
| V$_H$H polypeptide_29 with C18 diacid fatty acid conjugation | 1.5 |
| V$_H$H polypeptide_30, Cys substitution T215C | 1.9 |
| V$_H$H polypeptide_30 with C18 diacid fatty acid conjugation | 1.2 |
| V$_H$H polypeptide_31, Cys substitution S217C | 1.8 |
| V$_H$H polypeptide_31 with C18 diacid fatty acid conjugation | 1.2 |
| V$_H$H polypeptide_32, Cys substitution D219C | 1.8 |
| V$_H$H polypeptide_32 with C18 diacid fatty acid conjugation | 1.0 |
| V$_H$H polypeptide_33, Cys substitution N220C | 2.1 |
| V$_H$H polypeptide_33 with C18 diacid fatty acid conjugation | 0.8 |
| V$_H$H polypeptide_34, Cys substitution S221C | 1.9 |
| V$_H$H polypeptide_34 with C18 diacid fatty acid conjugation | 0.7 |
| V$_H$H polypeptide_35, Cys substitution K222C | 1.9 |
| V$_H$H polypeptide_35 with C18 diacid fatty acid conjugation | 1.1 |
| V$_H$H polypeptide_36, Cys substitution S231C | 1.9 |
| V$_H$H polypeptide_36 with C18 diacid fatty acid conjugation | 1.9 |
| V$_H$H polypeptide_37, Cys substitution R233C | 1.9 |
| V$_H$H polypeptide_37 with C18 diacid fatty acid conjugation | 1.4 |
| V$_H$H polypeptide_38, Cys substitution Q56C | 1.1 |
| V$_H$H polypeptide_38 with C18 diacid fatty acid conjugation | 0.3 |
| V$_H$H polypeptide_39, Cys substitution A57C | 0.9 |
| V$_H$H polypeptide_39 with C18 diacid fatty acid conjugation | 0.4 |
| V$_H$H polypeptide_40, Cys substitution K60C | 1.7 |
| V$_H$H polypeptide_40 with C18 diacid fatty acid conjugation | 0.4 |
| V$_H$H polypeptide_41, Cys substitution D79C | 1.7 |
| V$_H$H polypeptide_41 with C18 diacid fatty acid conjugation | 0.7 |

Testing of different linkers L$_{1-2}$ fused recombinantly between the two anti-FIX and anti-FX V$_H$H fragments was performed to optimize composition (see table 12). The relative activity levels, expressed as the maximum thrombin peak height of the $V_H$H polypeptide relative to the maximum thrombin peak height of emicizumab SIA, of the $V_H$H polypeptides are set forward in table 12. From these data, $V_H$H polypeptides with linkers of hydrophobic composition generally displayed the highest relative activities, whereas $V_H$H polypeptides with linkers of acidic or hydrophilic composition displayed the lowest activities. $V_H$H polypeptides with linkers of mixed composition composed of QAPGQA, GQAPGQ or similar showed intermediate relative activities. The optimal linker composition would preferably contain both hydrophilic and hydrophobic amino acids, thus the QAPGQA linker, for example, was investigated further for chemical stability using MS analysis showing high stability under accelerated stress conditions at 37° C. for two weeks in an isotonic buffer and neutral pH.

Thus, a ratio of hydrophobic to hydrophilic amino acids of “40 to 60%” to “60 to 40%” is preferred. The indicated $V_H$H polypeptide all included the same set of activity boosting CDR mutations, but different set of pI-lowering mutations outside CDRs.

TABLE 12

TGT activity of $V_H$H polypeptides sequence with different linker $L_{1-2}$ characteristics

| $V_H$H polypeptide ID | Linker ($L_{1-2}$) sequence | TGT activity, max. peak ratio (relative to emicizumab SIA) |
|---|---|---|
| Emicizumab SIA | | 1.0 |
| Cmpd #41 | QAPGQA | 5.2 |
| Cmpd #42 | GIGIGIGIGI | 5.5 |
| Cmpd #43 | GTGTGTGTGT | 3.7 |
| Cmpd #44 | GVGVGVGVGV | 5.7 |
| Cmpd #45 | GQAPGQ | 4.9 |
| Cmpd #46 | GGGGSGGGS | 5.0 |
| Cmpd #47 | QAPGQA | 5.4 |
| Cmpd #48 | GLGLGLGLGL | 7.0 |
| Cmpd #49 | GTGTGTGTGT | 4.4 |
| Cmpd #50 | GVGVGVGVGV | 5.6 |
| Cmpd #51 | GGGGSGGGS | 4.1 |

TABLE 12-continued TGT activity of V$_H$H polypeptides sequence with different linker L$_{1-2}$ characteristics

| V$_H$H polypeptide ID | Linker (L$_{1-2}$) sequence | TGT activity, max. peak ratio (relative to emicizumab SIA) |
|---|---|---|
| Cmpd #52 | QAPGQA | 4.9 |
| Cmpd #53 | GEGEGEGEGE | 3.1 |
| Cmpd #54 | GLGLGLGLGL | 5.6 |
| Cmpd #55 | GTGTGTGTGT | 4.9 |
| Cmpd #56 | GVGVGVGVGV | 5.6 |
| Cmpd #57 | GQAPGQ | 6.9 |

Example 9: Formulation of Anti-FX/Anti-FIX(A) V$_H$H Polypeptide Derivatives with SNAC and NAM in Dosage Form Suitable for Peroral Administration To prepare for oral studies using liquid formulations with sodium N-(8-[2-hydroxybenzoyl] amino) caprylate (SNAC) and nicotinamide (NAM) as excipients, the following procedure was followed. SNAC was weighed to obtain a concentration of 200 mg/ml, NAM was weighed to obtain a concentration of 1 M, HEPES buffer was weighed to obtain a final concentration of 5 mM. Powders were transferred to a glass vial and MilliQ-H$_2$O was added accordingly. The solution was stirred with a magnetic stirrer until SNAC, NAM and magnesium stearate were dissolved. pH was measured and adjusted to pH 8 with 2 M NaOH. Thus, batches of purified and conjugated V$_H$H polypeptide derivatives of 2-5 mg/ml were liquid formulated with 200 mg/ml SNAC and with 1 M NAM final concentration.

To prepare for oral studies using tablets with SNAC and NAM, the following procedure was followed. Batches of purified V$_H$H polypeptide (derivatives) with or without fatty acid protractor conjugations were buffer exchanged into MilliQ-H$_2$O and pH adjusted to 8.0 using either 0.1 M NaOH or 0.1 M formic acid. V$_H$H polypeptide (derivatives) dissolved in MilliQ-H$_2$O were at concentrations from 0.5 to 4 mg/ml. Spray drying of V$_H$H polypeptide (derivatives) was conducted using Mini Spray Dryer B290 (BUCHI) with pump setting 5-6, feed flow: 2 ml/min, inlet temp: 80-85° C., outlet temp: 45-50° C., nozzle: 1.5 mm and aspiration: 100%.

To prepare tablets, powder was mixed to obtain desired compositions. The following tablet formulations were prepared.

Formulation #1
V$_H$H polypeptide (derivative): 10-20 mg
SNAC: 300 mg
NAM: 0 mg
Magnesium stearate: 5.5 mg Formulation #2
V$_H$H polypeptide derivative: 10-20 mg
SNAC: 300 mg
NAM: 200 mg
Magnesium stearate: 5.5 mg Formulation #3
V$_H$H polypeptide derivative: 20 mg
SNAC: 150 mg NAM: 100 mg
Magnesium stearate: 1.25 mg Powders mixed were weighed and punched for homogenic tablet using Kilian Style One (Romaco) with punch setting to simulate a rotary press.

Example 10: Peroral and Intravenous Pharmacokinetic Study in Rat Using Anti-FX/Anti-FIX(A) V$_H$H Polypeptides Derivatives with Different PI-CHANGING MUTATIONS The purpose of the present study was to investigate the effect of pI-changing mutations in anti-FX/FIX(a) V$_H$H polypeptide derivatives on pharmacokinetic parameters such as oral bioavailability.

Liquid formulations of anti-FX/FIX(a) V$_H$H polypeptide derivatives were dosed intravenously (IV) (IV formulation: 20 mM Hepes, 150 mM NaCl, pH 7.4) or prepared according to Example 9 and administered by oral gavage to parallel groups of Sprague Dawley rats acclimated at least one week in-house prior to study and kept in group cages with ad libitum access to standard food and water. Rats for oral dosing were fasted, with free access to water, in grid-bottomed cages from approx. 2 pm on the day prior to dosing (for a total of 18 hours). On the day of dosing, all rats were acclimated in the procedure room for 30 minutes.

Blood samples were collected immediately prior to dosing and subsequently at a number of different post-dose time points. Peroral (PO) dosed animals were kept fasted in grid-bottomed cages until 4 hrs post dosing. Plasma concentrations of V$_H$H polypeptide derivatives were measured using a gamma-Glu-based immunoassay, in which an anti-V$_H$H antibody (Novo Nordisk, Denmark) and an anti-gamma-Glu (Novo Nordisk, Denmark) towards the protraction moiety of the test molecule was used. Here, 96-well MaxiSorp plates (Nunc, 439454) were coated with 2 μg/ml anti-gamma-Glu antibody, washed and blocked using PBS; 0.05% tween20; 1% BSA; pH 7.4. After a wash step, compound specific calibrator (0, 2.7, 8.2, 24.7, 74, 222, 667, 2000 pM) in 1% rat EDTA plasma and rat EDTA plasma samples in a minimal dilution of 100× were incubated on the plate, where the V$_H$H polypeptide derivative was captured via the gamma-Glu protraction moiety. After an additional wash step, a biotinylated in-house V$_H$H specific antibody was added to the plate (0.5 nM) to make up the sandwich ELISA. After a final wash step, horseradish peroxidase (HRP)-streptavidin was added to the plate as the detection reagent. The amount of biotin labelled antibody bound to the $V_HH$ polypeptide derivative was detected following addition of a chromogenic substrate (e.g., TMB (3,3',5,5'-tetramethylbenzidine). Optical density was measured using a Spectrometer (e.g. a SpectraMax® M2 spectrometer (Molecular Devices)). The response was proportional to the concentration of peroxidase, which again was proportional to the concentration of the $V_HH$ polypeptide derivative. Based on these exposure data, non-compartmental pharmacokinetic parameters were calculated using either Phoenix WinNonlin or the open source statistical analysis software R (package 'NonCompart').

The following pI-lowering substitutions T28D, K43Q, K65Q, N84D, R148Q, N159D, K172Q, K194Q and N213D (based on consecutive numbering using cmpd #4 as template) introduced at surface exposed residues outside the CDRs, were tested in different combinations (leading to $V_HH$ polypeptide derivatives cmpd #59 to 64 and cmpd #5) and compared to non-pI adjusted $V_HH$ polypeptide derivative cmpd #4.

Results are given in tables 13 and 14 below for $V_HH$ derivatives and show an effect of lowering pI on peroral bioavailability.

Lowering of pI from approx. 8.36 to 5.85 increased bioavailability 5- to 10-fold (see table 13).

No effect of pI lowering on half-life was observed (see table 14).

Example 11: Intravenous Pharmacokinetic Study in Rat: Anti-FX/Anti-FIX(A) $V_HH$ Polypeptide (Derivatives) with Different Protractors The purpose of the present study was to investigate the effect of different protractors on pharmacokinetic parameters such as half-life on $V_HH$ polypeptide derivatives.

Liquid formulations of anti-FX/FIX(a) $V_HH$ polypeptide derivatives prepared according to Example 9 were dosed intravenously (IV) to parallel groups of Sprague Dawley rats; acclimated at least one week in-house prior to study and kept in group cages with ad libitum access to standard food and water. Rats for oral dosing were fasted, with free access to water, in grid-bottomed cages from app. 2 pm on the day prior to dosing (for a total of 18 hours). On the day of dosing, all rats were acclimated in the procedure room for 30 minutes. Blood samples were collected immediately prior to dosing and subsequently at a number of different post-dose time points. Plasma concentrations of $V_HH$ polypeptide (derivatives) were measured using a His-tag- or gamma-Glu-based immunoassay, in which an anti-$V_HH$ antibody (Novo Nordisk) towards the $V_HH$ polypeptide derivative together with an anti-His-tag antibody (R&D systems, MAB050) towards His-tag fused to the test molecule or an anti-gamma-Glu (Novo Nordisk, Denmark) towards the protraction moiety of the test molecule were used. The two immunoassay setups gave similar sensitivities, and the latter was used when the $V_HH$ polypeptide compound had no His-tag fused to the molecule. 96-well MaxiSorp plates (Nunc, 439454) were coated with the His-tag or the anti-gamma-Glu antibody, washed and blocked using PBS; 0.05% tween20; 1% BSA; pH 7.4. After a wash step, derivative specific calibrator (0, 2.7, 8.2, 24.7, 74, 222, 667, 2000 pM) in 1% rat EDTA plasma and rat EDTA plasma samples in a minimal dilution of 100× were incubated on the plate, where the $V_HH$ polypeptide derivative was captured via its His-tag or the gamma-Glu protraction moiety. After an additional wash step, a biotinylated in-house $V_HH$ specific antibody was added to the plate (0.5 nM) to make up the sandwich ELISA. After a final wash step, horseradish peroxidase (HRP)-streptavidin was added to the plate as the detection reagent. The amount of biotin labelled antibody bound to the $V_HH$ polypeptide derivative was detected following addition of a chromogenic substrate (e.g., TMB (3,3',5,5'-tetramethylbenzidine). Optical density readings were measured using a Spectrometer (e.g. a SpectraMax® M2 spectrometer (Molecular Devices)). The response was proportional to the concentration of peroxidase, which again was proportional to the concentration of the $V_HH$ polypeptide derivative. Based on these exposure data, non-compartmental pharmacokinetic parameters were calculated using

TABLE 13

Oral bioavailability data of $V_HH$ polypeptides derivatives with engineered pI mutations tested in PO rat model

| Derivative ID | Protractor, conjugation site | pI | N (PO group) | PO Dose (nmol/kg) | PO Bioavailability (%) |
|---|---|---|---|---|---|
| Cmpd #4 | C18 diacid, C-term Cys conjugation | 8.36 | 6 | 338 | 0.02 |
| Cmpd #59 | C18 diacid, C-term Cys conjugation | 6.57 | 7 | 214-230 | 0.04 |
| Cmpd #5 | C18 diacid, C-term Cys conjugation | 6.56 | 7 | 215-233 | 0.07 |
| Cmpd #60 | C18 diacid, C-term Cys conjugation | 6.42 | 7 | 166-167 | 0.14 |
| Cmpd #61 | C18 diacid, C-term Cys conjugation | 6.42 | 7 | 166-167 | 0.10 |
| Cmpd #62 | C18 diacid, C-term Cys conjugation | 6.09 | 7 | 190-208 | 0.19 |
| Cmpd #63 | C18 diacid, C-term Cys conjugation | 6.09 | 7 | 166-167 | 0.15 |
| Cmpd #64 | C18 diacid, C-term Cys conjugation | 5.85 | 6 | 338 | 0.12 |

TABLE 14

PK data of $V_HH$ polypeptide derivatives with engineered pI mutations tested in IV rat model

| Derivative ID | Protractor, conjugation site | pI | N (IV group) | IV Dose (nmol/kg) | IV MRTHL* (Days) |
|---|---|---|---|---|---|
| Cmpd #4 | C18 diacid, C-term Cys conjugation | 8.36 | 3 | 6.7 | 0.51 |
| Cmpd #59 | C18 diacid, C-term Cys conjugation | 6.57 | 3 | 6.6 | 0.51 |
| Cmpd #5 | C18 diacid, C-term Cys conjugation | 6.56 | 3 | 6.6 | 0.53 |
| Cmpd #60 | C18 diacid, C-term Cys conjugation | 6.42 | 3 | 6.6 | 0.57 |
| Cmpd #61 | C18 diacid, C-term Cys conjugation | 6.42 | 3 | 6.6 | 0.57 |
| Cmpd #62 | C18 diacid, C-term Cys conjugation | 6.09 | 3 | 6.6 | 0.72 |
| Cmpd #63 | C18 diacid, C-term Cys conjugation | 6.09 | 3 | 6.6 | 0.43 |
| Cmpd #64 | C18 diacid, C-term Cys conjugation | 5.85 | 3 | 6.7 | 0.48 |

*MRTHL: Mean residence time terminal half-life. MRTHL is calculated as MRT*ln(2).

either Phoenix WinNonlin or the open source statistical analysis software R (package 'NonCompart').

Results for $V_HH$ polypeptide derivatives with different protractor types are shown in table 15 below. Results show the effect of using different fatty acids and albumin-binding peptides as protractor on median residence time terminal half-life (MRTHL).

Increased half-life compared to non-protracted polypeptides was observed for $V_HH$ polypeptide derivatives having C18, C20 and tetrazole fatty acid side-chain conjugations (cmpd #66, cmpd #67 and cmpd #68: 3 to 4-fold increase), as well as for $V_HH$ polypeptide derivatives with albumin-binding peptide protractor fusions (cmpd #70, cmpd #71, cmpd #72 and cmpd #73: 1.9 to 3.6-fold increase) with an optimal effect of using a 30 residues long GlySer $L_P$ linker fused C-terminally between the albumin-binder peptide and the $V_HH$ polypeptide. The $V_HH$ polypeptide derivative, cmpd #65, with a short C12 fatty acid showed the lowest half-life. This indicates that to obtain an optimal protraction of $V_HH$ polypeptide derivatives, for prolonged half-life circulation, a fatty acid longer than C12 is preferable (such as e.g. C16, C18 or C20).

TABLE 15

PK data of $V_HH$ polypeptides with different protractors tested in IV rat model

| Derivative ID | Protractor and conjugation site | pI | N (IV group) | IV Dose (nmol/kg) | IV MRTHL* (Days) |
|---|---|---|---|---|---|
| Cmpd #64 | No protractor | 7.11 | 5 | 6.5 | 0.19 |
| Cmpd #65 | C12 diacid, C-term Cys conjugation | 7.74 | 5 | 6.6 | 0.11 |
| Cmpd #66 | C18 diacid, C-term Cys conjugation | 7.74 | 5 | 6.6 | 0.63 |
| Cmpd #67 | C20 diacid, C-term Cys conjugation | 7.74 | 5 | 6.6 | 0.75 |
| Cmpd #68 | Tetrazole diacid, C-term Cys conjugation | 7.74 | 5 | 6.6 | 0.71 |
| Cmpd #69 | No protractor | 8.36 | 3 | 6.9 | 0.13 |
| Cmpd #4 | C18 diacid, C-term Cys conjugation | 8.36 | 3 | 6.7 | 0.51 |
| Cmpd #70 | Albumin-binder peptide, 10-GlySer linker, N-term fusion | 7.11 | 2 | 6.7 | 0.36 |
| Cmpd #71 | Albumin-binder peptide, 30-GlySer linker, N-term fusion | 7.11 | 2 | 6.7 | 0.34 |
| Cmpd #72 | Albumin-binder peptide, 10-GlySer linker, C-term fusion | 7.18 | 2 | 6.7 | 0.36 |
| Cmpd #73 | Albumin-binder peptide, 30-GlySer linker, C-term fusion | 7.18 | 2 | 6.7 | 0.70 |

*MRTHL: Mean residence time terminal half-life. MRTHL is calculated as MRT*ln(2).

Example 12: Peroral and Intravenous Pharmacokinetic Study in Dog: Anti-FX/Anti-FIX(A) $V_HH$ Polypeptide (Derivatives) Formulated with SNAC and NAM The purpose of the present study was to investigate the effect of fatty acid protraction on half-life, and if lowering of pI leads to enhanced oral bioavailability.

Appropriate formulations of anti-FX/FIX(a) $V_HH$ polypeptide (derivatives) were dosed intravenously or prepared as tablets and dosed perorally, respectively, to groups of Beagle dogs. The dogs were dosed in the morning after overnight fasting and kept fasting for 3-5 hours after a single dosing. In a subsets of oral studies the dogs were given a s.c. dosing of approximately 3 nmol/kg of glucagon 10 min prior to oral dosing. Blood samples were collected immediately prior to dosing and subsequently at a number of different post-dose time points. Plasma concentrations of $V_HH$ polypeptides were measured using a His-tag-based or gamma-Glu-linker based immunoassay, in which an anti-$V_HH$ antibody (Novo Nordisk, Denmark) towards the $V_HH$ polypeptide together with an anti-His-tag antibody (R&D systems, MAB050) towards His-tag fused to the test molecule or an anti-gamma-Glu (Novo Nordisk, Denmark) towards the protraction moiety of the test molecule were used. The two immunoassay setups gave similar sensitivities, and the latter was used when the $V_HH$ polypeptide compound had no His-tag fused to the molecule. 96-well MaxiSorp plates (Nunc, 439454) were coated with the antibody, washed and blocked using PBS; 0.05% tween20; 1% BSA; pH 7.4. After a wash step, compound specific calibrator (0, 2.7, 8.2, 24.7, 74, 222, 667, 2000 pM) in 1% dog EDTA plasma and dog EDTA plasma samples in a minimal dilution of 100× were incubated on the plate, where the $V_HH$ polypeptide compound was captured via its His-tag or the gamma-Glu linker motif. After an additional wash step, a biotinylated in-house $V_HH$ specific antibody was added to the plate (0.5 nM) to make up the sandwich ELISA. After a final wash step, horseradish peroxidase (HRP)-streptavidin was added to the plate as the detection reagent. The amount of biotin labelled antibody bound to the $V_HH$ polypeptide compound was detected following addition of a chromogenic substrate (e.g., TMB (3,3',5,5'-tetramethylbenzidine). Optical density readings were measured using a Spectrometer (e.g. a SpectraMax® M2 spectrometer (Molecular Devices)). The response was proportional to the concentration of peroxidase, which again was proportional to the concentration of the $V_HH$ polypeptide compound. Based on these exposure data, non-compartmental pharmacokinetic parameters were calculated using either Phoenix WinNonlin or the open source statistical analysis software R (package 'NonCompart'). § indicate a s.c. dosing of approximately 3 nmol/kg of glucagon 10 min prior to oral dosing.

Results are given in tables 16 and 17 below for three C18 diacid conjugated $V_HH$ polypeptide derivatives and confirms a) an effect of fatty acid protraction on half-life, and
b) that lowering of pI leads to enhanced oral bioavailability.

Thus, the observed half-lives in dog increased by 370 to 710-fold when the $V_HH$ polypeptide derivatives were conjugated with the indicated fatty acid as compared to a non-protracted compound. The compound cmpd #6 with two C16 diacid fatty acid conjugations in a C-terminal linker displayed the highest increase in half-life of approx. 7.6 days.

In dog, the SNAC:NAM formulation increased the oral bioavailability 2- to 8-fold compared to SNAC formulation alone. Thus, adding NAM to the oral formulation had a pronounced effect enabling the oral bioavailability to and above a level that is clinically relevant i.e. approx. 0.1%.

Overall considering the potency, the mean residence time and the oral bioavailability, the $V_HH$ polypeptide derivatives as disclosed herein would be expected to be useful in the treatment of haemophilia A with or without inhibitors and acquired haemophilia A, when administered perorally.

TABLE 16

Oral bioavailability data of V$_H$H polypeptide (derivatives) with engineered pI mutations and fatty acid side-chain conjugations tested in dog model

| Derivative ID | Protractor, conjugation site | pI | N (PO group) | PO Formulation | PO Dose (nmol/kg) | PO Bioavailability (%) |
|---|---|---|---|---|---|---|
| Cmpd #4 | C18 diacid, C-term Cys conjugation | 8.36 | 7 | "Formulation #1" | 83-216 | 0.02 |
| Cmpd #74[§] | No protractor | 7.74 | 6 | "Formulation #1" | 86 | 0.05 |
| Cmpd #61 | C18 diacid, C-term Cys conjugation | 6.09 | 7 | "Formulation #2" | 114-225 | 0.16 |
| Cmpd #63 | C18 diacid, C-term Cys conjugation | 5.85 | 7 | "Formulation #2" | 132-249 | 0.13 |
| Cmpd #6[§] | x2 C16 diacid, C-term Cys conjugation | 5.61 | 5 | "Formulation #2" | 99-152 | 0.09 |
| Cmpd #15[§] | x2 C16 diacid, C-term Cys conjugation | 4.89 | 6 | "Formulation #3" | 54-71 | 0.24 |

TABLE 17

PK data of V$_H$H polypeptides with engineered pI mutations and fatty acid side-chain conjugations tested in IV dog model

| Derivative ID | Protractor, conjugation site | pI | N (IV group) | IV Dose (nmol/kg) | IV MRTHL* (Days) |
|---|---|---|---|---|---|
| Cmpd #4 | C18 diacid, C-term Cys conjugation | 8.36 | 2 | 6.5-6.9 | 3.7 |
| Cmpd #74 | No protractor | 7.74 | 3 | 1.9-2.0 | <0.01 |
| Cmpd #61 | C18 diacid, C-term Cys conjugation | 6.09 | 2 | 6.5-6.6 | 4.5 |
| Cmpd #63 | C18 diacid, C-term Cys conjugation | 5.85 | 2 | 6.6-6.7 | 4.5 |
| Cmpd #6 | x2 C16 diacid, C-term Cys conjugations | 5.61 | 3 | 1.7-2.3 | 7.1 |
| Cmpd #15 | x2 C16 diacid, C-term Cys conjugation | 4.89 | 2 | 2.6 | 4.1 |

*MRTHL: Mean residence time terminal half-life. MRTHL is calculated as MRT*ln(2).

Example 13: Intravenous Pharmacokinetic Study in Pig: C18 Conjugated Anti-FX/Anti-FIX(A) V$_H$H Polypeptide (Derivatives)

The purpose of the present study was to investigate the pharmacokinetic effect of V$_H$H polypeptide (derivatives) with and without a C18 diacid protractor group.

Appropriate formulations of anti-FX/FIX(a) V$_H$H polypeptide (derivatives) were dosed intravenously (IV) and subcutaneously (SC), respectively, to groups of minipigs (Sus scrofa domesticus). Blood samples were collected immediately prior to dosing and subsequently at a number of different post-dose time points. Plasma concentrations of V$_H$H polypeptide (derivatives) were measured using a His-tag-based or gamma-Glu-based immunoassay, in which an anti-V$_H$H antibody (Novo Nordisk) towards the V$_H$H polypeptide (derivative) together with an anti-His-tag antibody (R&D systems, MAB050) towards His-tag fused to the test molecule or an anti-gamma-Glu (Novo Nordisk, Denmark) towards the protraction moiety of the test molecule were used. The two immunoassay setups gave similar sensitivities, and the latter was used when the V$_H$H polypeptide compound had no His-tag fused to the molecule. 96-well MaxiSorp plates (Nunc, 439454) were coated with the His-tag or the anti-gamma-Glu antibody, washed and blocked using PBS; 0.05% tween20; 1% BSA; pH 7.4. After a wash step, derivative specific calibrator (0, 2.7, 8.2, 24.7, 74, 222, 667, 2000 pM) in 1% pig EDTA plasma and pig EDTA plasma samples in a minimal dilution of 100x were incubated on the plate, where the V$_H$H polypeptide derivative was captured via its His-tag or the gamma-Glu protraction moiety. After an additional wash step, a biotinylated in-house V$_H$H specific antibody was added to the plate (0.5 nM) to make up the sandwich ELISA. After a final wash step, horseradish peroxidase (HRP)-streptavidin was added to the plate as the detection reagent. The amount of biotin labelled antibody bound to the V$_H$H polypeptide derivative was detected following addition of a chromogenic substrate (e.g., TMB (3,3',5,5'-tetramethylbenzidine). Optical density readings were measured using a Spectrometer (e.g. a SpectraMax® M2 spectrometer (Molecular Devices)). The response was proportional to the concentration of peroxidase, which again was proportional to the concentration of the V$_H$H polypeptide derivative. Non-compartmental pharmacokinetic parameters were calculated using the open source statistical analysis software R (package 'NonCompart'). Results are shown in table 18 below for V$_H$H polypeptides with and without a fatty acid protractor confirming an effect on half-life of fatty acid protractor conjugations for half-life extension as observed in examples 11, 12 and 13.

Thus, the observed half-lives in pig increased approx. 15 to 20-fold when the V$_H$H polypeptides were conjugated with a fatty acid C18 diacid protractor compared to non-protracted V$_H$H compounds.

TABLE 18

PK data of V$_H$H polypeptides with engineered pI mutations and fatty acid protractor conjugations tested in pig model.

| Derivative ID | Protractor, conjugation site | pI | N (IV or SC group) | Dose (nmol/kg) | IV MRTHL* (Days) |
|---|---|---|---|---|---|
| Cmpd #75 | No protractor | 8.95 | 3 (SC) | 30 | 0.59 |
| Cmpd #75 | No protractor | 8.95 | 2 (IV) | 30 | 0.24 |
| Cmpd #4 | C18 diacid, C-term Cys | 8.36 | 3 (IV) | 5.3 | 3.6 |
| Cmpd #63 | C18 diacid, C-term Cys | 5.85 | 3 (IV) | 4.8 | 4.7 |

* MRTHL: Mean residence time terminal half-life. MRTHL is calculated as MRT*ln(2).

Example 14: Pharmacodynamic Effect of Optimized Anti-FX/Anti-FIX(A) Polypeptide Derivatives in Mouse Tail-Vein Transection (TVT) Bleeding Model In vivo efficacy was tested in HA mouse models of moderate bleeding. In the TVT model, it has previously been shown that FVIII administration reduces bleeding to the same level observed for wild-type mice. To overcome the lack of mouse cross-species reactivity of compounds testes, HA mice were supplemented with human FIX and FX before the bleeding experiments. At the end of the bleeding period, total blood loss was determined by spectrophotometric haemoglobin measurement. Plasma levels of indicated V$_H$H polypeptide derivatives and FIX were quantified by a luminescent oxygen channelling assay using anti-$V_HH$ (Novo Nordisk, Denmark) and anti-gammaGlu-linker antibodies (Novo Nordisk, Denmark) and anti-FIX antibodies (LS-B7226, LSBio, and FIX-2F24, in-house clone), respectively. FX levels were quantified by a commercial FX ELISA (KSP134, Nordic Biosite). From dose—response studies with the indicated $V_HH$ polypeptide derivatives, EC50-values were determined by fitting of data to a three-parameter inverse log(dose) response equation with shared plateau values (>0). Automatic outlier elimination with a 1% ROUT coefficient was applied and sum of squares was weighted by (blood-loss) using GraphPad Prism software (version 9.0.1).

Dose-response studies showed a significant reduction in blood loss, reaching blood loss levels observed in wild-type mice for the tested $V_HH$ polypeptide derivatives compared to vehicle group and wild-type, non-haemophilic group, respectively, as shown in table 19. Estimates of $EC_{50}$ effective dose ranges are presented in table 20 showing high potency, as 50% effect were observed at low nmole per kg dosage for all 3 compounds tested.

TABLE 19

Effect of anti-FX/anti-FIX(a) polypeptide derivatives in TVT bleeding mouse model

| Derivative #/dose (µmole/kg) | Bleeding time (min, AVE ± SD, n = 6) | Blood loss (nmole, AVE ± SD, n = 6) |
|---|---|---|
| Vehicle | 21.0 ± 3.5 | 4594 ± 1326 |
| Wild-type, non-haemophilic | 5.4 ± 0.4 | 879 ± 438 |
| Cmpd#4 | | |
| 0.003 µmole/kg | 25.8 ± 3.0 | 6979 ± 1281 |
| 0.005 µmole/kg | 23.2 ± 6.7 | 6204 ± 1496 |
| 0.006 µmole/kg | 19.7 ± 11.2 | 5232 ± 3698 |
| 0.010 µmole/kg | 13.9 ± 8.7 | 2973 ± 2973 |
| 0.013 µmole/kg | 11.0 ± 8.6 | 2264 ± 2264 |
| Cmpd#6 | | |
| 0.003 µmole/kg | 26.4 ± 4.4 | 7445 ± 1053 |
| 0.005 µmole/kg | 18.4 ± 6.7 | 5143 ± 1861 |
| 0.006 µmole/kg | 11.8 ± 9.6 | 3771 ± 3374 |
| 0.010 µmole/kg | 19.2 ± 10.9 | 4532 ± 3277 |
| 0.013 µmole/kg | 7.1 ± 4.3 | 1024 ± 1050 |
| Cmpd#15 | | |
| 0.0065 µmole/kg | 9.5 ± 7.3 | 2408 ± 2391 |
| 0.0065 µmole/kg | 14.8 ± 8.3 | 4545 ± 2417 |
| 0.0097 µmole/kg | 7.0 ± 4.7 | 1223 ± 1163 |
| 0.0129 µmole/kg | 6.9 ± 1.7 | 1438 ± 798 |

TABLE 20

$EC_{50}$ estimates of anti-FX/anti-FIX(a) polypeptide derivatives from TVT bleeding mouse model

| Derivative ID | Bleeding time $EC_{50}$ (µmole/kg) | Blood loss $EC_{50}$ (µmole/kg) |
|---|---|---|
| Cmpd#4 | 0.0097 | 0.0094 |
| Cmpd#6 | 0.0077 | 0.0087 |
| Cmpd#15 | 0.0047 | 0.0060 |

Example 15: Ex Vivo Activity Determination of an Optimized Anti-FX/Anti-FIX(A) $V_HH$ Polypeptide Derivative Post Peroral Dosing Following a pharmacokinetic (PK) study in wild-type dogs from example 12 to characterize PO dosing of cmpd #6, chromogenic activity was determined at two separate time points at 30 minutes and 90 minutes post dosing. The measured FVIII-mimicking, chromogenic activity was compared to the plasma exposure of cmpd #6 to determine the fraction of active $V_HH$ polypeptide derivative in serum post PO dosing.

Chromogenic activity of cmpd #6 was determined using a commercial FVIII chromogenic activity assay (FVIII:C, Hyphen Biomed, France) to analyse dog serum samples. For the calibration curve, cmpd #6 was spiked into 10% dog serum and serum samples were analysed with 10-times dilution using the same assay. The final activity results were corrected with 10-fold for the 10-fold dilution. Plasma exposure levels of cmpd #6 were quantified by a luminescent oxygen channelling (LOCI) assay using anti-$V_HH$ (Novo Nordisk, Denmark) and anti-gammaGlu-linker antibodies (Novo Nordisk, Denmark). The data is summarized in table 21. FVIII:C chromogenic activity was measurable in serum 30 and 90 minutes post dosing and quantification of cmpd #6 based on chromogenic activity is similar to estimation based on cmpd #6 plasma exposure measurements using LOCI assay. Any discrepancies in cmpd #6 quantification is predicted to be caused by differences in assay sensitivity. The data show that the PO administrated $V_HH$ polypeptide derivative is fully active upon oral uptake in dog, indicating that the concept of making an orally available FVIII mimetic drug to treat patients, suffering from for example haemophilia A, is possible.

TABLE 21

Ex vivo activity of anti-FX/anti-FIX(a) polypeptide derivative post PO dosing

| Time post peroral dose | Animal | FVIII: C chromogenic activity (pM, serum) | Cmpd#6 exposure (pM, plasma) | Activity/ exposure Ratio % |
|---|---|---|---|---|
| 30 minutes | Animal 1 | 633 | 414 | 153% |
| | Animal 2 | 1740 | 905 | 192% |
| | Animal 3 | 445 | 247 | 180% |
| | Animal 4 | 1930 | 1490 | 129% |
| 90 minutes | Animal 1 | 1640 | 1290 | 127% |
| | Animal 2 | 3820 | 3130 | 122% |
| | Animal 3 | 2470 | 2110 | 117% |
| | Animal 4 | 7920 | 6550 | 121% |

Example 16: Crystallization and Paratope/Epitope Mapping of Anti-FX $V_HH$ Fragment Cmpd #76

The purpose of the present study was to determine the paratope and epitope residues of the $V_HH$ fragment designated Cmpd #76 ($V_HH$-1.15).

Crystallisation

Crystals of the $V_HH$ fragment Cmpd #76 produced using CHO mixed in a 1:4 molar ratio with a synthetic peptide N-term-NPFDLLD-C-term, corresponding to the activation peptide sequence aa31-37 of human FX (purchased from Apigenex) as identified in example 4, were grown using the sitting drop vapour diffusion technique. A protein solution of 250 nl 5.75 mg/ml complex in 20 mM Tris-HCl, pH 7.4, 50 mM NaCl was mixed with 250 nl of 4% (v/v) Tacsimate (1.8305 M Malonic acid, 0.25 M Ammonium citrate tribasic, 0.12 M Succinic acid, 0.3 M DL-Malic acid, 0.4 M Sodium acetate trihydrate, 0.5 M Sodium formate, and 0.16 M Ammonium tartrate dibasic) pH 5.0, 12% (w/v) Polyethylene glycol 3350 as precipitant and incubated over 80 µl precipitant. After 5 days of incubation at 18° C., the crystallisation plate was transferred to 5° C. Crystals appeared within three months.

Diffraction Data Collection

The crystal was cryo protected in precipitant added 20% ethylene glycol prior to flash cooling in liquid nitrogen. Diffraction data were collected at 100K at the Swiss Light Source beamline X10SA (1.0000 Å wavelength) using an Eiger2 16M pixel detector from Dectris. Autoindexing, integration and scaling of the data were performed with programmes from the XDS package (diffracting data statistics are summarised in Table 22).

Structure Determination and Refinement

The asymmetric unit contains two Cmpd #76:FX AP 31-37 complexes. The structure was determined by molecular replacement using Phaser as implemented in the programme suite Phenix using a previous determined crystal structure of a related $V_HH$ as a search model, see example 6. The correct amino acid sequence of Cmpd #76 was introduced and FX AP 31-37 was model built manually in the difference electron density map, all using COOT. During rounds of refinement in Phenix and manual rebuilding in COOT, O-glycosylation on threonine residue 117 and sulphation of tyrosine residue 109 were observed and modelled. The refinement statistics are found in Table 22.

TABLE 22

Data collection and refinement statistics

| | |
|---|---|
| Wavelength (Å) | 1 |
| Resolution range (Å) | 41.89-1.7 (1.761-1.7) |
| Space group | P 4$_1$ 2$_1$ 2 |
| Unit cell (Å, deg) | 66.54 66.54 161.74 90 90 90 |
| Total reflections | 534639 (54552) |
| Unique reflections | 40883 (4000) |
| Multiplicity | 13.1 (13.6) |
| Completeness (%) | 99.59 (99.48) |
| Mean I/sigma(I) | 17.03 (0.83) |
| Wilson B-factor (Å$^2$) | 35.51 |
| R-merge | 0.07098 (3.508) |
| R-meas | 0.07398 (3.642) |
| R-pim | 0.0206 (0.9736) |
| CC1/2 | 0.999 (0.72) |
| CC* | 1 (0.915) |
| Reflections used in refinement | 40750 (3981) |
| Reflections used for R-free | 1993 (193) |
| R-work | 0.1828 (0.3798) |
| R-free | 0.2077 (0.4038) |
| CC(work) | 0.963 (0.862) |
| CC(free) | 0.949 (0.702) |
| Number of non-hydrogen atoms | 2225 |
| macromolecules | 1958 |
| ligands | 84 |
| solvent | 217 |
| Protein residues | 254 |
| RMS(bonds) | 0.010 |
| RMS(angles) | 1.15 |
| Ramachandran favored (%) | 96.67 |
| Ramachandran allowed (%) | 2.92 |
| Ramachandran outliers (%) | 0.42 |
| Rotamer outliers (%) | 0.50 |
| Clashscore | 3.59 |
| Average B-factor (Å$^2$) | 47.24 |
| macromolecules | 46.21 |
| ligands | 71.05 |
| solvent | 51.13 |
| Number of TLS groups | 1 |

Statistics for the highest-resolution shell are shown in parentheses.

Determination of the Epitope and Paratope

The epitope of the synthetic peptide, defined as the FX activation peptide residues characterized by having a heavy atom (i.e. a non-hydrogen atom) within a distance of 4.0 Å from a heavy atom in the $V_HH$ polypeptide Cmpd #76, comprises the following residues from the synthetic peptide N173, P174, F175, L177, L178 and D179 according to the corresponding FX activation peptide sequence based on consecutive numbering (SEQ ID NO:2).

The paratope of $V_HH$ fragment Cmpd #76, defined as Cmpd #76 residues characterized by having a heavy atom (i.e. a non-hydrogen atom) within a distance of 4.0 Å from a heavy atom in the synthetic peptide, comprises the following residues from Cmpd #76: A33, M34, G35, W47, V48, A49, A50, I51, S52, S57, T58, N59, Y60, A61, A97, A98, D99, G105, L107, Y109 (SEQ ID NO:734) (consecutive numbering).

Example 17: Crystallization and Paratope/Epitope Mapping of Anti-FX $V_H$H Fragment Cmpd #77

The purpose of the present study was to determine the paratope and epitope residues of the $V_H$H fragment designated Cmpd #77 ($V_H$H1.13).

Crystallisation

Crystals of the $V_H$H fragment Cmpd #77 produced from CHO mixed in a 1:4 molar ratio with a synthetic peptide N-term-NPFDLLD-C-term, corresponding to the activation peptide sequence aa31-37 of human FX (synthesized by Apigenex) were grown using the sitting drop vapour diffusion technique. A protein solution of 250 nl 6.1 mg/ml complex in 20 mM Tris-HCl, pH 7.4, 50 mM NaCl was mixed with 250 nl of 3% (v/v) Tacsimate (1.8305 M Malonic acid, 0.25 M Ammonium citrate tribasic, 0.12 M Succinic acid, 0.3 M DL-Malic acid, 0.4 M Sodium acetate trihydrate, 0.5 M Sodium formate, and 0.16 M Ammonium tartrate dibasic) pH 4.0, 11% (w/v) PEG 3350 as precipitant and incubated over 80 µl precipitant. Crystal appeared 4 days of incubation at 5° C.

Diffraction Data Collection

The crystal was cryo protected in precipitant added 20% ethylene glycol prior to flash cooling in liquid nitrogen. Diffraction data were collected at 100K at the Swiss Light Source beamline X10SA (1.0000 Å wavelength) using an Eiger2 16M pixel detector from Dectris. Autoindexing, integration and scaling of the data were performed with programmes from the XDS package (diffracting data statistics are summarised in Table 23).

Structure Determination and Refinement

The asymmetric unit contains two Cmpd #77:FX AP 31-37 complexes. The structure was determined by molecular replacement using Phaser as implemented in the programme suite Phenix using the full asymmetric unit from the crystal structure of Cmpd #76:FX AP 31-37 in Example 16 as search model. The correct amino acid sequence of Cmpd #77 was introduced and rounds of refinement in Phenix and manual rebuilding in COOT were applied. The refinement statistics are found in Table 23.

TABLE 23

Data collection and refinement statistics

| | |
|---|---|
| Wavelength (Å) | 1.0000 |
| Resolution range (Å) | 32.88-1.7 (1.761-1.7) |
| Space group | P 4$_1$ 2$_1$ 2 |
| Unit cell Å, deg) | 58.99 58.99 160.25 90 90 90 |
| Total reflections | 418459 (41888) |
| Unique reflections | 31790 (3080) |
| Multiplicity | 13.2 (13.6) |
| Completeness (%) | 98.90 (97.90) |
| Mean I/sigma(I) | 16.44 (1.79) |
| Wilson B-factor (Å$^2$) | 26.81 |
| R-merge | 0.08787 (1.558) |
| R-meas | 0.09151 (1.618) |

TABLE 23-continued

| Data collection and refinement statistics | |
|---|---|
| R-pim | 0.02521 (0.4322) |
| CC1/2 | 0.999 (0.762) |
| CC* | 1 (0.93) |
| Reflections used in refinement | 31765 (3079) |
| Reflections used for R-free | 1588 (154) |
| R-work | 0.1717 (0.2765) |
| R-free | 0.2112 (0.3009) |
| CC(work) | 0.960 (0.903) |
| CC(free) | 0.935 (0.883) |
| Number of non-hydrogen atoms | 2253 |
| macromolecules | 1971 |
| ligands | 50 |
| solvent | 232 |
| Protein residues | 254 |
| RMS(bonds) | 0.011 |
| RMS(angles) | 1.03 |
| Ramachandran favored (%) | 98.33 |
| Ramachandran allowed (%) | 1.67 |
| Ramachandran outliers (%) | 0.00 |
| Rotamer outliers (%) | 0.49 |
| Clashscore | 3.83 |
| Average B-factor (Å$^2$) | 35.30 |
| macromolecules | 33.83 |
| ligands | 66.50 |
| solvent | 41.00 |
| Number of TLS groups | 1 |

Statistics for the highest-resolution shell are shown in parentheses.

Determination of the Epitope and Paratope

The epitope of the synthetic peptide, defined as the FX activation peptide residues characterized by having a heavy atom (i.e. a non-hydrogen atom) within a distance of 4.0 Å from a heavy atom in the V$_H$H fragment Cmpd #77, comprises the following residues from the synthetic peptide N173, P174, F175, L177, L178 and D179 according to the corresponding FX activation peptide sequence based on consecutive numbering (SEQ ID NO:2).

The paratope of V$_H$H fragment Cmpd #77, defined as Cmpd #77 residues characterized by having a heavy atom (i.e. a non-hydrogen atom) within a distance of 4.0 Å from a heavy atom in the synthetic peptide, comprises the following residues from Cmpd #77: A33, M34, G35, W47, V48, A49, A50, I51, S52, S57, T58, N59, Y60, A61, A97, A98, D99, G105, L107, Y109 (SEQ ID NO:735) (consecutive numbering).

Example 18: Steady State FXA Generation Kinetics of Bispecific V$_H$H Polypeptide Derivatives The purpose of the present study was to determine the procoagulant activity of anti-FIXa/FX bispecific V$_H$H polypeptide derivatives based on their ability to promote FX activation by FIXa in the presence of a procoagulant phospholipid membrane. The compounds tested are listed in Table 24 and emicizumab SIA was included for comparison.

The steady state FXa generation activity of each compound is reported as the parameters of Michaelis-Menten kinetics (Michaelis constant (K M) and the first order rate constant ($k_{cat}/K_M$)) at a given compound concentration. The compounds, the final assay concentration of which are shown in Table 24, were pre-incubation with 0.1 nM human plasma-derived FIXa (Haematologic Technologies Inc, USA) and 20 µM 25:75 phosphatidyl serine:phosphatidyl choline phospholipid vesicles (Haematologic Technologies Inc, USA) in assay buffer (50 mM HEPES, 100 mM NaCl, 5 mM CaCl$_2$, 0.1% (w/v) PEG8000, pH 7.3+1 mg/ml BSA) for 5 min. Activation was then initiated by addition of a two-fold dilution series of human plasma-derived FX (Haematologic Technologies Inc, USA) starting at 500 nM. Following activation at room temperature for 7 minutes, the reaction (50 µl) was quenched by addition of 25 µl quench buffer (50 mM HEPES, 100 mM NaCl, 60 mM EDTA, 0.1% PEG8000, pH 7.3+1 mg/ml BSA). The amount of FXa generated was determined by addition of 25 µl 2 mM S-2765 chromogenic substrate (Chromogenix, Sweden) and measurement of chromogenic substrate conversion by absorbance measurement at 405 nm (DOD/min) in a microplate reader. Similarly, FX activation by free FIXa was determined at a FIXa concentration of 10 nM and a reaction time of 5 to 10 min. To covert the measured absorption at 405 nm to a corresponding FXa concentration, a FXa standard curve from 0-5 nM (50 µl) were added 25 µl quench buffer and 25 µl 2 mM S-2765 chromogenic substrate before absorption at 405 nm was recorded as described above. Linear regression of DOD/min as a function of FXa concentration produces a slope which can be used for converting measured ΔOD/min into FXa generation rate:

$$FXa \text{ generation rate} = (\Delta DOD/min)/(slope_{FXa\ standard\ curve} * \text{reaction time})$$

Michaelis-Menten steady state kinetic parameters are determined by fitting FXa generation rate as a function of FX (substrate) concentration to the following equation:

$$FXa \text{ generation rate} = (k_{cat}*[FIXa]_t*[FX]_t)/(K_M+[FX]_t)$$

where $k_{cat}$ is the enzymatic efficiency (min$^{-1}$), [FIXa]$_t$ is the total FIXa (enzyme) concentration (nM), [FX]$_t$ is the total FX (substrate) concentration (nM) and K$_M$ is the Michaelis constant (nM). Table 24 lists the steady state kinetic constants determined for each tested compound as well as the concentration tested.

TABLE 24

| Determined steady state enzyme kinetic constants | | | |
|---|---|---|---|
| V$_H$H polypeptide derivative ID/ antibody name | Concentration tested (nM) | K$_M$ (nM) | k$_{cat}$/K$_M$ (1/(min * nM)) |
| Cmpd #21 | 5 | 3.9 | 0.27 |
| Cmpd #8 | 5 | 4.8 | 0.27 |
| Cmpd #17 | 5 | 9.0 | 0.15 |
| Cmpd #19 | 5 | 8.2 | 0.30 |
| Cmpd #16 | 5 | 7.1 | 0.14 |
| Cmpd #15 | 5 | 6.9 | 0.25 |
| Cmpd #13 | 5 | 6.2 | 0.18 |
| Cmpd #6 | 5 | 5.9 | 0.33 |
| Emicizumab-SIA | 300 | 53.5 | 0.03 |
| Free FIXa (10 nM) | N/A | 281.5 | 0.00012 |

CONCLUSION

The tested anti-FIXa/FX bispecific V$_H$H polypeptide derivatives all decrease K$_M$ from 281.5 nM of free FIXa to between 3.9-9.0 nM when supplemented to a final concentration of 5 nM, and further increase the catalytic efficiency from 0.00012 min$^{-1}$ nM$^{-1}$ to between 0.14-0.33 min$^{-1}$nM$^{-1}$. In comparison, emicizumab-SIA at 300 nM decrease K$_M$ to 53.5 nM.

The reduced K$_M$ values reflect an improved assembly (spatial arrangement) of FIX(a)/FX leading to a significant potency increase of the V$_H$H polypeptide derivatives. All compounds are tested in expected pharmacological relevant concentrations.

The invention claimed is:

1. A procoagulant $V_HH$ polypeptide derivative comprising a first $V_HH$ capable of binding to Factor IX (SEQ ID NO:1) or the activated form thereof, a second $V_HH$ capable of binding to Factor X (SEQ ID NO:2), a linker ($L_{1-2}$) linking said first $V_HH$ and said second $V_HH$, and a C-terminal extension (E) having SEQ ID NO:9, having the formula (N- to C-terminal): "second $V_HH$"-$L_{1-2}$-"first $V_HH$"-E, further comprising a first and a second protraction moiety attached to E,
wherein 1)
said first $V_HH$ comprises
CDR1:
    (SEQ ID NO: 172)
IYTMS, CDR2:
    (SEQ ID NO: 173)
GLRWTDSSTEYADSVKG,
and CDR3:
    (SEQ ID NO: 174)
DRSFLFAQALGATKNYEY;
and said second $V_HH$ comprises
CDR1:
    (SEQ ID NO: 152)
RYAMG,

CDR2:
    (SEQ ID NO: 153)
AISRRGGSTNYADSVKG,

CDR3:
    (SEQ ID NO: 154)
DDSVGDGYLDY;
or 2)
said first $V_HH$ comprises
CDR1:
    (SEQ ID NO: 132)
IYTMS, CDR2:
    (SEQ ID NO: 133)
GLRWTDSSTEYADSVKG,
and CDR3:
    (SEQ ID NO: 134)
DRSFLFAQALGATKNYEY;
and said second $V_HH$ comprises
CDR1:
    (SEQ ID NO: 128)
RLAMG,

CDR2:
    (SEQ ID NO: 129)
AISRRGGSTNYADSVKG,

CDR3:
    (SEQ ID NO: 130)
DDSVGDGYLDY.

2. The $V_HH$ polypeptide derivative according to claim 1, comprising SEQ ID NO:629 and wherein said first protraction moiety comprises the structure:

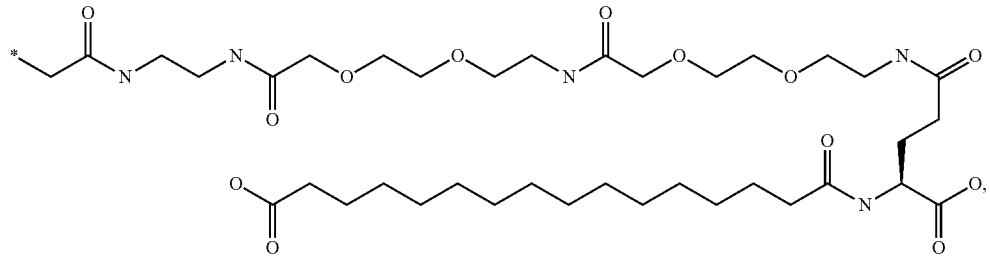

and wherein said second protraction moiety comprises the structure:

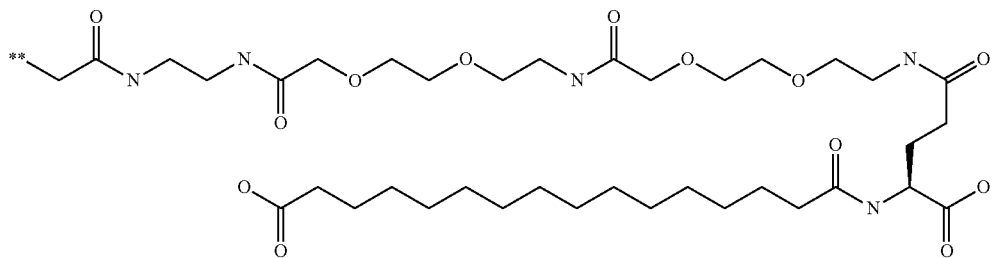

wherein '*' is Cys (C) in position 257 of SEQ ID NO:629, and
wherein '**' is Cys (C) in position 259 of SEQ ID NO:629.

3. The $V_HH$ polypeptide derivative according to claim 1, wherein said $V_HH$ polypeptide derivative is a bispecific $V_HH$ polypeptide derivative.

4. A pharmaceutical composition comprising the $V_HH$ polypeptide derivative according to claim 2 and a pharmaceutically acceptable excipient.

5. The pharmaceutical composition according to claim 4, wherein said composition comprises a salt of N-(8-(2-hydroxybenzoyl)amino) caprylic acid.

6. The pharmaceutical composition according to claim 5, wherein said salt of N-(8-(2-hydroxybenzoyl)amino) caprylic acid is sodium N-(8-(2-hydroxybenzoyl)amino) caprylate (SNAC) and wherein said composition further comprises nicotinamide (NAM).

7. A method of treating haemophilia A with or without inhibitors or acquired haemophilia A, comprising administering to a patient in need thereof the $V_HH$ polypeptide derivative of claim 2.

8. A method of treating haemophilia A with or without inhibitors or acquired haemophilia A, comprising administering to a patient in need thereof pharmaceutical composition of claim 4.

9. A method of treating haemophilia A with or without inhibitors or acquired haemophilia A, comprising perorally administering to a patient in need thereof pharmaceutical composition of claim 6.

* * * * *

SEQUENCE LISTING

```
Sequence total quantity: 739
SEQ ID NO: 1              moltype = AA  length = 415
FEATURE                   Location/Qualifiers
source                    1..415
                          mol_type = protein
                          organism = Homo sapiens
SEQUENCE: 1
YNSGKLEEFV QGNLERECME EKCSFEEARE VFENTERTTE FWKQYVDGDQ CESNPCLNGG   60
SCKDDINSYE CWCPFGFEGK NCELDVTCNI KNGRCEQFCK NSADNKVVCS CTEGYRLAEN  120
QKSCEPAVPF PCGRVSVSQT SKLTRAEAVF PDVDYVNSTE AETILDNITQ STQSFNDFTR  180
VVGGEDAKPG QFPWQVVLNG KVDAFCGGSI VNEKWIVTAA HCVETGVKIT VVAGEHNIEE  240
TEHTEQKRNV IRIIPHHNYN AAINKYNHDI ALLELDEPLV LNSYVTPICI ADKEYTNIFL  300
KFGSGYVSGW GRVFHKGRSA LVLQYLRVPL VDRATCLRST KFTIYNNMFC AGFHEGGRDS  360
CQGDSGGPHV TEVEGTSFLT GIISWGEECA MKGKYGIYTK VSRYVNWIKE KTKLT       415

SEQ ID NO: 2              moltype = AA  length = 448
FEATURE                   Location/Qualifiers
source                    1..448
                          mol_type = protein
                          organism = Homo sapiens
SEQUENCE: 2
ANSFLEEMKK GHLERECMEE TCSYEEAREV FEDSDKTNEF WNKYKDGDQC ETSPCQNQGK   60
CKDGLGEYTC TCLEGFEGKN CELFTRKLCS LDNGDCDQFC HEEQNSVVCS CARGYTLADN  120
GKACIPTGPY PCGKQTLERR KRSVAQATSS SGEAPDSITW KPYDAADLDP TENPFDLLDF  180
NQTQPERGDN NLTRIVGGQE CKDGECPWQA LLINEENEGF CGGTILSEFY ILTAAHCLYQ  240
AKRFKVRVGD RNTEQEEGGE AVHEVEVVIK HNRFTKETYD FDIAVLRLKT PITFRMNVAP  300
ACLPERDWAE STLMTQKTGI VSGFGRTHEK GRQSTRLKML EVPYVDRNSC KLSSSFIITQ  360
NMFCAGYDTK QEDACQGDSG GPHVTRFKDT YFVTGIVSWG EGCARKGKYG IYTKVTAFLK  420
WIDRSMKTRG LPKAKSHAPE VITSSPLK                                     448

SEQ ID NO: 3              moltype = AA  length = 30
FEATURE                   Location/Qualifiers
REGION                    1..30
                          note = Synthetic
source                    1..30
                          mol_type = protein
                          organism = synthetic construct
SEQUENCE: 3
QRLMEDICLP RWGCLWEDDF GGGGSGGGGS                                    30

SEQ ID NO: 4              moltype = AA  length = 50
FEATURE                   Location/Qualifiers
REGION                    1..50
                          note = Synthetic
source                    1..50
                          mol_type = protein
                          organism = synthetic construct
SEQUENCE: 4
QRLMEDICLP RWGCLWEDDF GGGGSGGGGS GGGGSGGGGS GGGGSGGGGS               50

SEQ ID NO: 5              moltype = AA  length = 34
FEATURE                   Location/Qualifiers
REGION                    1..34
                          note = Synthetic
source                    1..34
                          mol_type = protein
                          organism = synthetic construct
SEQUENCE: 5
AAADYKDHDG DYKDHDIDYK DDDDKGAAHH HHHH                                34

SEQ ID NO: 6              moltype = AA  length = 6
FEATURE                   Location/Qualifiers
REGION                    1..6
                          note = Synthetic
source                    1..6
                          mol_type = protein
                          organism = synthetic construct
SEQUENCE: 6
HHHHHH                                                                6

SEQ ID NO: 7              moltype = AA  length = 12
FEATURE                   Location/Qualifiers
REGION                    1..12
                          note = Synthetic
source                    1..12
                          mol_type = protein
                          organism = synthetic construct
SEQUENCE: 7
```

```
GGGGSCHHHH HH                                                          12

SEQ ID NO: 8              moltype = AA   length = 13
FEATURE                   Location/Qualifiers
REGION                    1..13
                          note = Synthetic
source                    1..13
                          mol_type = protein
                          organism = synthetic construct
SEQUENCE: 8
GGGGCSCHHH HHH                                                         13

SEQ ID NO: 9              moltype = AA   length = 6
FEATURE                   Location/Qualifiers
REGION                    1..6
                          note = Synthetic
source                    1..6
                          mol_type = protein
                          organism = synthetic construct
SEQUENCE: 9
GQACPC                                                                 6

SEQ ID NO: 10             moltype = AA   length = 16
FEATURE                   Location/Qualifiers
REGION                    1..16
                          note = Synthetic
source                    1..16
                          mol_type = protein
                          organism = synthetic construct
SEQUENCE: 10
GGGGSGGGSC HHHHHH                                                      16

SEQ ID NO: 11             moltype = AA   length = 11
FEATURE                   Location/Qualifiers
REGION                    1..11
                          note = Synthetic
source                    1..11
                          mol_type = protein
                          organism = synthetic construct
SEQUENCE: 11
GGGGSHHHHH H                                                           11

SEQ ID NO: 12             moltype = AA   length = 41
FEATURE                   Location/Qualifiers
REGION                    1..41
                          note = Synthetic
source                    1..41
                          mol_type = protein
                          organism = synthetic construct
SEQUENCE: 12
GGGGSHHHHH HGGGGSGGGG SQRLMEDICL PRWGCLWEDD F                          41

SEQ ID NO: 13             moltype = AA   length = 61
FEATURE                   Location/Qualifiers
REGION                    1..61
                          note = Synthetic
source                    1..61
                          mol_type = protein
                          organism = synthetic construct
SEQUENCE: 13
GGGGSHHHHH HGGGGSGGGG SGGGGSGGGG SGGGGSGGGG SQRLMEDICL PRWGCLWEDD      60
F                                                                      61

SEQ ID NO: 14             moltype = AA   length = 9
FEATURE                   Location/Qualifiers
REGION                    1..9
                          note = Synthetic
source                    1..9
                          mol_type = protein
                          organism = synthetic construct
SEQUENCE: 14
GGGGSGGGS                                                              9

SEQ ID NO: 15             moltype = AA   length = 5
FEATURE                   Location/Qualifiers
REGION                    1..5
                          note = Synthetic
source                    1..5
                          mol_type = protein
```

```
                                       -continued
                    organism = synthetic construct
SEQUENCE: 15
QAPGQ                                                                    5

SEQ ID NO: 16       moltype = AA   length = 6
FEATURE             Location/Qualifiers
REGION              1..6
                    note = Synthetic
source              1..6
                    mol_type = protein
                    organism = synthetic construct
SEQUENCE: 16
QAPGQA                                                                   6

SEQ ID NO: 17       moltype = AA   length = 10
FEATURE             Location/Qualifiers
REGION              1..10
                    note = Synthetic
source              1..10
                    mol_type = protein
                    organism = synthetic construct
SEQUENCE: 17
GIGIGIGIGI                                                              10

SEQ ID NO: 18       moltype = AA   length = 10
FEATURE             Location/Qualifiers
REGION              1..10
                    note = Synthetic
source              1..10
                    mol_type = protein
                    organism = synthetic construct
SEQUENCE: 18
GTGTGTGTGT                                                              10

SEQ ID NO: 19       moltype = AA   length = 10
FEATURE             Location/Qualifiers
REGION              1..10
                    note = Synthetic
source              1..10
                    mol_type = protein
                    organism = synthetic construct
SEQUENCE: 19
GVGVGVGVGV                                                              10

SEQ ID NO: 20       moltype = AA   length = 6
FEATURE             Location/Qualifiers
REGION              1..6
                    note = Synthetic
source              1..6
                    mol_type = protein
                    organism = synthetic construct
SEQUENCE: 20
GQAPGQ                                                                   6

SEQ ID NO: 21       moltype = AA   length = 10
FEATURE             Location/Qualifiers
REGION              1..10
                    note = Synthetic
source              1..10
                    mol_type = protein
                    organism = synthetic construct
SEQUENCE: 21
GLGLGLGLGL                                                              10

SEQ ID NO: 22       moltype = AA   length = 9
FEATURE             Location/Qualifiers
REGION              1..9
                    note = Synthetic
source              1..9
                    mol_type = protein
                    organism = synthetic construct
SEQUENCE: 22
GGGGSGGGS                                                                9

SEQ ID NO: 23       moltype = AA   length = 10
FEATURE             Location/Qualifiers
REGION              1..10
                    note = Synthetic
source              1..10
```

```
                        mol_type = protein
                        organism = synthetic construct
SEQUENCE: 23
GEGEGEGEGE                                                                       10

SEQ ID NO: 24           moltype = AA   length = 24
FEATURE                 Location/Qualifiers
REGION                  1..24
                        note = Synthetic
source                  1..24
                        mol_type = protein
                        organism = synthetic construct
SEQUENCE: 24
GSGGGGSGGG GSGSGGGGSG GGGS                                                       24

SEQ ID NO: 25           moltype = AA   length = 10
FEATURE                 Location/Qualifiers
REGION                  1..10
                        note = Synthetic
source                  1..10
                        mol_type = protein
                        organism = synthetic construct
SEQUENCE: 25
GGGGSGGGGS                                                                       10

SEQ ID NO: 26           moltype = AA   length = 30
FEATURE                 Location/Qualifiers
REGION                  1..30
                        note = Synthetic
source                  1..30
                        mol_type = protein
                        organism = synthetic construct
SEQUENCE: 26
GGGGSGGGGS GGGGSGGGGS GGGGSGGGGS                                                 30

SEQ ID NO: 27           moltype = AA   length = 120
FEATURE                 Location/Qualifiers
REGION                  1..120
                        note = Synthetic
source                  1..120
                        mol_type = protein
                        organism = synthetic construct
SEQUENCE: 27
EVQLVESGGG LVQPGGSLRL SCAASGSIGA FDAMGWYRQA PGKQRELVAG IMVSRGNTNY                60
TDSVKGRFTI SRDNAKNTVY LQMNSLKPED TAVYYCKAVK RPGPGYLEVW GQGTLVTVSS               120

SEQ ID NO: 28           moltype = AA   length = 5
FEATURE                 Location/Qualifiers
REGION                  1..5
                        note = Synthetic
source                  1..5
                        mol_type = protein
                        organism = synthetic construct
SEQUENCE: 28
FDAMG                                                                             5

SEQ ID NO: 29           moltype = AA   length = 17
FEATURE                 Location/Qualifiers
REGION                  1..17
                        note = Synthetic
source                  1..17
                        mol_type = protein
                        organism = synthetic construct
SEQUENCE: 29
GIMVSRGNTN YTDSVKG                                                               17

SEQ ID NO: 30           moltype = AA   length = 11
FEATURE                 Location/Qualifiers
REGION                  1..11
                        note = Synthetic
source                  1..11
                        mol_type = protein
                        organism = synthetic construct
SEQUENCE: 30
VKRPGPGYLE V                                                                     11

SEQ ID NO: 31           moltype = AA   length = 120
FEATURE                 Location/Qualifiers
REGION                  1..120
```

```
                        note = Synthetic
source                  1..120
                        mol_type = protein
                        organism = synthetic construct
SEQUENCE: 31
EVQLVESGGG VVQPGGSLRL SCVASGRTFS RYAMGWFRQA PGKEREFVAA ISRRGGSTNY      60
ADSVKGRFTI SRDNSKNTVY LQMNSLRPED TALYYCAADY SSGDGYLDYW GQGTLVTVSS     120

SEQ ID NO: 32           moltype = AA   length = 5
FEATURE                 Location/Qualifiers
REGION                  1..5
                        note = Synthetic
source                  1..5
                        mol_type = protein
                        organism = synthetic construct
SEQUENCE: 32
RYAMG                                                                   5

SEQ ID NO: 33           moltype = AA   length = 17
FEATURE                 Location/Qualifiers
REGION                  1..17
                        note = Synthetic
source                  1..17
                        mol_type = protein
                        organism = synthetic construct
SEQUENCE: 33
AISRRGGSTN YADSVKG                                                     17

SEQ ID NO: 34           moltype = AA   length = 11
FEATURE                 Location/Qualifiers
REGION                  1..11
                        note = Synthetic
source                  1..11
                        mol_type = protein
                        organism = synthetic construct
SEQUENCE: 34
DYSSGDGYLD Y                                                           11

SEQ ID NO: 35           moltype = AA   length = 127
FEATURE                 Location/Qualifiers
REGION                  1..127
                        note = Synthetic
source                  1..127
                        mol_type = protein
                        organism = synthetic construct
SEQUENCE: 35
EVQLVESGGG VVQPGGSLRL SCAASGRTFN IYTMSWFRQA PGKERELVAG LRWTDSSTEY      60
ADSVKGRATI SRDNSKTTVY LQMNSLRPED TALYYCAADR SFLFAQAMGA TKNYEYWGQG     120
TLVTVSS                                                               127

SEQ ID NO: 36           moltype = AA   length = 5
FEATURE                 Location/Qualifiers
REGION                  1..5
                        note = Synthetic
source                  1..5
                        mol_type = protein
                        organism = synthetic construct
SEQUENCE: 36
IYTMS                                                                   5

SEQ ID NO: 37           moltype = AA   length = 17
FEATURE                 Location/Qualifiers
REGION                  1..17
                        note = Synthetic
source                  1..17
                        mol_type = protein
                        organism = synthetic construct
SEQUENCE: 37
GLRWTDSSTE YADSVKG                                                     17

SEQ ID NO: 38           moltype = AA   length = 18
FEATURE                 Location/Qualifiers
REGION                  1..18
                        note = Synthetic
source                  1..18
                        mol_type = protein
                        organism = synthetic construct
SEQUENCE: 38
DRSFLFAQAM GATKNYEY                                                    18
```

```
SEQ ID NO: 39          moltype = AA   length = 120
FEATURE                Location/Qualifiers
REGION                 1..120
                       note = Synthetic
source                 1..120
                       mol_type = protein
                       organism = synthetic construct
SEQUENCE: 39
DVQLVESGGG VVQPGGSLRL SCAASGRTHS RYAMGWFRQA PGKEREFVAA ISRRGGSTNY    60
ADSVKGRFTI SRDNSKNTVY LQMNSLRPED TALYYCAADD SSGDGYLDYW GQGTLVTVSS   120

SEQ ID NO: 40          moltype = AA   length = 5
FEATURE                Location/Qualifiers
REGION                 1..5
                       note = Synthetic
source                 1..5
                       mol_type = protein
                       organism = synthetic construct
SEQUENCE: 40
RYAMG                                                                 5

SEQ ID NO: 41          moltype = AA   length = 17
FEATURE                Location/Qualifiers
REGION                 1..17
                       note = Synthetic
source                 1..17
                       mol_type = protein
                       organism = synthetic construct
SEQUENCE: 41
AISRRGGSTN YADSVKG                                                   17

SEQ ID NO: 42          moltype = AA   length = 11
FEATURE                Location/Qualifiers
REGION                 1..11
                       note = Synthetic
source                 1..11
                       mol_type = protein
                       organism = synthetic construct
SEQUENCE: 42
DDSSGDGYLD Y                                                         11

SEQ ID NO: 43          moltype = AA   length = 127
FEATURE                Location/Qualifiers
REGION                 1..127
                       note = Synthetic
source                 1..127
                       mol_type = protein
                       organism = synthetic construct
SEQUENCE: 43
EVQLVESGGG VVQPGGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                             127

SEQ ID NO: 44          moltype = AA   length = 5
FEATURE                Location/Qualifiers
REGION                 1..5
                       note = Synthetic
source                 1..5
                       mol_type = protein
                       organism = synthetic construct
SEQUENCE: 44
IYTMS                                                                 5

SEQ ID NO: 45          moltype = AA   length = 17
FEATURE                Location/Qualifiers
REGION                 1..17
                       note = Synthetic
source                 1..17
                       mol_type = protein
                       organism = synthetic construct
SEQUENCE: 45
GLRWTDSSTE YADSVKG                                                   17

SEQ ID NO: 46          moltype = AA   length = 18
FEATURE                Location/Qualifiers
REGION                 1..18
                       note = Synthetic
source                 1..18
```

-continued

```
                            mol_type = protein
                            organism = synthetic construct
SEQUENCE: 46
DRSFLFAQAL GATKNYEY                                                           18

SEQ ID NO: 47               moltype = AA   length = 120
FEATURE                     Location/Qualifiers
REGION                      1..120
                            note = Synthetic
source                      1..120
                            mol_type = protein
                            organism = synthetic construct
SEQUENCE: 47
DVQLVESGGG VVQPGGSLQL SCAASGRTHS RYAMGWFRQA PGQEREFVAA ISRRGGSTNY              60
ADSVKGRFTI SRDNSKNTVY LQMDSLRPED TALYYCAADD SSGDGYLDYW GQGTLVTVSS             120

SEQ ID NO: 48               moltype = AA   length = 5
FEATURE                     Location/Qualifiers
REGION                      1..5
                            note = Synthetic
source                      1..5
                            mol_type = protein
                            organism = synthetic construct
SEQUENCE: 48
RYAMG                                                                          5

SEQ ID NO: 49               moltype = AA   length = 17
FEATURE                     Location/Qualifiers
REGION                      1..17
                            note = Synthetic
source                      1..17
                            mol_type = protein
                            organism = synthetic construct
SEQUENCE: 49
AISRRGGSTN YADSVKG                                                            17

SEQ ID NO: 50               moltype = AA   length = 11
FEATURE                     Location/Qualifiers
REGION                      1..11
                            note = Synthetic
source                      1..11
                            mol_type = protein
                            organism = synthetic construct
SEQUENCE: 50
DDSSGDGYLD Y                                                                  11

SEQ ID NO: 51               moltype = AA   length = 127
FEATURE                     Location/Qualifiers
REGION                      1..127
                            note = Synthetic
source                      1..127
                            mol_type = protein
                            organism = synthetic construct
SEQUENCE: 51
EVQLVESGGG VVQPGGSLQL SCAASGRTFN IYTMSWFRQA PGQEREFVAG LRWTDSSTEY              60
ADSVKGRFTI SRDNSKNTVY LQMDSLRPED TALYYCAADR SFLFAQALGA TKNYEYWGQG             120
TLVTVSS                                                                      127

SEQ ID NO: 52               moltype = AA   length = 5
FEATURE                     Location/Qualifiers
REGION                      1..5
                            note = Synthetic
source                      1..5
                            mol_type = protein
                            organism = synthetic construct
SEQUENCE: 52
IYTMS                                                                          5

SEQ ID NO: 53               moltype = AA   length = 17
FEATURE                     Location/Qualifiers
REGION                      1..17
                            note = Synthetic
source                      1..17
                            mol_type = protein
                            organism = synthetic construct
SEQUENCE: 53
GLRWTDSSTE YADSVKG                                                            17

SEQ ID NO: 54               moltype = AA   length = 18
```

```
FEATURE                 Location/Qualifiers
REGION                  1..18
                        note = Synthetic
source                  1..18
                        mol_type = protein
                        organism = synthetic construct
SEQUENCE: 54
DRSFLFAQAL GATKNYEY                                                      18

SEQ ID NO: 55           moltype = AA  length = 120
FEATURE                 Location/Qualifiers
REGION                  1..120
                        note = Synthetic
source                  1..120
                        mol_type = protein
                        organism = synthetic construct
SEQUENCE: 55
DVQLVESGGG VVQPGGSLQL SCAASGRTHS RYAMGWFRQA PGQEREFVAA ISRRGGSTNY         60
ADSVKGRFTI SRDNSKNTVY LQMDSLRPED TALYYCAADD SSGDGYLDYW GQGTLVTVSS        120

SEQ ID NO: 56           moltype = AA  length = 5
FEATURE                 Location/Qualifiers
REGION                  1..5
                        note = Synthetic
source                  1..5
                        mol_type = protein
                        organism = synthetic construct
SEQUENCE: 56
RYAMG                                                                     5

SEQ ID NO: 57           moltype = AA  length = 17
FEATURE                 Location/Qualifiers
REGION                  1..17
                        note = Synthetic
source                  1..17
                        mol_type = protein
                        organism = synthetic construct
SEQUENCE: 57
AISRRGGSTN YADSVKG                                                       17

SEQ ID NO: 58           moltype = AA  length = 11
FEATURE                 Location/Qualifiers
REGION                  1..11
                        note = Synthetic
source                  1..11
                        mol_type = protein
                        organism = synthetic construct
SEQUENCE: 58
DDSSGDGYLD Y                                                             11

SEQ ID NO: 59           moltype = AA  length = 127
FEATURE                 Location/Qualifiers
REGION                  1..127
                        note = Synthetic
source                  1..127
                        mol_type = protein
                        organism = synthetic construct
SEQUENCE: 59
EVQLVESGGG VVQPGGSLQL SCAASGRTFN IYTMSWFRQA PGQEREFVAG LRWTDSSTEY         60
ADSVKGRFTI SRDNSKNTVY LQMDSLRPED TALYYCAADR SFLFAQALGA TKNYEYWGQG        120
TLVTVSS                                                                 127

SEQ ID NO: 60           moltype = AA  length = 5
FEATURE                 Location/Qualifiers
REGION                  1..5
                        note = Synthetic
source                  1..5
                        mol_type = protein
                        organism = synthetic construct
SEQUENCE: 60
IYTMS                                                                     5

SEQ ID NO: 61           moltype = AA  length = 17
FEATURE                 Location/Qualifiers
REGION                  1..17
                        note = Synthetic
source                  1..17
                        mol_type = protein
                        organism = synthetic construct
```

```
SEQUENCE: 61
GLRWTDSSTE YADSVKG                                                    17

SEQ ID NO: 62          moltype = AA  length = 18
FEATURE                Location/Qualifiers
REGION                 1..18
                       note = Synthetic
source                 1..18
                       mol_type = protein
                       organism = synthetic construct
SEQUENCE: 62
DRSFLFAQAL GATKNYEY                                                   18

SEQ ID NO: 63          moltype = AA  length = 120
FEATURE                Location/Qualifiers
REGION                 1..120
                       note = Synthetic
source                 1..120
                       mol_type = protein
                       organism = synthetic construct
SEQUENCE: 63
DVQLVESGGG VVQPGGSLQL SCAASGGTKS RYAMGWFRQA PGQEREFVAA ISRRGGSTNY      60
ADSVKGRFTI SRDNSKNTVY LQMDSLRPED TALYYCAADD SVGDGYLDYW GQGTLVTVSS     120

SEQ ID NO: 64          moltype = AA  length = 5
FEATURE                Location/Qualifiers
REGION                 1..5
                       note = Synthetic
source                 1..5
                       mol_type = protein
                       organism = synthetic construct
SEQUENCE: 64
RYAMG                                                                  5

SEQ ID NO: 65          moltype = AA  length = 17
FEATURE                Location/Qualifiers
REGION                 1..17
                       note = Synthetic
source                 1..17
                       mol_type = protein
                       organism = synthetic construct
SEQUENCE: 65
AISRRGGSTN YADSVKG                                                    17

SEQ ID NO: 66          moltype = AA  length = 11
FEATURE                Location/Qualifiers
REGION                 1..11
                       note = Synthetic
source                 1..11
                       mol_type = protein
                       organism = synthetic construct
SEQUENCE: 66
DDSVGDGYLD Y                                                          11

SEQ ID NO: 67          moltype = AA  length = 127
FEATURE                Location/Qualifiers
REGION                 1..127
                       note = Synthetic
source                 1..127
                       mol_type = protein
                       organism = synthetic construct
SEQUENCE: 67
EVQLVESGGG VVQPGGSLRL SCAASGRTFN IYTMSWFRQA PGQEREFVAG LRWTDSSTEY      60
ADSVKGRFTI SRDNSKNTVY LQMNSLRPED TALYYCAADR SFLFAQALGA TKNYEYWGQG     120
TLVTVSS                                                              127

SEQ ID NO: 68          moltype = AA  length = 5
FEATURE                Location/Qualifiers
REGION                 1..5
                       note = Synthetic
source                 1..5
                       mol_type = protein
                       organism = synthetic construct
SEQUENCE: 68
IYTMS                                                                  5

SEQ ID NO: 69          moltype = AA  length = 17
FEATURE                Location/Qualifiers
REGION                 1..17
```

```
                        note = Synthetic
source                  1..17
                        mol_type = protein
                        organism = synthetic construct
SEQUENCE: 69
GLRWTDSSTE YADSVKG                                                          17

SEQ ID NO: 70           moltype = AA   length = 18
FEATURE                 Location/Qualifiers
REGION                  1..18
                        note = Synthetic
source                  1..18
                        mol_type = protein
                        organism = synthetic construct
SEQUENCE: 70
DRSFLFAQAL GATKNYEY                                                         18

SEQ ID NO: 71           moltype = AA   length = 120
FEATURE                 Location/Qualifiers
REGION                  1..120
                        note = Synthetic
source                  1..120
                        mol_type = protein
                        organism = synthetic construct
SEQUENCE: 71
DVQLVESGGG VVQPGGSLQL SCAASGGTKS RYAMGWFRQA PGQEREFVAA ISRRGGSTNY            60
ADSVKGRFTI SRDNSKNTVY LQMDSLRPED TALYYCAADD SVGDGYLDYW GQGTLVTVSS           120

SEQ ID NO: 72           moltype = AA   length = 5
FEATURE                 Location/Qualifiers
REGION                  1..5
                        note = Synthetic
source                  1..5
                        mol_type = protein
                        organism = synthetic construct
SEQUENCE: 72
RYAMG                                                                        5

SEQ ID NO: 73           moltype = AA   length = 17
FEATURE                 Location/Qualifiers
REGION                  1..17
                        note = Synthetic
source                  1..17
                        mol_type = protein
                        organism = synthetic construct
SEQUENCE: 73
AISRRGGSTN YADSVKG                                                          17

SEQ ID NO: 74           moltype = AA   length = 11
FEATURE                 Location/Qualifiers
REGION                  1..11
                        note = Synthetic
source                  1..11
                        mol_type = protein
                        organism = synthetic construct
SEQUENCE: 74
DDSVGDGYLD Y                                                                11

SEQ ID NO: 75           moltype = AA   length = 127
FEATURE                 Location/Qualifiers
REGION                  1..127
                        note = Synthetic
source                  1..127
                        mol_type = protein
                        organism = synthetic construct
SEQUENCE: 75
EVQLVESGGG VVQPGGSLQL SCAASGRTFN IYTMSWFRQA PGQEREFVAG LRWTDSSTEY            60
ADSVKGRFTI SRDNSKNTVY LQMDSLRPED TALYYCAADR SFLFAQALGA TKNYEYWGQG           120
TLVTVSS                                                                    127

SEQ ID NO: 76           moltype = AA   length = 5
FEATURE                 Location/Qualifiers
REGION                  1..5
                        note = Synthetic
source                  1..5
                        mol_type = protein
                        organism = synthetic construct
SEQUENCE: 76
IYTMS                                                                        5
```

```
SEQ ID NO: 77            moltype = AA  length = 17
FEATURE                  Location/Qualifiers
REGION                   1..17
                         note = Synthetic
source                   1..17
                         mol_type = protein
                         organism = synthetic construct
SEQUENCE: 77
GLRWTDSSTE YADSVKG                                                          17

SEQ ID NO: 78            moltype = AA  length = 18
FEATURE                  Location/Qualifiers
REGION                   1..18
                         note = Synthetic
source                   1..18
                         mol_type = protein
                         organism = synthetic construct
SEQUENCE: 78
DRSFLFAQAL GATKNYEY                                                         18

SEQ ID NO: 79            moltype = AA  length = 120
FEATURE                  Location/Qualifiers
REGION                   1..120
                         note = Synthetic
source                   1..120
                         mol_type = protein
                         organism = synthetic construct
SEQUENCE: 79
DVQLVESGGG VVQPGGSLQL SCAASGGTKS RYAMGWFRQA PGQEREFVAA ISRRGGSTNY            60
ADSVKGRFTI SRDNSKNTVY LDMDDLRPED TALYYCAADD SVGDGYLDYW GQGTLVTVSS           120

SEQ ID NO: 80            moltype = AA  length = 5
FEATURE                  Location/Qualifiers
REGION                   1..5
                         note = Synthetic
source                   1..5
                         mol_type = protein
                         organism = synthetic construct
SEQUENCE: 80
RYAMG                                                                        5

SEQ ID NO: 81            moltype = AA  length = 17
FEATURE                  Location/Qualifiers
REGION                   1..17
                         note = Synthetic
source                   1..17
                         mol_type = protein
                         organism = synthetic construct
SEQUENCE: 81
AISRRGGSTN YADSVKG                                                          17

SEQ ID NO: 82            moltype = AA  length = 11
FEATURE                  Location/Qualifiers
REGION                   1..11
                         note = Synthetic
source                   1..11
                         mol_type = protein
                         organism = synthetic construct
SEQUENCE: 82
DDSVGDGYLD Y                                                                11

SEQ ID NO: 83            moltype = AA  length = 127
FEATURE                  Location/Qualifiers
REGION                   1..127
                         note = Synthetic
source                   1..127
                         mol_type = protein
                         organism = synthetic construct
SEQUENCE: 83
EVQLVESGGG VVQPGGSLRL SCAASGRTFN IYTMSWFRQD PGQEREFVAG LRWTDSSTEY            60
ADSVKGRFTI SRDNSKNTVY LQMNSLRPED TALYYCAADR SFLFAQALGA TKNYEYWGQG           120
TLVTVSS                                                                    127

SEQ ID NO: 84            moltype = AA  length = 5
FEATURE                  Location/Qualifiers
REGION                   1..5
                         note = Synthetic
source                   1..5
```

```
                        mol_type = protein
                        organism = synthetic construct
SEQUENCE: 84
IYTMS                                                                    5

SEQ ID NO: 85           moltype = AA   length = 17
FEATURE                 Location/Qualifiers
REGION                  1..17
                        note = Synthetic
source                  1..17
                        mol_type = protein
                        organism = synthetic construct
SEQUENCE: 85
GLRWTDSSTE YADSVKG                                                      17

SEQ ID NO: 86           moltype = AA   length = 18
FEATURE                 Location/Qualifiers
REGION                  1..18
                        note = Synthetic
source                  1..18
                        mol_type = protein
                        organism = synthetic construct
SEQUENCE: 86
DRSFLFAQAL GATKNYEY                                                     18

SEQ ID NO: 87           moltype = AA   length = 120
FEATURE                 Location/Qualifiers
REGION                  1..120
                        note = Synthetic
source                  1..120
                        mol_type = protein
                        organism = synthetic construct
SEQUENCE: 87
DVQLVESGGG VVQPGGSLQL SCAASGGTKR RLAMGWFRQA PGQEREWVAA ISRRGGSTNY        60
ADSVKGRFTI SRDNSKNTVY LQMDSLRPED TALYYCAADD SVGDGYLDYW GQGTLVTVSS       120

SEQ ID NO: 88           moltype = AA   length = 5
FEATURE                 Location/Qualifiers
REGION                  1..5
                        note = Synthetic
source                  1..5
                        mol_type = protein
                        organism = synthetic construct
SEQUENCE: 88
RLAMG                                                                    5

SEQ ID NO: 89           moltype = AA   length = 17
FEATURE                 Location/Qualifiers
REGION                  1..17
                        note = Synthetic
source                  1..17
                        mol_type = protein
                        organism = synthetic construct
SEQUENCE: 89
AISRRGGSTN YADSVKG                                                      17

SEQ ID NO: 90           moltype = AA   length = 11
FEATURE                 Location/Qualifiers
REGION                  1..11
                        note = Synthetic
source                  1..11
                        mol_type = protein
                        organism = synthetic construct
SEQUENCE: 90
DDSVGDGYLD Y                                                            11

SEQ ID NO: 91           moltype = AA   length = 127
FEATURE                 Location/Qualifiers
REGION                  1..127
                        note = Synthetic
source                  1..127
                        mol_type = protein
                        organism = synthetic construct
SEQUENCE: 91
EVQLVESGGG VVQPGGSLRL SCAASGRTFN IYTMSWFRQA PGQEREFVAG LRWTDSSTEY        60
ADSVKGRFTI SRDNSKNTVY LQMNSLRPED TALYYCAADR SFLFAQALGA TKNYEYWGQG       120
TLVTVSS                                                                127

SEQ ID NO: 92           moltype = AA   length = 5
```

```
FEATURE              Location/Qualifiers
REGION               1..5
                     note = Synthetic
source               1..5
                     mol_type = protein
                     organism = synthetic construct
SEQUENCE: 92
IYTMS                                                                     5

SEQ ID NO: 93        moltype = AA  length = 17
FEATURE              Location/Qualifiers
REGION               1..17
                     note = Synthetic
source               1..17
                     mol_type = protein
                     organism = synthetic construct
SEQUENCE: 93
GLRWTDSSTE YADSVKG                                                       17

SEQ ID NO: 94        moltype = AA  length = 18
FEATURE              Location/Qualifiers
REGION               1..18
                     note = Synthetic
source               1..18
                     mol_type = protein
                     organism = synthetic construct
SEQUENCE: 94
DRSFLFAQAL GATKNYEY                                                      18

SEQ ID NO: 95        moltype = AA  length = 120
FEATURE              Location/Qualifiers
REGION               1..120
                     note = Synthetic
source               1..120
                     mol_type = protein
                     organism = synthetic construct
SEQUENCE: 95
DVQLVESGGG VVQPGGSLQL SCAASGGTKR RLAMGWFRQA PGQEREFVAA ISRRGGSTNY         60
ADSVKGRFTI SRDNSKNTVY LDMDDLRPED TALYYCAADD SVGDGYLDYW GQGTLVTVSS        120

SEQ ID NO: 96        moltype = AA  length = 5
FEATURE              Location/Qualifiers
REGION               1..5
                     note = Synthetic
source               1..5
                     mol_type = protein
                     organism = synthetic construct
SEQUENCE: 96
RLAMG                                                                     5

SEQ ID NO: 97        moltype = AA  length = 17
FEATURE              Location/Qualifiers
REGION               1..17
                     note = Synthetic
source               1..17
                     mol_type = protein
                     organism = synthetic construct
SEQUENCE: 97
AISRRGGSTN YADSVKG                                                       17

SEQ ID NO: 98        moltype = AA  length = 11
FEATURE              Location/Qualifiers
REGION               1..11
                     note = Synthetic
source               1..11
                     mol_type = protein
                     organism = synthetic construct
SEQUENCE: 98
DDSVGDGYLD Y                                                             11

SEQ ID NO: 99        moltype = AA  length = 127
FEATURE              Location/Qualifiers
REGION               1..127
                     note = Synthetic
source               1..127
                     mol_type = protein
                     organism = synthetic construct
SEQUENCE: 99
EVQLVESGGG VVQPGGSLRL SCAASGRTFN IYTMSWFRQD PGQEREFVAG LRWTDSSTEY         60
```

```
ADSVKGRFTI SRDNSKNTVY LQMNSLRPED TALYYCAADR SFLFAQALGA TKNYEYWGQG   120
TLVTVSS                                                           127

SEQ ID NO: 100          moltype = AA  length = 5
FEATURE                 Location/Qualifiers
REGION                  1..5
                        note = Synthetic
source                  1..5
                        mol_type = protein
                        organism = synthetic construct
SEQUENCE: 100
IYTMS                                                             5

SEQ ID NO: 101          moltype = AA  length = 17
FEATURE                 Location/Qualifiers
REGION                  1..17
                        note = Synthetic
source                  1..17
                        mol_type = protein
                        organism = synthetic construct
SEQUENCE: 101
GLRWTDSSTE YADSVKG                                                17

SEQ ID NO: 102          moltype = AA  length = 18
FEATURE                 Location/Qualifiers
REGION                  1..18
                        note = Synthetic
source                  1..18
                        mol_type = protein
                        organism = synthetic construct
SEQUENCE: 102
DRSFLFAQAL GATKNYEY                                               18

SEQ ID NO: 103          moltype = AA  length = 120
FEATURE                 Location/Qualifiers
REGION                  1..120
                        note = Synthetic
source                  1..120
                        mol_type = protein
                        organism = synthetic construct
SEQUENCE: 103
DVQLVESGGG VVQPGGSLQL SCAASGGTKR RLAMGWFRQA PGQEREFVAA ISRRGGSTNY   60
ADSVKGRFTI SRDNSKNTVY LDMDDLRPED TALYYCAADD SVGDGYLDYW GQGTLVTVSS  120

SEQ ID NO: 104          moltype = AA  length = 5
FEATURE                 Location/Qualifiers
REGION                  1..5
                        note = Synthetic
source                  1..5
                        mol_type = protein
                        organism = synthetic construct
SEQUENCE: 104
RLAMG                                                             5

SEQ ID NO: 105          moltype = AA  length = 17
FEATURE                 Location/Qualifiers
REGION                  1..17
                        note = Synthetic
source                  1..17
                        mol_type = protein
                        organism = synthetic construct
SEQUENCE: 105
AISRRGGSTN YADSVKG                                                17

SEQ ID NO: 106          moltype = AA  length = 11
FEATURE                 Location/Qualifiers
REGION                  1..11
                        note = Synthetic
source                  1..11
                        mol_type = protein
                        organism = synthetic construct
SEQUENCE: 106
DDSVGDGYLD Y                                                      11

SEQ ID NO: 107          moltype = AA  length = 127
FEATURE                 Location/Qualifiers
REGION                  1..127
                        note = Synthetic
source                  1..127
```

```
                        mol_type = protein
                        organism = synthetic construct
SEQUENCE: 107
EVQLVESGGG VVQPGGSLQL SCAASGRTFN IYTMSWFRQD PGQEREFVAG LRWTDSSTEY    60
ADSVKGRFTI SRDNSKNTVY LQMDSLRPED TALYYCAADR SFLFAQALGA TKNYEYWGQG   120
TLVTVSS                                                             127

SEQ ID NO: 108          moltype = AA   length = 5
FEATURE                 Location/Qualifiers
REGION                  1..5
                        note = Synthetic
source                  1..5
                        mol_type = protein
                        organism = synthetic construct
SEQUENCE: 108
IYTMS                                                                 5

SEQ ID NO: 109          moltype = AA   length = 17
FEATURE                 Location/Qualifiers
REGION                  1..17
                        note = Synthetic
source                  1..17
                        mol_type = protein
                        organism = synthetic construct
SEQUENCE: 109
GLRWTDSSTE YADSVKG                                                   17

SEQ ID NO: 110          moltype = AA   length = 18
FEATURE                 Location/Qualifiers
REGION                  1..18
                        note = Synthetic
source                  1..18
                        mol_type = protein
                        organism = synthetic construct
SEQUENCE: 110
DRSFLFAQAL GATKNYEY                                                  18

SEQ ID NO: 111          moltype = AA   length = 120
FEATURE                 Location/Qualifiers
REGION                  1..120
                        note = Synthetic
source                  1..120
                        mol_type = protein
                        organism = synthetic construct
SEQUENCE: 111
DVQLVESGGG VVQPGGSLQL SCAASGGTKR RLAMGWFRQA PGQEREWVAA ISRRGGSTNY    60
ADSVKGRFTI SRDNSKNTVY LDMDDLRPED TALYYCAADD SVGDGYLDYW GQGTLVTVSS   120

SEQ ID NO: 112          moltype = AA   length = 5
FEATURE                 Location/Qualifiers
REGION                  1..5
                        note = Synthetic
source                  1..5
                        mol_type = protein
                        organism = synthetic construct
SEQUENCE: 112
RLAMG                                                                 5

SEQ ID NO: 113          moltype = AA   length = 17
FEATURE                 Location/Qualifiers
REGION                  1..17
                        note = Synthetic
source                  1..17
                        mol_type = protein
                        organism = synthetic construct
SEQUENCE: 113
AISRRGGSTN YADSVKG                                                   17

SEQ ID NO: 114          moltype = AA   length = 11
FEATURE                 Location/Qualifiers
REGION                  1..11
                        note = Synthetic
source                  1..11
                        mol_type = protein
                        organism = synthetic construct
SEQUENCE: 114
DDSVGDGYLD Y                                                         11

SEQ ID NO: 115          moltype = AA   length = 127
```

```
FEATURE                 Location/Qualifiers
REGION                  1..127
                        note = Synthetic
source                  1..127
                        mol_type = protein
                        organism = synthetic construct
SEQUENCE: 115
EVQLVESGGG VVQPGGSLQL SCAASGRTFN IYTMSWFRQD PGQEREFVAG LRWTDSSTEY     60
ADSVKGRFTI SRDNSKNTVY LQMDSLRPED TALYYCAADR SFLFAQALGA TKNYEYWGQG    120
TLVTVSS                                                              127

SEQ ID NO: 116          moltype = AA  length = 5
FEATURE                 Location/Qualifiers
REGION                  1..5
                        note = Synthetic
source                  1..5
                        mol_type = protein
                        organism = synthetic construct
SEQUENCE: 116
IYTMS                                                                  5

SEQ ID NO: 117          moltype = AA  length = 17
FEATURE                 Location/Qualifiers
REGION                  1..17
                        note = Synthetic
source                  1..17
                        mol_type = protein
                        organism = synthetic construct
SEQUENCE: 117
GLRWTDSSTE YADSVKG                                                    17

SEQ ID NO: 118          moltype = AA  length = 18
FEATURE                 Location/Qualifiers
REGION                  1..18
                        note = Synthetic
source                  1..18
                        mol_type = protein
                        organism = synthetic construct
SEQUENCE: 118
DRSFLFAQAL GATKNYEY                                                   18

SEQ ID NO: 119          moltype = AA  length = 120
FEATURE                 Location/Qualifiers
REGION                  1..120
                        note = Synthetic
source                  1..120
                        mol_type = protein
                        organism = synthetic construct
SEQUENCE: 119
DVQLVESGGG VVQPGGSLQL SCAASGGTKR RLAMGWFRQA PGQEREFVAA ISRRGGSTNY     60
ADSVKGRFTI SRDNSKNTVY LQMDSLRPED TALYYCAADD SVGDGYLDYW GQGTLVTVSS    120

SEQ ID NO: 120          moltype = AA  length = 5
FEATURE                 Location/Qualifiers
REGION                  1..5
                        note = Synthetic
source                  1..5
                        mol_type = protein
                        organism = synthetic construct
SEQUENCE: 120
RLAMG                                                                  5

SEQ ID NO: 121          moltype = AA  length = 17
FEATURE                 Location/Qualifiers
REGION                  1..17
                        note = Synthetic
source                  1..17
                        mol_type = protein
                        organism = synthetic construct
SEQUENCE: 121
AISRRGGSTN YADSVKG                                                    17

SEQ ID NO: 122          moltype = AA  length = 11
FEATURE                 Location/Qualifiers
REGION                  1..11
                        note = Synthetic
source                  1..11
                        mol_type = protein
                        organism = synthetic construct
```

```
SEQUENCE: 122
DDSVGDGYLD Y                                                          11

SEQ ID NO: 123           moltype = AA  length = 127
FEATURE                  Location/Qualifiers
REGION                   1..127
                         note = Synthetic
source                   1..127
                         mol_type = protein
                         organism = synthetic construct
SEQUENCE: 123
EVQLVESGGG VVQPGGSLQL SCAASGRTFN IYTMSWFRQA PGQEREFVAG LRWTDSSTEY      60
ADSVKGRFTI SRDNSKNTVY LQMDSLRPED TALYYCAADR SFLFAQALGA TKNYEYWGQG     120
TLVTVSS                                                              127

SEQ ID NO: 124           moltype = AA  length = 5
FEATURE                  Location/Qualifiers
REGION                   1..5
                         note = Synthetic
source                   1..5
                         mol_type = protein
                         organism = synthetic construct
SEQUENCE: 124
IYTMS                                                                 5

SEQ ID NO: 125           moltype = AA  length = 17
FEATURE                  Location/Qualifiers
REGION                   1..17
                         note = Synthetic
source                   1..17
                         mol_type = protein
                         organism = synthetic construct
SEQUENCE: 125
GLRWTDSSTE YADSVKG                                                    17

SEQ ID NO: 126           moltype = AA  length = 18
FEATURE                  Location/Qualifiers
REGION                   1..18
                         note = Synthetic
source                   1..18
                         mol_type = protein
                         organism = synthetic construct
SEQUENCE: 126
DRSFLFAQAL GATKNYEY                                                   18

SEQ ID NO: 127           moltype = AA  length = 120
FEATURE                  Location/Qualifiers
REGION                   1..120
                         note = Synthetic
source                   1..120
                         mol_type = protein
                         organism = synthetic construct
SEQUENCE: 127
DVQLVESGGG VVQPGGSLQL SCAASGGTKR RLAMGWFRQA PGQEREWVAA ISRRGGSTNY      60
ADSVKGRFTI SRDNSKNTVY LQMDSLRPED TALYYCAADD SVGDGYLDYW GQGTLVTVSS     120

SEQ ID NO: 128           moltype = AA  length = 5
FEATURE                  Location/Qualifiers
REGION                   1..5
                         note = Synthetic
source                   1..5
                         mol_type = protein
                         organism = synthetic construct
SEQUENCE: 128
RLAMG                                                                 5

SEQ ID NO: 129           moltype = AA  length = 17
FEATURE                  Location/Qualifiers
REGION                   1..17
                         note = Synthetic
source                   1..17
                         mol_type = protein
                         organism = synthetic construct
SEQUENCE: 129
AISRRGGSTN YADSVKG                                                    17

SEQ ID NO: 130           moltype = AA  length = 11
FEATURE                  Location/Qualifiers
REGION                   1..11
```

```
                          note = Synthetic
source                    1..11
                          mol_type = protein
                          organism = synthetic construct
SEQUENCE: 130
DDSVGDGYLD Y                                                              11

SEQ ID NO: 131            moltype = AA  length = 127
FEATURE                   Location/Qualifiers
REGION                    1..127
                          note = Synthetic
source                    1..127
                          mol_type = protein
                          organism = synthetic construct
SEQUENCE: 131
EVQLVESGGG VVQPGGSLQL SCAASGRTFN IYTMSWFRQA PGQEREFVAG LRWTDSSTEY          60
ADSVKGRFTI SRDNSKNTVY LQMDSLRPED TALYYCAADR SFLFAQALGA TKNYEYWGQG          120
TLVTVSS                                                                   127

SEQ ID NO: 132            moltype = AA  length = 5
FEATURE                   Location/Qualifiers
REGION                    1..5
                          note = Synthetic
source                    1..5
                          mol_type = protein
                          organism = synthetic construct
SEQUENCE: 132
IYTMS                                                                     5

SEQ ID NO: 133            moltype = AA  length = 17
FEATURE                   Location/Qualifiers
REGION                    1..17
                          note = Synthetic
source                    1..17
                          mol_type = protein
                          organism = synthetic construct
SEQUENCE: 133
GLRWTDSSTE YADSVKG                                                        17

SEQ ID NO: 134            moltype = AA  length = 18
FEATURE                   Location/Qualifiers
REGION                    1..18
                          note = Synthetic
source                    1..18
                          mol_type = protein
                          organism = synthetic construct
SEQUENCE: 134
DRSFLFAQAL GATKNYEY                                                       18

SEQ ID NO: 135            moltype = AA  length = 120
FEATURE                   Location/Qualifiers
REGION                    1..120
                          note = Synthetic
source                    1..120
                          mol_type = protein
                          organism = synthetic construct
SEQUENCE: 135
DVQLVESGGG VVQPGGSLQL SCAASGGTKR RLAMGWFRQA PGQEREWVAA ISRRGGSTNY          60
ADSVKGRFTI SRDNSKNTVY LDMDDLRPED TALYYCAADD SVGDGYLDYW GQGTLVTVSS          120

SEQ ID NO: 136            moltype = AA  length = 5
FEATURE                   Location/Qualifiers
REGION                    1..5
                          note = Synthetic
source                    1..5
                          mol_type = protein
                          organism = synthetic construct
SEQUENCE: 136
RLAMG                                                                     5

SEQ ID NO: 137            moltype = AA  length = 17
FEATURE                   Location/Qualifiers
REGION                    1..17
                          note = Synthetic
source                    1..17
                          mol_type = protein
                          organism = synthetic construct
SEQUENCE: 137
AISRRGGSTN YADSVKG                                                        17
```

```
SEQ ID NO: 138          moltype = AA  length = 11
FEATURE                 Location/Qualifiers
REGION                  1..11
                        note = Synthetic
source                  1..11
                        mol_type = protein
                        organism = synthetic construct
SEQUENCE: 138
DDSVGDGYLD Y                                                               11

SEQ ID NO: 139          moltype = AA  length = 127
FEATURE                 Location/Qualifiers
REGION                  1..127
                        note = Synthetic
source                  1..127
                        mol_type = protein
                        organism = synthetic construct
SEQUENCE: 139
EVQLVESGGG VVQPGGSLRL SCAASGRYFN IYTMSWFRQD PGQEREFVAG LRWTDSSTEY           60
ADSVKGRFTI SRDNSKNTVY LQMNSLRPED TALYYCAADR SFLFAQALGA TKNYEYWGQG          120
TLVTVSS                                                                   127

SEQ ID NO: 140          moltype = AA  length = 5
FEATURE                 Location/Qualifiers
REGION                  1..5
                        note = Synthetic
source                  1..5
                        mol_type = protein
                        organism = synthetic construct
SEQUENCE: 140
IYTMS                                                                       5

SEQ ID NO: 141          moltype = AA  length = 17
FEATURE                 Location/Qualifiers
REGION                  1..17
                        note = Synthetic
source                  1..17
                        mol_type = protein
                        organism = synthetic construct
SEQUENCE: 141
GLRWTDSSTE YADSVKG                                                         17

SEQ ID NO: 142          moltype = AA  length = 18
FEATURE                 Location/Qualifiers
REGION                  1..18
                        note = Synthetic
source                  1..18
                        mol_type = protein
                        organism = synthetic construct
SEQUENCE: 142
DRSFLFAQAL GATKNYEY                                                        18

SEQ ID NO: 143          moltype = AA  length = 120
FEATURE                 Location/Qualifiers
REGION                  1..120
                        note = Synthetic
source                  1..120
                        mol_type = protein
                        organism = synthetic construct
SEQUENCE: 143
DVQLVESGGG VVQPGGSLQL SCAASGGTKS RYAMGWFRQA PGQEREWVAA ISRRGGSTNY           60
ADSVKGRFTI SRDNSKNTVY LDMDDLRPED TALYYCAADD SVGDGYLDYW GQGTLVTVSS          120

SEQ ID NO: 144          moltype = AA  length = 5
FEATURE                 Location/Qualifiers
REGION                  1..5
                        note = Synthetic
source                  1..5
                        mol_type = protein
                        organism = synthetic construct
SEQUENCE: 144
RYAMG                                                                       5

SEQ ID NO: 145          moltype = AA  length = 17
FEATURE                 Location/Qualifiers
REGION                  1..17
                        note = Synthetic
source                  1..17
```

```
                        mol_type = protein
                        organism = synthetic construct
SEQUENCE: 145
AISRRGGSTN YADSVKG                                                    17

SEQ ID NO: 146          moltype = AA   length = 11
FEATURE                 Location/Qualifiers
REGION                  1..11
                        note = Synthetic
source                  1..11
                        mol_type = protein
                        organism = synthetic construct
SEQUENCE: 146
DDSVGDGYLD Y                                                          11

SEQ ID NO: 147          moltype = AA   length = 127
FEATURE                 Location/Qualifiers
REGION                  1..127
                        note = Synthetic
source                  1..127
                        mol_type = protein
                        organism = synthetic construct
SEQUENCE: 147
EVQLVESGGG VVQPGGSLQL SCAASGRTFN IYTMSWFRQD PGQEREFVAG LRWTDSSTEY      60
ADSVKGRFTI SRDNSKNTVY LQMDSLRPED TALYYCAADR SFLFAQALGA TKNYEYWGQG     120
TLVTVSS                                                              127

SEQ ID NO: 148          moltype = AA   length = 5
FEATURE                 Location/Qualifiers
REGION                  1..5
                        note = Synthetic
source                  1..5
                        mol_type = protein
                        organism = synthetic construct
SEQUENCE: 148
IYTMS                                                                  5

SEQ ID NO: 149          moltype = AA   length = 17
FEATURE                 Location/Qualifiers
REGION                  1..17
                        note = Synthetic
source                  1..17
                        mol_type = protein
                        organism = synthetic construct
SEQUENCE: 149
GLRWTDSSTE YADSVKG                                                    17

SEQ ID NO: 150          moltype = AA   length = 18
FEATURE                 Location/Qualifiers
REGION                  1..18
                        note = Synthetic
source                  1..18
                        mol_type = protein
                        organism = synthetic construct
SEQUENCE: 150
DRSFLFAQAL GATKNYEY                                                   18

SEQ ID NO: 151          moltype = AA   length = 120
FEATURE                 Location/Qualifiers
REGION                  1..120
                        note = Synthetic
source                  1..120
                        mol_type = protein
                        organism = synthetic construct
SEQUENCE: 151
DVQLVESGGG VVQPGGSLQL SCAASGGTKS RYAMGWFRQA PGQEREWVAA ISRRGGSTNY      60
ADSVKGRFTI SRDNSKNTVY LDMDDLRPED TALYYCAADD SVGDGYLDYW GQGTLVTVSS     120

SEQ ID NO: 152          moltype = AA   length = 5
FEATURE                 Location/Qualifiers
REGION                  1..5
                        note = Synthetic
source                  1..5
                        mol_type = protein
                        organism = synthetic construct
SEQUENCE: 152
RYAMG                                                                  5

SEQ ID NO: 153          moltype = AA   length = 17
```

```
FEATURE                 Location/Qualifiers
REGION                  1..17
                        note = Synthetic
source                  1..17
                        mol_type = protein
                        organism = synthetic construct
SEQUENCE: 153
AISRRGGSTN YADSVKG                                                      17

SEQ ID NO: 154          moltype = AA  length = 11
FEATURE                 Location/Qualifiers
REGION                  1..11
                        note = Synthetic
source                  1..11
                        mol_type = protein
                        organism = synthetic construct
SEQUENCE: 154
DDSVGDGYLD Y                                                            11

SEQ ID NO: 155          moltype = AA  length = 127
FEATURE                 Location/Qualifiers
REGION                  1..127
                        note = Synthetic
source                  1..127
                        mol_type = protein
                        organism = synthetic construct
SEQUENCE: 155
EVQLVESGGG VVQPGGSLRL SCAASGRTFN IYTMSWFRQD PGQEREFVAG LRWTDSSTEY        60
ADSVKGRFTI SRDNSKNTVY LQMNSLRPED TALYYCAADR SFLFAQALGA TKNYEYWGQG       120
TLVTVSS                                                                127

SEQ ID NO: 156          moltype = AA  length = 5
FEATURE                 Location/Qualifiers
REGION                  1..5
                        note = Synthetic
source                  1..5
                        mol_type = protein
                        organism = synthetic construct
SEQUENCE: 156
IYTMS                                                                   5

SEQ ID NO: 157          moltype = AA  length = 17
FEATURE                 Location/Qualifiers
REGION                  1..17
                        note = Synthetic
source                  1..17
                        mol_type = protein
                        organism = synthetic construct
SEQUENCE: 157
GLRWTDSSTE YADSVKG                                                      17

SEQ ID NO: 158          moltype = AA  length = 18
FEATURE                 Location/Qualifiers
REGION                  1..18
                        note = Synthetic
source                  1..18
                        mol_type = protein
                        organism = synthetic construct
SEQUENCE: 158
DRSFLFAQAL GATKNYEY                                                     18

SEQ ID NO: 159          moltype = AA  length = 120
FEATURE                 Location/Qualifiers
REGION                  1..120
                        note = Synthetic
source                  1..120
                        mol_type = protein
                        organism = synthetic construct
SEQUENCE: 159
DVQLVESGGG VVQPGGSLQL SCAASGGTKS RYAMGWFRQA PGQEREWVAA ISRRGGSTNY        60
ADSVKGRFTI SRDNSKNTVY LQMDSLRPED TALYYCAADD SVGDGYLDYW GQGTLVTVSS       120

SEQ ID NO: 160          moltype = AA  length = 5
FEATURE                 Location/Qualifiers
REGION                  1..5
                        note = Synthetic
source                  1..5
                        mol_type = protein
                        organism = synthetic construct
```

```
SEQUENCE: 160
RYAMG                                                                    5

SEQ ID NO: 161          moltype = AA  length = 17
FEATURE                 Location/Qualifiers
REGION                  1..17
                        note = Synthetic
source                  1..17
                        mol_type = protein
                        organism = synthetic construct
SEQUENCE: 161
AISRRGGSTN YADSVKG                                                      17

SEQ ID NO: 162          moltype = AA  length = 11
FEATURE                 Location/Qualifiers
REGION                  1..11
                        note = Synthetic
source                  1..11
                        mol_type = protein
                        organism = synthetic construct
SEQUENCE: 162
DDSVGDGYLD Y                                                            11

SEQ ID NO: 163          moltype = AA  length = 127
FEATURE                 Location/Qualifiers
REGION                  1..127
                        note = Synthetic
source                  1..127
                        mol_type = protein
                        organism = synthetic construct
SEQUENCE: 163
EVQLVESGGG VVQPGGSLQL SCAASGRTFN IYTMSWFRQA PGQEREFVAG LRWTDSSTEY        60
ADSVKGRFTI SRDNSKNTVY LQMDSLRPED TALYYCAADR SFLFAQALGA TKNYEYWGQG       120
TLVTVSS                                                                127

SEQ ID NO: 164          moltype = AA  length = 5
FEATURE                 Location/Qualifiers
REGION                  1..5
                        note = Synthetic
source                  1..5
                        mol_type = protein
                        organism = synthetic construct
SEQUENCE: 164
IYTMS                                                                    5

SEQ ID NO: 165          moltype = AA  length = 17
FEATURE                 Location/Qualifiers
REGION                  1..17
                        note = Synthetic
source                  1..17
                        mol_type = protein
                        organism = synthetic construct
SEQUENCE: 165
GLRWTDSSTE YADSVKG                                                      17

SEQ ID NO: 166          moltype = AA  length = 18
FEATURE                 Location/Qualifiers
REGION                  1..18
                        note = Synthetic
source                  1..18
                        mol_type = protein
                        organism = synthetic construct
SEQUENCE: 166
DRSFLFAQAL GATKNYEY                                                     18

SEQ ID NO: 167          moltype = AA  length = 120
FEATURE                 Location/Qualifiers
REGION                  1..120
                        note = Synthetic
source                  1..120
                        mol_type = protein
                        organism = synthetic construct
SEQUENCE: 167
DVQLVESGGG VVQPGGSLQL SCAASGGTKS RYAMGWFRQA PGQEREWVAA ISRRGGSTNY        60
ADSVKGRFTI SRDNSKNTVY LQMDSLRPED TALYYCAADD SVGDGYLDYW GQGTLVTVSS       120

SEQ ID NO: 168          moltype = AA  length = 5
FEATURE                 Location/Qualifiers
REGION                  1..5
```

```
                            note = Synthetic
source                      1..5
                            mol_type = protein
                            organism = synthetic construct
SEQUENCE: 168
RYAMG                                                                       5

SEQ ID NO: 169              moltype = AA  length = 17
FEATURE                     Location/Qualifiers
REGION                      1..17
                            note = Synthetic
source                      1..17
                            mol_type = protein
                            organism = synthetic construct
SEQUENCE: 169
AISRRGGSTN YADSVKG                                                         17

SEQ ID NO: 170              moltype = AA  length = 11
FEATURE                     Location/Qualifiers
REGION                      1..11
                            note = Synthetic
source                      1..11
                            mol_type = protein
                            organism = synthetic construct
SEQUENCE: 170
DDSVGDGYLD Y                                                               11

SEQ ID NO: 171              moltype = AA  length = 127
FEATURE                     Location/Qualifiers
REGION                      1..127
                            note = Synthetic
source                      1..127
                            mol_type = protein
                            organism = synthetic construct
SEQUENCE: 171
EVQLVESGGG VVQPGGSLRL SCAASGRTFN IYTMSWFRQA PGQEREFVAG LRWTDSSTEY           60
ADSVKGRFTI SRDNSKNTVY LQMNSLRPED TALYYCAADR SFLFAQALGA TKNYEYWGQG          120
TLVTVSS                                                                   127

SEQ ID NO: 172              moltype = AA  length = 5
FEATURE                     Location/Qualifiers
REGION                      1..5
                            note = Synthetic
source                      1..5
                            mol_type = protein
                            organism = synthetic construct
SEQUENCE: 172
IYTMS                                                                       5

SEQ ID NO: 173              moltype = AA  length = 17
FEATURE                     Location/Qualifiers
REGION                      1..17
                            note = Synthetic
source                      1..17
                            mol_type = protein
                            organism = synthetic construct
SEQUENCE: 173
GLRWTDSSTE YADSVKG                                                         17

SEQ ID NO: 174              moltype = AA  length = 18
FEATURE                     Location/Qualifiers
REGION                      1..18
                            note = Synthetic
source                      1..18
                            mol_type = protein
                            organism = synthetic construct
SEQUENCE: 174
DRSFLFAQAL GATKNYEY                                                        18

SEQ ID NO: 175              moltype = AA  length = 120
FEATURE                     Location/Qualifiers
REGION                      1..120
                            note = Synthetic
source                      1..120
                            mol_type = protein
                            organism = synthetic construct
SEQUENCE: 175
DVQLVESGGG VVQPGGSLQL SCAASGGTKS RYAMGWFRQA PGQEREFVAA ISRRGGSTNY           60
ADSVKGRFTI SRDNSKNTVY LDMDDLRPED TALYYCAADD SVGDGYLDYW GQGTLVTVSS          120
```

```
SEQ ID NO: 176          moltype = AA   length = 5
FEATURE                 Location/Qualifiers
REGION                  1..5
                        note = Synthetic
source                  1..5
                        mol_type = protein
                        organism = synthetic construct
SEQUENCE: 176
RYAMG                                                                    5

SEQ ID NO: 177          moltype = AA   length = 17
FEATURE                 Location/Qualifiers
REGION                  1..17
                        note = Synthetic
source                  1..17
                        mol_type = protein
                        organism = synthetic construct
SEQUENCE: 177
AISRRGGSTN YADSVKG                                                      17

SEQ ID NO: 178          moltype = AA   length = 11
FEATURE                 Location/Qualifiers
REGION                  1..11
                        note = Synthetic
source                  1..11
                        mol_type = protein
                        organism = synthetic construct
SEQUENCE: 178
DDSVGDGYLD Y                                                            11

SEQ ID NO: 179          moltype = AA   length = 127
FEATURE                 Location/Qualifiers
REGION                  1..127
                        note = Synthetic
source                  1..127
                        mol_type = protein
                        organism = synthetic construct
SEQUENCE: 179
EVQLVESGGG VVQPGGSLQL SCAASGRTFN IYTMSWFRQD PGQEREFVAG LRWTDSSTEY        60
ADSVKGRFTI SRDNSKNTVY LQMDSLRPED TALYYCAADR SFLFAQALGA TKNYEYWGQG       120
TLVTVSS                                                                127

SEQ ID NO: 180          moltype = AA   length = 5
FEATURE                 Location/Qualifiers
REGION                  1..5
                        note = Synthetic
source                  1..5
                        mol_type = protein
                        organism = synthetic construct
SEQUENCE: 180
IYTMS                                                                    5

SEQ ID NO: 181          moltype = AA   length = 17
FEATURE                 Location/Qualifiers
REGION                  1..17
                        note = Synthetic
source                  1..17
                        mol_type = protein
                        organism = synthetic construct
SEQUENCE: 181
GLRWTDSSTE YADSVKG                                                      17

SEQ ID NO: 182          moltype = AA   length = 18
FEATURE                 Location/Qualifiers
REGION                  1..18
                        note = Synthetic
source                  1..18
                        mol_type = protein
                        organism = synthetic construct
SEQUENCE: 182
DRSFLFAQAL GATKNYEY                                                     18

SEQ ID NO: 183          moltype = AA   length = 120
FEATURE                 Location/Qualifiers
REGION                  1..120
                        note = Synthetic
source                  1..120
                        mol_type = protein
```

```
                        organism = synthetic construct
SEQUENCE: 183
DVQLVESGGG VVQPGGSLQL SCAASGGTKR RLAMGWFRQA PGQEREWVAA ISRRGGSTNY        60
ADSVKGRFTI SRDNSKNTVY LDMDDLRPED TALYYCAADD SVGDGYLDYW GQGTLVTVSS       120

SEQ ID NO: 184          moltype = AA  length = 5
FEATURE                 Location/Qualifiers
REGION                  1..5
                        note = Synthetic
source                  1..5
                        mol_type = protein
                        organism = synthetic construct
SEQUENCE: 184
RLAMG                                                                    5

SEQ ID NO: 185          moltype = AA  length = 17
FEATURE                 Location/Qualifiers
REGION                  1..17
                        note = Synthetic
source                  1..17
                        mol_type = protein
                        organism = synthetic construct
SEQUENCE: 185
AISRRGGSTN YADSVKG                                                      17

SEQ ID NO: 186          moltype = AA  length = 11
FEATURE                 Location/Qualifiers
REGION                  1..11
                        note = Synthetic
source                  1..11
                        mol_type = protein
                        organism = synthetic construct
SEQUENCE: 186
DDSVGDGYLD Y                                                            11

SEQ ID NO: 187          moltype = AA  length = 127
FEATURE                 Location/Qualifiers
REGION                  1..127
                        note = Synthetic
source                  1..127
                        mol_type = protein
                        organism = synthetic construct
SEQUENCE: 187
EVQLVESGGG VVQPGGSLRL SCAASGRTFN IYTMSWFRQD PGQEREFVAG LRWTDSSTEY        60
ADSVKGRFTI SRDNSKNTVY LQMNSLRPED TALYYCAADR SFLFAQALGA TKNYEYWGQG       120
TLVTVSS                                                                127

SEQ ID NO: 188          moltype = AA  length = 5
FEATURE                 Location/Qualifiers
REGION                  1..5
                        note = Synthetic
source                  1..5
                        mol_type = protein
                        organism = synthetic construct
SEQUENCE: 188
IYTMS                                                                    5

SEQ ID NO: 189          moltype = AA  length = 17
FEATURE                 Location/Qualifiers
REGION                  1..17
                        note = Synthetic
source                  1..17
                        mol_type = protein
                        organism = synthetic construct
SEQUENCE: 189
GLRWTDSSTE YADSVKG                                                      17

SEQ ID NO: 190          moltype = AA  length = 18
FEATURE                 Location/Qualifiers
REGION                  1..18
                        note = Synthetic
source                  1..18
                        mol_type = protein
                        organism = synthetic construct
SEQUENCE: 190
DRSFLFAQAL GATKNYEY                                                     18

SEQ ID NO: 191          moltype = AA  length = 120
FEATURE                 Location/Qualifiers
```

```
REGION                  1..120
                        note = Synthetic
source                  1..120
                        mol_type = protein
                        organism = synthetic construct
SEQUENCE: 191
DVQLVESGGG VVQPGGSLRL SCAASGRTFS RYAMGWFRQA PGKEREFVAA ISRRGGSTNY    60
ADSVKGRFTI SRDNSKNTVY LQMNSLRPED TALYYCAADY SSGDGYLDYW GQGTLVTVSS   120

SEQ ID NO: 192          moltype = AA  length = 5
FEATURE                 Location/Qualifiers
REGION                  1..5
                        note = Synthetic
source                  1..5
                        mol_type = protein
                        organism = synthetic construct
SEQUENCE: 192
RYAMG                                                                 5

SEQ ID NO: 193          moltype = AA  length = 17
FEATURE                 Location/Qualifiers
REGION                  1..17
                        note = Synthetic
source                  1..17
                        mol_type = protein
                        organism = synthetic construct
SEQUENCE: 193
AISRRGGSTN YADSVKG                                                   17

SEQ ID NO: 194          moltype = AA  length = 11
FEATURE                 Location/Qualifiers
REGION                  1..11
                        note = Synthetic
source                  1..11
                        mol_type = protein
                        organism = synthetic construct
SEQUENCE: 194
DYSSGDGYLD Y                                                         11

SEQ ID NO: 195          moltype = AA  length = 127
FEATURE                 Location/Qualifiers
REGION                  1..127
                        note = Synthetic
source                  1..127
                        mol_type = protein
                        organism = synthetic construct
SEQUENCE: 195
EVQLVESGGG VVQPGGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                             127

SEQ ID NO: 196          moltype = AA  length = 5
FEATURE                 Location/Qualifiers
REGION                  1..5
                        note = Synthetic
source                  1..5
                        mol_type = protein
                        organism = synthetic construct
SEQUENCE: 196
IYTMS                                                                 5

SEQ ID NO: 197          moltype = AA  length = 17
FEATURE                 Location/Qualifiers
REGION                  1..17
                        note = Synthetic
source                  1..17
                        mol_type = protein
                        organism = synthetic construct
SEQUENCE: 197
GLRWTDSSTE YADSVKG                                                   17

SEQ ID NO: 198          moltype = AA  length = 18
FEATURE                 Location/Qualifiers
REGION                  1..18
                        note = Synthetic
source                  1..18
                        mol_type = protein
                        organism = synthetic construct
SEQUENCE: 198
```

```
DRSFLFAQAL GATKNYEY                                                          18

SEQ ID NO: 199          moltype = AA   length = 120
FEATURE                 Location/Qualifiers
REGION                  1..120
                        note = Synthetic
source                  1..120
                        mol_type = protein
                        organism = synthetic construct
SEQUENCE: 199
DVQLVESGGG VVQPGGSLRL SCAASGRTFS RYAMGWFRQA PGKEREFVAA ISRRGGSTNY   60
ADSVKGRFTI SRDNSKNTVY LQMNSLRPED TALYYCAADY SSGDGYLDYW GQGTLVTVSS  120

SEQ ID NO: 200          moltype = AA   length = 5
FEATURE                 Location/Qualifiers
REGION                  1..5
                        note = Synthetic
source                  1..5
                        mol_type = protein
                        organism = synthetic construct
SEQUENCE: 200
RYAMG                                                                         5

SEQ ID NO: 201          moltype = AA   length = 17
FEATURE                 Location/Qualifiers
REGION                  1..17
                        note = Synthetic
source                  1..17
                        mol_type = protein
                        organism = synthetic construct
SEQUENCE: 201
AISRRGGSTN YADSVKG                                                           17

SEQ ID NO: 202          moltype = AA   length = 11
FEATURE                 Location/Qualifiers
REGION                  1..11
                        note = Synthetic
source                  1..11
                        mol_type = protein
                        organism = synthetic construct
SEQUENCE: 202
DYSSGDGYLD Y                                                                 11

SEQ ID NO: 203          moltype = AA   length = 127
FEATURE                 Location/Qualifiers
REGION                  1..127
                        note = Synthetic
source                  1..127
                        mol_type = protein
                        organism = synthetic construct
SEQUENCE: 203
EVQLVESGGG VVQPGGSLRL SCAASGRTFN IYTMSWFRQA PGKEREFVAG LRWTDSSTEY   60
ADSVKGRFTI SRDNSKNTVY LQMNSLRPED TALYYCAADR SFLFAQALGA TKNYEYWGQG  120
TLVTVSS                                                                     127

SEQ ID NO: 204          moltype = AA   length = 5
FEATURE                 Location/Qualifiers
REGION                  1..5
                        note = Synthetic
source                  1..5
                        mol_type = protein
                        organism = synthetic construct
SEQUENCE: 204
IYTMS                                                                         5

SEQ ID NO: 205          moltype = AA   length = 17
FEATURE                 Location/Qualifiers
REGION                  1..17
                        note = Synthetic
source                  1..17
                        mol_type = protein
                        organism = synthetic construct
SEQUENCE: 205
GLRWTDSSTE YADSVKG                                                           17

SEQ ID NO: 206          moltype = AA   length = 18
FEATURE                 Location/Qualifiers
REGION                  1..18
                        note = Synthetic
```

```
source                  1..18
                        mol_type = protein
                        organism = synthetic construct
SEQUENCE: 206
DRSFLFAQAL GATKNYEY                                                  18

SEQ ID NO: 207          moltype = AA   length = 120
FEATURE                 Location/Qualifiers
REGION                  1..120
                        note = Synthetic
source                  1..120
                        mol_type = protein
                        organism = synthetic construct
SEQUENCE: 207
DVQLVESGGG VVCPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120

SEQ ID NO: 208          moltype = AA   length = 5
FEATURE                 Location/Qualifiers
REGION                  1..5
                        note = Synthetic
source                  1..5
                        mol_type = protein
                        organism = synthetic construct
SEQUENCE: 208
RLAMG                                                                 5

SEQ ID NO: 209          moltype = AA   length = 17
FEATURE                 Location/Qualifiers
REGION                  1..17
                        note = Synthetic
source                  1..17
                        mol_type = protein
                        organism = synthetic construct
SEQUENCE: 209
AISRRGGSTN YADSVKG                                                   17

SEQ ID NO: 210          moltype = AA   length = 11
FEATURE                 Location/Qualifiers
REGION                  1..11
                        note = Synthetic
source                  1..11
                        mol_type = protein
                        organism = synthetic construct
SEQUENCE: 210
DDSSGDGYLD Y                                                         11

SEQ ID NO: 211          moltype = AA   length = 127
FEATURE                 Location/Qualifiers
REGION                  1..127
                        note = Synthetic
source                  1..127
                        mol_type = protein
                        organism = synthetic construct
SEQUENCE: 211
EVQLVESGGG VVQPGGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                             127

SEQ ID NO: 212          moltype = AA   length = 5
FEATURE                 Location/Qualifiers
REGION                  1..5
                        note = Synthetic
source                  1..5
                        mol_type = protein
                        organism = synthetic construct
SEQUENCE: 212
IYTMS                                                                 5

SEQ ID NO: 213          moltype = AA   length = 17
FEATURE                 Location/Qualifiers
REGION                  1..17
                        note = Synthetic
source                  1..17
                        mol_type = protein
                        organism = synthetic construct
SEQUENCE: 213
GLRWTDSSTE YADSVKG                                                   17
```

```
SEQ ID NO: 214          moltype = AA   length = 18
FEATURE                 Location/Qualifiers
REGION                  1..18
                        note = Synthetic
source                  1..18
                        mol_type = protein
                        organism = synthetic construct
SEQUENCE: 214
DRSFLFAQAL GATKNYEY                                                  18

SEQ ID NO: 215          moltype = AA   length = 120
FEATURE                 Location/Qualifiers
REGION                  1..120
                        note = Synthetic
source                  1..120
                        mol_type = protein
                        organism = synthetic construct
SEQUENCE: 215
DVQLVESGGG VVCPGGSLRL SCAASGRTFS RLAMGWFRQA PGKEREFVAA ISRRGGSTNY     60
ADSVKGRFTI SRDNSKNTVY LQMNSLRPED TALYYCAADD SSGDGYLDYW GQGTLVTVSS    120

SEQ ID NO: 216          moltype = AA   length = 5
FEATURE                 Location/Qualifiers
REGION                  1..5
                        note = Synthetic
source                  1..5
                        mol_type = protein
                        organism = synthetic construct
SEQUENCE: 216
RLAMG                                                                 5

SEQ ID NO: 217          moltype = AA   length = 17
FEATURE                 Location/Qualifiers
REGION                  1..17
                        note = Synthetic
source                  1..17
                        mol_type = protein
                        organism = synthetic construct
SEQUENCE: 217
AISRRGGSTN YADSVKG                                                   17

SEQ ID NO: 218          moltype = AA   length = 11
FEATURE                 Location/Qualifiers
REGION                  1..11
                        note = Synthetic
source                  1..11
                        mol_type = protein
                        organism = synthetic construct
SEQUENCE: 218
DDSSGDGYLD Y                                                         11

SEQ ID NO: 219          moltype = AA   length = 127
FEATURE                 Location/Qualifiers
REGION                  1..127
                        note = Synthetic
source                  1..127
                        mol_type = protein
                        organism = synthetic construct
SEQUENCE: 219
EVQLVESGGG VVQPGGSLRL SCAASGRTFN IYTMSWFRQA PGKEREFVAG LRWTDSSTEY     60
ADSVKGRFTI SRDNSKNTVY LQMNSLRPED TALYYCAADR SFLFAQALGA TKNYEYWGQG    120
TLVTVSS                                                              127

SEQ ID NO: 220          moltype = AA   length = 5
FEATURE                 Location/Qualifiers
REGION                  1..5
                        note = Synthetic
source                  1..5
                        mol_type = protein
                        organism = synthetic construct
SEQUENCE: 220
IYTMS                                                                 5

SEQ ID NO: 221          moltype = AA   length = 17
FEATURE                 Location/Qualifiers
REGION                  1..17
                        note = Synthetic
source                  1..17
                        mol_type = protein
```

```
                                organism = synthetic construct
SEQUENCE: 221
GLRWTDSSTE YADSVKG                                                              17

SEQ ID NO: 222          moltype = AA  length = 18
FEATURE                 Location/Qualifiers
REGION                  1..18
                        note = Synthetic
source                  1..18
                        mol_type = protein
                        organism = synthetic construct
SEQUENCE: 222
DRSFLFAQAL GATKNYEY                                                             18

SEQ ID NO: 223          moltype = AA  length = 120
FEATURE                 Location/Qualifiers
REGION                  1..120
                        note = Synthetic
source                  1..120
                        mol_type = protein
                        organism = synthetic construct
SEQUENCE: 223
DVQLVESGGG VVQPGGSLRL SCAASGRTFS RLAMGWFRQA PGKEREFVAA ISRRGGSTNY               60
ADSVKGRFTI SRDNSKNTVY LQMNSLRPED TALYYCAADD SSGDGYLDYW GQGTLVTVSS              120

SEQ ID NO: 224          moltype = AA  length = 5
FEATURE                 Location/Qualifiers
REGION                  1..5
                        note = Synthetic
source                  1..5
                        mol_type = protein
                        organism = synthetic construct
SEQUENCE: 224
RLAMG                                                                            5

SEQ ID NO: 225          moltype = AA  length = 17
FEATURE                 Location/Qualifiers
REGION                  1..17
                        note = Synthetic
source                  1..17
                        mol_type = protein
                        organism = synthetic construct
SEQUENCE: 225
AISRRGGSTN YADSVKG                                                              17

SEQ ID NO: 226          moltype = AA  length = 11
FEATURE                 Location/Qualifiers
REGION                  1..11
                        note = Synthetic
source                  1..11
                        mol_type = protein
                        organism = synthetic construct
SEQUENCE: 226
DDSSGDGYLD Y                                                                    11

SEQ ID NO: 227          moltype = AA  length = 127
FEATURE                 Location/Qualifiers
REGION                  1..127
                        note = Synthetic
source                  1..127
                        mol_type = protein
                        organism = synthetic construct
SEQUENCE: 227
EVQLVESGGG VCQPGGSLRL SCAASGRTFN IYTMSWFRQA PGKEREFVAG LRWTDSSTEY               60
ADSVKGRFTI SRDNSKNTVY LQMNSLRPED TALYYCAADR SFLFAQALGA TKNYEYWGQG              120
TLVTVSS                                                                        127

SEQ ID NO: 228          moltype = AA  length = 5
FEATURE                 Location/Qualifiers
REGION                  1..5
                        note = Synthetic
source                  1..5
                        mol_type = protein
                        organism = synthetic construct
SEQUENCE: 228
IYTMS                                                                            5

SEQ ID NO: 229          moltype = AA  length = 17
FEATURE                 Location/Qualifiers
```

```
REGION                  1..17
                        note = Synthetic
source                  1..17
                        mol_type = protein
                        organism = synthetic construct
SEQUENCE: 229
GLRWTDSSTE YADSVKG                                                      17

SEQ ID NO: 230          moltype = AA   length = 18
FEATURE                 Location/Qualifiers
REGION                  1..18
                        note = Synthetic
source                  1..18
                        mol_type = protein
                        organism = synthetic construct
SEQUENCE: 230
DRSFLFAQAL GATKNYEY                                                     18

SEQ ID NO: 231          moltype = AA   length = 120
FEATURE                 Location/Qualifiers
REGION                  1..120
                        note = Synthetic
source                  1..120
                        mol_type = protein
                        organism = synthetic construct
SEQUENCE: 231
DVQLVESGGG VVQPGGSLRL SCAASGRTFS RLAMGWFRQA PGKEREFVAA ISRRGGSTNY        60
ADSVKGRFTI SRDNSKNTVY LQMNSLRPED TALYYCAADD SSGDGYLDYW GQGTLVTVSS       120

SEQ ID NO: 232          moltype = AA   length = 5
FEATURE                 Location/Qualifiers
REGION                  1..5
                        note = Synthetic
source                  1..5
                        mol_type = protein
                        organism = synthetic construct
SEQUENCE: 232
RLAMG                                                                    5

SEQ ID NO: 233          moltype = AA   length = 17
FEATURE                 Location/Qualifiers
REGION                  1..17
                        note = Synthetic
source                  1..17
                        mol_type = protein
                        organism = synthetic construct
SEQUENCE: 233
AISRRGGSTN YADSVKG                                                      17

SEQ ID NO: 234          moltype = AA   length = 11
FEATURE                 Location/Qualifiers
REGION                  1..11
                        note = Synthetic
source                  1..11
                        mol_type = protein
                        organism = synthetic construct
SEQUENCE: 234
DDSSGDGYLD Y                                                            11

SEQ ID NO: 235          moltype = AA   length = 127
FEATURE                 Location/Qualifiers
REGION                  1..127
                        note = Synthetic
source                  1..127
                        mol_type = protein
                        organism = synthetic construct
SEQUENCE: 235
EVQLVESGGG VCQPGGSLRL SCAASGRTFN IYTMSWFRQA PGKEREFVAG LRWTDSSTEY        60
ADSVKGRFTI SRDNSKNTVY LQMNSLRPED TALYYCAADR SFLFAQALGA TKNYEYWGQG       120
TLVTVSS                                                                127

SEQ ID NO: 236          moltype = AA   length = 5
FEATURE                 Location/Qualifiers
REGION                  1..5
                        note = Synthetic
source                  1..5
                        mol_type = protein
                        organism = synthetic construct
SEQUENCE: 236
```

```
IYTMS                                                                          5

SEQ ID NO: 237          moltype = AA  length = 17
FEATURE                 Location/Qualifiers
REGION                  1..17
                        note = Synthetic
source                  1..17
                        mol_type = protein
                        organism = synthetic construct
SEQUENCE: 237
GLRWTDSSTE YADSVKG                                                            17

SEQ ID NO: 238          moltype = AA  length = 18
FEATURE                 Location/Qualifiers
REGION                  1..18
                        note = Synthetic
source                  1..18
                        mol_type = protein
                        organism = synthetic construct
SEQUENCE: 238
DRSFLFAQAL GATKNYEY                                                           18

SEQ ID NO: 239          moltype = AA  length = 120
FEATURE                 Location/Qualifiers
REGION                  1..120
                        note = Synthetic
source                  1..120
                        mol_type = protein
                        organism = synthetic construct
SEQUENCE: 239
DVQLVESGGG VVQPGGSLRL SCAASGRTFS RLAMGWFRQA PGKEREFVAA ISRRGGSTNY             60
ADSVKGRFTI SRDNSKNTVY LQMNSLRPED TALYYCAADD SSGDGYLDYW GQGTLVTVSS            120

SEQ ID NO: 240          moltype = AA  length = 5
FEATURE                 Location/Qualifiers
REGION                  1..5
                        note = Synthetic
source                  1..5
                        mol_type = protein
                        organism = synthetic construct
SEQUENCE: 240
RLAMG                                                                          5

SEQ ID NO: 241          moltype = AA  length = 17
FEATURE                 Location/Qualifiers
REGION                  1..17
                        note = Synthetic
source                  1..17
                        mol_type = protein
                        organism = synthetic construct
SEQUENCE: 241
AISRRGGSTN YADSVKG                                                            17

SEQ ID NO: 242          moltype = AA  length = 11
FEATURE                 Location/Qualifiers
REGION                  1..11
                        note = Synthetic
source                  1..11
                        mol_type = protein
                        organism = synthetic construct
SEQUENCE: 242
DDSSGDGYLD Y                                                                  11

SEQ ID NO: 243          moltype = AA  length = 127
FEATURE                 Location/Qualifiers
REGION                  1..127
                        note = Synthetic
source                  1..127
                        mol_type = protein
                        organism = synthetic construct
SEQUENCE: 243
EVQLVESGGG VVQCGGSLRL SCAASGRTFN IYTMSWFRQA PGKEREFVAG LRWTDSSTEY             60
ADSVKGRFTI SRDNSKNTVY LQMNSLRPED TALYYCAADR SFLFAQALGA TKNYEYWGQG            120
TLVTVSS                                                                      127

SEQ ID NO: 244          moltype = AA  length = 5
FEATURE                 Location/Qualifiers
REGION                  1..5
                        note = Synthetic
```

```
source                  1..5
                        mol_type = protein
                        organism = synthetic construct
SEQUENCE: 244
IYTMS                                                                    5

SEQ ID NO: 245          moltype = AA   length = 17
FEATURE                 Location/Qualifiers
REGION                  1..17
                        note = Synthetic
source                  1..17
                        mol_type = protein
                        organism = synthetic construct
SEQUENCE: 245
GLRWTDSSTE YADSVKG                                                      17

SEQ ID NO: 246          moltype = AA   length = 18
FEATURE                 Location/Qualifiers
REGION                  1..18
                        note = Synthetic
source                  1..18
                        mol_type = protein
                        organism = synthetic construct
SEQUENCE: 246
DRSFLFAQAL GATKNYEY                                                     18

SEQ ID NO: 247          moltype = AA   length = 120
FEATURE                 Location/Qualifiers
REGION                  1..120
                        note = Synthetic
source                  1..120
                        mol_type = protein
                        organism = synthetic construct
SEQUENCE: 247
DVQLVESGGG VVQPGGSLRL SCAASGRTFS RLAMGWFRQA PGKEREFVAA ISRRGGSTNY        60
ADSVKGRFTI SRDNSKNTVY LQMNSLRPED TALYYCAADD SSGDGYLDYW GQGTLVTVSS       120

SEQ ID NO: 248          moltype = AA   length = 5
FEATURE                 Location/Qualifiers
REGION                  1..5
                        note = Synthetic
source                  1..5
                        mol_type = protein
                        organism = synthetic construct
SEQUENCE: 248
RLAMG                                                                    5

SEQ ID NO: 249          moltype = AA   length = 17
FEATURE                 Location/Qualifiers
REGION                  1..17
                        note = Synthetic
source                  1..17
                        mol_type = protein
                        organism = synthetic construct
SEQUENCE: 249
AISRRGGSTN YADSVKG                                                      17

SEQ ID NO: 250          moltype = AA   length = 11
FEATURE                 Location/Qualifiers
REGION                  1..11
                        note = Synthetic
source                  1..11
                        mol_type = protein
                        organism = synthetic construct
SEQUENCE: 250
DDSSGDGYLD Y                                                            11

SEQ ID NO: 251          moltype = AA   length = 127
FEATURE                 Location/Qualifiers
REGION                  1..127
                        note = Synthetic
source                  1..127
                        mol_type = protein
                        organism = synthetic construct
SEQUENCE: 251
EVQLVESGGG VVQCGGSLRL SCAASGRTFN IYTMSWFRQA PGKEREFVAG LRWTDSSTEY        60
ADSVKGRFTI SRDNSKNTVY LQMNSLRPED TALYYCAADR SFLFAQALGA TKNYEYWGQG       120
TLVTVSS                                                                127
```

-continued

```
SEQ ID NO: 252           moltype = AA   length = 5
FEATURE                  Location/Qualifiers
REGION                   1..5
                         note = Synthetic
source                   1..5
                         mol_type = protein
                         organism = synthetic construct
SEQUENCE: 252
IYTMS                                                                   5

SEQ ID NO: 253           moltype = AA   length = 17
FEATURE                  Location/Qualifiers
REGION                   1..17
                         note = Synthetic
source                   1..17
                         mol_type = protein
                         organism = synthetic construct
SEQUENCE: 253
GLRWTDSSTE YADSVKG                                                     17

SEQ ID NO: 254           moltype = AA   length = 18
FEATURE                  Location/Qualifiers
REGION                   1..18
                         note = Synthetic
source                   1..18
                         mol_type = protein
                         organism = synthetic construct
SEQUENCE: 254
DRSFLFAQAL GATKNYEY                                                    18

SEQ ID NO: 255           moltype = AA   length = 120
FEATURE                  Location/Qualifiers
REGION                   1..120
                         note = Synthetic
source                   1..120
                         mol_type = protein
                         organism = synthetic construct
SEQUENCE: 255
DVQLVESGGG VVQPGGSLRL SCAASGRTFS RLAMGWFRQA PGKEREFVAA ISRRGGSTNY       60
ADSVKGRFTI SRDNSKNTVY LQMNSLRPED TALYYCAADD SSGDGYLDYW GQGTLVTVSS      120

SEQ ID NO: 256           moltype = AA   length = 5
FEATURE                  Location/Qualifiers
REGION                   1..5
                         note = Synthetic
source                   1..5
                         mol_type = protein
                         organism = synthetic construct
SEQUENCE: 256
RLAMG                                                                   5

SEQ ID NO: 257           moltype = AA   length = 17
FEATURE                  Location/Qualifiers
REGION                   1..17
                         note = Synthetic
source                   1..17
                         mol_type = protein
                         organism = synthetic construct
SEQUENCE: 257
AISRRGGSTN YADSVKG                                                     17

SEQ ID NO: 258           moltype = AA   length = 11
FEATURE                  Location/Qualifiers
REGION                   1..11
                         note = Synthetic
source                   1..11
                         mol_type = protein
                         organism = synthetic construct
SEQUENCE: 258
DDSSGDGYLD Y                                                           11

SEQ ID NO: 259           moltype = AA   length = 127
FEATURE                  Location/Qualifiers
REGION                   1..127
                         note = Synthetic
source                   1..127
                         mol_type = protein
                         organism = synthetic construct
SEQUENCE: 259
```

```
EVQLVESGGG VVQPCGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                            127

SEQ ID NO: 260          moltype = AA   length = 5
FEATURE                 Location/Qualifiers
REGION                  1..5
                        note = Synthetic
source                  1..5
                        mol_type = protein
                        organism = synthetic construct
SEQUENCE: 260
IYTMS                                                                5

SEQ ID NO: 261          moltype = AA   length = 17
FEATURE                 Location/Qualifiers
REGION                  1..17
                        note = Synthetic
source                  1..17
                        mol_type = protein
                        organism = synthetic construct
SEQUENCE: 261
GLRWTDSSTE YADSVKG                                                  17

SEQ ID NO: 262          moltype = AA   length = 18
FEATURE                 Location/Qualifiers
REGION                  1..18
                        note = Synthetic
source                  1..18
                        mol_type = protein
                        organism = synthetic construct
SEQUENCE: 262
DRSFLFAQAL GATKNYEY                                                 18

SEQ ID NO: 263          moltype = AA   length = 120
FEATURE                 Location/Qualifiers
REGION                  1..120
                        note = Synthetic
source                  1..120
                        mol_type = protein
                        organism = synthetic construct
SEQUENCE: 263
DVQLVESGGG VVQPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120

SEQ ID NO: 264          moltype = AA   length = 5
FEATURE                 Location/Qualifiers
REGION                  1..5
                        note = Synthetic
source                  1..5
                        mol_type = protein
                        organism = synthetic construct
SEQUENCE: 264
RLAMG                                                                5

SEQ ID NO: 265          moltype = AA   length = 17
FEATURE                 Location/Qualifiers
REGION                  1..17
                        note = Synthetic
source                  1..17
                        mol_type = protein
                        organism = synthetic construct
SEQUENCE: 265
AISRRGGSTN YADSVKG                                                  17

SEQ ID NO: 266          moltype = AA   length = 11
FEATURE                 Location/Qualifiers
REGION                  1..11
                        note = Synthetic
source                  1..11
                        mol_type = protein
                        organism = synthetic construct
SEQUENCE: 266
DDSSGDGYLD Y                                                        11

SEQ ID NO: 267          moltype = AA   length = 127
FEATURE                 Location/Qualifiers
REGION                  1..127
                        note = Synthetic
```

```
                        source                  1..127
                                                mol_type = protein
                                                organism = synthetic construct
SEQUENCE: 267
EVQLVESGGG VVQPCGSLRL SCAASGRTFN IYTMSWFRQA PGKEREFVAG LRWTDSSTEY          60
ADSVKGRFTI SRDNSKNTVY LQMNSLRPED TALYYCAADR SFLFAQALGA TKNYEYWGQG         120
TLVTVSS                                                                  127

SEQ ID NO: 268          moltype = AA  length = 5
FEATURE                 Location/Qualifiers
REGION                  1..5
                        note = Synthetic
source                  1..5
                        mol_type = protein
                        organism = synthetic construct
SEQUENCE: 268
IYTMS                                                                      5

SEQ ID NO: 269          moltype = AA  length = 17
FEATURE                 Location/Qualifiers
REGION                  1..17
                        note = Synthetic
source                  1..17
                        mol_type = protein
                        organism = synthetic construct
SEQUENCE: 269
GLRWTDSSTE YADSVKG                                                        17

SEQ ID NO: 270          moltype = AA  length = 18
FEATURE                 Location/Qualifiers
REGION                  1..18
                        note = Synthetic
source                  1..18
                        mol_type = protein
                        organism = synthetic construct
SEQUENCE: 270
DRSFLFAQAL GATKNYEY                                                       18

SEQ ID NO: 271          moltype = AA  length = 120
FEATURE                 Location/Qualifiers
REGION                  1..120
                        note = Synthetic
source                  1..120
                        mol_type = protein
                        organism = synthetic construct
SEQUENCE: 271
DVQLVESGGG VVQPGGSLRL SCAASGRTFS RLAMGWFRQA PGKEREFVAA ISRRGGSTNY          60
ADSVKGRFTI SRDNSKNTVY LQMNSLRPED TALYYCAADD SSGDGYLDYW GQGTLVTVSS         120

SEQ ID NO: 272          moltype = AA  length = 5
FEATURE                 Location/Qualifiers
REGION                  1..5
                        note = Synthetic
source                  1..5
                        mol_type = protein
                        organism = synthetic construct
SEQUENCE: 272
RLAMG                                                                      5

SEQ ID NO: 273          moltype = AA  length = 17
FEATURE                 Location/Qualifiers
REGION                  1..17
                        note = Synthetic
source                  1..17
                        mol_type = protein
                        organism = synthetic construct
SEQUENCE: 273
AISRRGGSTN YADSVKG                                                        17

SEQ ID NO: 274          moltype = AA  length = 11
FEATURE                 Location/Qualifiers
REGION                  1..11
                        note = Synthetic
source                  1..11
                        mol_type = protein
                        organism = synthetic construct
SEQUENCE: 274
DDSSGDGYLD Y                                                              11
```

```
SEQ ID NO: 275         moltype = AA  length = 127
FEATURE                Location/Qualifiers
REGION                 1..127
                       note = Synthetic
source                 1..127
                       mol_type = protein
                       organism = synthetic construct
SEQUENCE: 275
EVQLVESGGG VVQPGGSLRL SCAASGRTFN IYTMSWFRQA PCKEREFVAG LRWTDSSTEY   60
ADSVKGRFTI SRDNSKNTVY LQMNSLRPED TALYYCAADR SFLFAQALGA TKNYEYWGQG  120
TLVTVSS                                                           127

SEQ ID NO: 276         moltype = AA  length = 5
FEATURE                Location/Qualifiers
REGION                 1..5
                       note = Synthetic
source                 1..5
                       mol_type = protein
                       organism = synthetic construct
SEQUENCE: 276
IYTMS                                                               5

SEQ ID NO: 277         moltype = AA  length = 17
FEATURE                Location/Qualifiers
REGION                 1..17
                       note = Synthetic
source                 1..17
                       mol_type = protein
                       organism = synthetic construct
SEQUENCE: 277
GLRWTDSSTE YADSVKG                                                 17

SEQ ID NO: 278         moltype = AA  length = 18
FEATURE                Location/Qualifiers
REGION                 1..18
                       note = Synthetic
source                 1..18
                       mol_type = protein
                       organism = synthetic construct
SEQUENCE: 278
DRSFLFAQAL GATKNYEY                                                18

SEQ ID NO: 279         moltype = AA  length = 120
FEATURE                Location/Qualifiers
REGION                 1..120
                       note = Synthetic
source                 1..120
                       mol_type = protein
                       organism = synthetic construct
SEQUENCE: 279
DVQLVESGGG VVQPGGSLRL SCAASGRTFS RLAMGWFRQA PGKEREFVAA ISRRGGSTNY   60
ADSVKGRFTI SRDNSKNTVY LQMNSLRPED TALYYCAADD SSGDGYLDYW GQGTLVTVSS  120

SEQ ID NO: 280         moltype = AA  length = 5
FEATURE                Location/Qualifiers
REGION                 1..5
                       note = Synthetic
source                 1..5
                       mol_type = protein
                       organism = synthetic construct
SEQUENCE: 280
RLAMG                                                               5

SEQ ID NO: 281         moltype = AA  length = 17
FEATURE                Location/Qualifiers
REGION                 1..17
                       note = Synthetic
source                 1..17
                       mol_type = protein
                       organism = synthetic construct
SEQUENCE: 281
AISRRGGSTN YADSVKG                                                 17

SEQ ID NO: 282         moltype = AA  length = 11
FEATURE                Location/Qualifiers
REGION                 1..11
                       note = Synthetic
source                 1..11
                       mol_type = protein
```

```
                            organism = synthetic construct
SEQUENCE: 282
DDSSGDGYLD Y                                                                11

SEQ ID NO: 283          moltype = AA  length = 127
FEATURE                 Location/Qualifiers
REGION                  1..127
                        note = Synthetic
source                  1..127
                        mol_type = protein
                        organism = synthetic construct
SEQUENCE: 283
EVQLVESGGG VVQPGGSLRL SCAASGRTFN IYTMSWFRQA PCKEREFVAG LRWTDSSTEY            60
ADSVKGRFTI SRDNSKNTVY LQMNSLRPED TALYYCAADR SFLFAQALGA TKNYEYWGQG           120
TLVTVSS                                                                    127

SEQ ID NO: 284          moltype = AA  length = 5
FEATURE                 Location/Qualifiers
REGION                  1..5
                        note = Synthetic
source                  1..5
                        mol_type = protein
                        organism = synthetic construct
SEQUENCE: 284
IYTMS                                                                       5

SEQ ID NO: 285          moltype = AA  length = 17
FEATURE                 Location/Qualifiers
REGION                  1..17
                        note = Synthetic
source                  1..17
                        mol_type = protein
                        organism = synthetic construct
SEQUENCE: 285
GLRWTDSSTE YADSVKG                                                          17

SEQ ID NO: 286          moltype = AA  length = 18
FEATURE                 Location/Qualifiers
REGION                  1..18
                        note = Synthetic
source                  1..18
                        mol_type = protein
                        organism = synthetic construct
SEQUENCE: 286
DRSFLFAQAL GATKNYEY                                                         18

SEQ ID NO: 287          moltype = AA  length = 120
FEATURE                 Location/Qualifiers
REGION                  1..120
                        note = Synthetic
source                  1..120
                        mol_type = protein
                        organism = synthetic construct
SEQUENCE: 287
DVQLVESGGG VVQPGGSLRL SCAASGRTFS RLAMGWFRQA PGKEREFVAA ISRRGGSTNY            60
ADSVKGRFTI SRDNSKNTVY LQMNSLRPED TALYYCAADD SSGDGYLDYW GQGTLVTVSS           120

SEQ ID NO: 288          moltype = AA  length = 5
FEATURE                 Location/Qualifiers
REGION                  1..5
                        note = Synthetic
source                  1..5
                        mol_type = protein
                        organism = synthetic construct
SEQUENCE: 288
RLAMG                                                                       5

SEQ ID NO: 289          moltype = AA  length = 17
FEATURE                 Location/Qualifiers
REGION                  1..17
                        note = Synthetic
source                  1..17
                        mol_type = protein
                        organism = synthetic construct
SEQUENCE: 289
AISRRGGSTN YADSVKG                                                          17

SEQ ID NO: 290          moltype = AA  length = 11
FEATURE                 Location/Qualifiers
```

```
REGION                    1..11
                          note = Synthetic
source                    1..11
                          mol_type = protein
                          organism = synthetic construct
SEQUENCE: 290
DDSSGDGYLD Y                                                              11

SEQ ID NO: 291            moltype = AA   length = 127
FEATURE                   Location/Qualifiers
REGION                    1..127
                          note = Synthetic
source                    1..127
                          mol_type = protein
                          organism = synthetic construct
SEQUENCE: 291
EVQLVESGGG VVQPGGSLRL SCAASGRTFN IYTMSWFRQA PGKCREFVAG LRWTDSSTEY          60
ADSVKGRFTI SRDNSKNTVY LQMNSLRPED TALYYCAADR SFLFAQALGA TKNYEYWGQG         120
TLVTVSS                                                                  127

SEQ ID NO: 292            moltype = AA   length = 5
FEATURE                   Location/Qualifiers
REGION                    1..5
                          note = Synthetic
source                    1..5
                          mol_type = protein
                          organism = synthetic construct
SEQUENCE: 292
IYTMS                                                                      5

SEQ ID NO: 293            moltype = AA   length = 17
FEATURE                   Location/Qualifiers
REGION                    1..17
                          note = Synthetic
source                    1..17
                          mol_type = protein
                          organism = synthetic construct
SEQUENCE: 293
GLRWTDSSTE YADSVKG                                                        17

SEQ ID NO: 294            moltype = AA   length = 18
FEATURE                   Location/Qualifiers
REGION                    1..18
                          note = Synthetic
source                    1..18
                          mol_type = protein
                          organism = synthetic construct
SEQUENCE: 294
DRSFLFAQAL GATKNYEY                                                       18

SEQ ID NO: 295            moltype = AA   length = 120
FEATURE                   Location/Qualifiers
REGION                    1..120
                          note = Synthetic
source                    1..120
                          mol_type = protein
                          organism = synthetic construct
SEQUENCE: 295
DVQLVESGGG VVQPGGSLRL SCAASGRTFS RLAMGWFRQA PGKEREFVAA ISRRGGSTNY          60
ADSVKGRFTI SRDNSKNTVY LQMNSLRPED TALYYCAADD SSGDGYLDYW GQGTLVTVSS         120

SEQ ID NO: 296            moltype = AA   length = 5
FEATURE                   Location/Qualifiers
REGION                    1..5
                          note = Synthetic
source                    1..5
                          mol_type = protein
                          organism = synthetic construct
SEQUENCE: 296
RLAMG                                                                      5

SEQ ID NO: 297            moltype = AA   length = 17
FEATURE                   Location/Qualifiers
REGION                    1..17
                          note = Synthetic
source                    1..17
                          mol_type = protein
                          organism = synthetic construct
SEQUENCE: 297
```

```
AISRRGGSTN YADSVKG                                                            17

SEQ ID NO: 298          moltype = AA   length = 11
FEATURE                 Location/Qualifiers
REGION                  1..11
                        note = Synthetic
source                  1..11
                        mol_type = protein
                        organism = synthetic construct
SEQUENCE: 298
DDSSGDGYLD Y                                                                  11

SEQ ID NO: 299          moltype = AA   length = 127
FEATURE                 Location/Qualifiers
REGION                  1..127
                        note = Synthetic
source                  1..127
                        mol_type = protein
                        organism = synthetic construct
SEQUENCE: 299
EVQLVESGGG VVQPGGSLRL SCAASGRTFN IYTMSWFRQA PGKCREFVAG LRWTDSSTEY             60
ADSVKGRFTI SRDNSKNTVY LQMNSLRPED TALYYCAADR SFLFAQALGA TKNYEYWGQG            120
TLVTVSS                                                                     127

SEQ ID NO: 300          moltype = AA   length = 5
FEATURE                 Location/Qualifiers
REGION                  1..5
                        note = Synthetic
source                  1..5
                        mol_type = protein
                        organism = synthetic construct
SEQUENCE: 300
IYTMS                                                                         5

SEQ ID NO: 301          moltype = AA   length = 17
FEATURE                 Location/Qualifiers
REGION                  1..17
                        note = Synthetic
source                  1..17
                        mol_type = protein
                        organism = synthetic construct
SEQUENCE: 301
GLRWTDSSTE YADSVKG                                                           17

SEQ ID NO: 302          moltype = AA   length = 18
FEATURE                 Location/Qualifiers
REGION                  1..18
                        note = Synthetic
source                  1..18
                        mol_type = protein
                        organism = synthetic construct
SEQUENCE: 302
DRSFLFAQAL GATKNYEY                                                          18

SEQ ID NO: 303          moltype = AA   length = 120
FEATURE                 Location/Qualifiers
REGION                  1..120
                        note = Synthetic
source                  1..120
                        mol_type = protein
                        organism = synthetic construct
SEQUENCE: 303
DVQLVESGGG VVQPGGSLRL SCAASGRTFS RLAMGWFRQA PGKEREFVAA ISRRGGSTNY             60
ADSVKGRFTI SRDNSKNTVY LQMNSLRPED TALYYCAADD SSGDGYLDYW GQGTLVTVSS            120

SEQ ID NO: 304          moltype = AA   length = 5
FEATURE                 Location/Qualifiers
REGION                  1..5
                        note = Synthetic
source                  1..5
                        mol_type = protein
                        organism = synthetic construct
SEQUENCE: 304
RLAMG                                                                         5

SEQ ID NO: 305          moltype = AA   length = 17
FEATURE                 Location/Qualifiers
REGION                  1..17
                        note = Synthetic
```

```
source                   1..17
                         mol_type = protein
                         organism = synthetic construct
SEQUENCE: 305
AISRRGGSTN YADSVKG                                                    17

SEQ ID NO: 306           moltype = AA  length = 11
FEATURE                  Location/Qualifiers
REGION                   1..11
                         note = Synthetic
source                   1..11
                         mol_type = protein
                         organism = synthetic construct
SEQUENCE: 306
DDSSGDGYLD Y                                                          11

SEQ ID NO: 307           moltype = AA  length = 127
FEATURE                  Location/Qualifiers
REGION                   1..127
                         note = Synthetic
source                   1..127
                         mol_type = protein
                         organism = synthetic construct
SEQUENCE: 307
EVQLVESGGG VVQPGGSLRL SCAASGRTFN IYTMSWFRQA PGKEREFVAG LRWTDSSTEY      60
ADCVKGRFTI SRDNSKNTVY LQMNSLRPED TALYYCAADR SFLFAQALGA TKNYEYWGQG     120
TLVTVSS                                                              127

SEQ ID NO: 308           moltype = AA  length = 5
FEATURE                  Location/Qualifiers
REGION                   1..5
                         note = Synthetic
source                   1..5
                         mol_type = protein
                         organism = synthetic construct
SEQUENCE: 308
IYTMS                                                                  5

SEQ ID NO: 309           moltype = AA  length = 17
FEATURE                  Location/Qualifiers
REGION                   1..17
                         note = Synthetic
source                   1..17
                         mol_type = protein
                         organism = synthetic construct
SEQUENCE: 309
GLRWTDSSTE YADCVKG                                                    17

SEQ ID NO: 310           moltype = AA  length = 18
FEATURE                  Location/Qualifiers
REGION                   1..18
                         note = Synthetic
source                   1..18
                         mol_type = protein
                         organism = synthetic construct
SEQUENCE: 310
DRSFLFAQAL GATKNYEY                                                   18

SEQ ID NO: 311           moltype = AA  length = 120
FEATURE                  Location/Qualifiers
REGION                   1..120
                         note = Synthetic
source                   1..120
                         mol_type = protein
                         organism = synthetic construct
SEQUENCE: 311
DVQLVESGGG VVQPGGSLRL SCAASGRTFS RLAMGWFRQA PGKEREFVAA ISRRGGSTNY      60
ADSVKGRFTI SRDNSKNTVY LQMNSLRPED TALYYCAADD SSGDGYLDYW GQGTLVTVSS     120

SEQ ID NO: 312           moltype = AA  length = 5
FEATURE                  Location/Qualifiers
REGION                   1..5
                         note = Synthetic
source                   1..5
                         mol_type = protein
                         organism = synthetic construct
SEQUENCE: 312
RLAMG                                                                  5
```

```
SEQ ID NO: 313          moltype = AA  length = 17
FEATURE                 Location/Qualifiers
REGION                  1..17
                        note = Synthetic
source                  1..17
                        mol_type = protein
                        organism = synthetic construct
SEQUENCE: 313
AISRRGGSTN YADSVKG                                                       17

SEQ ID NO: 314          moltype = AA  length = 11
FEATURE                 Location/Qualifiers
REGION                  1..11
                        note = Synthetic
source                  1..11
                        mol_type = protein
                        organism = synthetic construct
SEQUENCE: 314
DDSSGDGYLD Y                                                             11

SEQ ID NO: 315          moltype = AA  length = 127
FEATURE                 Location/Qualifiers
REGION                  1..127
                        note = Synthetic
source                  1..127
                        mol_type = protein
                        organism = synthetic construct
SEQUENCE: 315
EVQLVESGGG VVQPGGSLRL SCAASGRTFN IYTMSWFRQA PGKEREFVAG LRWTDSSTEY         60
ADCVKGRFTI SRDNSKNTVY LQMNSLRPED TALYYCAADR SFLFAQALGA TKNYEYWGQG        120
TLVTVSS                                                                 127

SEQ ID NO: 316          moltype = AA  length = 5
FEATURE                 Location/Qualifiers
REGION                  1..5
                        note = Synthetic
source                  1..5
                        mol_type = protein
                        organism = synthetic construct
SEQUENCE: 316
IYTMS                                                                    5

SEQ ID NO: 317          moltype = AA  length = 17
FEATURE                 Location/Qualifiers
REGION                  1..17
                        note = Synthetic
source                  1..17
                        mol_type = protein
                        organism = synthetic construct
SEQUENCE: 317
GLRWTDSSTE YADCVKG                                                       17

SEQ ID NO: 318          moltype = AA  length = 18
FEATURE                 Location/Qualifiers
REGION                  1..18
                        note = Synthetic
source                  1..18
                        mol_type = protein
                        organism = synthetic construct
SEQUENCE: 318
DRSFLFAQAL GATKNYEY                                                      18

SEQ ID NO: 319          moltype = AA  length = 120
FEATURE                 Location/Qualifiers
REGION                  1..120
                        note = Synthetic
source                  1..120
                        mol_type = protein
                        organism = synthetic construct
SEQUENCE: 319
DVQLVESGGG VVQPGGSLRL SCAASGRTFS RLAMGWFRQA PGKEREFVAA ISRRGGSTNY         60
ADSVKGRFTI SRDNSKNTVY LQMNSLRPED TALYYCAADD SSGDGYLDYW GQGTLVTVSS        120

SEQ ID NO: 320          moltype = AA  length = 5
FEATURE                 Location/Qualifiers
REGION                  1..5
                        note = Synthetic
source                  1..5
                        mol_type = protein
```

```
                        organism = synthetic construct
SEQUENCE: 320
RLAMG                                                                   5

SEQ ID NO: 321          moltype = AA   length = 17
FEATURE                 Location/Qualifiers
REGION                  1..17
                        note = Synthetic
source                  1..17
                        mol_type = protein
                        organism = synthetic construct
SEQUENCE: 321
AISRRGGSTN YADSVKG                                                     17

SEQ ID NO: 322          moltype = AA   length = 11
FEATURE                 Location/Qualifiers
REGION                  1..11
                        note = Synthetic
source                  1..11
                        mol_type = protein
                        organism = synthetic construct
SEQUENCE: 322
DDSSGDGYLD Y                                                           11

SEQ ID NO: 323          moltype = AA   length = 127
FEATURE                 Location/Qualifiers
REGION                  1..127
                        note = Synthetic
source                  1..127
                        mol_type = protein
                        organism = synthetic construct
SEQUENCE: 323
EVQLVESGGG VVQPGGSLRL SCAASGRTFN IYTMSWFRQA PGKEREFVAG LRWTDSSTEY       60
ADSVKGRFTI SRDNSKNTVY LQMNCLRPED TALYYCAADR SFLFAQALGA TKNYEYWGQG      120
TLVTVSS                                                               127

SEQ ID NO: 324          moltype = AA   length = 5
FEATURE                 Location/Qualifiers
REGION                  1..5
                        note = Synthetic
source                  1..5
                        mol_type = protein
                        organism = synthetic construct
SEQUENCE: 324
IYTMS                                                                   5

SEQ ID NO: 325          moltype = AA   length = 17
FEATURE                 Location/Qualifiers
REGION                  1..17
                        note = Synthetic
source                  1..17
                        mol_type = protein
                        organism = synthetic construct
SEQUENCE: 325
GLRWTDSSTE YADSVKG                                                     17

SEQ ID NO: 326          moltype = AA   length = 18
FEATURE                 Location/Qualifiers
REGION                  1..18
                        note = Synthetic
source                  1..18
                        mol_type = protein
                        organism = synthetic construct
SEQUENCE: 326
DRSFLFAQAL GATKNYEY                                                    18

SEQ ID NO: 327          moltype = AA   length = 120
FEATURE                 Location/Qualifiers
REGION                  1..120
                        note = Synthetic
source                  1..120
                        mol_type = protein
                        organism = synthetic construct
SEQUENCE: 327
DVQLVESGGG VVQPGGSLRL SCAASGRTFS RLAMGWFRQA PGKEREFVAA ISRRGGSTNY       60
ADSVKGRFTI SRDNSKNTVY LQMNSLRPED TALYYCAADD SSGDGYLDYW GQGTLVTVSS      120

SEQ ID NO: 328          moltype = AA   length = 5
FEATURE                 Location/Qualifiers
```

```
REGION                   1..5
                         note = Synthetic
source                   1..5
                         mol_type = protein
                         organism = synthetic construct
SEQUENCE: 328
RLAMG                                                                       5

SEQ ID NO: 329           moltype = AA  length = 17
FEATURE                  Location/Qualifiers
REGION                   1..17
                         note = Synthetic
source                   1..17
                         mol_type = protein
                         organism = synthetic construct
SEQUENCE: 329
AISRRGGSTN YADSVKG                                                         17

SEQ ID NO: 330           moltype = AA  length = 11
FEATURE                  Location/Qualifiers
REGION                   1..11
                         note = Synthetic
source                   1..11
                         mol_type = protein
                         organism = synthetic construct
SEQUENCE: 330
DDSSGDGYLD Y                                                               11

SEQ ID NO: 331           moltype = AA  length = 127
FEATURE                  Location/Qualifiers
REGION                   1..127
                         note = Synthetic
source                   1..127
                         mol_type = protein
                         organism = synthetic construct
SEQUENCE: 331
EVQLVESGGG VVQPGGSLRL SCAASGRTFN IYTMSWFRQA PGKEREFVAG LRWTDSSTEY           60
ADSVKGRFTI SRDNSKNTVY LQMNCLRPED TALYYCAADR SFLFAQALGA TKNYEYWGQG          120
TLVTVSS                                                                   127

SEQ ID NO: 332           moltype = AA  length = 5
FEATURE                  Location/Qualifiers
REGION                   1..5
                         note = Synthetic
source                   1..5
                         mol_type = protein
                         organism = synthetic construct
SEQUENCE: 332
IYTMS                                                                       5

SEQ ID NO: 333           moltype = AA  length = 17
FEATURE                  Location/Qualifiers
REGION                   1..17
                         note = Synthetic
source                   1..17
                         mol_type = protein
                         organism = synthetic construct
SEQUENCE: 333
GLRWTDSSTE YADSVKG                                                         17

SEQ ID NO: 334           moltype = AA  length = 18
FEATURE                  Location/Qualifiers
REGION                   1..18
                         note = Synthetic
source                   1..18
                         mol_type = protein
                         organism = synthetic construct
SEQUENCE: 334
DRSFLFAQAL GATKNYEY                                                        18

SEQ ID NO: 335           moltype = AA  length = 120
FEATURE                  Location/Qualifiers
REGION                   1..120
                         note = Synthetic
source                   1..120
                         mol_type = protein
                         organism = synthetic construct
SEQUENCE: 335
DVQLVESGGG VVQPGGSLQL SCAASGRTHS RLAMGWFRQA PGQEREFVAA ISRRGGSTNY           60
```

```
ADSVKGRFTI SRDNSKNTVY LQMDSLRPED TALYYCAADD SSGDGYLDYW GQGTLVTVSS   120

SEQ ID NO: 336          moltype = AA  length = 5
FEATURE                 Location/Qualifiers
REGION                  1..5
                        note = Synthetic
source                  1..5
                        mol_type = protein
                        organism = synthetic construct
SEQUENCE: 336
RLAMG                                                                5

SEQ ID NO: 337          moltype = AA  length = 17
FEATURE                 Location/Qualifiers
REGION                  1..17
                        note = Synthetic
source                  1..17
                        mol_type = protein
                        organism = synthetic construct
SEQUENCE: 337
AISRRGGSTN YADSVKG                                                  17

SEQ ID NO: 338          moltype = AA  length = 11
FEATURE                 Location/Qualifiers
REGION                  1..11
                        note = Synthetic
source                  1..11
                        mol_type = protein
                        organism = synthetic construct
SEQUENCE: 338
DDSSGDGYLD Y                                                        11

SEQ ID NO: 339          moltype = AA  length = 127
FEATURE                 Location/Qualifiers
REGION                  1..127
                        note = Synthetic
source                  1..127
                        mol_type = protein
                        organism = synthetic construct
SEQUENCE: 339
EVQLVESGGG VVQPGGSLQL SCAASGRTFN IYTMSWFRQA PGQEREFVAG LRWTDSSTEY    60
ADSVKGRFTI SRDNSKNTVY LQMDSLRPED TALYYCAADR SFLFAQALGA TKNYEYWGQG   120
TLVTVSS                                                            127

SEQ ID NO: 340          moltype = AA  length = 5
FEATURE                 Location/Qualifiers
REGION                  1..5
                        note = Synthetic
source                  1..5
                        mol_type = protein
                        organism = synthetic construct
SEQUENCE: 340
IYTMS                                                                5

SEQ ID NO: 341          moltype = AA  length = 17
FEATURE                 Location/Qualifiers
REGION                  1..17
                        note = Synthetic
source                  1..17
                        mol_type = protein
                        organism = synthetic construct
SEQUENCE: 341
GLRWTDSSTE YADSVKG                                                  17

SEQ ID NO: 342          moltype = AA  length = 18
FEATURE                 Location/Qualifiers
REGION                  1..18
                        note = Synthetic
source                  1..18
                        mol_type = protein
                        organism = synthetic construct
SEQUENCE: 342
DRSFLFAQAL GATKNYEY                                                 18

SEQ ID NO: 343          moltype = AA  length = 120
FEATURE                 Location/Qualifiers
REGION                  1..120
                        note = Synthetic
source                  1..120
```

```
                            mol_type = protein
                            organism = synthetic construct
SEQUENCE: 343
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 344              moltype = AA   length = 5
FEATURE                     Location/Qualifiers
REGION                      1..5
                            note = Synthetic
source                      1..5
                            mol_type = protein
                            organism = synthetic construct
SEQUENCE: 344
RLAMG                                                                 5

SEQ ID NO: 345              moltype = AA   length = 17
FEATURE                     Location/Qualifiers
REGION                      1..17
                            note = Synthetic
source                      1..17
                            mol_type = protein
                            organism = synthetic construct
SEQUENCE: 345
AISRRGGSTN YADSVKG                                                   17

SEQ ID NO: 346              moltype = AA   length = 11
FEATURE                     Location/Qualifiers
REGION                      1..11
                            note = Synthetic
source                      1..11
                            mol_type = protein
                            organism = synthetic construct
SEQUENCE: 346
DDSSGDGYLD Y                                                         11

SEQ ID NO: 347              moltype = AA   length = 127
FEATURE                     Location/Qualifiers
REGION                      1..127
                            note = Synthetic
source                      1..127
                            mol_type = protein
                            organism = synthetic construct
SEQUENCE: 347
EVQLVESGGG VVQPGGSLQL SCAASGRTFN IYTMSWFRQA PGQEREFVAG LRWTDSSTEY    60
ADSVKGRFTI SRDNSKNTVY LQMDSLRPED TALYYCAADR SFLFAQALGA TKNYEYWGQG   120
TLVTVSS                                                             127

SEQ ID NO: 348              moltype = AA   length = 5
FEATURE                     Location/Qualifiers
REGION                      1..5
                            note = Synthetic
source                      1..5
                            mol_type = protein
                            organism = synthetic construct
SEQUENCE: 348
IYTMS                                                                 5

SEQ ID NO: 349              moltype = AA   length = 17
FEATURE                     Location/Qualifiers
REGION                      1..17
                            note = Synthetic
source                      1..17
                            mol_type = protein
                            organism = synthetic construct
SEQUENCE: 349
GLRWTDSSTE YADSVKG                                                   17

SEQ ID NO: 350              moltype = AA   length = 18
FEATURE                     Location/Qualifiers
REGION                      1..18
                            note = Synthetic
source                      1..18
                            mol_type = protein
                            organism = synthetic construct
SEQUENCE: 350
DRSFLFAQAL GATKNYEY                                                  18

SEQ ID NO: 351              moltype = AA   length = 120
```

```
FEATURE                 Location/Qualifiers
REGION                  1..120
                        note = Synthetic
source                  1..120
                        mol_type = protein
                        organism = synthetic construct
SEQUENCE: 351
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 352          moltype = AA   length = 5
FEATURE                 Location/Qualifiers
REGION                  1..5
                        note = Synthetic
source                  1..5
                        mol_type = protein
                        organism = synthetic construct
SEQUENCE: 352
RLAMG                                                                 5

SEQ ID NO: 353          moltype = AA   length = 17
FEATURE                 Location/Qualifiers
REGION                  1..17
                        note = Synthetic
source                  1..17
                        mol_type = protein
                        organism = synthetic construct
SEQUENCE: 353
AISRRGGSTN YADSVKG                                                   17

SEQ ID NO: 354          moltype = AA   length = 11
FEATURE                 Location/Qualifiers
REGION                  1..11
                        note = Synthetic
source                  1..11
                        mol_type = protein
                        organism = synthetic construct
SEQUENCE: 354
DDSSGDGYLD Y                                                         11

SEQ ID NO: 355          moltype = AA   length = 127
FEATURE                 Location/Qualifiers
REGION                  1..127
                        note = Synthetic
source                  1..127
                        mol_type = protein
                        organism = synthetic construct
SEQUENCE: 355
EVQLVESGGG VVQPGGSLQL SCAASGRTFN IYTMSWFRQA PGQEREFVAG LRWTDSSTEY    60
ADSVKGRFTI SRDNSKNTVY LQMDSLRPED TALYYCAADR SFLFAQALGA TKNYEYWGQG   120
TLVTVSS                                                             127

SEQ ID NO: 356          moltype = AA   length = 5
FEATURE                 Location/Qualifiers
REGION                  1..5
                        note = Synthetic
source                  1..5
                        mol_type = protein
                        organism = synthetic construct
SEQUENCE: 356
IYTMS                                                                 5

SEQ ID NO: 357          moltype = AA   length = 17
FEATURE                 Location/Qualifiers
REGION                  1..17
                        note = Synthetic
source                  1..17
                        mol_type = protein
                        organism = synthetic construct
SEQUENCE: 357
GLRWTDSSTE YADSVKG                                                   17

SEQ ID NO: 358          moltype = AA   length = 18
FEATURE                 Location/Qualifiers
REGION                  1..18
                        note = Synthetic
source                  1..18
                        mol_type = protein
                        organism = synthetic construct
```

```
SEQUENCE: 358
DRSFLFAQAL GATKNYEY                                               18

SEQ ID NO: 359        moltype = AA  length = 120
FEATURE               Location/Qualifiers
REGION                1..120
                      note = Synthetic
source                1..120
                      mol_type = protein
                      organism = synthetic construct
SEQUENCE: 359
DVQLVESGGG VVQPGGSLQL SCAASGRTHS RLAMGWFRQA PGQEREFVAA ISRRGGSTNY  60
ADSVKGRFTI SRDNSKNTVY LQMDSLRPED TALYYCAADD SSGDGYLDYW GQGTLVTVSS 120

SEQ ID NO: 360        moltype = AA  length = 5
FEATURE               Location/Qualifiers
REGION                1..5
                      note = Synthetic
source                1..5
                      mol_type = protein
                      organism = synthetic construct
SEQUENCE: 360
RLAMG                                                              5

SEQ ID NO: 361        moltype = AA  length = 17
FEATURE               Location/Qualifiers
REGION                1..17
                      note = Synthetic
source                1..17
                      mol_type = protein
                      organism = synthetic construct
SEQUENCE: 361
AISRRGGSTN YADSVKG                                                17

SEQ ID NO: 362        moltype = AA  length = 11
FEATURE               Location/Qualifiers
REGION                1..11
                      note = Synthetic
source                1..11
                      mol_type = protein
                      organism = synthetic construct
SEQUENCE: 362
DDSSGDGYLD Y                                                      11

SEQ ID NO: 363        moltype = AA  length = 127
FEATURE               Location/Qualifiers
REGION                1..127
                      note = Synthetic
source                1..127
                      mol_type = protein
                      organism = synthetic construct
SEQUENCE: 363
EVQLVESGGG VVQPGGSLQL SCAASGRTFN IYTMSWFRQA PGQEREFVAG LRWTDSSTEY  60
ADSVKGRFTI SRDNSKNTVY LQMDSLRPED TALYYCAADR SFLFAQALGA TKNYEYWGQG 120
TLVTVSS                                                          127

SEQ ID NO: 364        moltype = AA  length = 5
FEATURE               Location/Qualifiers
REGION                1..5
                      note = Synthetic
source                1..5
                      mol_type = protein
                      organism = synthetic construct
SEQUENCE: 364
IYTMS                                                              5

SEQ ID NO: 365        moltype = AA  length = 17
FEATURE               Location/Qualifiers
REGION                1..17
                      note = Synthetic
source                1..17
                      mol_type = protein
                      organism = synthetic construct
SEQUENCE: 365
GLRWTDSSTE YADSVKG                                                17

SEQ ID NO: 366        moltype = AA  length = 18
FEATURE               Location/Qualifiers
REGION                1..18
```

```
                        note = Synthetic
source                  1..18
                        mol_type = protein
                        organism = synthetic construct
SEQUENCE: 366
DRSFLFAQAL GATKNYEY                                                         18

SEQ ID NO: 367          moltype = AA  length = 120
FEATURE                 Location/Qualifiers
REGION                  1..120
                        note = Synthetic
source                  1..120
                        mol_type = protein
                        organism = synthetic construct
SEQUENCE: 367
DVQLVESGGG VVQPGGSLQL SCAASGRTHS RLAMGWFRQA PGQEREFVAA ISRRGGSTNY            60
ADSVKGRFTI SRDNSKNTVY LQMDSLRPED TALYYCAADD SSGDGYLDYW GQGTLVTVSS           120

SEQ ID NO: 368          moltype = AA  length = 5
FEATURE                 Location/Qualifiers
REGION                  1..5
                        note = Synthetic
source                  1..5
                        mol_type = protein
                        organism = synthetic construct
SEQUENCE: 368
RLAMG                                                                        5

SEQ ID NO: 369          moltype = AA  length = 17
FEATURE                 Location/Qualifiers
REGION                  1..17
                        note = Synthetic
source                  1..17
                        mol_type = protein
                        organism = synthetic construct
SEQUENCE: 369
AISRRGGSTN YADSVKG                                                          17

SEQ ID NO: 370          moltype = AA  length = 11
FEATURE                 Location/Qualifiers
REGION                  1..11
                        note = Synthetic
source                  1..11
                        mol_type = protein
                        organism = synthetic construct
SEQUENCE: 370
DDSSGDGYLD Y                                                                11

SEQ ID NO: 371          moltype = AA  length = 127
FEATURE                 Location/Qualifiers
REGION                  1..127
                        note = Synthetic
source                  1..127
                        mol_type = protein
                        organism = synthetic construct
SEQUENCE: 371
EVQLVESGGG VVQPGGSLQL SCAASGRTFN IYTMSWFRQA PGQEREFVAG LRWTDSSTEY            60
ADSVKGRFTI SRDNSKNTVY LQMDSLRPED TALYYCAADR SFLFAQALGA TKNYEYWGQG           120
TLVTVSS                                                                    127

SEQ ID NO: 372          moltype = AA  length = 5
FEATURE                 Location/Qualifiers
REGION                  1..5
                        note = Synthetic
source                  1..5
                        mol_type = protein
                        organism = synthetic construct
SEQUENCE: 372
IYTMS                                                                        5

SEQ ID NO: 373          moltype = AA  length = 17
FEATURE                 Location/Qualifiers
REGION                  1..17
                        note = Synthetic
source                  1..17
                        mol_type = protein
                        organism = synthetic construct
SEQUENCE: 373
GLRWTDSSTE YADSVKG                                                          17
```

```
SEQ ID NO: 374           moltype = AA   length = 18
FEATURE                  Location/Qualifiers
REGION                   1..18
                         note = Synthetic
source                   1..18
                         mol_type = protein
                         organism = synthetic construct
SEQUENCE: 374
DRSFLFAQAL GATKNYEY                                                    18

SEQ ID NO: 375           moltype = AA   length = 120
FEATURE                  Location/Qualifiers
REGION                   1..120
                         note = Synthetic
source                   1..120
                         mol_type = protein
                         organism = synthetic construct
SEQUENCE: 375
DVQLVESGGG VVQPGGSLQL SCAASGRTHS RLAMGWFRQA PGQEREFVAA ISRRGGSTNY       60
ADSVKGRFTI SRDNSKNTVY LQMDSLRPED TALYYCAADD SSGDGYLDYW GQGTLVTVSS      120

SEQ ID NO: 376           moltype = AA   length = 5
FEATURE                  Location/Qualifiers
REGION                   1..5
                         note = Synthetic
source                   1..5
                         mol_type = protein
                         organism = synthetic construct
SEQUENCE: 376
RLAMG                                                                   5

SEQ ID NO: 377           moltype = AA   length = 17
FEATURE                  Location/Qualifiers
REGION                   1..17
                         note = Synthetic
source                   1..17
                         mol_type = protein
                         organism = synthetic construct
SEQUENCE: 377
AISRRGGSTN YADSVKG                                                     17

SEQ ID NO: 378           moltype = AA   length = 11
FEATURE                  Location/Qualifiers
REGION                   1..11
                         note = Synthetic
source                   1..11
                         mol_type = protein
                         organism = synthetic construct
SEQUENCE: 378
DDSSGDGYLD Y                                                           11

SEQ ID NO: 379           moltype = AA   length = 127
FEATURE                  Location/Qualifiers
REGION                   1..127
                         note = Synthetic
source                   1..127
                         mol_type = protein
                         organism = synthetic construct
SEQUENCE: 379
EVQLVESGGG VVQPGGSLQL SCAASGRTFN IYTMSWFRQA PGQEREFVAG LRWTDSSTEY       60
ADSVKGRFTI SRDNSKNTVY LQMDSLRPED TALYYCAADR SFLFAKALGA TKNYEYWGQG      120
TLVTVSS                                                               127

SEQ ID NO: 380           moltype = AA   length = 5
FEATURE                  Location/Qualifiers
REGION                   1..5
                         note = Synthetic
source                   1..5
                         mol_type = protein
                         organism = synthetic construct
SEQUENCE: 380
IYTMS                                                                   5

SEQ ID NO: 381           moltype = AA   length = 17
FEATURE                  Location/Qualifiers
REGION                   1..17
                         note = Synthetic
source                   1..17
```

```
                        mol_type = protein
                        organism = synthetic construct
SEQUENCE: 381
GLRWTDSSTE YADSVKG                                                  17

SEQ ID NO: 382          moltype = AA   length = 18
FEATURE                 Location/Qualifiers
REGION                  1..18
                        note = Synthetic
source                  1..18
                        mol_type = protein
                        organism = synthetic construct
SEQUENCE: 382
DRSFLFAKAL GATKNYEY                                                 18

SEQ ID NO: 383          moltype = AA   length = 120
FEATURE                 Location/Qualifiers
REGION                  1..120
                        note = Synthetic
source                  1..120
                        mol_type = protein
                        organism = synthetic construct
SEQUENCE: 383
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 384          moltype = AA   length = 5
FEATURE                 Location/Qualifiers
REGION                  1..5
                        note = Synthetic
source                  1..5
                        mol_type = protein
                        organism = synthetic construct
SEQUENCE: 384
RLAMG                                                                5

SEQ ID NO: 385          moltype = AA   length = 17
FEATURE                 Location/Qualifiers
REGION                  1..17
                        note = Synthetic
source                  1..17
                        mol_type = protein
                        organism = synthetic construct
SEQUENCE: 385
AISRRGGSTN YADSVKG                                                  17

SEQ ID NO: 386          moltype = AA   length = 11
FEATURE                 Location/Qualifiers
REGION                  1..11
                        note = Synthetic
source                  1..11
                        mol_type = protein
                        organism = synthetic construct
SEQUENCE: 386
DDSSGDGYLD Y                                                        11

SEQ ID NO: 387          moltype = AA   length = 127
FEATURE                 Location/Qualifiers
REGION                  1..127
                        note = Synthetic
source                  1..127
                        mol_type = protein
                        organism = synthetic construct
SEQUENCE: 387
EVQLVESGGG VVQPGGSLQL SCAASGRTFN IYTMSWFRQA PGQEREFVAG LRWTDSSTEY    60
ADSVKGRFTI SRDNSKNTVY LQMDSLRPED TALYYCAADR SFLFAKALGA TKNYEYWGQG   120
TLVTVSS                                                            127

SEQ ID NO: 388          moltype = AA   length = 5
FEATURE                 Location/Qualifiers
REGION                  1..5
                        note = Synthetic
source                  1..5
                        mol_type = protein
                        organism = synthetic construct
SEQUENCE: 388
IYTMS                                                                5

SEQ ID NO: 389          moltype = AA   length = 17
```

```
FEATURE                 Location/Qualifiers
REGION                  1..17
                        note = Synthetic
source                  1..17
                        mol_type = protein
                        organism = synthetic construct
SEQUENCE: 389
GLRWTDSSTE YADSVKG                                                       17

SEQ ID NO: 390          moltype = AA  length = 18
FEATURE                 Location/Qualifiers
REGION                  1..18
                        note = Synthetic
source                  1..18
                        mol_type = protein
                        organism = synthetic construct
SEQUENCE: 390
DRSFLFAKAL GATKNYEY                                                      18

SEQ ID NO: 391          moltype = AA  length = 120
FEATURE                 Location/Qualifiers
REGION                  1..120
                        note = Synthetic
source                  1..120
                        mol_type = protein
                        organism = synthetic construct
SEQUENCE: 391
DVQLVESGGG VVQPGGSLQL SCAASGRTHS RLAMGWFRQA PGQEREFVAA ISRRGGSTNY        60
ADSVKGRFTI SRDNSKNTVY LQMDSLRPED TALYYCAADD SSGDGYLDYW GQGTLVTVSS       120

SEQ ID NO: 392          moltype = AA  length = 5
FEATURE                 Location/Qualifiers
REGION                  1..5
                        note = Synthetic
source                  1..5
                        mol_type = protein
                        organism = synthetic construct
SEQUENCE: 392
RLAMG                                                                     5

SEQ ID NO: 393          moltype = AA  length = 17
FEATURE                 Location/Qualifiers
REGION                  1..17
                        note = Synthetic
source                  1..17
                        mol_type = protein
                        organism = synthetic construct
SEQUENCE: 393
AISRRGGSTN YADSVKG                                                       17

SEQ ID NO: 394          moltype = AA  length = 11
FEATURE                 Location/Qualifiers
REGION                  1..11
                        note = Synthetic
source                  1..11
                        mol_type = protein
                        organism = synthetic construct
SEQUENCE: 394
DDSSGDGYLD Y                                                             11

SEQ ID NO: 395          moltype = AA  length = 127
FEATURE                 Location/Qualifiers
REGION                  1..127
                        note = Synthetic
source                  1..127
                        mol_type = protein
                        organism = synthetic construct
SEQUENCE: 395
EVQLVESGGG VVQPGGSLQL SCAASGRTFN IYTMSWFRQA PGQEREFVAG LRWTDSSTEY        60
ADSVKGRFTI SRDNSKNTVY LQMDSLRPED TALYYCAADR SFLFAKALGA TKNYEYWGQG       120
TLVTVSS                                                                 127

SEQ ID NO: 396          moltype = AA  length = 5
FEATURE                 Location/Qualifiers
REGION                  1..5
                        note = Synthetic
source                  1..5
                        mol_type = protein
                        organism = synthetic construct
```

```
SEQUENCE: 396
IYTMS                                                                5

SEQ ID NO: 397         moltype = AA  length = 17
FEATURE                Location/Qualifiers
REGION                 1..17
                       note = Synthetic
source                 1..17
                       mol_type = protein
                       organism = synthetic construct
SEQUENCE: 397
GLRWTDSSTE YADSVKG                                                  17

SEQ ID NO: 398         moltype = AA  length = 18
FEATURE                Location/Qualifiers
REGION                 1..18
                       note = Synthetic
source                 1..18
                       mol_type = protein
                       organism = synthetic construct
SEQUENCE: 398
DRSFLFAKAL GATKNYEY                                                 18

SEQ ID NO: 399         moltype = AA  length = 120
FEATURE                Location/Qualifiers
REGION                 1..120
                       note = Synthetic
source                 1..120
                       mol_type = protein
                       organism = synthetic construct
SEQUENCE: 399
DVQLVESGGG VVQPGGSLQL SCAASGRTHS RLAMGWFRQA PGQEREFVAA ISRRGGSTNY   60
ADSVKGRFTI SRDNSKNTVY LQMDSLRPED TALYYCAADD SSGDGYLDYW GQGTLVTVSS  120

SEQ ID NO: 400         moltype = AA  length = 5
FEATURE                Location/Qualifiers
REGION                 1..5
                       note = Synthetic
source                 1..5
                       mol_type = protein
                       organism = synthetic construct
SEQUENCE: 400
RLAMG                                                                5

SEQ ID NO: 401         moltype = AA  length = 17
FEATURE                Location/Qualifiers
REGION                 1..17
                       note = Synthetic
source                 1..17
                       mol_type = protein
                       organism = synthetic construct
SEQUENCE: 401
AISRRGGSTN YADSVKG                                                  17

SEQ ID NO: 402         moltype = AA  length = 11
FEATURE                Location/Qualifiers
REGION                 1..11
                       note = Synthetic
source                 1..11
                       mol_type = protein
                       organism = synthetic construct
SEQUENCE: 402
DDSSGDGYLD Y                                                        11

SEQ ID NO: 403         moltype = AA  length = 127
FEATURE                Location/Qualifiers
REGION                 1..127
                       note = Synthetic
source                 1..127
                       mol_type = protein
                       organism = synthetic construct
SEQUENCE: 403
EVQLVESGGG VVQPGGSLQL SCAASGRTFN IYTMSWFRQA PGQEREFVAG LRWTDSSTEY   60
ADSVKGRFTI SRDNSKNTVY LQMDSLRPED TALYYCAADR SFLFAKALGA TKNYEYWGQG  120
TLVTVSS                                                            127

SEQ ID NO: 404         moltype = AA  length = 5
FEATURE                Location/Qualifiers
REGION                 1..5
```

```
                        note = Synthetic
source                  1..5
                        mol_type = protein
                        organism = synthetic construct
SEQUENCE: 404
IYTMS                                                                     5

SEQ ID NO: 405          moltype = AA   length = 17
FEATURE                 Location/Qualifiers
REGION                  1..17
                        note = Synthetic
source                  1..17
                        mol_type = protein
                        organism = synthetic construct
SEQUENCE: 405
GLRWTDSSTE YADSVKG                                                        17

SEQ ID NO: 406          moltype = AA   length = 18
FEATURE                 Location/Qualifiers
REGION                  1..18
                        note = Synthetic
source                  1..18
                        mol_type = protein
                        organism = synthetic construct
SEQUENCE: 406
DRSFLFAKAL GATKNYEY                                                       18

SEQ ID NO: 407          moltype = AA   length = 120
FEATURE                 Location/Qualifiers
REGION                  1..120
                        note = Synthetic
source                  1..120
                        mol_type = protein
                        organism = synthetic construct
SEQUENCE: 407
DVQLVESGGG VVQPGGSLQL SCAASGRTHS RLAMGWFRQA PGQEREFVAA ISRRGGSTNY         60
ADSVKGRFTI SRDNSKNTVY LQMDSLRPED TALYYCAADD SSGDGYLDYW GQGTLVTVSS        120

SEQ ID NO: 408          moltype = AA   length = 5
FEATURE                 Location/Qualifiers
REGION                  1..5
                        note = Synthetic
source                  1..5
                        mol_type = protein
                        organism = synthetic construct
SEQUENCE: 408
RLAMG                                                                     5

SEQ ID NO: 409          moltype = AA   length = 17
FEATURE                 Location/Qualifiers
REGION                  1..17
                        note = Synthetic
source                  1..17
                        mol_type = protein
                        organism = synthetic construct
SEQUENCE: 409
AISRRGGSTN YADSVKG                                                        17

SEQ ID NO: 410          moltype = AA   length = 11
FEATURE                 Location/Qualifiers
REGION                  1..11
                        note = Synthetic
source                  1..11
                        mol_type = protein
                        organism = synthetic construct
SEQUENCE: 410
DDSSGDGYLD Y                                                              11

SEQ ID NO: 411          moltype = AA   length = 127
FEATURE                 Location/Qualifiers
REGION                  1..127
                        note = Synthetic
source                  1..127
                        mol_type = protein
                        organism = synthetic construct
SEQUENCE: 411
EVQLVESGGG VVQPGGSLQL SCAASGRTFN IYTMSWFRQA PGQEREFVAG LRWTDSSTEY         60
ADSVKGRFTI SRDNSKNTVY LQMDSLRPED TALYYCAADR SFLFAKALGA TKNYEYWGQG        120
TLVTVSS                                                                  127
```

```
SEQ ID NO: 412          moltype = AA   length = 5
FEATURE                 Location/Qualifiers
REGION                  1..5
                        note = Synthetic
source                  1..5
                        mol_type = protein
                        organism = synthetic construct
SEQUENCE: 412
IYTMS                                                                   5

SEQ ID NO: 413          moltype = AA   length = 17
FEATURE                 Location/Qualifiers
REGION                  1..17
                        note = Synthetic
source                  1..17
                        mol_type = protein
                        organism = synthetic construct
SEQUENCE: 413
GLRWTDSSTE YADSVKG                                                      17

SEQ ID NO: 414          moltype = AA   length = 18
FEATURE                 Location/Qualifiers
REGION                  1..18
                        note = Synthetic
source                  1..18
                        mol_type = protein
                        organism = synthetic construct
SEQUENCE: 414
DRSFLFAKAL GATKNYEY                                                     18

SEQ ID NO: 415          moltype = AA   length = 120
FEATURE                 Location/Qualifiers
REGION                  1..120
                        note = Synthetic
source                  1..120
                        mol_type = protein
                        organism = synthetic construct
SEQUENCE: 415
DVQLVESGGG VVQPGGSLQL SCAASGRTHS RLAMGWFRQA PGQEREFVAA ISRRGGSTNY       60
ADSVKGRFTI SRDNSKNTVY LQMDSLRPED TALYYCAADD SSGDGYLDYW GQGTLVTVSS       120

SEQ ID NO: 416          moltype = AA   length = 5
FEATURE                 Location/Qualifiers
REGION                  1..5
                        note = Synthetic
source                  1..5
                        mol_type = protein
                        organism = synthetic construct
SEQUENCE: 416
RLAMG                                                                   5

SEQ ID NO: 417          moltype = AA   length = 17
FEATURE                 Location/Qualifiers
REGION                  1..17
                        note = Synthetic
source                  1..17
                        mol_type = protein
                        organism = synthetic construct
SEQUENCE: 417
AISRRGGSTN YADSVKG                                                      17

SEQ ID NO: 418          moltype = AA   length = 11
FEATURE                 Location/Qualifiers
REGION                  1..11
                        note = Synthetic
source                  1..11
                        mol_type = protein
                        organism = synthetic construct
SEQUENCE: 418
DDSSGDGYLD Y                                                            11

SEQ ID NO: 419          moltype = AA   length = 127
FEATURE                 Location/Qualifiers
REGION                  1..127
                        note = Synthetic
source                  1..127
                        mol_type = protein
                        organism = synthetic construct
```

```
SEQUENCE: 419
EVQLVESGGG VVQPGGSLQL SCAASGRTFN IYTMSWFRQA PGQEREFVAG LRWTDSSTEY    60
ADSVKGRFTI SRDNSKNTVY LQMDSPRPED TALYYCAADR SFLFAKALGA TKNYEYWGQG   120
TLVTVSS                                                            127

SEQ ID NO: 420          moltype = AA  length = 5
FEATURE                 Location/Qualifiers
REGION                  1..5
                        note = Synthetic
source                  1..5
                        mol_type = protein
                        organism = synthetic construct
SEQUENCE: 420
IYTMS                                                                5

SEQ ID NO: 421          moltype = AA  length = 17
FEATURE                 Location/Qualifiers
REGION                  1..17
                        note = Synthetic
source                  1..17
                        mol_type = protein
                        organism = synthetic construct
SEQUENCE: 421
GLRWTDSSTE YADSVKG                                                  17

SEQ ID NO: 422          moltype = AA  length = 18
FEATURE                 Location/Qualifiers
REGION                  1..18
                        note = Synthetic
source                  1..18
                        mol_type = protein
                        organism = synthetic construct
SEQUENCE: 422
DRSFLFAKAL GATKNYEY                                                 18

SEQ ID NO: 423          moltype = AA  length = 120
FEATURE                 Location/Qualifiers
REGION                  1..120
                        note = Synthetic
source                  1..120
                        mol_type = protein
                        organism = synthetic construct
SEQUENCE: 423
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 424          moltype = AA  length = 5
FEATURE                 Location/Qualifiers
REGION                  1..5
                        note = Synthetic
source                  1..5
                        mol_type = protein
                        organism = synthetic construct
SEQUENCE: 424
RLAMG                                                                5

SEQ ID NO: 425          moltype = AA  length = 17
FEATURE                 Location/Qualifiers
REGION                  1..17
                        note = Synthetic
source                  1..17
                        mol_type = protein
                        organism = synthetic construct
SEQUENCE: 425
AISRRGGSTN YADSVKG                                                  17

SEQ ID NO: 426          moltype = AA  length = 11
FEATURE                 Location/Qualifiers
REGION                  1..11
                        note = Synthetic
source                  1..11
                        mol_type = protein
                        organism = synthetic construct
SEQUENCE: 426
DDSSGDGYLD Y                                                        11

SEQ ID NO: 427          moltype = AA  length = 127
FEATURE                 Location/Qualifiers
REGION                  1..127
```

```
                        note = Synthetic
source                  1..127
                        mol_type = protein
                        organism = synthetic construct
SEQUENCE: 427
EVQLVESGGG VVQPGGSLQL SCAASGRTFN IYTMSWFRQA PGQEREFVAG LRWTDSSTEY    60
ADSVKGRFTI SRDNSKNTVY LQMDSPRPED TALYYCAADR SFLFAKALGA TKNYEYWGQG   120
TLVTVSS                                                             127

SEQ ID NO: 428          moltype = AA  length = 5
FEATURE                 Location/Qualifiers
REGION                  1..5
                        note = Synthetic
source                  1..5
                        mol_type = protein
                        organism = synthetic construct
SEQUENCE: 428
IYTMS                                                                 5

SEQ ID NO: 429          moltype = AA  length = 17
FEATURE                 Location/Qualifiers
REGION                  1..17
                        note = Synthetic
source                  1..17
                        mol_type = protein
                        organism = synthetic construct
SEQUENCE: 429
GLRWTDSSTE YADSVKG                                                   17

SEQ ID NO: 430          moltype = AA  length = 18
FEATURE                 Location/Qualifiers
REGION                  1..18
                        note = Synthetic
source                  1..18
                        mol_type = protein
                        organism = synthetic construct
SEQUENCE: 430
DRSFLFAKAL GATKNYEY                                                  18

SEQ ID NO: 431          moltype = AA  length = 120
FEATURE                 Location/Qualifiers
REGION                  1..120
                        note = Synthetic
source                  1..120
                        mol_type = protein
                        organism = synthetic construct
SEQUENCE: 431
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 432          moltype = AA  length = 5
FEATURE                 Location/Qualifiers
REGION                  1..5
                        note = Synthetic
source                  1..5
                        mol_type = protein
                        organism = synthetic construct
SEQUENCE: 432
RLAMG                                                                 5

SEQ ID NO: 433          moltype = AA  length = 17
FEATURE                 Location/Qualifiers
REGION                  1..17
                        note = Synthetic
source                  1..17
                        mol_type = protein
                        organism = synthetic construct
SEQUENCE: 433
AISRRGGSTN YADSVKG                                                   17

SEQ ID NO: 434          moltype = AA  length = 11
FEATURE                 Location/Qualifiers
REGION                  1..11
                        note = Synthetic
source                  1..11
                        mol_type = protein
                        organism = synthetic construct
SEQUENCE: 434
DDSSGDGYLD Y                                                         11
```

```
SEQ ID NO: 435          moltype = AA   length = 127
FEATURE                 Location/Qualifiers
REGION                  1..127
                        note = Synthetic
source                  1..127
                        mol_type = protein
                        organism = synthetic construct
SEQUENCE: 435
EVQLVESGGG VVQPGGSLQL SCAASGRTFN IYTMSWFRQA PGQEREFVAG LRWTDSSTEY    60
ADSVKGRFTI SRDNSKNTVY LQMDSPRPED TALYYCAADR SFLFAKALGA TKNYEYWGQG   120
TLVTVSS                                                             127

SEQ ID NO: 436          moltype = AA   length = 5
FEATURE                 Location/Qualifiers
REGION                  1..5
                        note = Synthetic
source                  1..5
                        mol_type = protein
                        organism = synthetic construct
SEQUENCE: 436
IYTMS                                                                 5

SEQ ID NO: 437          moltype = AA   length = 17
FEATURE                 Location/Qualifiers
REGION                  1..17
                        note = Synthetic
source                  1..17
                        mol_type = protein
                        organism = synthetic construct
SEQUENCE: 437
GLRWTDSSTE YADSVKG                                                   17

SEQ ID NO: 438          moltype = AA   length = 18
FEATURE                 Location/Qualifiers
REGION                  1..18
                        note = Synthetic
source                  1..18
                        mol_type = protein
                        organism = synthetic construct
SEQUENCE: 438
DRSFLFAKAL GATKNYEY                                                  18

SEQ ID NO: 439          moltype = AA   length = 120
FEATURE                 Location/Qualifiers
REGION                  1..120
                        note = Synthetic
source                  1..120
                        mol_type = protein
                        organism = synthetic construct
SEQUENCE: 439
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 440          moltype = AA   length = 5
FEATURE                 Location/Qualifiers
REGION                  1..5
                        note = Synthetic
source                  1..5
                        mol_type = protein
                        organism = synthetic construct
SEQUENCE: 440
RLAMG                                                                 5

SEQ ID NO: 441          moltype = AA   length = 17
FEATURE                 Location/Qualifiers
REGION                  1..17
                        note = Synthetic
source                  1..17
                        mol_type = protein
                        organism = synthetic construct
SEQUENCE: 441
AISRRGGSTN YADSVKG                                                   17

SEQ ID NO: 442          moltype = AA   length = 11
FEATURE                 Location/Qualifiers
REGION                  1..11
                        note = Synthetic
source                  1..11
```

```
                        mol_type = protein
                        organism = synthetic construct
SEQUENCE: 442
DDSSGDGYLD Y                                                            11

SEQ ID NO: 443          moltype = AA   length = 127
FEATURE                 Location/Qualifiers
REGION                  1..127
                        note = Synthetic
source                  1..127
                        mol_type = protein
                        organism = synthetic construct
SEQUENCE: 443
EVQLVESGGG VVQPGGSLQL SCAASGRTFN IYTMSWFRQA PGQEREFVAG LRWTDSSTEY        60
ADSVKGRFTI SRDNSKNTVY LQMDSPRPED TALYYCAADR SFLFAKALGA TKNYEYWGQG       120
TLVTVSS                                                                127

SEQ ID NO: 444          moltype = AA   length = 5
FEATURE                 Location/Qualifiers
REGION                  1..5
                        note = Synthetic
source                  1..5
                        mol_type = protein
                        organism = synthetic construct
SEQUENCE: 444
IYTMS                                                                    5

SEQ ID NO: 445          moltype = AA   length = 17
FEATURE                 Location/Qualifiers
REGION                  1..17
                        note = Synthetic
source                  1..17
                        mol_type = protein
                        organism = synthetic construct
SEQUENCE: 445
GLRWTDSSTE YADSVKG                                                      17

SEQ ID NO: 446          moltype = AA   length = 18
FEATURE                 Location/Qualifiers
REGION                  1..18
                        note = Synthetic
source                  1..18
                        mol_type = protein
                        organism = synthetic construct
SEQUENCE: 446
DRSFLFAKAL GATKNYEY                                                     18

SEQ ID NO: 447          moltype = AA   length = 120
FEATURE                 Location/Qualifiers
REGION                  1..120
                        note = Synthetic
source                  1..120
                        mol_type = protein
                        organism = synthetic construct
SEQUENCE: 447
DVQLVESGGG VVQPGGSLQL SCAASGRTHS RLAMGWFRQA PGQEREFVAA ISRRGGSTNY        60
ADSVKGRFTI SRDNSKNTVY LQMDSLRPED TALYYCAADD SSGDGYLDYW GQGTLVTVSS       120

SEQ ID NO: 448          moltype = AA   length = 5
FEATURE                 Location/Qualifiers
REGION                  1..5
                        note = Synthetic
source                  1..5
                        mol_type = protein
                        organism = synthetic construct
SEQUENCE: 448
RLAMG                                                                    5

SEQ ID NO: 449          moltype = AA   length = 17
FEATURE                 Location/Qualifiers
REGION                  1..17
                        note = Synthetic
source                  1..17
                        mol_type = protein
                        organism = synthetic construct
SEQUENCE: 449
AISRRGGSTN YADSVKG                                                      17

SEQ ID NO: 450          moltype = AA   length = 11
```

```
FEATURE              Location/Qualifiers
REGION               1..11
                     note = Synthetic
source               1..11
                     mol_type = protein
                     organism = synthetic construct
SEQUENCE: 450
DDSSGDGYLD Y                                                                11

SEQ ID NO: 451       moltype = AA  length = 127
FEATURE              Location/Qualifiers
REGION               1..127
                     note = Synthetic
source               1..127
                     mol_type = protein
                     organism = synthetic construct
SEQUENCE: 451
EVQLVESGGG VVQPGGSLQL SCAASGRTFN IYTMSWFRQA PGQEREFVAG LRWTDSSTEY           60
ADSVKGRFTI SRDNSKNTVY LQMDSPRPED TALYYCAADR SFLFAKALGA TKNYEYWGQG          120
TLVTVSS                                                                   127

SEQ ID NO: 452       moltype = AA  length = 5
FEATURE              Location/Qualifiers
REGION               1..5
                     note = Synthetic
source               1..5
                     mol_type = protein
                     organism = synthetic construct
SEQUENCE: 452
IYTMS                                                                       5

SEQ ID NO: 453       moltype = AA  length = 17
FEATURE              Location/Qualifiers
REGION               1..17
                     note = Synthetic
source               1..17
                     mol_type = protein
                     organism = synthetic construct
SEQUENCE: 453
GLRWTDSSTE YADSVKG                                                         17

SEQ ID NO: 454       moltype = AA  length = 18
FEATURE              Location/Qualifiers
REGION               1..18
                     note = Synthetic
source               1..18
                     mol_type = protein
                     organism = synthetic construct
SEQUENCE: 454
DRSFLFAKAL GATKNYEY                                                        18

SEQ ID NO: 455       moltype = AA  length = 120
FEATURE              Location/Qualifiers
REGION               1..120
                     note = Synthetic
source               1..120
                     mol_type = protein
                     organism = synthetic construct
SEQUENCE: 455
DVQLVESGGG VVQPGGSLQL SCAASGRTHS RLAMGWFRQA PGQEREFVAA ISRRGGSTNY           60
ADSVKGRFTI SRDNSKNTVY LQMDSLRPED TALYYCAADD SSGDGYLDYW GQGTLVTVSS          120

SEQ ID NO: 456       moltype = AA  length = 5
FEATURE              Location/Qualifiers
REGION               1..5
                     note = Synthetic
source               1..5
                     mol_type = protein
                     organism = synthetic construct
SEQUENCE: 456
RLAMG                                                                       5

SEQ ID NO: 457       moltype = AA  length = 17
FEATURE              Location/Qualifiers
REGION               1..17
                     note = Synthetic
source               1..17
                     mol_type = protein
                     organism = synthetic construct
```

```
SEQUENCE: 457
AISRRGGSTN YADSVKG                                                    17

SEQ ID NO: 458         moltype = AA  length = 11
FEATURE                Location/Qualifiers
REGION                 1..11
                       note = Synthetic
source                 1..11
                       mol_type = protein
                       organism = synthetic construct
SEQUENCE: 458
DDSSGDGYLD Y                                                          11

SEQ ID NO: 459         moltype = AA  length = 127
FEATURE                Location/Qualifiers
REGION                 1..127
                       note = Synthetic
source                 1..127
                       mol_type = protein
                       organism = synthetic construct
SEQUENCE: 459
EVQLVESGGG VVQPGGSLQL SCAASGRTFN IYTMSWFRQA PGQEREFVAG LRWTDSSTEY      60
ADSVKGRFTI SRDNSKNTVY LQMDSPRPED TALYYCAADR SFLFAKALGA TKNYEYWGQG     120
TLVTVSS                                                              127

SEQ ID NO: 460         moltype = AA  length = 5
FEATURE                Location/Qualifiers
REGION                 1..5
                       note = Synthetic
source                 1..5
                       mol_type = protein
                       organism = synthetic construct
SEQUENCE: 460
IYTMS                                                                  5

SEQ ID NO: 461         moltype = AA  length = 17
FEATURE                Location/Qualifiers
REGION                 1..17
                       note = Synthetic
source                 1..17
                       mol_type = protein
                       organism = synthetic construct
SEQUENCE: 461
GLRWTDSSTE YADSVKG                                                    17

SEQ ID NO: 462         moltype = AA  length = 18
FEATURE                Location/Qualifiers
REGION                 1..18
                       note = Synthetic
source                 1..18
                       mol_type = protein
                       organism = synthetic construct
SEQUENCE: 462
DRSFLFAKAL GATKNYEY                                                   18

SEQ ID NO: 463         moltype = AA  length = 120
FEATURE                Location/Qualifiers
REGION                 1..120
                       note = Synthetic
source                 1..120
                       mol_type = protein
                       organism = synthetic construct
SEQUENCE: 463
DVQLVESGGG VVQPGGSLQL SCAASGRTHS RLAMGWFRQA PGQEREFVAA ISRRGGSTNY      60
ADSVKGRFTI SRDNSKNTVY LQMDSLRPED TALYYCAADD SSGDGYLDYW GQGTLVTVSS     120

SEQ ID NO: 464         moltype = AA  length = 5
FEATURE                Location/Qualifiers
REGION                 1..5
                       note = Synthetic
source                 1..5
                       mol_type = protein
                       organism = synthetic construct
SEQUENCE: 464
RLAMG                                                                  5

SEQ ID NO: 465         moltype = AA  length = 17
FEATURE                Location/Qualifiers
REGION                 1..17
```

```
                        note = Synthetic
source                  1..17
                        mol_type = protein
                        organism = synthetic construct
SEQUENCE: 465
AISRRGGSTN YADSVKG                                                      17

SEQ ID NO: 466          moltype = AA  length = 11
FEATURE                 Location/Qualifiers
REGION                  1..11
                        note = Synthetic
source                  1..11
                        mol_type = protein
                        organism = synthetic construct
SEQUENCE: 466
DDSSGDGYLD Y                                                            11

SEQ ID NO: 467          moltype = AA  length = 127
FEATURE                 Location/Qualifiers
REGION                  1..127
                        note = Synthetic
source                  1..127
                        mol_type = protein
                        organism = synthetic construct
SEQUENCE: 467
EVQLVESGGG VVQPGGSLQL SCAASGRTFN IYTMSWFRQA PGQEREFVAG LRWTDSSTEY        60
ADSVKGRFTI SRDNSKNTVY LQMDSPRPED TALYYCAADR SFLFAKALGA TKNYEYWGQG       120
TLVTVSS                                                                127

SEQ ID NO: 468          moltype = AA  length = 5
FEATURE                 Location/Qualifiers
REGION                  1..5
                        note = Synthetic
source                  1..5
                        mol_type = protein
                        organism = synthetic construct
SEQUENCE: 468
IYTMS                                                                    5

SEQ ID NO: 469          moltype = AA  length = 17
FEATURE                 Location/Qualifiers
REGION                  1..17
                        note = Synthetic
source                  1..17
                        mol_type = protein
                        organism = synthetic construct
SEQUENCE: 469
GLRWTDSSTE YADSVKG                                                      17

SEQ ID NO: 470          moltype = AA  length = 18
FEATURE                 Location/Qualifiers
REGION                  1..18
                        note = Synthetic
source                  1..18
                        mol_type = protein
                        organism = synthetic construct
SEQUENCE: 470
DRSFLFAKAL GATKNYEY                                                     18

SEQ ID NO: 471          moltype = AA  length = 120
FEATURE                 Location/Qualifiers
REGION                  1..120
                        note = Synthetic
source                  1..120
                        mol_type = protein
                        organism = synthetic construct
SEQUENCE: 471
DVQLVESGGG VVQPGGDLRL SCAASGRTHS RYAMGWFRQA PGQEREFVAA ISRRGGSTNY        60
ADSVKGRFTI SRDESKNTVY LQMNSLRPED TALYYCAADD SSGDGYLDYW GQGTLVTVSS       120

SEQ ID NO: 472          moltype = AA  length = 5
FEATURE                 Location/Qualifiers
REGION                  1..5
                        note = Synthetic
source                  1..5
                        mol_type = protein
                        organism = synthetic construct
SEQUENCE: 472
RYAMG                                                                    5
```

```
SEQ ID NO: 473          moltype = AA  length = 17
FEATURE                 Location/Qualifiers
REGION                  1..17
                        note = Synthetic
source                  1..17
                        mol_type = protein
                        organism = synthetic construct
SEQUENCE: 473
AISRRGGSTN YADSVKG                                                         17

SEQ ID NO: 474          moltype = AA  length = 11
FEATURE                 Location/Qualifiers
REGION                  1..11
                        note = Synthetic
source                  1..11
                        mol_type = protein
                        organism = synthetic construct
SEQUENCE: 474
DDSSGDGYLD Y                                                               11

SEQ ID NO: 475          moltype = AA  length = 127
FEATURE                 Location/Qualifiers
REGION                  1..127
                        note = Synthetic
source                  1..127
                        mol_type = protein
                        organism = synthetic construct
SEQUENCE: 475
EVQLVESGGG VVQPGGDLRL SCAASGRTFN IYTMSWFRQA PGQEREFVAG LRWTDSSTEY           60
ADSVKGRFTI SRDESKNTVY LQMNSLRPED TALYYCAADR SFLFAQALGA TKNYEYWGQG         120
TLVTVSS                                                                  127

SEQ ID NO: 476          moltype = AA  length = 5
FEATURE                 Location/Qualifiers
REGION                  1..5
                        note = Synthetic
source                  1..5
                        mol_type = protein
                        organism = synthetic construct
SEQUENCE: 476
IYTMS                                                                       5

SEQ ID NO: 477          moltype = AA  length = 17
FEATURE                 Location/Qualifiers
REGION                  1..17
                        note = Synthetic
source                  1..17
                        mol_type = protein
                        organism = synthetic construct
SEQUENCE: 477
GLRWTDSSTE YADSVKG                                                         17

SEQ ID NO: 478          moltype = AA  length = 18
FEATURE                 Location/Qualifiers
REGION                  1..18
                        note = Synthetic
source                  1..18
                        mol_type = protein
                        organism = synthetic construct
SEQUENCE: 478
DRSFLFAQAL GATKNYEY                                                        18

SEQ ID NO: 479          moltype = AA  length = 120
FEATURE                 Location/Qualifiers
REGION                  1..120
                        note = Synthetic
source                  1..120
                        mol_type = protein
                        organism = synthetic construct
SEQUENCE: 479
DVQLVESGGG VVQPGGSLQL SCAASGRTFS RLAMGWFRQA PGQEREFVAA ISRRGGSTNY           60
ADSVKGRFTI SRDNSKNTVY LQMDSLRPED TALYYCAADD SSGDGYLDYW GQGTLVTVSS         120

SEQ ID NO: 480          moltype = AA  length = 5
FEATURE                 Location/Qualifiers
REGION                  1..5
                        note = Synthetic
source                  1..5
```

```
                        mol_type = protein
                        organism = synthetic construct
SEQUENCE: 480
RLAMG                                                                    5

SEQ ID NO: 481          moltype = AA  length = 17
FEATURE                 Location/Qualifiers
REGION                  1..17
                        note = Synthetic
source                  1..17
                        mol_type = protein
                        organism = synthetic construct
SEQUENCE: 481
AISRRGGSTN YADSVKG                                                      17

SEQ ID NO: 482          moltype = AA  length = 11
FEATURE                 Location/Qualifiers
REGION                  1..11
                        note = Synthetic
source                  1..11
                        mol_type = protein
                        organism = synthetic construct
SEQUENCE: 482
DDSSGDGYLD Y                                                            11

SEQ ID NO: 483          moltype = AA  length = 127
FEATURE                 Location/Qualifiers
REGION                  1..127
                        note = Synthetic
source                  1..127
                        mol_type = protein
                        organism = synthetic construct
SEQUENCE: 483
EVQLVESGGG VVQPGGSLQL SCAASGRTFN IYTMSWFRQA PGQEREFVAG LRWTDSSTEY        60
ADSVKGRFTI SRDNSKNTVY LQMDSLRPED TALYYCAADR SFLFAQALGA TKNYEYWGQG       120
TLVTVSS                                                                127

SEQ ID NO: 484          moltype = AA  length = 5
FEATURE                 Location/Qualifiers
REGION                  1..5
                        note = Synthetic
source                  1..5
                        mol_type = protein
                        organism = synthetic construct
SEQUENCE: 484
IYTMS                                                                    5

SEQ ID NO: 485          moltype = AA  length = 17
FEATURE                 Location/Qualifiers
REGION                  1..17
                        note = Synthetic
source                  1..17
                        mol_type = protein
                        organism = synthetic construct
SEQUENCE: 485
GLRWTDSSTE YADSVKG                                                      17

SEQ ID NO: 486          moltype = AA  length = 18
FEATURE                 Location/Qualifiers
REGION                  1..18
                        note = Synthetic
source                  1..18
                        mol_type = protein
                        organism = synthetic construct
SEQUENCE: 486
DRSFLFAQAL GATKNYEY                                                     18

SEQ ID NO: 487          moltype = AA  length = 120
FEATURE                 Location/Qualifiers
REGION                  1..120
                        note = Synthetic
source                  1..120
                        mol_type = protein
                        organism = synthetic construct
SEQUENCE: 487
DVQLVESGGG VVQPGGDLRL SCAASGRTFS RLAMGWFRQA PGQEREFVAA ISRRGGSTNY        60
ADSVKGRFTI SRDESKNTVY LQMNSLRPED TALYYCAADD SSGDGYLDYW GQGTLVTVSS       120

SEQ ID NO: 488          moltype = AA  length = 5
```

```
FEATURE                 Location/Qualifiers
REGION                  1..5
                        note = Synthetic
source                  1..5
                        mol_type = protein
                        organism = synthetic construct
SEQUENCE: 488
RLAMG                                                                   5

SEQ ID NO: 489          moltype = AA  length = 17
FEATURE                 Location/Qualifiers
REGION                  1..17
                        note = Synthetic
source                  1..17
                        mol_type = protein
                        organism = synthetic construct
SEQUENCE: 489
AISRRGGSTN YADSVKG                                                     17

SEQ ID NO: 490          moltype = AA  length = 11
FEATURE                 Location/Qualifiers
REGION                  1..11
                        note = Synthetic
source                  1..11
                        mol_type = protein
                        organism = synthetic construct
SEQUENCE: 490
DDSSGDGYLD Y                                                           11

SEQ ID NO: 491          moltype = AA  length = 127
FEATURE                 Location/Qualifiers
REGION                  1..127
                        note = Synthetic
source                  1..127
                        mol_type = protein
                        organism = synthetic construct
SEQUENCE: 491
EVQLVESGGG VVQPGGDLRL SCAASGRTFN IYTMSWFRQA PGQEREFVAG LRWTDSSTEY       60
ADSVKGRFTI SRDESKNTVY LQMNSLRPED TALYYCAADR SFLFAQALGA TKNYEYWGQG     120
TLVTVSS                                                              127

SEQ ID NO: 492          moltype = AA  length = 5
FEATURE                 Location/Qualifiers
REGION                  1..5
                        note = Synthetic
source                  1..5
                        mol_type = protein
                        organism = synthetic construct
SEQUENCE: 492
IYTMS                                                                   5

SEQ ID NO: 493          moltype = AA  length = 17
FEATURE                 Location/Qualifiers
REGION                  1..17
                        note = Synthetic
source                  1..17
                        mol_type = protein
                        organism = synthetic construct
SEQUENCE: 493
GLRWTDSSTE YADSVKG                                                     17

SEQ ID NO: 494          moltype = AA  length = 18
FEATURE                 Location/Qualifiers
REGION                  1..18
                        note = Synthetic
source                  1..18
                        mol_type = protein
                        organism = synthetic construct
SEQUENCE: 494
DRSFLFAQAL GATKNYEY                                                    18

SEQ ID NO: 495          moltype = AA  length = 120
FEATURE                 Location/Qualifiers
REGION                  1..120
                        note = Synthetic
source                  1..120
                        mol_type = protein
                        organism = synthetic construct
SEQUENCE: 495
```

```
DVQLVESGGG VVQPGGSLQL SCAASGRTHD RYAMGWFRQA PGQEREFVAA ISRRGGSTNY    60
ADSVKGRFTI SRDNSKNTVY LQMDSLRPED TALYYCAADD SSGDGYLDYW GQGTLVTVSS   120

SEQ ID NO: 496          moltype = AA  length = 5
FEATURE                 Location/Qualifiers
REGION                  1..5
                        note = Synthetic
source                  1..5
                        mol_type = protein
                        organism = synthetic construct
SEQUENCE: 496
RYAMG                                                                5

SEQ ID NO: 497          moltype = AA  length = 17
FEATURE                 Location/Qualifiers
REGION                  1..17
                        note = Synthetic
source                  1..17
                        mol_type = protein
                        organism = synthetic construct
SEQUENCE: 497
AISRRGGSTN YADSVKG                                                  17

SEQ ID NO: 498          moltype = AA  length = 11
FEATURE                 Location/Qualifiers
REGION                  1..11
                        note = Synthetic
source                  1..11
                        mol_type = protein
                        organism = synthetic construct
SEQUENCE: 498
DDSSGDGYLD Y                                                        11

SEQ ID NO: 499          moltype = AA  length = 127
FEATURE                 Location/Qualifiers
REGION                  1..127
                        note = Synthetic
source                  1..127
                        mol_type = protein
                        organism = synthetic construct
SEQUENCE: 499
EVQLVESGGG VVQPGGSLQL SCAASGRTFD IYTMSWFRQA PGQEREFVAG LRWTDSSTEY    60
ADSVKGRFTI SRDNSKNTVY LQMDSLRPED TALYYCAADR SFLFAQALGA TKNYEYWGQG   120
TLVTVSS                                                            127

SEQ ID NO: 500          moltype = AA  length = 5
FEATURE                 Location/Qualifiers
REGION                  1..5
                        note = Synthetic
source                  1..5
                        mol_type = protein
                        organism = synthetic construct
SEQUENCE: 500
IYTMS                                                                5

SEQ ID NO: 501          moltype = AA  length = 17
FEATURE                 Location/Qualifiers
REGION                  1..17
                        note = Synthetic
source                  1..17
                        mol_type = protein
                        organism = synthetic construct
SEQUENCE: 501
GLRWTDSSTE YADSVKG                                                  17

SEQ ID NO: 502          moltype = AA  length = 18
FEATURE                 Location/Qualifiers
REGION                  1..18
                        note = Synthetic
source                  1..18
                        mol_type = protein
                        organism = synthetic construct
SEQUENCE: 502
DRSFLFAQAL GATKNYEY                                                 18

SEQ ID NO: 503          moltype = AA  length = 120
FEATURE                 Location/Qualifiers
REGION                  1..120
                        note = Synthetic
```

```
source                    1..120
                          mol_type = protein
                          organism = synthetic construct
SEQUENCE: 503
DVQLVESGGG VVQPGGSLRL SCAASGRTHD RYAMGWFRQA PGQEREFVAA ISRRGGSTNY    60
ADSVQGRFTI SRDNSKNTVY LQMDSLRPED TALYYCAADD SSGDGYLDYW GQGTLVTVSS   120

SEQ ID NO: 504            moltype = AA  length = 5
FEATURE                   Location/Qualifiers
REGION                    1..5
                          note = Synthetic
source                    1..5
                          mol_type = protein
                          organism = synthetic construct
SEQUENCE: 504
RYAMG                                                                5

SEQ ID NO: 505            moltype = AA  length = 17
FEATURE                   Location/Qualifiers
REGION                    1..17
                          note = Synthetic
source                    1..17
                          mol_type = protein
                          organism = synthetic construct
SEQUENCE: 505
AISRRGGSTN YADSVQG                                                  17

SEQ ID NO: 506            moltype = AA  length = 11
FEATURE                   Location/Qualifiers
REGION                    1..11
                          note = Synthetic
source                    1..11
                          mol_type = protein
                          organism = synthetic construct
SEQUENCE: 506
DDSSGDGYLD Y                                                        11

SEQ ID NO: 507            moltype = AA  length = 127
FEATURE                   Location/Qualifiers
REGION                    1..127
                          note = Synthetic
source                    1..127
                          mol_type = protein
                          organism = synthetic construct
SEQUENCE: 507
EVQLVESGGG VVQPGGSLRL SCAASGRTFD IYTMSWFRQA PGQEREFVAG LRWTDSSTEY    60
ADSVQGRFTI SRDNSKNTVY LQMDSLRPED TALYYCAADR SFLFAQALGA TKNYEYWGQG   120
TLVTVSS                                                            127

SEQ ID NO: 508            moltype = AA  length = 5
FEATURE                   Location/Qualifiers
REGION                    1..5
                          note = Synthetic
source                    1..5
                          mol_type = protein
                          organism = synthetic construct
SEQUENCE: 508
IYTMS                                                                5

SEQ ID NO: 509            moltype = AA  length = 17
FEATURE                   Location/Qualifiers
REGION                    1..17
                          note = Synthetic
source                    1..17
                          mol_type = protein
                          organism = synthetic construct
SEQUENCE: 509
GLRWTDSSTE YADSVQG                                                  17

SEQ ID NO: 510            moltype = AA  length = 18
FEATURE                   Location/Qualifiers
REGION                    1..18
                          note = Synthetic
source                    1..18
                          mol_type = protein
                          organism = synthetic construct
SEQUENCE: 510
DRSFLFAQAL GATKNYEY                                                 18
```

```
SEQ ID NO: 511              moltype = AA  length = 120
FEATURE                     Location/Qualifiers
REGION                      1..120
                            note = Synthetic
source                      1..120
                            mol_type = protein
                            organism = synthetic construct
SEQUENCE: 511
DVQLVESGGG VVQPGGSLRL SCAASGRTFD RLAMGWFRQA PGQEREFVAA ISRRGGSTNY    60
ADSVQGRFTI SRDNSKNTVY LQMDSLRPED TALYYCAADD SSGDGYLDYW GQGTLVTVSS   120

SEQ ID NO: 512              moltype = AA  length = 5
FEATURE                     Location/Qualifiers
REGION                      1..5
                            note = Synthetic
source                      1..5
                            mol_type = protein
                            organism = synthetic construct
SEQUENCE: 512
RLAMG                                                                 5

SEQ ID NO: 513              moltype = AA  length = 17
FEATURE                     Location/Qualifiers
REGION                      1..17
                            note = Synthetic
source                      1..17
                            mol_type = protein
                            organism = synthetic construct
SEQUENCE: 513
AISRRGGSTN YADSVQG                                                   17

SEQ ID NO: 514              moltype = AA  length = 11
FEATURE                     Location/Qualifiers
REGION                      1..11
                            note = Synthetic
source                      1..11
                            mol_type = protein
                            organism = synthetic construct
SEQUENCE: 514
DDSSGDGYLD Y                                                         11

SEQ ID NO: 515              moltype = AA  length = 127
FEATURE                     Location/Qualifiers
REGION                      1..127
                            note = Synthetic
source                      1..127
                            mol_type = protein
                            organism = synthetic construct
SEQUENCE: 515
EVQLVESGGG VVQPGGSLRL SCAASGRTFD IYTMSWFRQA PGQEREFVAG LRWTDSSTEY    60
ADSVQGRFTI SRDNSKNTVY LQMDSLRPED TALYYCAADR SFLFAQALGA TKNYEYWGQG   120
TLVTVSS                                                             127

SEQ ID NO: 516              moltype = AA  length = 5
FEATURE                     Location/Qualifiers
REGION                      1..5
                            note = Synthetic
source                      1..5
                            mol_type = protein
                            organism = synthetic construct
SEQUENCE: 516
IYTMS                                                                 5

SEQ ID NO: 517              moltype = AA  length = 17
FEATURE                     Location/Qualifiers
REGION                      1..17
                            note = Synthetic
source                      1..17
                            mol_type = protein
                            organism = synthetic construct
SEQUENCE: 517
GLRWTDSSTE YADSVQG                                                   17

SEQ ID NO: 518              moltype = AA  length = 18
FEATURE                     Location/Qualifiers
REGION                      1..18
                            note = Synthetic
source                      1..18
                            mol_type = protein
```

```
                        organism = synthetic construct
SEQUENCE: 518
DRSFLFAQAL GATKNYEY                                                    18

SEQ ID NO: 519          moltype = AA  length = 120
FEATURE                 Location/Qualifiers
REGION                  1..120
                        note = Synthetic
source                  1..120
                        mol_type = protein
                        organism = synthetic construct
SEQUENCE: 519
DVQLVESGGG VVQPGGSLRL SCAASGRTFS RLAMGWFRQA PGKEREFVAA ISRRGGSTNY       60
ADSVKGRFTI SRDNSKNTVY LQMNSLRPED TALYYCAADD SSGDGYLDYW GQGTLVTVSS      120

SEQ ID NO: 520          moltype = AA  length = 5
FEATURE                 Location/Qualifiers
REGION                  1..5
                        note = Synthetic
source                  1..5
                        mol_type = protein
                        organism = synthetic construct
SEQUENCE: 520
RLAMG                                                                   5

SEQ ID NO: 521          moltype = AA  length = 17
FEATURE                 Location/Qualifiers
REGION                  1..17
                        note = Synthetic
source                  1..17
                        mol_type = protein
                        organism = synthetic construct
SEQUENCE: 521
AISRRGGSTN YADSVKG                                                     17

SEQ ID NO: 522          moltype = AA  length = 11
FEATURE                 Location/Qualifiers
REGION                  1..11
                        note = Synthetic
source                  1..11
                        mol_type = protein
                        organism = synthetic construct
SEQUENCE: 522
DDSSGDGYLD Y                                                           11

SEQ ID NO: 523          moltype = AA  length = 127
FEATURE                 Location/Qualifiers
REGION                  1..127
                        note = Synthetic
source                  1..127
                        mol_type = protein
                        organism = synthetic construct
SEQUENCE: 523
EVQLVESGGG VVQPGGSLRL SCAASGRTFN IYTMSWFRQA PGKEREFVAG LRWTDSSTEY       60
ADSVKGRFTI SRDNSKNTVY LQMNSLRPED TALYYCAADR SFLFAQALGA TKNYEYWGQG      120
TLVTVSS                                                               127

SEQ ID NO: 524          moltype = AA  length = 5
FEATURE                 Location/Qualifiers
REGION                  1..5
                        note = Synthetic
source                  1..5
                        mol_type = protein
                        organism = synthetic construct
SEQUENCE: 524
IYTMS                                                                   5

SEQ ID NO: 525          moltype = AA  length = 17
FEATURE                 Location/Qualifiers
REGION                  1..17
                        note = Synthetic
source                  1..17
                        mol_type = protein
                        organism = synthetic construct
SEQUENCE: 525
GLRWTDSSTE YADSVKG                                                     17

SEQ ID NO: 526          moltype = AA  length = 18
FEATURE                 Location/Qualifiers
```

```
REGION                   1..18
                         note = Synthetic
source                   1..18
                         mol_type = protein
                         organism = synthetic construct
SEQUENCE: 526
DRSFLFAQAL GATKNYEY                                                    18

SEQ ID NO: 527           moltype = AA  length = 120
FEATURE                  Location/Qualifiers
REGION                   1..120
                         note = Synthetic
source                   1..120
                         mol_type = protein
                         organism = synthetic construct
SEQUENCE: 527
DVQLVESGGG VVQPGGSLRL SCAASGRTFS RLAMGWFRQA PGKEREFVAA ISRRGGSTNY       60
ADSVKGRFTI SRDNSKNTVY LQMNSLRPED TALYYCAADD SSGDGYLDYW GQGTLVTVSS      120

SEQ ID NO: 528           moltype = AA  length = 5
FEATURE                  Location/Qualifiers
REGION                   1..5
                         note = Synthetic
source                   1..5
                         mol_type = protein
                         organism = synthetic construct
SEQUENCE: 528
RLAMG                                                                   5

SEQ ID NO: 529           moltype = AA  length = 17
FEATURE                  Location/Qualifiers
REGION                   1..17
                         note = Synthetic
source                   1..17
                         mol_type = protein
                         organism = synthetic construct
SEQUENCE: 529
AISRRGGSTN YADSVKG                                                     17

SEQ ID NO: 530           moltype = AA  length = 11
FEATURE                  Location/Qualifiers
REGION                   1..11
                         note = Synthetic
source                   1..11
                         mol_type = protein
                         organism = synthetic construct
SEQUENCE: 530
DDSSGDGYLD Y                                                           11

SEQ ID NO: 531           moltype = AA  length = 127
FEATURE                  Location/Qualifiers
REGION                   1..127
                         note = Synthetic
source                   1..127
                         mol_type = protein
                         organism = synthetic construct
SEQUENCE: 531
EVQLVESGGG VVQPGGSLRL SCAASGRTFN IYTMSWFRQA PGKEREFVAG LRWTDSSTEY       60
ADSVKGRFTI SRDNSKNTVY LQMNSLRPED TALYYCAADR SFLFAQALGA TKNYEYWGQG      120
TLVTVSS                                                               127

SEQ ID NO: 532           moltype = AA  length = 5
FEATURE                  Location/Qualifiers
REGION                   1..5
                         note = Synthetic
source                   1..5
                         mol_type = protein
                         organism = synthetic construct
SEQUENCE: 532
IYTMS                                                                   5

SEQ ID NO: 533           moltype = AA  length = 17
FEATURE                  Location/Qualifiers
REGION                   1..17
                         note = Synthetic
source                   1..17
                         mol_type = protein
                         organism = synthetic construct
SEQUENCE: 533
```

```
GLRWTDSSTE YADSVKG                                                          17

SEQ ID NO: 534          moltype = AA  length = 18
FEATURE                 Location/Qualifiers
REGION                  1..18
                        note = Synthetic
source                  1..18
                        mol_type = protein
                        organism = synthetic construct
SEQUENCE: 534
DRSFLFAQAL GATKNYEY                                                         18

SEQ ID NO: 535          moltype = AA  length = 120
FEATURE                 Location/Qualifiers
REGION                  1..120
                        note = Synthetic
source                  1..120
                        mol_type = protein
                        organism = synthetic construct
SEQUENCE: 535
DVQLVESGGG VVQPGGSLRL SCAASGRTFS RLAMGWFRQA PGKEREFVAA ISRRGGSTNY            60
ADSVKGRFTI SRDNSKNTVY LQMNSLRPED TALYYCAADD SSGDGYLDYW GQGTLVTVSS           120

SEQ ID NO: 536          moltype = AA  length = 5
FEATURE                 Location/Qualifiers
REGION                  1..5
                        note = Synthetic
source                  1..5
                        mol_type = protein
                        organism = synthetic construct
SEQUENCE: 536
RLAMG                                                                        5

SEQ ID NO: 537          moltype = AA  length = 17
FEATURE                 Location/Qualifiers
REGION                  1..17
                        note = Synthetic
source                  1..17
                        mol_type = protein
                        organism = synthetic construct
SEQUENCE: 537
AISRRGGSTN YADSVKG                                                          17

SEQ ID NO: 538          moltype = AA  length = 11
FEATURE                 Location/Qualifiers
REGION                  1..11
                        note = Synthetic
source                  1..11
                        mol_type = protein
                        organism = synthetic construct
SEQUENCE: 538
DDSSGDGYLD Y                                                                11

SEQ ID NO: 539          moltype = AA  length = 127
FEATURE                 Location/Qualifiers
REGION                  1..127
                        note = Synthetic
source                  1..127
                        mol_type = protein
                        organism = synthetic construct
SEQUENCE: 539
EVQLVESGGG VVQPGGSLRL SCAASGRTFN IYTMSWFRQA PGKEREFVAG LRWTDSSTEY            60
ADSVKGRFTI SRDNSKNTVY LQMNSLRPED TALYYCAADR SFLFAQALGA TKNYEYWGQG           120
TLVTVSS                                                                    127

SEQ ID NO: 540          moltype = AA  length = 5
FEATURE                 Location/Qualifiers
REGION                  1..5
                        note = Synthetic
source                  1..5
                        mol_type = protein
                        organism = synthetic construct
SEQUENCE: 540
IYTMS                                                                        5

SEQ ID NO: 541          moltype = AA  length = 17
FEATURE                 Location/Qualifiers
REGION                  1..17
                        note = Synthetic
```

```
source                  1..17
                        mol_type = protein
                        organism = synthetic construct
SEQUENCE: 541
GLRWTDSSTE YADSVKG                                                        17

SEQ ID NO: 542          moltype = AA   length = 18
FEATURE                 Location/Qualifiers
REGION                  1..18
                        note = Synthetic
source                  1..18
                        mol_type = protein
                        organism = synthetic construct
SEQUENCE: 542
DRSFLFAQAL GATKNYEY                                                       18

SEQ ID NO: 543          moltype = AA   length = 120
FEATURE                 Location/Qualifiers
REGION                  1..120
                        note = Synthetic
source                  1..120
                        mol_type = protein
                        organism = synthetic construct
SEQUENCE: 543
DVQLVESGGG VVQPGGSLRL SCAASGRTFS RLAMGWFRQA PGKEREFVAA ISRRGGSTNY          60
ADSVKGRFTI SRDNSKNTVY LQMNSLRPED TALYYCAADD SSGDGYLDYW GQGTLVTVSS         120

SEQ ID NO: 544          moltype = AA   length = 5
FEATURE                 Location/Qualifiers
REGION                  1..5
                        note = Synthetic
source                  1..5
                        mol_type = protein
                        organism = synthetic construct
SEQUENCE: 544
RLAMG                                                                      5

SEQ ID NO: 545          moltype = AA   length = 17
FEATURE                 Location/Qualifiers
REGION                  1..17
                        note = Synthetic
source                  1..17
                        mol_type = protein
                        organism = synthetic construct
SEQUENCE: 545
AISRRGGSTN YADSVKG                                                        17

SEQ ID NO: 546          moltype = AA   length = 11
FEATURE                 Location/Qualifiers
REGION                  1..11
                        note = Synthetic
source                  1..11
                        mol_type = protein
                        organism = synthetic construct
SEQUENCE: 546
DDSSGDGYLD Y                                                              11

SEQ ID NO: 547          moltype = AA   length = 127
FEATURE                 Location/Qualifiers
REGION                  1..127
                        note = Synthetic
source                  1..127
                        mol_type = protein
                        organism = synthetic construct
SEQUENCE: 547
EVQLVESGGG VVQPGGSLRL SCAASGRTFN IYTMSWFRQA PGKEREFVAG LRWTDSSTEY          60
ADSVKGRFTI SRDNSKNTVY LQMNSLRPED TALYYCAADR SFLFAQALGA TKNYEYWGQG         120
TLVTVSS                                                                  127

SEQ ID NO: 548          moltype = AA   length = 5
FEATURE                 Location/Qualifiers
REGION                  1..5
                        note = Synthetic
source                  1..5
                        mol_type = protein
                        organism = synthetic construct
SEQUENCE: 548
IYTMS                                                                      5
```

```
SEQ ID NO: 549            moltype = AA   length = 17
FEATURE                   Location/Qualifiers
REGION                    1..17
                          note = Synthetic
source                    1..17
                          mol_type = protein
                          organism = synthetic construct
SEQUENCE: 549
GLRWTDSSTE YADSVKG                                                            17

SEQ ID NO: 550            moltype = AA   length = 18
FEATURE                   Location/Qualifiers
REGION                    1..18
                          note = Synthetic
source                    1..18
                          mol_type = protein
                          organism = synthetic construct
SEQUENCE: 550
DRSFLFAQAL GATKNYEY                                                           18

SEQ ID NO: 551            moltype = AA   length = 120
FEATURE                   Location/Qualifiers
REGION                    1..120
                          note = Synthetic
source                    1..120
                          mol_type = protein
                          organism = synthetic construct
SEQUENCE: 551
DVQLVESGGG VVQPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120

SEQ ID NO: 552            moltype = AA   length = 5
FEATURE                   Location/Qualifiers
REGION                    1..5
                          note = Synthetic
source                    1..5
                          mol_type = protein
                          organism = synthetic construct
SEQUENCE: 552
RLAMG                                                                          5

SEQ ID NO: 553            moltype = AA   length = 17
FEATURE                   Location/Qualifiers
REGION                    1..17
                          note = Synthetic
source                    1..17
                          mol_type = protein
                          organism = synthetic construct
SEQUENCE: 553
AISRRGGSTN YADSVKG                                                            17

SEQ ID NO: 554            moltype = AA   length = 11
FEATURE                   Location/Qualifiers
REGION                    1..11
                          note = Synthetic
source                    1..11
                          mol_type = protein
                          organism = synthetic construct
SEQUENCE: 554
DDSSGDGYLD Y                                                                  11

SEQ ID NO: 555            moltype = AA   length = 127
FEATURE                   Location/Qualifiers
REGION                    1..127
                          note = Synthetic
source                    1..127
                          mol_type = protein
                          organism = synthetic construct
SEQUENCE: 555
EVQLVESGGG VVQPGGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                                      127

SEQ ID NO: 556            moltype = AA   length = 5
FEATURE                   Location/Qualifiers
REGION                    1..5
                          note = Synthetic
source                    1..5
                          mol_type = protein
```

```
                                     organism = synthetic construct
SEQUENCE: 556
IYTMS                                                                        5

SEQ ID NO: 557          moltype = AA  length = 17
FEATURE                 Location/Qualifiers
REGION                  1..17
                        note = Synthetic
source                  1..17
                        mol_type = protein
                        organism = synthetic construct
SEQUENCE: 557
GLRWTDSSTE YADSVKG                                                          17

SEQ ID NO: 558          moltype = AA  length = 18
FEATURE                 Location/Qualifiers
REGION                  1..18
                        note = Synthetic
source                  1..18
                        mol_type = protein
                        organism = synthetic construct
SEQUENCE: 558
DRSFLFAQAL GATKNYEY                                                         18

SEQ ID NO: 559          moltype = AA  length = 120
FEATURE                 Location/Qualifiers
REGION                  1..120
                        note = Synthetic
source                  1..120
                        mol_type = protein
                        organism = synthetic construct
SEQUENCE: 559
DVQLVESGGG VVQPGGSLRL SCAASGRTHS RYAMGWFRQA PGKEREFVAA ISRRGGSTNY           60
ADSVKGRFTI SRDNSKNTVY LQMNSLRPED TALYYCAADD SSGDGYLDYW GQGTLVTVSS          120

SEQ ID NO: 560          moltype = AA  length = 5
FEATURE                 Location/Qualifiers
REGION                  1..5
                        note = Synthetic
source                  1..5
                        mol_type = protein
                        organism = synthetic construct
SEQUENCE: 560
RYAMG                                                                        5

SEQ ID NO: 561          moltype = AA  length = 17
FEATURE                 Location/Qualifiers
REGION                  1..17
                        note = Synthetic
source                  1..17
                        mol_type = protein
                        organism = synthetic construct
SEQUENCE: 561
AISRRGGSTN YADSVKG                                                          17

SEQ ID NO: 562          moltype = AA  length = 11
FEATURE                 Location/Qualifiers
REGION                  1..11
                        note = Synthetic
source                  1..11
                        mol_type = protein
                        organism = synthetic construct
SEQUENCE: 562
DDSSGDGYLD Y                                                                11

SEQ ID NO: 563          moltype = AA  length = 127
FEATURE                 Location/Qualifiers
REGION                  1..127
                        note = Synthetic
source                  1..127
                        mol_type = protein
                        organism = synthetic construct
SEQUENCE: 563
EVQLVESGGG VVQPGGSLRL SCAASGRTFN IYTMSWFRQA PGKEREFVAG LRWTDSSTEY           60
ADSVKGRFTI SRDNSKNTVY LQMNSLRPED TALYYCAADR SFLFAQALGA TKNYEYWGQG          120
TLVTVSS                                                                    127

SEQ ID NO: 564          moltype = AA  length = 5
FEATURE                 Location/Qualifiers
```

```
REGION                  1..5
                        note = Synthetic
source                  1..5
                        mol_type = protein
                        organism = synthetic construct
SEQUENCE: 564
IYTMS                                                                   5

SEQ ID NO: 565          moltype = AA  length = 17
FEATURE                 Location/Qualifiers
REGION                  1..17
                        note = Synthetic
source                  1..17
                        mol_type = protein
                        organism = synthetic construct
SEQUENCE: 565
GLRWTDSSTE YADSVKG                                                      17

SEQ ID NO: 566          moltype = AA  length = 18
FEATURE                 Location/Qualifiers
REGION                  1..18
                        note = Synthetic
source                  1..18
                        mol_type = protein
                        organism = synthetic construct
SEQUENCE: 566
DRSFLFAQAL GATKNYEY                                                     18

SEQ ID NO: 567          moltype = AA  length = 120
FEATURE                 Location/Qualifiers
REGION                  1..120
                        note = Synthetic
source                  1..120
                        mol_type = protein
                        organism = synthetic construct
SEQUENCE: 567
DVQLVESGGG VVQPGGSLRL SCAASGRTFS RLAMGWFRQA PGKEREFVAA ISRRGGSTNY        60
ADSVKGRFTI SRDNSKNTVY LQMNSLRPED TALYYCAADD SSGDGYLDYW GQGTLVTVSS        120

SEQ ID NO: 568          moltype = AA  length = 5
FEATURE                 Location/Qualifiers
REGION                  1..5
                        note = Synthetic
source                  1..5
                        mol_type = protein
                        organism = synthetic construct
SEQUENCE: 568
RLAMG                                                                   5

SEQ ID NO: 569          moltype = AA  length = 17
FEATURE                 Location/Qualifiers
REGION                  1..17
                        note = Synthetic
source                  1..17
                        mol_type = protein
                        organism = synthetic construct
SEQUENCE: 569
AISRRGGSTN YADSVKG                                                      17

SEQ ID NO: 570          moltype = AA  length = 11
FEATURE                 Location/Qualifiers
REGION                  1..11
                        note = Synthetic
source                  1..11
                        mol_type = protein
                        organism = synthetic construct
SEQUENCE: 570
DDSSGDGYLD Y                                                            11

SEQ ID NO: 571          moltype = AA  length = 127
FEATURE                 Location/Qualifiers
REGION                  1..127
                        note = Synthetic
source                  1..127
                        mol_type = protein
                        organism = synthetic construct
SEQUENCE: 571
EVQLVESGGG VVQPGGSLRL SCAASGRTFN IYTMSWFRQA PGKEREFVAG LRWTDSSTEY        60
ADSVKGRFTI SRDNSKNTVY LQMNSLRPED TALYYCAADR SFLFAQALGA TKNYEYWGQG       120
```

```
TLVTVSS                                                              127

SEQ ID NO: 572          moltype = AA  length = 5
FEATURE                 Location/Qualifiers
REGION                  1..5
                        note = Synthetic
source                  1..5
                        mol_type = protein
                        organism = synthetic construct
SEQUENCE: 572
IYTMS                                                                  5

SEQ ID NO: 573          moltype = AA  length = 17
FEATURE                 Location/Qualifiers
REGION                  1..17
                        note = Synthetic
source                  1..17
                        mol_type = protein
                        organism = synthetic construct
SEQUENCE: 573
GLRWTDSSTE YADSVKG                                                    17

SEQ ID NO: 574          moltype = AA  length = 18
FEATURE                 Location/Qualifiers
REGION                  1..18
                        note = Synthetic
source                  1..18
                        mol_type = protein
                        organism = synthetic construct
SEQUENCE: 574
DRSFLFAQAL GATKNYEY                                                   18

SEQ ID NO: 575          moltype = AA  length = 120
FEATURE                 Location/Qualifiers
REGION                  1..120
                        note = Synthetic
source                  1..120
                        mol_type = protein
                        organism = synthetic construct
SEQUENCE: 575
DVQLVESGGG VVQPGGSLRL SCAASGRTFS RLAMGWFRQA PGKEREFVAA ISRRGGSTNY      60
ADSVKGRFTI SRDNSKNTVY LQMNSLRPED TALYYCAADD SSGDGYLDYW GQGTLVTVSS     120

SEQ ID NO: 576          moltype = AA  length = 5
FEATURE                 Location/Qualifiers
REGION                  1..5
                        note = Synthetic
source                  1..5
                        mol_type = protein
                        organism = synthetic construct
SEQUENCE: 576
RLAMG                                                                  5

SEQ ID NO: 577          moltype = AA  length = 17
FEATURE                 Location/Qualifiers
REGION                  1..17
                        note = Synthetic
source                  1..17
                        mol_type = protein
                        organism = synthetic construct
SEQUENCE: 577
AISRRGGSTN YADSVKG                                                    17

SEQ ID NO: 578          moltype = AA  length = 11
FEATURE                 Location/Qualifiers
REGION                  1..11
                        note = Synthetic
source                  1..11
                        mol_type = protein
                        organism = synthetic construct
SEQUENCE: 578
DDSSGDGYLD Y                                                          11

SEQ ID NO: 579          moltype = AA  length = 127
FEATURE                 Location/Qualifiers
REGION                  1..127
                        note = Synthetic
source                  1..127
                        mol_type = protein
```

```
                        organism = synthetic construct
SEQUENCE: 579
EVQLVESGGG VVQPGGSLRL SCAASGRTFN IYTMSWFRQA PGKEREFVAG LRWTDSSTEY   60
ADSVKGRFTI SRDNSKNTVY LQMNSLRPED TALYYCAADR SFLFAQALGA TKNYEYWGQG  120
TLVTVSS                                                           127

SEQ ID NO: 580          moltype = AA   length = 5
FEATURE                 Location/Qualifiers
REGION                  1..5
                        note = Synthetic
source                  1..5
                        mol_type = protein
                        organism = synthetic construct
SEQUENCE: 580
IYTMS                                                               5

SEQ ID NO: 581          moltype = AA   length = 17
FEATURE                 Location/Qualifiers
REGION                  1..17
                        note = Synthetic
source                  1..17
                        mol_type = protein
                        organism = synthetic construct
SEQUENCE: 581
GLRWTDSSTE YADSVKG                                                 17

SEQ ID NO: 582          moltype = AA   length = 18
FEATURE                 Location/Qualifiers
REGION                  1..18
                        note = Synthetic
source                  1..18
                        mol_type = protein
                        organism = synthetic construct
SEQUENCE: 582
DRSFLFAQAL GATKNYEY                                                18

SEQ ID NO: 583          moltype = AA   length = 120
FEATURE                 Location/Qualifiers
REGION                  1..120
                        note = Synthetic
source                  1..120
                        mol_type = protein
                        organism = synthetic construct
SEQUENCE: 583
DVQLVESGGG VVQPGGSLRL SCAASGRTFS RLAMGWFRQA PGKEREFVAA ISRRGGSTNY   60
ADSVKGRFTI SRDNSKNTVY LQMNSLRPED TALYYCAADD SSGDGYLDYW GQGTLVTVSS  120

SEQ ID NO: 584          moltype = AA   length = 5
FEATURE                 Location/Qualifiers
REGION                  1..5
                        note = Synthetic
source                  1..5
                        mol_type = protein
                        organism = synthetic construct
SEQUENCE: 584
RLAMG                                                               5

SEQ ID NO: 585          moltype = AA   length = 17
FEATURE                 Location/Qualifiers
REGION                  1..17
                        note = Synthetic
source                  1..17
                        mol_type = protein
                        organism = synthetic construct
SEQUENCE: 585
AISRRGGSTN YADSVKG                                                 17

SEQ ID NO: 586          moltype = AA   length = 11
FEATURE                 Location/Qualifiers
REGION                  1..11
                        note = Synthetic
source                  1..11
                        mol_type = protein
                        organism = synthetic construct
SEQUENCE: 586
DDSSGDGYLD Y                                                       11

SEQ ID NO: 587          moltype = AA   length = 127
FEATURE                 Location/Qualifiers
```

```
REGION                   1..127
                         note = Synthetic
source                   1..127
                         mol_type = protein
                         organism = synthetic construct
SEQUENCE: 587
EVQLVESGGG VVQPGGSLRL SCAASGRTFN IYTMSWFRQA PGKEREFVAG LRWTDSSTEY    60
ADSVKGRFTI SRDNSKNTVY LQMNSLRPED TALYYCAADR SFLFAQALGA TKNYEYWGQG   120
TLVTVSS                                                             127

SEQ ID NO: 588           moltype = AA  length = 5
FEATURE                  Location/Qualifiers
REGION                   1..5
                         note = Synthetic
source                   1..5
                         mol_type = protein
                         organism = synthetic construct
SEQUENCE: 588
IYTMS                                                                 5

SEQ ID NO: 589           moltype = AA  length = 17
FEATURE                  Location/Qualifiers
REGION                   1..17
                         note = Synthetic
source                   1..17
                         mol_type = protein
                         organism = synthetic construct
SEQUENCE: 589
GLRWTDSSTE YADSVKG                                                   17

SEQ ID NO: 590           moltype = AA  length = 18
FEATURE                  Location/Qualifiers
REGION                   1..18
                         note = Synthetic
source                   1..18
                         mol_type = protein
                         organism = synthetic construct
SEQUENCE: 590
DRSFLFAQAL GATKNYEY                                                  18

SEQ ID NO: 591           moltype = AA  length = 120
FEATURE                  Location/Qualifiers
REGION                   1..120
                         note = Synthetic
source                   1..120
                         mol_type = protein
                         organism = synthetic construct
SEQUENCE: 591
DVQLVESGGG VVQPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120

SEQ ID NO: 592           moltype = AA  length = 5
FEATURE                  Location/Qualifiers
REGION                   1..5
                         note = Synthetic
source                   1..5
                         mol_type = protein
                         organism = synthetic construct
SEQUENCE: 592
RLAMG                                                                 5

SEQ ID NO: 593           moltype = AA  length = 17
FEATURE                  Location/Qualifiers
REGION                   1..17
                         note = Synthetic
source                   1..17
                         mol_type = protein
                         organism = synthetic construct
SEQUENCE: 593
AISRRGGSTN YADSVKG                                                   17

SEQ ID NO: 594           moltype = AA  length = 11
FEATURE                  Location/Qualifiers
REGION                   1..11
                         note = Synthetic
source                   1..11
                         mol_type = protein
                         organism = synthetic construct
SEQUENCE: 594
```

```
DDSSGDGYLD Y                                                                  11

SEQ ID NO: 595         moltype = AA  length = 127
FEATURE                Location/Qualifiers
REGION                 1..127
                       note = Synthetic
source                 1..127
                       mol_type = protein
                       organism = synthetic construct
SEQUENCE: 595
EVQLVESGGG VVQPGGSLRL SCAASGRTFN IYTMSWFRQA PGKEREFVAG LRWTDSSTEY             60
ADSVKGRFTI SRDNSKNTVY LQMNSLRPED TALYYCAADR SFLFAQALGA TKNYEYWGQG            120
TLVTVSS                                                                     127

SEQ ID NO: 596         moltype = AA  length = 5
FEATURE                Location/Qualifiers
REGION                 1..5
                       note = Synthetic
source                 1..5
                       mol_type = protein
                       organism = synthetic construct
SEQUENCE: 596
IYTMS                                                                         5

SEQ ID NO: 597         moltype = AA  length = 17
FEATURE                Location/Qualifiers
REGION                 1..17
                       note = Synthetic
source                 1..17
                       mol_type = protein
                       organism = synthetic construct
SEQUENCE: 597
GLRWTDSSTE YADSVKG                                                           17

SEQ ID NO: 598         moltype = AA  length = 18
FEATURE                Location/Qualifiers
REGION                 1..18
                       note = Synthetic
source                 1..18
                       mol_type = protein
                       organism = synthetic construct
SEQUENCE: 598
DRSFLFAQAL GATKNYEY                                                          18

SEQ ID NO: 599         moltype = AA  length = 114
FEATURE                Location/Qualifiers
REGION                 1..114
                       note = Synthetic
source                 1..114
                       mol_type = protein
                       organism = synthetic construct
SEQUENCE: 599
DVQLVESGGG VVQPGGSLRL SCAASGIVWP INNMGWYRQA PGKQRELVAE FTSGGNTNYA             60
DSVKGRFTIS RGNDENTIYL QMNSLRPEDT ALYYCKIYWG RDYWGQGTLV TVSS                  114

SEQ ID NO: 600         moltype = AA  length = 5
FEATURE                Location/Qualifiers
REGION                 1..5
                       note = Synthetic
source                 1..5
                       mol_type = protein
                       organism = synthetic construct
SEQUENCE: 600
INNMG                                                                         5

SEQ ID NO: 601         moltype = AA  length = 16
FEATURE                Location/Qualifiers
REGION                 1..16
                       note = Synthetic
source                 1..16
                       mol_type = protein
                       organism = synthetic construct
SEQUENCE: 601
EFTSGGNTNY ADSVKG                                                            16

SEQ ID NO: 602         moltype = AA  length = 6
FEATURE                Location/Qualifiers
REGION                 1..6
                       note = Synthetic
```

```
source                        1..6
                              mol_type = protein
                              organism = synthetic construct
SEQUENCE: 602
YWGRDY                                                                    6

SEQ ID NO: 603                moltype = AA  length = 125
FEATURE                       Location/Qualifiers
REGION                        1..125
                              note = Synthetic
source                        1..125
                              mol_type = protein
                              organism = synthetic construct
SEQUENCE: 603
EVQLVESGGG VVQPGGSLRL SCAASGRNFG DYNMAWFRQA PGKEREFVAG ITWSGGSTRY          60
ADSVKGRFTI SRDNSKNTVY LQMNSLRPED TALYYCASGN GRLSILIMSD NYFSWGQGTL         120
VTVSS                                                                   125

SEQ ID NO: 604                moltype = AA  length = 5
FEATURE                       Location/Qualifiers
REGION                        1..5
                              note = Synthetic
source                        1..5
                              mol_type = protein
                              organism = synthetic construct
SEQUENCE: 604
DYNMA                                                                     5

SEQ ID NO: 605                moltype = AA  length = 17
FEATURE                       Location/Qualifiers
REGION                        1..17
                              note = Synthetic
source                        1..17
                              mol_type = protein
                              organism = synthetic construct
SEQUENCE: 605
GITWSGGSTR YADSVKG                                                       17

SEQ ID NO: 606                moltype = AA  length = 16
FEATURE                       Location/Qualifiers
REGION                        1..16
                              note = Synthetic
source                        1..16
                              mol_type = protein
                              organism = synthetic construct
SEQUENCE: 606
GNGRLSILIM SDNYFS                                                        16

SEQ ID NO: 607                moltype = AA  length = 120
FEATURE                       Location/Qualifiers
REGION                        1..120
                              note = Synthetic
source                        1..120
                              mol_type = protein
                              organism = synthetic construct
SEQUENCE: 607
DVQLVESGGG VVQPGGSLRL SCVASGRTFS RYAMGWFRQA PGKEREFVAA ISRRGGSTNY         60
ADSVKGRFTI SRDNSKNTVY LQMNSLRPED TALYYCAADY SSGDGYLDYW GQGTLVTVSS        120

SEQ ID NO: 608                moltype = AA  length = 5
FEATURE                       Location/Qualifiers
REGION                        1..5
                              note = Synthetic
source                        1..5
                              mol_type = protein
                              organism = synthetic construct
SEQUENCE: 608
RYAMG                                                                     5

SEQ ID NO: 609                moltype = AA  length = 17
FEATURE                       Location/Qualifiers
REGION                        1..17
                              note = Synthetic
source                        1..17
                              mol_type = protein
                              organism = synthetic construct
SEQUENCE: 609
AISRRGGSTN YADSVKG                                                       17
```

```
SEQ ID NO: 610            moltype = AA  length = 11
FEATURE                   Location/Qualifiers
REGION                    1..11
                          note = Synthetic
source                    1..11
                          mol_type = protein
                          organism = synthetic construct
SEQUENCE: 610
DYSSGDGYLD Y                                                           11

SEQ ID NO: 611            moltype = AA  length = 127
FEATURE                   Location/Qualifiers
REGION                    1..127
                          note = Synthetic
source                    1..127
                          mol_type = protein
                          organism = synthetic construct
SEQUENCE: 611
EVQLVESGGG VVQPGGSLRL SCAASGRTFN IYTMSWFRQA PGKERELVAG LRWTDSSTEY       60
ADSVKGRATI SRDNSKTTVY LQMNSLRPED TALYYCAADR SFLFAQAMGA TKNYEYWGQG      120
TLVTVSS                                                               127

SEQ ID NO: 612            moltype = AA  length = 5
FEATURE                   Location/Qualifiers
REGION                    1..5
                          note = Synthetic
source                    1..5
                          mol_type = protein
                          organism = synthetic construct
SEQUENCE: 612
IYTMS                                                                   5

SEQ ID NO: 613            moltype = AA  length = 17
FEATURE                   Location/Qualifiers
REGION                    1..17
                          note = Synthetic
source                    1..17
                          mol_type = protein
                          organism = synthetic construct
SEQUENCE: 613
GLRWTDSSTE YADSVKG                                                     17

SEQ ID NO: 614            moltype = AA  length = 18
FEATURE                   Location/Qualifiers
REGION                    1..18
                          note = Synthetic
source                    1..18
                          mol_type = protein
                          organism = synthetic construct
SEQUENCE: 614
DRSFLFAQAM GATKNYEY                                                    18

SEQ ID NO: 615            moltype = AA  length = 154
FEATURE                   Location/Qualifiers
REGION                    1..154
                          note = Synthetic
source                    1..154
                          mol_type = protein
                          organism = synthetic construct
SEQUENCE: 615
EVQLVESGGG LVQPGGSLRL SCAASGSIGA FDAMGWYRQA PGKQRELVAG IMVSRGNTNY       60
TDSVKGRFTI SRDNAKNTVY LQMNSLKPED TAVYYCKAVK RPGPGYLEVW GQGTLVTVSS      120
AAADYKDHDG DYKDHDIDYK DDDDKGAAHH HHHH                                  154

SEQ ID NO: 616            moltype = AA  length = 133
FEATURE                   Location/Qualifiers
REGION                    1..133
                          note = Synthetic
source                    1..133
                          mol_type = protein
                          organism = synthetic construct
SEQUENCE: 616
EVQLVESGGG VVQPGGSLRL SCAASGRTFN IYTMSWFRQA PGKERELVAG LRWTDSSTEY       60
ADSVKGRATI SRDNSKTTVY LQMNSLRPED TALYYCAADR SFLFAQAMGA TKNYEYWGQG      120
TLVTVSSHHH HHH                                                        133

SEQ ID NO: 617            moltype = AA  length = 126
FEATURE                   Location/Qualifiers
REGION                    1..126
```

```
                        note = Synthetic
source                  1..126
                        mol_type = protein
                        organism = synthetic construct
SEQUENCE: 617
EVQLVESGGG VVQPGGSLRL SCVASGRTFS RYAMGWFRQA PGKEREFVAA ISRRGGSTNY   60
ADSVKGRFTI SRDNSKNTVY LQMNSLRPED TALYYCAADY SSGDGYLDYW GQGTLVTVSS  120
HHHHHH                                                             126

SEQ ID NO: 618          moltype = AA   length = 268
FEATURE                 Location/Qualifiers
REGION                  1..268
                        note = Synthetic
source                  1..268
                        mol_type = protein
                        organism = synthetic construct
SEQUENCE: 618
DVQLVESGGG VVQPGGSLRL SCAASGRTHS RYAMGWFRQA PGKEREFVAA ISRRGGSTNY   60
ADSVKGRFTI SRDNSKNTVY LQMNSLRPED TALYYCAADD SSGDGYLDYW GQGTLVTVSS  120
GGGGSGGGSE VQLVESGGGV VQPGGSLRLS CAASGRTFNI YTMSWFRQAP GKEREFVAGL  180
RWTDSSTEYA DSVKGRFTIS RDNSKNTVYL QMNSLRPEDT ALYYCAADRS FLFAQALGAT  240
KNYEYWGQGT LVTVSSGGGG SCHHHHHH                                     268

SEQ ID NO: 619          moltype = AA   length = 268
FEATURE                 Location/Qualifiers
REGION                  1..268
                        note = Synthetic
source                  1..268
                        mol_type = protein
                        organism = synthetic construct
SEQUENCE: 619
DVQLVESGGG VVQPGGSLQL SCAASGRTHS RYAMGWFRQA PGQEREFVAA ISRRGGSTNY   60
ADSVKGRFTI SRDNSKNTVY LQMDSLRPED TALYYCAADD SSGDGYLDYW GQGTLVTVSS  120
GGGGSGGGSE VQLVESGGGV VQPGGSLQLS CAASGRTFNI YTMSWFRQAP GQEREFVAGL  180
RWTDSSTEYA DSVKGRFTIS RDNSKNTVYL QMDSLRPEDT ALYYCAADRS FLFAQALGAT  240
KNYEYWGQGT LVTVSSGGGG SCHHHHHH                                     268

SEQ ID NO: 620          moltype = AA   length = 269
FEATURE                 Location/Qualifiers
REGION                  1..269
                        note = Synthetic
source                  1..269
                        mol_type = protein
                        organism = synthetic construct
SEQUENCE: 620
DVQLVESGGG VVQPGGSLQL SCAASGRTHS RYAMGWFRQA PGQEREFVAA ISRRGGSTNY   60
ADSVKGRFTI SRDNSKNTVY LQMDSLRPED TALYYCAADD SSGDGYLDYW GQGTLVTVSS  120
GGGGSGGGSE VQLVESGGGV VQPGGSLQLS CAASGRTFNI YTMSWFRQAP GQEREFVAGL  180
RWTDSSTEYA DSVKGRFTIS RDNSKNTVYL QMDSLRPEDT ALYYCAADRS FLFAQALGAT  240
KNYEYWGQGT LVTVSSGGGG CSCHHHHHH                                    269

SEQ ID NO: 621          moltype = AA   length = 259
FEATURE                 Location/Qualifiers
REGION                  1..259
                        note = Synthetic
source                  1..259
                        mol_type = protein
                        organism = synthetic construct
SEQUENCE: 621
DVQLVESGGG VVQPGGSLQL SCAASGGTKS RYAMGWFRQA PGQEREFVAA ISRRGGSTNY   60
ADSVKGRFTI SRDNSKNTVY LQMDSLRPED TALYYCAADD SVGDGYLDYW GQGTLVTVSS  120
GQAPGQEVQL VESGGGVVQP GGSLRLSCAA SGRTFNIYTM SWFRQAPGQE REFVAGLRWT  180
DSSTEYADSV KGRFTISRDN SKNTVYLQMN SLRPEDTALY YCAADRSFLF AQALGATKNY  240
EYWGQGTLVT VSSGQACPC                                               259

SEQ ID NO: 622          moltype = AA   length = 259
FEATURE                 Location/Qualifiers
REGION                  1..259
                        note = Synthetic
source                  1..259
                        mol_type = protein
                        organism = synthetic construct
SEQUENCE: 622
DVQLVESGGG VVQPGGSLQL SCAASGGTKS RYAMGWFRQA PGQEREFVAA ISRRGGSTNY   60
ADSVKGRFTI SRDNSKNTVY LQMDSLRPED TALYYCAADD SVGDGYLDYW GQGTLVTVSS  120
GQAPGQEVQL VESGGGVVQP GGSLQLSCAA SGRTFNIYTM SWFRQAPGQE REFVAGLRWT  180
DSSTEYADSV KGRFTISRDN SKNTVYLQMD SLRPEDTALY YCAADRSFLF AQALGATKNY  240
EYWGQGTLVT VSSGQACPC                                               259
```

```
SEQ ID NO: 623          moltype = AA  length = 259
FEATURE                 Location/Qualifiers
REGION                  1..259
                        note = Synthetic
source                  1..259
                        mol_type = protein
                        organism = synthetic construct
SEQUENCE: 623
DVQLVESGGG VVQPGGSLQL SCAASGGTKS RYAMGWFRQA PGQEREFVAA ISRRGGSTNY   60
ADSVKGRFTI SRDNSKNTVY LDMDDLRPED TALYYCAADD SVGDGYLDYW GQGTLVTVSS  120
GQAPGQEVQL VESGGGVVQP GGSLRLSCAA SGRTFNIYTM SWFRQDPGQE REFVAGLRWT  180
DSSTEYADSV KGRFTISRDN SKNTVYLQMN SLRPEDTALY YCAADRSFLF AQALGATKNY  240
EYWGQGTLVT VSSGQACPC                                              259

SEQ ID NO: 624          moltype = AA  length = 259
FEATURE                 Location/Qualifiers
REGION                  1..259
                        note = Synthetic
source                  1..259
                        mol_type = protein
                        organism = synthetic construct
SEQUENCE: 624
DVQLVESGGG VVQPGGSLQL SCAASGGTKR RLAMGWFRQA PGQEREWVAA ISRRGGSTNY   60
ADSVKGRFTI SRDNSKNTVY LQMDSLRPED TALYYCAADD SVGDGYLDYW GQGTLVTVSS  120
GQAPGQEVQL VESGGGVVQP GGSLRLSCAA SGRTFNIYTM SWFRQAPGQE REFVAGLRWT  180
DSSTEYADSV KGRFTISRDN SKNTVYLQMN SLRPEDTALY YCAADRSFLF AQALGATKNY  240
EYWGQGTLVT VSSGQACPC                                              259

SEQ ID NO: 625          moltype = AA  length = 259
FEATURE                 Location/Qualifiers
REGION                  1..259
                        note = Synthetic
source                  1..259
                        mol_type = protein
                        organism = synthetic construct
SEQUENCE: 625
DVQLVESGGG VVQPGGSLQL SCAASGGTKR RLAMGWFRQA PGQEREFVAA ISRRGGSTNY   60
ADSVKGRFTI SRDNSKNTVY LDMDDLRPED TALYYCAADD SVGDGYLDYW GQGTLVTVSS  120
GQAPGQEVQL VESGGGVVQP GGSLRLSCAA SGRTFNIYTM SWFRQDPGQE REFVAGLRWT  180
DSSTEYADSV KGRFTISRDN SKNTVYLQMN SLRPEDTALY YCAADRSFLF AQALGATKNY  240
EYWGQGTLVT VSSGQACPC                                              259

SEQ ID NO: 626          moltype = AA  length = 259
FEATURE                 Location/Qualifiers
REGION                  1..259
                        note = Synthetic
source                  1..259
                        mol_type = protein
                        organism = synthetic construct
SEQUENCE: 626
DVQLVESGGG VVQPGGSLQL SCAASGGTKR RLAMGWFRQA PGQEREFVAA ISRRGGSTNY   60
ADSVKGRFTI SRDNSKNTVY LDMDDLRPED TALYYCAADD SVGDGYLDYW GQGTLVTVSS  120
GQAPGQEVQL VESGGGVVQP GGSLQLSCAA SGRTFNIYTM SWFRQDPGQE REFVAGLRWT  180
DSSTEYADSV KGRFTISRDN SKNTVYLQMD SLRPEDTALY YCAADRSFLF AQALGATKNY  240
EYWGQGTLVT VSSGQACPC                                              259

SEQ ID NO: 627          moltype = AA  length = 259
FEATURE                 Location/Qualifiers
REGION                  1..259
                        note = Synthetic
source                  1..259
                        mol_type = protein
                        organism = synthetic construct
SEQUENCE: 627
DVQLVESGGG VVQPGGSLQL SCAASGGTKR RLAMGWFRQA PGQEREWVAA ISRRGGSTNY   60
ADSVKGRFTI SRDNSKNTVY LDMDDLRPED TALYYCAADD SVGDGYLDYW GQGTLVTVSS  120
GQAPGQEVQL VESGGGVVQP GGSLQLSCAA SGRTFNIYTM SWFRQDPGQE REFVAGLRWT  180
DSSTEYADSV KGRFTISRDN SKNTVYLQMD SLRPEDTALY YCAADRSFLF AQALGATKNY  240
EYWGQGTLVT VSSGQACPC                                              259

SEQ ID NO: 628          moltype = AA  length = 259
FEATURE                 Location/Qualifiers
REGION                  1..259
                        note = Synthetic
source                  1..259
                        mol_type = protein
                        organism = synthetic construct
SEQUENCE: 628
DVQLVESGGG VVQPGGSLQL SCAASGGTKR RLAMGWFRQA PGQEREFVAA ISRRGGSTNY   60
```

```
ADSVKGRFTI SRDNSKNTVY LQMDSLRPED TALYYCAADD SVGDGYLDYW GQGTLVTVSS    120
GQAPGQEVQL VESGGGVVQP GGSLQLSCAA SGRTFNIYTM SWFRQAPGQE REFVAGLRWT    180
DSSTEYADSV KGRFTISRDN SKNTVYLQMD SLRPEDTALY YCAADRSFLF AQALGATKNY    240
EYWGQGTLVT VSSGQACPC                                                259

SEQ ID NO: 629          moltype = AA  length = 259
FEATURE                 Location/Qualifiers
REGION                  1..259
                        note = Synthetic
source                  1..259
                        mol_type = protein
                        organism = synthetic construct
SEQUENCE: 629
DVQLVESGGG VVQPGGSLQL SCAASGGTKR RLAMGWFRQA PGQEREWVAA ISRRGGSTNY    60
ADSVKGRFTI SRDNSKNTVY LQMDSLRPED TALYYCAADD SVGDGYLDYW GQGTLVTVSS    120
GQAPGQEVQL VESGGGVVQP GGSLQLSCAA SGRTFNIYTM SWFRQAPGQE REFVAGLRWT    180
DSSTEYADSV KGRFTISRDN SKNTVYLQMD SLRPEDTALY YCAADRSFLF AQALGATKNY    240
EYWGQGTLVT VSSGQACPC                                                259

SEQ ID NO: 630          moltype = AA  length = 259
FEATURE                 Location/Qualifiers
REGION                  1..259
                        note = Synthetic
source                  1..259
                        mol_type = protein
                        organism = synthetic construct
SEQUENCE: 630
DVQLVESGGG VVQPGGSLQL SCAASGGTKR RLAMGWFRQA PGQEREWVAA ISRRGGSTNY    60
ADSVKGRFTI SRDNSKNTVY LDMDDLRPED TALYYCAADD SVGDGYLDYW GQGTLVTVSS    120
GQAPGQEVQL VESGGGVVQP GGSLRLSCAA SGRYFNIYTM SWFRQDPGQE REFVAGLRWT    180
DSSTEYADSV KGRFTISRDN SKNTVYLQMN SLRPEDTALY YCAADRSFLF AQALGATKNY    240
EYWGQGTLVT VSSGQACPC                                                259

SEQ ID NO: 631          moltype = AA  length = 259
FEATURE                 Location/Qualifiers
REGION                  1..259
                        note = Synthetic
source                  1..259
                        mol_type = protein
                        organism = synthetic construct
SEQUENCE: 631
DVQLVESGGG VVQPGGSLQL SCAASGGTKS RYAMGWFRQA PGQEREWVAA ISRRGGSTNY    60
ADSVKGRFTI SRDNSKNTVY LDMDDLRPED TALYYCAADD SVGDGYLDYW GQGTLVTVSS    120
GQAPGQEVQL VESGGGVVQP GGSLQLSCAA SGRTFNIYTM SWFRQDPGQE REFVAGLRWT    180
DSSTEYADSV KGRFTISRDN SKNTVYLQMD SLRPEDTALY YCAADRSFLF AQALGATKNY    240
EYWGQGTLVT VSSGQACPC                                                259

SEQ ID NO: 632          moltype = AA  length = 259
FEATURE                 Location/Qualifiers
REGION                  1..259
                        note = Synthetic
source                  1..259
                        mol_type = protein
                        organism = synthetic construct
SEQUENCE: 632
DVQLVESGGG VVQPGGSLQL SCAASGGTKS RYAMGWFRQA PGQEREWVAA ISRRGGSTNY    60
ADSVKGRFTI SRDNSKNTVY LDMDDLRPED TALYYCAADD SVGDGYLDYW GQGTLVTVSS    120
GQAPGQEVQL VESGGGVVQP GGSLRLSCAA SGRTFNIYTM SWFRQDPGQE REFVAGLRWT    180
DSSTEYADSV KGRFTISRDN SKNTVYLQMN SLRPEDTALY YCAADRSFLF AQALGATKNY    240
EYWGQGTLVT VSSGQACPC                                                259

SEQ ID NO: 633          moltype = AA  length = 259
FEATURE                 Location/Qualifiers
REGION                  1..259
                        note = Synthetic
source                  1..259
                        mol_type = protein
                        organism = synthetic construct
SEQUENCE: 633
DVQLVESGGG VVQPGGSLQL SCAASGGTKS RYAMGWFRQA PGQEREWVAA ISRRGGSTNY    60
ADSVKGRFTI SRDNSKNTVY LQMDSLRPED TALYYCAADD SVGDGYLDYW GQGTLVTVSS    120
GQAPGQEVQL VESGGGVVQP GGSLQLSCAA SGRTFNIYTM SWFRQAPGQE REFVAGLRWT    180
DSSTEYADSV KGRFTISRDN SKNTVYLQMD SLRPEDTALY YCAADRSFLF AQALGATKNY    240
EYWGQGTLVT VSSGQACPC                                                259

SEQ ID NO: 634          moltype = AA  length = 259
FEATURE                 Location/Qualifiers
REGION                  1..259
                        note = Synthetic
```

```
source                          1..259
                                mol_type = protein
                                organism = synthetic construct
SEQUENCE: 634
DVQLVESGGG VVQPGGSLQL SCAASGGTKS RYAMGWFRQA PGQEREWVAA ISRRGGSTNY    60
ADSVKGRFTI SRDNSKNTVY LQMDSLRPED TALYYCAADD SVGDGYLDYW GQGTLVTVSS   120
GQAPGQEVQL VESGGGVVQP GGSLRLSCAA SGRTFNIYTM SWFRQAPGQE REFVAGLRWT   180
DSSTEYADSV KGRFTISRDN SKNTVYLQMN SLRPEDTALY YCAADRSFLF AQALGATKNY   240
EYWGQGTLVT VSSGQACPC                                                259

SEQ ID NO: 635          moltype = AA   length = 259
FEATURE                 Location/Qualifiers
REGION                  1..259
                        note = Synthetic
source                  1..259
                        mol_type = protein
                        organism = synthetic construct
SEQUENCE: 635
DVQLVESGGG VVQPGGSLQL SCAASGGTKS RYAMGWFRQA PGQEREFVAA ISRRGGSTNY    60
ADSVKGRFTI SRDNSKNTVY LDMDDLRPED TALYYCAADD SVGDGYLDYW GQGTLVTVSS   120
GQAPGQEVQL VESGGGVVQP GGSLQLSCAA SGRTFNIYTM SWFRQDPGQE REFVAGLRWT   180
DSSTEYADSV KGRFTISRDN SKNTVYLQMD SLRPEDTALY YCAADRSFLF AQALGATKNY   240
EYWGQGTLVT VSSGQACPC                                                259

SEQ ID NO: 636          moltype = AA   length = 259
FEATURE                 Location/Qualifiers
REGION                  1..259
                        note = Synthetic
source                  1..259
                        mol_type = protein
                        organism = synthetic construct
SEQUENCE: 636
DVQLVESGGG VVQPGGSLQL SCAASGGTKR RLAMGWFRQA PGQEREWVAA ISRRGGSTNY    60
ADSVKGRFTI SRDNSKNTVY LDMDDLRPED TALYYCAADD SVGDGYLDYW GQGTLVTVSS   120
GQAPGQEVQL VESGGGVVQP GGSLRLSCAA SGRTFNIYTM SWFRQDPGQE REFVAGLRWT   180
DSSTEYADSV KGRFTISRDN SKNTVYLQMN SLRPEDTALY YCAADRSFLF AQALGATKNY   240
EYWGQGTLVT VSSGQACPC                                                259

SEQ ID NO: 637          moltype = AA   length = 289
FEATURE                 Location/Qualifiers
REGION                  1..289
                        note = Synthetic
source                  1..289
                        mol_type = protein
                        organism = synthetic construct
SEQUENCE: 637
EDQVDPRLID GKGGGGSDVQ LVESGGGVVQ PGGSLRLSCA ASGRTFSRYA MGWFRQAPGK    60
EREFVAAISR RGGSTNYADS VKGRFTISRD NSKNTVYLQM NSLRPEDTAL YYCAADYSSG   120
DGYLDYWGQG TLVTVSSGGG GSGGGSEVQL VESGGGVVQP GGSLRLSCAA SGRTFNIYTM   180
SWFRQAPGKE REFVAGLRWT DSSTEYADSV KGRFTISRDN SKNTVYLQMN SLRPEDTALY   240
YCAADRSFLF AQALGATKNY EYWGQGTLVT VSSGGGGSGG GSCHHHHHH               289

SEQ ID NO: 638          moltype = AA   length = 289
FEATURE                 Location/Qualifiers
REGION                  1..289
                        note = Synthetic
source                  1..289
                        mol_type = protein
                        organism = synthetic construct
SEQUENCE: 638
EDQVDPRLID GKGGGGSDVQ LVESGGGVVQ PGGSLRLSCA ASGRTFSRYA MGWFRQAPGK    60
EREFVAAISR RGGSTNYADS VKGRFTISRD NSKNTVYLQM NSLRPEDTAL YYCAADYSSG   120
DGYLDYWGQG TLVTVSSGGG GSGGGSEVQL VESGGGVVQP GGSLRLSCAA SGRTFNIYTM   180
SWFRQAPGKE REFVAGLRWT DSSTEYADSV KGRFTISRDN SKNTVYLQMN SLRPEDTALY   240
YCAADRSFLF AQALGATKNY EYWGQGTLVT VSSGGGGSGG GSCHHHHHH               289

SEQ ID NO: 639          moltype = AA   length = 284
FEATURE                 Location/Qualifiers
REGION                  1..284
                        note = Synthetic
source                  1..284
                        mol_type = protein
                        organism = synthetic construct
SEQUENCE: 639
EDQVDPRLID GKGGGGSDVQ LVESGGGVVC PGGSLRLSCA ASGRTFSRLA MGWFRQAPGK    60
EREFVAAISR RGGSTNYADS VKGRFTISRD NSKNTVYLQM NSLRPEDTAL YYCAADDSSG   120
DGYLDYWGQG TLVTVSSGGG GSGGGSEVQL VESGGGVVQP GGSLRLSCAA SGRTFNIYTM   180
SWFRQAPGKE REFVAGLRWT DSSTEYADSV KGRFTISRDN SKNTVYLQMN SLRPEDTALY   240
YCAADRSFLF AQALGATKNY EYWGQGTLVT VSSGGGGSHH HHHH                    284
```

```
SEQ ID NO: 640          moltype = AA  length = 284
FEATURE                 Location/Qualifiers
REGION                  1..284
                        note = Synthetic
source                  1..284
                        mol_type = protein
                        organism = synthetic construct
SEQUENCE: 640
EDQVDPRLID GKGGGGSDVQ LVESGGGVVC PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP GGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 641          moltype = AA  length = 284
FEATURE                 Location/Qualifiers
REGION                  1..284
                        note = Synthetic
source                  1..284
                        mol_type = protein
                        organism = synthetic construct
SEQUENCE: 641
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVCQP GGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 642          moltype = AA  length = 284
FEATURE                 Location/Qualifiers
REGION                  1..284
                        note = Synthetic
source                  1..284
                        mol_type = protein
                        organism = synthetic construct
SEQUENCE: 642
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVCQP GGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 643          moltype = AA  length = 284
FEATURE                 Location/Qualifiers
REGION                  1..284
                        note = Synthetic
source                  1..284
                        mol_type = protein
                        organism = synthetic construct
SEQUENCE: 643
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVC GGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 644          moltype = AA  length = 284
FEATURE                 Location/Qualifiers
REGION                  1..284
                        note = Synthetic
source                  1..284
                        mol_type = protein
                        organism = synthetic construct
SEQUENCE: 644
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQC GGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 645          moltype = AA  length = 284
FEATURE                 Location/Qualifiers
REGION                  1..284
                        note = Synthetic
source                  1..284
                        mol_type = protein
                        organism = synthetic construct
SEQUENCE: 645
```

```
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP CGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 646          moltype = AA   length = 284
FEATURE                 Location/Qualifiers
REGION                  1..284
                        note = Synthetic
source                  1..284
                        mol_type = protein
                        organism = synthetic construct
SEQUENCE: 646
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP CGSLRLSCAA SGRTFNIYTM  180
SWFRQAPGKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 647          moltype = AA   length = 284
FEATURE                 Location/Qualifiers
REGION                  1..284
                        note = Synthetic
source                  1..284
                        mol_type = protein
                        organism = synthetic construct
SEQUENCE: 647
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP GGSLRLSCAA SGRTFNIYTM  180
SWFRQAPCKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 648          moltype = AA   length = 284
FEATURE                 Location/Qualifiers
REGION                  1..284
                        note = Synthetic
source                  1..284
                        mol_type = protein
                        organism = synthetic construct
SEQUENCE: 648
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP GGSLRLSCAA SGRTFNIYTM  180
SWFRQAPCKE REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 649          moltype = AA   length = 284
FEATURE                 Location/Qualifiers
REGION                  1..284
                        note = Synthetic
source                  1..284
                        mol_type = protein
                        organism = synthetic construct
SEQUENCE: 649
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP GGSLRLSCAA SGRTFNIYTM  180
SWFRQAPGKC REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 650          moltype = AA   length = 284
FEATURE                 Location/Qualifiers
REGION                  1..284
                        note = Synthetic
source                  1..284
                        mol_type = protein
                        organism = synthetic construct
SEQUENCE: 650
EDQVDPRLID GKGGGGSDVQ LVESGGGVVQ PGGSLRLSCA ASGRTFSRLA MGWFRQAPGK   60
EREFVAAISR RGGSTNYADS VKGRFTISRD NSKNTVYLQM NSLRPEDTAL YYCAADDSSG  120
DGYLDYWGQG TLVTVSSGGG GSGGGSEVQL VESGGGVVQP GGSLRLSCAA SGRTFNIYTM  180
SWFRQAPGKC REFVAGLRWT DSSTEYADSV KGRFTISRDN SKNTVYLQMN SLRPEDTALY  240
YCAADRSFLF AQALGATKNY EYWGQGTLVT VSSGGGGSHH HHHH                  284

SEQ ID NO: 651          moltype = AA   length = 284
FEATURE                 Location/Qualifiers
REGION                  1..284
```

```
SEQ ID NO: 651                moltype = AA  length = 284
FEATURE                       Location/Qualifiers
REGION                        1..284
                              note = Synthetic
source                        1..284
                              mol_type = protein
                              organism = synthetic construct
SEQUENCE: 651
EDQVDPRLID GKGGGGSDVQ LVESGGGVVQ PGGSLRLSCA ASGRTFSRLA MGWFRQAPGK  60
EREFVAAISR RGGSTNYADS VKGRFTISRD NSKNTVYLQM NSLRPEDTAL YYCAADDSSG 120
DGYLDYWGQG TLVTVSSGGG GSGGGSEVQL VESGGGVVQP GGSLRLSCAA SGRTFNIYTM 180
SWFRQAPGKE REFVAGLRWT DSSTEYADCV KGRFTISRDN SKNTVYLQMN SLRPEDTALY 240
YCAADRSFLF AQALGATKNY EYWGQGTLVT VSSGGGGSHH HHHH            284

SEQ ID NO: 652                moltype = AA  length = 284
FEATURE                       Location/Qualifiers
REGION                        1..284
                              note = Synthetic
source                        1..284
                              mol_type = protein
                              organism = synthetic construct
SEQUENCE: 652
EDQVDPRLID GKGGGGSDVQ LVESGGGVVQ PGGSLRLSCA ASGRTFSRLA MGWFRQAPGK  60
EREFVAAISR RGGSTNYADS VKGRFTISRD NSKNTVYLQM NSLRPEDTAL YYCAADDSSG 120
DGYLDYWGQG TLVTVSSGGG GSGGGSEVQL VESGGGVVQP GGSLRLSCAA SGRTFNIYTM 180
SWFRQAPGKE REFVAGLRWT DSSTEYADCV KGRFTISRDN SKNTVYLQMN SLRPEDTALY 240
YCAADRSFLF AQALGATKNY EYWGQGTLVT VSSGGGGSHH HHHH            284

SEQ ID NO: 653                moltype = AA  length = 284
FEATURE                       Location/Qualifiers
REGION                        1..284
                              note = Synthetic
source                        1..284
                              mol_type = protein
                              organism = synthetic construct
SEQUENCE: 653
EDQVDPRLID GKGGGGSDVQ LVESGGGVVQ PGGSLRLSCA ASGRTFSRLA MGWFRQAPGK  60
EREFVAAISR RGGSTNYADS VKGRFTISRD NSKNTVYLQM NSLRPEDTAL YYCAADDSSG 120
DGYLDYWGQG TLVTVSSGGG GSGGGSEVQL VESGGGVVQP GGSLRLSCAA SGRTFNIYTM 180
SWFRQAPGKE REFVAGLRWT DSSTEYADSV KGRFTISRDN SKNTVYLQMN CLRPEDTALY 240
YCAADRSFLF AQALGATKNY EYWGQGTLVT VSSGGGGSHH HHHH            284

SEQ ID NO: 654                moltype = AA  length = 284
FEATURE                       Location/Qualifiers
REGION                        1..284
                              note = Synthetic
source                        1..284
                              mol_type = protein
                              organism = synthetic construct
SEQUENCE: 654
EDQVDPRLID GKGGGGSDVQ LVESGGGVVQ PGGSLRLSCA ASGRTFSRLA MGWFRQAPGK  60
EREFVAAISR RGGSTNYADS VKGRFTISRD NSKNTVYLQM NSLRPEDTAL YYCAADDSSG 120
DGYLDYWGQG TLVTVSSGGG GSGGGSEVQL VESGGGVVQP GGSLRLSCAA SGRTFNIYTM 180
SWFRQAPGKE REFVAGLRWT DSSTEYADSV KGRFTISRDN SKNTVYLQMN CLRPEDTALY 240
YCAADRSFLF AQALGATKNY EYWGQGTLVT VSSGGGGSHH HHHH            284

SEQ ID NO: 655                moltype = AA  length = 265
FEATURE                       Location/Qualifiers
REGION                        1..265
                              note = Synthetic
source                        1..265
                              mol_type = protein
                              organism = synthetic construct
SEQUENCE: 655
DVQLVESGGG VVQPGGSLQL SCAASGRTHS RLAMGWFRQA PGQEREFVAA ISRRGGSTNY  60
ADSVKGRFTI SRDNSKNTVY LQMDSLRPED TALYYCAADD SSGDGYLDYW GQGTLVTVSS 120
QAPGQAEVQL VESGGGVVQP GGSLQLSCAA SGRTFNIYTM SWFRQAPGQE REFVAGLRWT 180
DSSTEYADSV KGRFTISRDN SKNTVYLQMD SLRPEDTALY YCAADRSFLF AQALGATKNY 240
EYWGQGTLVT VSSGGGGSCH HHHHH                                 265

SEQ ID NO: 656                moltype = AA  length = 269
FEATURE                       Location/Qualifiers
REGION                        1..269
                              note = Synthetic
source                        1..269
                              mol_type = protein
                              organism = synthetic construct
SEQUENCE: 656
DVQLVESGGG VVQPGGSLQL SCAASGRTHS RLAMGWFRQA PGQEREFVAA ISRRGGSTNY  60
ADSVKGRFTI SRDNSKNTVY LQMDSLRPED TALYYCAADD SSGDGYLDYW GQGTLVTVSS 120
GIGIGIGIGI EVQLVESGGG VVQPGGSLQL SCAASGRTFN IYTMSWFRQA PGQEREFVAG 180
LRWTDSSTEY ADSVKGRFTI SRDNSKNTVY LQMDSLRPED TALYYCAADR SFLFAQALGA 240
```

-continued

```
TKNYEYWGQG TLVTVSSGGG GSCHHHHHH                                                   269

SEQ ID NO: 657            moltype = AA   length = 269
FEATURE                   Location/Qualifiers
REGION                    1..269
                          note = Synthetic
source                    1..269
                          mol_type = protein
                          organism = synthetic construct
SEQUENCE: 657
DVQLVESGGG VVQPGGSLQL SCAASGRTHS RLAMGWFRQA PGQEREFVAA ISRRGGSTNY                   60
ADSVKGRFTI SRDNSKNTVY LQMDSLRPED TALYYCAADD SSGDGYLDYW GQGTLVTVSS                  120
GTGTGTGTGT EVQLVESGGG VVQPGGSLQL SCAASGRTFN IYTMSWFRQA PGQEREFVAG                  180
LRWTDSSTEY ADSVKGRFTI SRDNSKNTVY LQMDSLRPED TALYYCAADR SFLFAQALGA                  240
TKNYEYWGQG TLVTVSSGGG GSCHHHHHH                                                   269

SEQ ID NO: 658            moltype = AA   length = 269
FEATURE                   Location/Qualifiers
REGION                    1..269
                          note = Synthetic
source                    1..269
                          mol_type = protein
                          organism = synthetic construct
SEQUENCE: 658
DVQLVESGGG VVQPGGSLQL SCAASGRTHS RLAMGWFRQA PGQEREFVAA ISRRGGSTNY                   60
ADSVKGRFTI SRDNSKNTVY LQMDSLRPED TALYYCAADD SSGDGYLDYW GQGTLVTVSS                  120
GVGVGVGVGV EVQLVESGGG VVQPGGSLQL SCAASGRTFN IYTMSWFRQA PGQEREFVAG                  180
LRWTDSSTEY ADSVKGRFTI SRDNSKNTVY LQMDSLRPED TALYYCAADR SFLFAQALGA                  240
TKNYEYWGQG TLVTVSSGGG GSCHHHHHH                                                   269

SEQ ID NO: 659            moltype = AA   length = 265
FEATURE                   Location/Qualifiers
REGION                    1..265
                          note = Synthetic
source                    1..265
                          mol_type = protein
                          organism = synthetic construct
SEQUENCE: 659
DVQLVESGGG VVQPGGSLQL SCAASGRTHS RLAMGWFRQA PGQEREFVAA ISRRGGSTNY                   60
ADSVKGRFTI SRDNSKNTVY LQMDSLRPED TALYYCAADD SSGDGYLDYW GQGTLVTVSS                  120
GQAPGQEVQL VESGGGVVQP GGSLQLSCAA SGRTFNIYTM SWFRQAPGQE REFVAGLRWT                  180
DSSTEYADSV KGRFTISRDN SKNTVYLQMD SLRPEDTALY YCAADRSFLF AQALGATKNY                  240
EYWGQGTLVT VSSGGGGSCH HHHHH                                                       265

SEQ ID NO: 660            moltype = AA   length = 268
FEATURE                   Location/Qualifiers
REGION                    1..268
                          note = Synthetic
source                    1..268
                          mol_type = protein
                          organism = synthetic construct
SEQUENCE: 660
DVQLVESGGG VVQPGGSLQL SCAASGRTHS RLAMGWFRQA PGQEREFVAA ISRRGGSTNY                   60
ADSVKGRFTI SRDNSKNTVY LQMDSLRPED TALYYCAADD SSGDGYLDYW GQGTLVTVSS                  120
GGGGSGGGSE VQLVESGGGV VQPGGSLQLS CAASGRTFNI YTMSWFRQAP GQEREFVAGL                  180
RWTDSSTEYA DSVKGRFTIS RDNSKNTVYL QMDSLRPEDT ALYYCAADRS FLFAKALGAT                  240
KNYEYWGQGT LVTVSSGGGG SCHHHHHH                                                    268

SEQ ID NO: 661            moltype = AA   length = 265
FEATURE                   Location/Qualifiers
REGION                    1..265
                          note = Synthetic
source                    1..265
                          mol_type = protein
                          organism = synthetic construct
SEQUENCE: 661
DVQLVESGGG VVQPGGSLQL SCAASGRTHS RLAMGWFRQA PGQEREFVAA ISRRGGSTNY                   60
ADSVKGRFTI SRDNSKNTVY LQMDSLRPED TALYYCAADD SSGDGYLDYW GQGTLVTVSS                  120
QAPGQAEVQL VESGGGVVQP GGSLQLSCAA SGRTFNIYTM SWFRQAPGQE REFVAGLRWT                  180
DSSTEYADSV KGRFTISRDN SKNTVYLQMD SLRPEDTALY YCAADRSFLF AKALGATKNY                  240
EYWGQGTLVT VSSGGGGSCH HHHH                                                        265

SEQ ID NO: 662            moltype = AA   length = 269
FEATURE                   Location/Qualifiers
REGION                    1..269
                          note = Synthetic
source                    1..269
                          mol_type = protein
                          organism = synthetic construct
```

```
SEQUENCE: 662
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GLGLGLGLGL EVQLVESGGG VVQPGGSLQL SCAASGRTFN IYTMSWFRQA PGQEREFVAG   180
LRWTDSSTEY ADSVKGRFTI SRDNSKNTVY LQMDSLRPED TALYYCAADR SFLFAKALGA   240
TKNYEYWGQG TLVTVSSGGG GSCHHHHHH                                    269

SEQ ID NO: 663           moltype = AA  length = 269
FEATURE                  Location/Qualifiers
REGION                   1..269
                         note = Synthetic
source                   1..269
                         mol_type = protein
                         organism = synthetic construct
SEQUENCE: 663
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GTGTGTGTGT EVQLVESGGG VVQPGGSLQL SCAASGRTFN IYTMSWFRQA PGQEREFVAG   180
LRWTDSSTEY ADSVKGRFTI SRDNSKNTVY LQMDSLRPED TALYYCAADR SFLFAKALGA   240
TKNYEYWGQG TLVTVSSGGG GSCHHHHHH                                    269

SEQ ID NO: 664           moltype = AA  length = 269
FEATURE                  Location/Qualifiers
REGION                   1..269
                         note = Synthetic
source                   1..269
                         mol_type = protein
                         organism = synthetic construct
SEQUENCE: 664
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GVGVGVGVGV EVQLVESGGG VVQPGGSLQL SCAASGRTFN IYTMSWFRQA PGQEREFVAG   180
LRWTDSSTEY ADSVKGRFTI SRDNSKNTVY LQMDSLRPED TALYYCAADR SFLFAKALGA   240
TKNYEYWGQG TLVTVSSGGG GSCHHHHHH                                    269

SEQ ID NO: 665           moltype = AA  length = 268
FEATURE                  Location/Qualifiers
REGION                   1..268
                         note = Synthetic
source                   1..268
                         mol_type = protein
                         organism = synthetic construct
SEQUENCE: 665
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GGGGSGGGSE VQLVESGGGV VQPGGSLQLS CAASGRTFNI YTMSWFRQAP GQEREFVAGL   180
RWTDSSTEYA DSVKGRFTIS RDNSKNTVYL QMDSPRPEDT ALYYCAADRS FLFAKALGAT   240
KNYEYWGQGT LVTVSSGGGG SCHHHHHH                                     268

SEQ ID NO: 666           moltype = AA  length = 265
FEATURE                  Location/Qualifiers
REGION                   1..265
                         note = Synthetic
source                   1..265
                         mol_type = protein
                         organism = synthetic construct
SEQUENCE: 666
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
QAPGQAEVQL VESGGGVVQP GGSLQLSCAA SGRTFNIYTM SWFRQAPGQE REFVAGLRWT   180
DSSTEYADSV KGRFTISRDN SKNTVYLQMD SPRPEDTALY YCAADRSFLF AKALGATKNY   240
EYWGQGTLVT VSSGGGGSCH HHHH                                         265

SEQ ID NO: 667           moltype = AA  length = 269
FEATURE                  Location/Qualifiers
REGION                   1..269
                         note = Synthetic
source                   1..269
                         mol_type = protein
                         organism = synthetic construct
SEQUENCE: 667
DVQLVESGGG VVQPGGSLQL SCAASGRTHS RLAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GEGEGEGEGE EVQLVESGGG VVQPGGSLQL SCAASGRTFN IYTMSWFRQA PGQEREFVAG   180
LRWTDSSTEY ADSVKGRFTI SRDNSKNTVY LQMDSPRPED TALYYCAADR SFLFAKALGA   240
TKNYEYWGQG TLVTVSSGGG GSCHHHHHH                                    269

SEQ ID NO: 668           moltype = AA  length = 269
FEATURE                  Location/Qualifiers
```

| | | |
|---|---|---|
| REGION | 1..269 | |
| | note = Synthetic | |
| source | 1..269 | |
| | mol_type = protein | |
| | organism = synthetic construct | |

SEQUENCE: 668
DVQLVESGGG VVQPGGSLQL SCAASGRTHS RLAMGWFRQA PGQEREFVAA ISRRGGSTNY 60
ADSVKGRFTI SRDNSKNTVY LQMDSLRPED TALYYCAADD SSGDGYLDYW GQGTLVTVSS 120
GLGLGLGLGL EVQLVESGGG VVQPGGSLQL SCAASGRTFN IYTMSWFRQA PGQEREFVAG 180
LRWTDSSTEY ADSVKGRFTI SRDNSKNTVY LQMDSPRPED TALYYCAADR SFLFAKALGA 240
TKNYEYWGQG TLVTVSSGGG GSCHHHHHH 269

| | | |
|---|---|---|
| SEQ ID NO: 669 | moltype = AA length = 269 | |
| FEATURE | Location/Qualifiers | |
| REGION | 1..269 | |
| | note = Synthetic | |
| source | 1..269 | |
| | mol_type = protein | |
| | organism = synthetic construct | |

SEQUENCE: 669
DVQLVESGGG VVQPGGSLQL SCAASGRTHS RLAMGWFRQA PGQEREFVAA ISRRGGSTNY 60
ADSVKGRFTI SRDNSKNTVY LQMDSLRPED TALYYCAADD SSGDGYLDYW GQGTLVTVSS 120
GTGTGTGTGT EVQLVESGGG VVQPGGSLQL SCAASGRTFN IYTMSWFRQA PGQEREFVAG 180
LRWTDSSTEY ADSVKGRFTI SRDNSKNTVY LQMDSPRPED TALYYCAADR SFLFAKALGA 240
TKNYEYWGQG TLVTVSSGGG GSCHHHHHH 269

| | | |
|---|---|---|
| SEQ ID NO: 670 | moltype = AA length = 269 | |
| FEATURE | Location/Qualifiers | |
| REGION | 1..269 | |
| | note = Synthetic | |
| source | 1..269 | |
| | mol_type = protein | |
| | organism = synthetic construct | |

SEQUENCE: 670
DVQLVESGGG VVQPGGSLQL SCAASGRTHS RLAMGWFRQA PGQEREFVAA ISRRGGSTNY 60
ADSVKGRFTI SRDNSKNTVY LQMDSLRPED TALYYCAADD SSGDGYLDYW GQGTLVTVSS 120
GVGVGVGVGV EVQLVESGGG VVQPGGSLQL SCAASGRTFN IYTMSWFRQA PGQEREFVAG 180
LRWTDSSTEY ADSVKGRFTI SRDNSKNTVY LQMDSPRPED TALYYCAADR SFLFAKALGA 240
TKNYEYWGQG TLVTVSSGGG GSCHHHHHH 269

| | | |
|---|---|---|
| SEQ ID NO: 671 | moltype = AA length = 265 | |
| FEATURE | Location/Qualifiers | |
| REGION | 1..265 | |
| | note = Synthetic | |
| source | 1..265 | |
| | mol_type = protein | |
| | organism = synthetic construct | |

SEQUENCE: 671
DVQLVESGGG VVQPGGSLQL SCAASGRTHS RLAMGWFRQA PGQEREFVAA ISRRGGSTNY 60
ADSVKGRFTI SRDNSKNTVY LQMDSLRPED TALYYCAADD SSGDGYLDYW GQGTLVTVSS 120
GQAPGQEVQL VESGGGVVQP GGSLQLSCAA SGRTFNIYTM SWFRQAPGQE REFVAGLRWT 180
DSSTEYADSV KGRFTISRDN SKNTVYLQMD SPRPEDTALY YCAADRSFLF AKALGATKNY 240
EYWGQGTLVT VSSGGGGSCH HHHH 265

| | | |
|---|---|---|
| SEQ ID NO: 672 | moltype = AA length = 268 | |
| FEATURE | Location/Qualifiers | |
| REGION | 1..268 | |
| | note = Synthetic | |
| source | 1..268 | |
| | mol_type = protein | |
| | organism = synthetic construct | |

SEQUENCE: 672
DVQLVESGGG VVQPGGDLRL SCAASGRTHS RYAMGWFRQA PGQEREFVAA ISRRGGSTNY 60
ADSVKGRFTI SRDESKNTVY LQMNSLRPED TALYYCAADD SSGDGYLDYW GQGTLVTVSS 120
GGGGSGGGSE VQLVESGGGV VQPGGDLRLS CAASGRTFNI YTMSWFRQAP GQEREFVAGL 180
RWTDSSTEYA DSVKGRFTIS RDESKNTVYL QMNSLRPEDT ALYYCAADRS FLFAQALGAT 240
KNYEYWGQGT LVTVSSGGGG SCHHHHHH 268

| | | |
|---|---|---|
| SEQ ID NO: 673 | moltype = AA length = 268 | |
| FEATURE | Location/Qualifiers | |
| REGION | 1..268 | |
| | note = Synthetic | |
| source | 1..268 | |
| | mol_type = protein | |
| | organism = synthetic construct | |

SEQUENCE: 673
DVQLVESGGG VVQPGGSLQL SCAASGRTFS RLAMGWFRQA PGQEREFVAA ISRRGGSTNY 60
ADSVKGRFTI SRDNSKNTVY LQMDSLRPED TALYYCAADD SSGDGYLDYW GQGTLVTVSS 120
GGGGSGGGSE VQLVESGGGV VQPGGSLQLS CAASGRTFNI YTMSWFRQAP GQEREFVAGL 180

```
RWTDSSTEYA DSVKGRFTIS RDNSKNTVYL QMDSLRPEDT ALYYCAADRS FLFAQALGAT    240
KNYEYWGQGT LVTVSSGGGG SCHHHHHH                                      268

SEQ ID NO: 674           moltype = AA  length = 268
FEATURE                  Location/Qualifiers
REGION                   1..268
                         note = Synthetic
source                   1..268
                         mol_type = protein
                         organism = synthetic construct
SEQUENCE: 674
DVQLVESGGG VVQPGGDLRL SCAASGRTFS RLAMGWFRQA PGQEREFVAA ISRRGGSTNY    60
ADSVKGRFTI SRDESKNTVY LQMNSLRPED TALYYCAADD SSGDGYLDYW GQGTLVTVSS   120
GGGGSGGGSE VQLVESGGGV VQPGGDLRLS CAASGRTFNI YTMSWFRQAP GQEREFVAGL   180
RWTDSSTEYA DSVKGRFTIS RDESKNTVYL QMNSLRPEDT ALYYCAADRS FLFAQALGAT   240
KNYEYWGQGT LVTVSSGGGG SCHHHHHH                                      268

SEQ ID NO: 675           moltype = AA  length = 268
FEATURE                  Location/Qualifiers
REGION                   1..268
                         note = Synthetic
source                   1..268
                         mol_type = protein
                         organism = synthetic construct
SEQUENCE: 675
DVQLVESGGG VVQPGGSLQL SCAASGRTHD RYAMGWFRQA PGQEREFVAA ISRRGGSTNY    60
ADSVKGRFTI SRDNSKNTVY LQMDSLRPED TALYYCAADD SSGDGYLDYW GQGTLVTVSS   120
GGGGSGGGSE VQLVESGGGV VQPGGSLQLS CAASGRTFDI YTMSWFRQAP GQEREFVAGL   180
RWTDSSTEYA DSVKGRFTIS RDNSKNTVYL QMDSLRPEDT ALYYCAADRS FLFAQALGAT   240
KNYEYWGQGT LVTVSSGGGG SCHHHHHH                                      268

SEQ ID NO: 676           moltype = AA  length = 268
FEATURE                  Location/Qualifiers
REGION                   1..268
                         note = Synthetic
source                   1..268
                         mol_type = protein
                         organism = synthetic construct
SEQUENCE: 676
DVQLVESGGG VVQPGGSLRL SCAASGRTHD RYAMGWFRQA PGQEREFVAA ISRRGGSTNY    60
ADSVQGRFTI SRDNSKNTVY LQMDSLRPED TALYYCAADD SSGDGYLDYW GQGTLVTVSS   120
GGGGSGGGSE VQLVESGGGV VQPGGSLRLS CAASGRTFDI YTMSWFRQAP GQEREFVAGL   180
RWTDSSTEYA DSVQGRFTIS RDNSKNTVYL QMDSLRPEDT ALYYCAADRS FLFAQALGAT   240
KNYEYWGQGT LVTVSSGGGG SCHHHHHH                                      268

SEQ ID NO: 677           moltype = AA  length = 268
FEATURE                  Location/Qualifiers
REGION                   1..268
                         note = Synthetic
source                   1..268
                         mol_type = protein
                         organism = synthetic construct
SEQUENCE: 677
DVQLVESGGG VVQPGGSLRL SCAASGRTFD RLAMGWFRQA PGQEREFVAA ISRRGGSTNY    60
ADSVQGRFTI SRDMSKNTVY LQMDSLRPED TALYYCAADD SSGDGYLDYW GQGTLVTVSS   120
GGGGSGGGSE VQLVESGGGV VQPGGSLRLS CAASGRTFDI YTMSWFRQAP GQEREFVAGL   180
RWTDSSTEYA DSVQGRFTIS RDNSKNTVYL QMDSLRPEDT ALYYCAADRS FLFAQALGAT   240
KNYEYWGQGT LVTVSSGGGG SCHHHHHH                                      268

SEQ ID NO: 678           moltype = AA  length = 289
FEATURE                  Location/Qualifiers
REGION                   1..289
                         note = Synthetic
source                   1..289
                         mol_type = protein
                         organism = synthetic construct
SEQUENCE: 678
EDQVDPRLID GKGGGGSDVQ LVESGGGVVQ PGGSLRLSCA ASGRTFSRLA MGWFRQAPGK    60
EREFVAAISR RGGSTNYADS VKGRFTISRD NSKNTVYLQM NSLRPEDTAL YYCAADDSSG   120
DGYLDYWGQG TLVTVSSGGG GSGGGSEVQL VESGGGVVQP GGSLRLSCAA SGRTFNIYTM   180
SWFRQAPGKE REFVAGLRWT DSSTEYADSV KGRFTISRDN SKNTVYLQMN SLRPEDTALY   240
YCAADRSFLF AQALGATKNY EYWGQGTLVT VSSGGGGSGG GSCHHHHHH               289

SEQ ID NO: 679           moltype = AA  length = 289
FEATURE                  Location/Qualifiers
REGION                   1..289
                         note = Synthetic
source                   1..289
                         mol_type = protein
```

```
                        organism = synthetic construct
SEQUENCE: 679
EDQVDPRLID GKGGGGSDVQ LVESGGGVVQ PGGSLRLSCA ASGRTFSRLA MGWFRQAPGK       60
EREFVAAISR RGGSTNYADS VKGRFTISRD NSKNTVYLQM NSLRPEDTAL YYCAADDSSG      120
DGYLDYWGQG TLVTVSSGGG GSGGGGSEVQ LVESGGGVVQ PGGSLRLSCAA SGRTFNIYTM     180
SWFRQAPGKE REFVAGLRWT DSSTEYADSV KGRFTISRDN SKNTVYLQMN SLRPEDTALY      240
YCAADRSFLF AQALGATKNY EYWGQGTLVT VSSGGGGSGG GSCHHHHHH                  289

SEQ ID NO: 680          moltype = AA  length = 289
FEATURE                 Location/Qualifiers
REGION                  1..289
                        note = Synthetic
source                  1..289
                        mol_type = protein
                        organism = synthetic construct
SEQUENCE: 680
EDQVDPRLID GKGGGGSDVQ LVESGGGVVQ PGGSLRLSCA ASGRTFSRLA MGWFRQAPGK       60
EREFVAAISR RGGSTNYADS VKGRFTISRD NSKNTVYLQM NSLRPEDTAL YYCAADDSSG      120
DGYLDYWGQG TLVTVSSGGG GSGGGGSEVQ LVESGGGVVQP GGSLRLSCAA SGRTFNIYTM     180
SWFRQAPGKE REFVAGLRWT DSSTEYADSV KGRFTISRDN SKNTVYLQMN SLRPEDTALY      240
YCAADRSFLF AQALGATKNY EYWGQGTLVT VSSGGGGSGG GSCHHHHHH                  289

SEQ ID NO: 681          moltype = AA  length = 289
FEATURE                 Location/Qualifiers
REGION                  1..289
                        note = Synthetic
source                  1..289
                        mol_type = protein
                        organism = synthetic construct
SEQUENCE: 681
EDQVDPRLID GKGGGGSDVQ LVESGGGVVQ PGGSLRLSCA ASGRTFSRLA MGWFRQAPGK       60
EREFVAAISR RGGSTNYADS VKGRFTISRD NSKNTVYLQM NSLRPEDTAL YYCAADDSSG      120
DGYLDYWGQG TLVTVSSGGG GSGGGGSEVQ LVESGGGVVQP GGSLRLSCAA SGRTFNIYTM     180
SWFRQAPGKE REFVAGLRWT DSSTEYADSV KGRFTISRDN SKNTVYLQMN SLRPEDTALY      240
YCAADRSFLF AQALGATKNY EYWGQGTLVT VSSGGGGSGG GSCHHHHHH                  289

SEQ ID NO: 682          moltype = AA  length = 289
FEATURE                 Location/Qualifiers
REGION                  1..289
                        note = Synthetic
source                  1..289
                        mol_type = protein
                        organism = synthetic construct
SEQUENCE: 682
EDQVDPRLID GKGGGGSDVQ LVESGGGVVQ PGGSLRLSCA ASGRTFSRLA MGWFRQAPGK       60
EREFVAAISR RGGSTNYADS VKGRFTISRD NSKNTVYLQM NSLRPEDTAL YYCAADDSSG      120
DGYLDYWGQG TLVTVSSGGG GSGGGGSEVQ LVESGGGVVQP GGSLRLSCAA SGRTFNIYTM     180
SWFRQAPGKE REFVAGLRWT DSSTEYADSV KGRFTISRDN SKNTVYLQMN SLRPEDTALY      240
YCAADRSFLF AQALGATKNY EYWGQGTLVT VSSGGGGSGG GSCHHHHHH                  289

SEQ ID NO: 683          moltype = AA  length = 268
FEATURE                 Location/Qualifiers
REGION                  1..268
                        note = Synthetic
source                  1..268
                        mol_type = protein
                        organism = synthetic construct
SEQUENCE: 683
DVQLVESGGG VVQPGGSLRL SCAASGRTHS RYAMGWFRQA PGKEREFVAA ISRRGGSTNY       60
ADSVKGRFTI SRDNSKNTVY LQMNSLRPED TALYYCAADD SSGDGYLDYW GQGTLVTVSS      120
GGGGSGGGSE VQLVESGGGV VQPGGSLRLS CAASGRTFNI YTMSWFRQAP GKEREFVAGL      180
RWTDSSTEYA DSVKGRFTIS RDNSKNTVYL QMNSLRPEDT ALYYCAADRS FLFAQALGAT      240
KNYEYWGQGT LVTVSSGGGG SCHHHHHH                                         268

SEQ ID NO: 684          moltype = AA  length = 297
FEATURE                 Location/Qualifiers
REGION                  1..297
                        note = Synthetic
source                  1..297
                        mol_type = protein
                        organism = synthetic construct
SEQUENCE: 684
QRLMEDICLP RWGCLWEDDF GGGGSGGGGS DVQLVESGGG VVQPGGSLRL SCAASGRTFS       60
RLAMGWFRQA PGKEREFVAA ISRRGGSTNY ADSVKGRFTI SRDNSKNTVY LQMNSLRPED      120
TALYYCAADD SSGDGYLDYW GQGTLVTVSS GGGGSGGGSE VQLVESGGGV VQPGGSLRLS      180
CAASGRTFNI YTMSWFRQAP GKEREFVAGL RWTDSSTEYA DSVKGRFTIS RDNSKNTVYL      240
QMNSLRPEDT ALYYCAADRS FLFAQALGAT KNYEYWGQGT LVTVSSGGGG SHHHHHH         297

SEQ ID NO: 685          moltype = AA  length = 317
```

```
FEATURE                 Location/Qualifiers
REGION                  1..317
                        note = Synthetic
source                  1..317
                        mol_type = protein
                        organism = synthetic construct
SEQUENCE: 685
QRLMEDICLP RWGCLWEDDF GGGGSGGGGS GGGGSGGGGS GGGGSGGGGS DVQLVESGGG    60
VVQPGGSLRL SCAASGRTFS RLAMGWFRQA PGKEREFVAA ISRRGGSTNY ADSVKGRFTI   120
SRDNSKNTVY LQMNSLRPED TALYYCAADD SSGDGYLDYW GQGTLVTVSS GGGGSGGGSE   180
VQLVESGGGV VQPGGSLRLS CAASGRTFNI YTMSWFRQAP GKEREFVAGL RWTDSSTEYA   240
DSVKGRFTIS RDNSKNTVYL QMNSLRPEDT ALYYCAADRS FLFAQALGAT KNYEYWGQGT   300
LVTVSSGGGG SHHHHHH                                                 317

SEQ ID NO: 686          moltype = AA  length = 297
FEATURE                 Location/Qualifiers
REGION                  1..297
                        note = Synthetic
source                  1..297
                        mol_type = protein
                        organism = synthetic construct
SEQUENCE: 686
DVQLVESGGG VVQPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120
GGGGSGGGSE VQLVESGGGV VQPGGSLRLS CAASGRTFNI YTMSWFRQAP GKEREFVAGL   180
RWTDSSTEYA DSVKGRFTIS RDNSKNTVYL QMNSLRPEDT ALYYCAADRS FLFAQALGAT   240
KNYEYWGQGT LVTVSSGGGG SHHHHHHGGG GSGGGGSQRL MEDICLPRWG CLWEDDF      297

SEQ ID NO: 687          moltype = AA  length = 317
FEATURE                 Location/Qualifiers
REGION                  1..317
                        note = Synthetic
source                  1..317
                        mol_type = protein
                        organism = synthetic construct
SEQUENCE: 687
DVQLVESGGG VVQPGGSLRL SCAASGRTFS RLAMGWFRQA PGKEREFVAA ISRRGGSTNY    60
ADSVKGRFTI SRDNSKNTVY LQMNSLRPED TALYYCAADD SSGDGYLDYW GQGTLVTVSS   120
GGGGSGGGSE VQLVESGGGV VQPGGSLRLS CAASGRTFNI YTMSWFRQAP GKEREFVAGL   180
RWTDSSTEYA DSVKGRFTIS RDNSKNTVYL QMNSLRPEDT ALYYCAADRS FLFAQALGAT   240
KNYEYWGQGT LVTVSSGGGG SHHHHHHGGG GSGGGGSGGG GSGGGGSGGG GSGGGGSQRL   300
MEDICLPRWG CLWEDDF                                                 317

SEQ ID NO: 688          moltype = AA  length = 293
FEATURE                 Location/Qualifiers
REGION                  1..293
                        note = Synthetic
source                  1..293
                        mol_type = protein
                        organism = synthetic construct
SEQUENCE: 688
EDQVDPRLID GKGGGGSDVQ LVESGGGVVQ PGGSLRLSCA ASGIVWPINN MGWYRQAPGK    60
QRELVAEFTS GGNTNYADSV KGRFTISRGN DENTIYLQMN SLRPEDTALY YCKIYWGRDY   120
WGQGTLVTVS SGGGGSGGGG SGGGGSGGGG SGGGGSEVQL VESGGGVVQP GGSLRLSCAA   180
SGRNFGDYNM AWFRQAPGKE REFVAGITWS GGSTRYADSV KGRFTISRDN SKNTVYLQMN   240
SLRPEDTALY YCASGNGRLS ILIMSDNYFS WGQGTLVTVS SGGGGSCHHH HHH          293

SEQ ID NO: 689          moltype = AA  length = 257
FEATURE                 Location/Qualifiers
REGION                  1..257
                        note = Synthetic
source                  1..257
                        mol_type = protein
                        organism = synthetic construct
SEQUENCE: 689
DVQLVESGGG VVQPGGSLRL SCVASGRTFS RYAMGWFRQA PGKEREFVAA ISRRGGSTNY    60
ADSVKGRFTI SRDNSKNTVY LQMNSLRPED TALYYCAADY SSGDGYLDYW GQGTLVTVSS   120
GGGGSGGGSE VQLVESGGGV VQPGGSLRLS CAASGRTFNI YTMSWFRQAP GKERELVAGL   180
RWTDSSTEYA DSVKGRATIS RDNSKTTVYL QMNSLRPEDT ALYYCAADRS FLFAQAMGAT   240
KNYEYWGQGT LVTVSSA                                                 257

SEQ ID NO: 690          moltype = AA  length = 17
FEATURE                 Location/Qualifiers
REGION                  1..17
                        note = Synthetic
source                  1..17
                        mol_type = protein
                        organism = synthetic construct
SEQUENCE: 690
```

```
EDQVDPRLID GKGGGGS                                                  17

SEQ ID NO: 691        moltype = AA  length = 25
FEATURE               Location/Qualifiers
REGION                1..25
                      note = Synthetic
source                1..25
                      mol_type = protein
                      organism = synthetic construct
SEQUENCE: 691
GGGGSGGGGS GGGGSGGGGS GGGGS                                         25

SEQ ID NO: 692        moltype = AA  length = 8
FEATURE               Location/Qualifiers
source                1..8
                      mol_type = protein
                      organism = synthetic construct
SEQUENCE: 692
NPFDLLDF                                                            8

SEQ ID NO: 693        moltype = AA  length = 12
FEATURE               Location/Qualifiers
source                1..12
                      mol_type = protein
                      organism = synthetic construct
SEQUENCE: 693
SVAQATSSSG EA                                                       12

SEQ ID NO: 694        moltype = AA  length = 12
FEATURE               Location/Qualifiers
source                1..12
                      mol_type = protein
                      organism = synthetic construct
SEQUENCE: 694
VAQATSSSGE AP                                                       12

SEQ ID NO: 695        moltype = AA  length = 12
FEATURE               Location/Qualifiers
source                1..12
                      mol_type = protein
                      organism = synthetic construct
SEQUENCE: 695
AQATSSSGEA PD                                                       12

SEQ ID NO: 696        moltype = AA  length = 12
FEATURE               Location/Qualifiers
source                1..12
                      mol_type = protein
                      organism = synthetic construct
SEQUENCE: 696
QATSSSGEAP DS                                                       12

SEQ ID NO: 697        moltype = AA  length = 12
FEATURE               Location/Qualifiers
source                1..12
                      mol_type = protein
                      organism = synthetic construct
SEQUENCE: 697
ATSSSGEAPD SI                                                       12

SEQ ID NO: 698        moltype = AA  length = 12
FEATURE               Location/Qualifiers
source                1..12
                      mol_type = protein
                      organism = synthetic construct
SEQUENCE: 698
TSSSGEAPDS IT                                                       12

SEQ ID NO: 699        moltype = AA  length = 12
FEATURE               Location/Qualifiers
source                1..12
                      mol_type = protein
                      organism = synthetic construct
SEQUENCE: 699
SSSGEAPDSI TW                                                       12

SEQ ID NO: 700        moltype = AA  length = 12
FEATURE               Location/Qualifiers
source                1..12
```

```
                              mol_type = protein
                              organism = synthetic construct
SEQUENCE: 700
SSGEAPDSIT WK                                                          12

SEQ ID NO: 701                moltype = AA  length = 12
FEATURE                       Location/Qualifiers
source                        1..12
                              mol_type = protein
                              organism = synthetic construct
SEQUENCE: 701
SGEAPDSITW KP                                                          12

SEQ ID NO: 702                moltype = AA  length = 12
FEATURE                       Location/Qualifiers
source                        1..12
                              mol_type = protein
                              organism = synthetic construct
SEQUENCE: 702
GEAPDSITWK PY                                                          12

SEQ ID NO: 703                moltype = AA  length = 12
FEATURE                       Location/Qualifiers
source                        1..12
                              mol_type = protein
                              organism = synthetic construct
SEQUENCE: 703
EAPDSITWKP YD                                                          12

SEQ ID NO: 704                moltype = AA  length = 12
FEATURE                       Location/Qualifiers
source                        1..12
                              mol_type = protein
                              organism = synthetic construct
SEQUENCE: 704
APDSITWKPY DA                                                          12

SEQ ID NO: 705                moltype = AA  length = 12
FEATURE                       Location/Qualifiers
source                        1..12
                              mol_type = protein
                              organism = synthetic construct
SEQUENCE: 705
PDSITWKPYD AA                                                          12

SEQ ID NO: 706                moltype = AA  length = 12
FEATURE                       Location/Qualifiers
source                        1..12
                              mol_type = protein
                              organism = synthetic construct
SEQUENCE: 706
DSITWKPYDA AD                                                          12

SEQ ID NO: 707                moltype = AA  length = 12
FEATURE                       Location/Qualifiers
source                        1..12
                              mol_type = protein
                              organism = synthetic construct
SEQUENCE: 707
SITWKPYDAA DL                                                          12

SEQ ID NO: 708                moltype = AA  length = 12
FEATURE                       Location/Qualifiers
source                        1..12
                              mol_type = protein
                              organism = synthetic construct
SEQUENCE: 708
ITWKPYDAAD LD                                                          12

SEQ ID NO: 709                moltype = AA  length = 12
FEATURE                       Location/Qualifiers
source                        1..12
                              mol_type = protein
                              organism = synthetic construct
SEQUENCE: 709
TWKPYDAADL DP                                                          12

SEQ ID NO: 710                moltype = AA  length = 12
FEATURE                       Location/Qualifiers
```

```
source                    1..12
                          mol_type = protein
                          organism = synthetic construct
SEQUENCE: 710
WKPYDAADLD PT                                                               12

SEQ ID NO: 711            moltype = AA   length = 12
FEATURE                   Location/Qualifiers
source                    1..12
                          mol_type = protein
                          organism = synthetic construct
SEQUENCE: 711
KPYDAADLDP TE                                                               12

SEQ ID NO: 712            moltype = AA   length = 12
FEATURE                   Location/Qualifiers
source                    1..12
                          mol_type = protein
                          organism = synthetic construct
SEQUENCE: 712
PYDAADLDPT EN                                                               12

SEQ ID NO: 713            moltype = AA   length = 12
FEATURE                   Location/Qualifiers
source                    1..12
                          mol_type = protein
                          organism = synthetic construct
SEQUENCE: 713
YDAADLDPTE NP                                                               12

SEQ ID NO: 714            moltype = AA   length = 12
FEATURE                   Location/Qualifiers
source                    1..12
                          mol_type = protein
                          organism = synthetic construct
SEQUENCE: 714
DAADLDPTEN PF                                                               12

SEQ ID NO: 715            moltype = AA   length = 12
FEATURE                   Location/Qualifiers
source                    1..12
                          mol_type = protein
                          organism = synthetic construct
SEQUENCE: 715
AADLDPTENP FD                                                               12

SEQ ID NO: 716            moltype = AA   length = 12
FEATURE                   Location/Qualifiers
source                    1..12
                          mol_type = protein
                          organism = synthetic construct
SEQUENCE: 716
ADLDPTENPF DL                                                               12

SEQ ID NO: 717            moltype = AA   length = 12
FEATURE                   Location/Qualifiers
source                    1..12
                          mol_type = protein
                          organism = synthetic construct
SEQUENCE: 717
DLDPTENPFD LL                                                               12

SEQ ID NO: 718            moltype = AA   length = 12
FEATURE                   Location/Qualifiers
source                    1..12
                          mol_type = protein
                          organism = synthetic construct
SEQUENCE: 718
LDPTENPFDL LD                                                               12

SEQ ID NO: 719            moltype = AA   length = 12
FEATURE                   Location/Qualifiers
source                    1..12
                          mol_type = protein
                          organism = synthetic construct
SEQUENCE: 719
DPTENPFDLL DF                                                               12

SEQ ID NO: 720            moltype = AA   length = 12
```

```
                              -continued

FEATURE                 Location/Qualifiers
source                  1..12
                        mol_type = protein
                        organism = synthetic construct
SEQUENCE: 720
PTENPFDLLD FN                                                           12

SEQ ID NO: 721          moltype = AA  length = 12
FEATURE                 Location/Qualifiers
source                  1..12
                        mol_type = protein
                        organism = synthetic construct
SEQUENCE: 721
TENPFDLLDF NQ                                                           12

SEQ ID NO: 722          moltype = AA  length = 12
FEATURE                 Location/Qualifiers
source                  1..12
                        mol_type = protein
                        organism = synthetic construct
SEQUENCE: 722
ENPFDLLDFN QT                                                           12

SEQ ID NO: 723          moltype = AA  length = 12
FEATURE                 Location/Qualifiers
source                  1..12
                        mol_type = protein
                        organism = synthetic construct
SEQUENCE: 723
NPFDLLDFNQ TQ                                                           12

SEQ ID NO: 724          moltype = AA  length = 12
FEATURE                 Location/Qualifiers
source                  1..12
                        mol_type = protein
                        organism = synthetic construct
SEQUENCE: 724
PFDLLDFNQT QP                                                           12

SEQ ID NO: 725          moltype = AA  length = 12
FEATURE                 Location/Qualifiers
source                  1..12
                        mol_type = protein
                        organism = synthetic construct
SEQUENCE: 725
FDLLDFNQTQ PE                                                           12

SEQ ID NO: 726          moltype = AA  length = 12
FEATURE                 Location/Qualifiers
source                  1..12
                        mol_type = protein
                        organism = synthetic construct
SEQUENCE: 726
DLLDFNQTQP ER                                                           12

SEQ ID NO: 727          moltype = AA  length = 12
FEATURE                 Location/Qualifiers
source                  1..12
                        mol_type = protein
                        organism = synthetic construct
SEQUENCE: 727
LLDFNQTQPE RG                                                           12

SEQ ID NO: 728          moltype = AA  length = 12
FEATURE                 Location/Qualifiers
source                  1..12
                        mol_type = protein
                        organism = synthetic construct
SEQUENCE: 728
LDFNQTQPER GD                                                           12

SEQ ID NO: 729          moltype = AA  length = 12
FEATURE                 Location/Qualifiers
source                  1..12
                        mol_type = protein
                        organism = synthetic construct
SEQUENCE: 729
DFNQTQPERG DN                                                           12
```

| | | |
|---|---|---|
| SEQ ID NO: 730 | moltype = AA length = 12 | |
| FEATURE | Location/Qualifiers | |
| source | 1..12 | |
| | mol_type = protein | |
| | organism = synthetic construct | |
| SEQUENCE: 730 | | |
| FNQTQPERGD NN | | 12 |
| | | |
| SEQ ID NO: 731 | moltype = AA length = 12 | |
| FEATURE | Location/Qualifiers | |
| source | 1..12 | |
| | mol_type = protein | |
| | organism = synthetic construct | |
| SEQUENCE: 731 | | |
| NQTQPERGDN NL | | 12 |
| | | |
| SEQ ID NO: 732 | moltype = AA length = 12 | |
| FEATURE | Location/Qualifiers | |
| source | 1..12 | |
| | mol_type = protein | |
| | organism = synthetic construct | |
| SEQUENCE: 732 | | |
| QTQPERGDNN LT | | 12 |
| | | |
| SEQ ID NO: 733 | moltype = AA length = 12 | |
| FEATURE | Location/Qualifiers | |
| source | 1..12 | |
| | mol_type = protein | |
| | organism = synthetic construct | |
| SEQUENCE: 733 | | |
| TQPERGDNNL TR | | 12 |
| | | |
| SEQ ID NO: 734 | moltype = AA length = 131 | |
| FEATURE | Location/Qualifiers | |
| source | 1..131 | |
| | mol_type = protein | |
| | organism = synthetic construct | |
| SEQUENCE: 734 | | |
| DVQLVESGGG VVQPGGSLQL SCAASGGTKR RLAMGWFRQA PGQEREWVAA ISRRGGSTNY | | 60 |
| ADSVKGRFTI SRDNSKNTVY LQMDSLRPED TALYYCAADD SVGDGYLDYW GQGTLVTVSS | | 120 |
| GGGGSHHHHH H | | 131 |
| | | |
| SEQ ID NO: 735 | moltype = AA length = 131 | |
| FEATURE | Location/Qualifiers | |
| source | 1..131 | |
| | mol_type = protein | |
| | organism = synthetic construct | |
| SEQUENCE: 735 | | |
| DVQLVESGGG VVQPGGSLQL SCAASGGTKR RLAMGWFRQA PGQEREWVAA ISRRGGSTNY | | 60 |
| ADSVKGRFTI SRDNSKNTVY LDMDDLRPED TALYYCAADD SVGDGYLDYW GQGTLVTVSS | | 120 |
| GGGGSHHHHH H | | 131 |
| | | |
| SEQ ID NO: 736 | moltype = AA length = 20 | |
| FEATURE | Location/Qualifiers | |
| source | 1..20 | |
| | mol_type = protein | |
| | organism = synthetic construct | |
| SEQUENCE: 736 | | |
| QRLMEDICLP RWGCLWEDDF | | 20 |
| | | |
| SEQ ID NO: 737 | moltype = AA length = 18 | |
| FEATURE | Location/Qualifiers | |
| source | 1..18 | |
| | mol_type = protein | |
| | organism = synthetic construct | |
| SEQUENCE: 737 | | |
| RLIEDICLPR WGCLWEDD | | 18 |

```
SEQ ID NO: 738        moltype = AA   length = 16
FEATURE               Location/Qualifiers
source                1..16
                      mol_type = protein
                      organism = synthetic construct
SEQUENCE: 738
QRFCTGHFGG LYPCNG                                                    16

SEQ ID NO: 739        moltype = AA   length = 34
FEATURE               Location/Qualifiers
source                1..34
                      mol_type = protein
                      organism = synthetic construct
SEQUENCE: 739
FNMQQQRRFY EALHDPNLNE EQRNAKIKSI RDDN                                34
```

UNITED STATES PATENT AND TRADEMARK OFFICE
CERTIFICATE OF CORRECTION

| | | |
|---|---|---|
| PATENT NO. | : 12,098,400 B2 | Page 1 of 1 |
| APPLICATION NO. | : 18/219159 | |
| DATED | : September 24, 2024 | |
| INVENTOR(S) | : Andreas Vegge et al. | |

It is certified that error appears in the above-identified patent and that said Letters Patent is hereby corrected as shown below:

On the Title Page

At Column 1, item (72) Inventor section, Line number 6, please replace with "Per J. Greisen, Sammamish, WA (US);".

Signed and Sealed this
Seventeenth Day of June, 2025

Coke Morgan Stewart
*Acting Director of the United States Patent and Trademark Office*